(12) United States Patent
Rando et al.

(10) Patent No.: US 6,323,185 B1
(45) Date of Patent: *Nov. 27, 2001

(54) ANTI-VIRAL GUANOSINE-RICH OLIGONUCLEOTIDES AND METHOD OF TREATING HIV

(75) Inventors: Robert F. Rando; Susan Fennewald; Joseph G. Zendegui, all of The Woodlands; Joshua O. Ojwang, Spring; Michael E. Hogan, The Woodlands, all of TX (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/682,255

(22) Filed: Jul. 17, 1996

Related U.S. Application Data (6362) Continuation-in-part of application No. 08/535,168, filed as application No. PCT/US94/04529 on Apr. 25, 1994, now Pat. No. 6,184,369, application No. 08/682,255, which is a continuation-in-part of application No. 08/145,704, filed on Oct. 28, 1993, now Pat. No. 5,567,604, which is a continuation-in-part of application No. 08/053,027, filed on Apr. 23, 1993, now abandoned.

(60) Provisional application No. 60/001,505, filed on Jul. 19, 1995, provisional application No. 60/013,688, filed on Mar. 19, 1996, provisional application No. 60/014,007, filed on Mar. 25, 1996, provisional application No. 60/015,714, filed on Apr. 17, 1996, and provisional application No. 60/016,271, filed on Apr. 23, 1996.

(51) Int. Cl.[7] .............................. A61K 31/70; C07H 21/00
(52) U.S. Cl. ......................... 514/44; 536/23.1; 536/24.5; 435/6
(58) Field of Search ................... 514/44; 435/6; 536/23.1, 24.5

(56) References Cited

U.S. PATENT DOCUMENTS

| | | | |
|---|---|---|---|
| 3,687,808 | * | 8/1972 | Merigan et al. ..................... 536/23.1 |
| 4,388,306 | * | 6/1983 | Field et al. ............................ 424/177 |
| 4,981,957 | * | 1/1991 | LeBleu et al. ....................... 536/25.2 |
| 5,075,217 | * | 12/1991 | Weber ........................................ 435/6 |
| 5,176,996 | * | 1/1993 | Hogan et al. .............................. 435/6 |
| 5,334,711 | * | 8/1994 | Sproat et al. ........................ 536/24.5 |
| 5,397,702 | * | 3/1995 | Cahalan et al. ..................... 435/69.1 |
| 5,428,007 | * | 6/1995 | Fischer et al. ............................ 514/6 |
| 5,523,389 | | 6/1996 | Ecker et al. ......................... 536/23.1 |
| 5,567,604 | * | 10/1996 | Rando et al. .......................... 435/238 |
| 5,591,721 | | 1/1997 | Agrawal et al. ........................ 514/44 |
| 5,714,320 | * | 2/1998 | Kool ........................................... 435/6 |
| 6,013,639 | * | 1/2000 | Peyman et al. ........................ 514/44 |

FOREIGN PATENT DOCUMENTS

| | | |
|---|---|---|
| 0375408 | 6/1990 | (EP) . |
| 0713705A | 5/1996 | (EP) . |
| 8901036 * | 2/1989 | (WO) . |
| WO9408053 | 4/1994 | (WO) . |

OTHER PUBLICATIONS

He et al., "Characterization of Human Cytomegalovirus UL84 Early Gene and Identification of Its Putative Protein Product," *J. Virology*, 66(2), 1098–1108 (1992).*

Oram et al., "Use of Recombinant Plasmids to Investigate the Structure of the Human Cytomegalovirus Genome," *J. Gen. Virology*, 59, 111–129 (1982).*

Weston et al., "Sequence of the Short Unique Region, Short Repeats, and art of theLong Repeats of Human Cytomegalovirus," *J. Mol. Biology*, 192, 177–208 (1986).*

Tamashiro et al.(I), "Structure of the Heterogeneous L–S Junction Region of Human Cytomegalovirus Strain AD169 DNA," *J. Virology*, 52(2), 541–548 (1984).

Mocarski et al., "Structure and Variability of the α Sequence in the Genome of Human Cytomegalovirus (Towne Strain)," *J. Gen. Virology*, 68, 2223–2230 (1987).

Tamashiro et al.(II), "Terminal Structure and Heterogeneity in Human Cytomegalovirus Strain AD 169," *J. Virology*, 59(3), 591–604 (1986).

Henninghausen et al., "Nuclear Factor 1 Interacts with Five DNA Elements int eh Promoter Region of the Human Cytomegalovirus Major Immediate Early Gene," *EMBO J.*, 5(6), 1367–1371 (1986).

Rasmussen et al., "Sequences in Human Cytomegalovirus Which Hybridize with the Avian Retrovirus Oncogene v myc Are G+C Rich and Do Not Hybridize with the Human c–myc Gene," *Molecular & Cellular Biology*, 5(6), 1525–1530 (1985).

G. Zon, "Oligonucleotide Analogues as Potential Chemotherapeutic Agents," *Pharmaceutical Research*, 5(9), 539–549 (1988).

Miller et al., "Control of Ribonucleic Acid Function by Oligonucleoside Methylphosphonates," *Biochemie*, 67, 769–776 (1985).

Marshall et al., "Phosphorodithioate DNA as a Potential Therapeutic Drug," *Science*, 259, 1564–1570 (1993).

Gura, "Antisense has Growing Pains—Efforts to Develop Antisense Compounds for Cancer, AIDS, and Other Diseases Have Encountered Some Unexpected Questions About How the Drugs Really Work," *Science*, 270, 575–577 (1995).

Kreig et al., "CpG Motifs in Bacterial DNA Trigger Direct B–Cell Activation," *Nature*, 374, 546–549 (Apr. 6, 1995).

(List continued on next page.)

*Primary Examiner*—Gary Geist
*Assistant Examiner*—L Eric Crane

(57) ABSTRACT

A method and compositions for treating viral infection in vitro and in vivo using a guanosine-rich oligonucleotide. The oligonucleotides have sufficient guanosine to form a guanosine tetrad. Also provided are oligonucleotides of at least two runs of at least two guanosines. Also provided are guanosine-rich oligonucleotides and methods for treating viral infections in humans, and a method for designing guanosine-rich oligonucleotides having anti-viral activity and integrase inhibition activity.

17 Claims, 68 Drawing Sheets

OTHER PUBLICATIONS

Patick et al., "Antiviral and Resistance Studies of AG1343, an Orally Bioavailable Inhibitor of Human Immunodeficiency Virus Protease," *Antimicrobial Agents and Chemotherapy*, 40(2), 292–297 (Feb., 1996); supplied but not cited by applicant.*

Rusconi et al., "Naphthalene Sulfonate Polymers with CD4–Blocking and Anti–Human Immunodefiency Virus Type 1 Activities," *Antimicrobial Agents and Chemotherapy*, 40(1), 234–236 (Jan. 1996); supplied but not cited by applicant.*

Wallace et al.(I), "Pharmacokinetics and Distribution of a $^{33}$P–Labeled Anti–Human Immunodeficiency Virus Oligonucleotide (AR177) After Single–and Multiple–Dose Intravenous Administration to Rats," *J. Pharmacology and Experimental Therapeutics*, 280(3), 1480–1488 (1997); supplied but not cited by applicant.*

Wallace et al. (II), "Single–Dose Hemodynamic Toxicity and Pharmacokinetics of a Partial Phosphorothiate Anti–HIV Oligonucleotide (AR177) After Intravenous Administration to Cynomolgus Monkeys," *J. Pharmacology and Experimental Therapeutics*, 278(3), 1306–1312 (1996); supplied but not citied by applicant.*

Wallace et al. (III), "Repeat–Dose Toxicity and Pharmacokinetics of a Partial Phosphorothioate Anti–HIV Oligonucleotide (AR177) After Bolus Intravenous Adminstration to Cynomolgus Monkeys," *J. Pharmacology and Experimental Therapeutics*, 278(3), 1313–1317 (1987); supplied but not cited by applicant.*

Rando, "Clinical Trial Results of Aronex's Anti–HIV Oligonucleotide (AR177) and Recent Antisense Technology Advances," IBC's Fourth International Symposium on Antisense Therapeutics with New Applications for Genomics, International Business Communications, Inc., Wyndham Emerald Plaza Hotel, San Diego, CA Feb. 6–7, 1997; only abstract supplied; supplied but not cited by applicant.

Clinical Update, Hybridon, Inc. Worcester, MA, Feb. 10, 1997; press release apparently obtained from the Internet; supplied but not cited by applicant.

Hybridon Moves GEM® 91 into Confirmatory Clinical Trail in Advanced HIV–Positive Patient, Hybridon, Inc., Cambridge, MA, Feb. 10, 1997; original release date was Feb. 6–7, 1997 in San Diego, CA (See ref. RB supra); supplied but not cited by applicant.

Kahn et al., "Phase 1 Study of AR–177 (Zintevir), an HIV–1 Inhibitor with Significant Activity Against Integase Protein: Safety, Pharmacokinetics, Immunologic and Virologic Activity," Abstract of presentation at the 11th International Conference on Aids, Vancouver, BC, Jul. 7–12, 1996; supplied but not cited by applicant.

Kern, "Preclinical Evaluation of Antiviral Agents: In Vitro and Animal Model Testing," Ch. 3 in Antiviral Agents and Viral Disease in Man, Galasso et al. (eds.), Raven Press, Ltd., New York, NY 1990, pp. 87–114, only pp. 87 and 94–95 supplied.

Balzarini, J., "Suppression of the Breakthrough of Human Immunodeficiency Virus Type 1 (HIV–1) in Cell Culture by Thiocarboxanilide Derivatives When Used Individually or in Combination with Other HIV–1 Specific Inhibitos (i.e., TSAO Derivatives)," Proc. Natl. Acad. Sci. USA 92:5470–5474 (Jun. 1995).

Nagy, K. et al., "Antiviral Activity of Human Immunodeficiency Virus Type 1 Protease Inhibitors in a Single Cycle of Infection: Evidence for a Role of Protease in the Early Phase," J. Virol. 68:757–765 (Feb. 1994).

Nelson et al., "Bifunctional Oligonucleotide Probes Synthesized Using a Novel CPG Support are Able to Detect Single Base Pair Mutations," Nucleic Acids Research, 17:7187–7194 (1989) Issue No. 18.

Nelson et al., "A new and Versatile Reagent for Incorporation Multiple Primary Aliphatic Amines Into Synthetic Oligonucleotides," Nucleic Acids Research, 17:7187–7194 (1989) Issue No. 18.

Vlassov et al., "The Effect of Modification of Terminal Groups of Oligonucleotides on Their Stability in Mycoplasma Culture," Biopolim. Kletka, Vol. 7, No. 5 (Novosibirsk, USSR), pp. 37–41, see Biosis, Abstract No. 94–032, 483, (1984). Month of publication data is unavailable for this reference.

Zendugui et al., "In Vivo Stability and Kinetics of Absorption and Disposition of 3'–Phosphopropl Amine Oligonucleotides," Nucleic Acids Research, 20:307–314 (1992) Issue No. 2. Month of publication data is unavailable for this reference.

Agrawal S. et al., "Oligodeoxynucleoside Phosphoramidates and Phosphorothioates as Inhibitors of Human Immunodeficiency Virus" Proceedings of the National Academy of Science of USA, Vol. 85, Oct. 1, 1988, pp. 7079–7083.

Wyatt, J. et al., "Combinatorially selected guanosine–quartet structure is a potent inhibitor of human immunodeficiency virus envelope–mediated cell fusion" Proceedings of the National Academy of Sciences of USA., vol. 91, Feb. 1994.

Rando, R. et al., "Suppression of human immunodeficiency virus type 1 activity in vitro by oligonucleotides which form intramolecular tetrads" Journal of Biological Chemistry., vol. 270, Jan. 27, 1995, pp. 1754–1760.

Supplementary Partial European Search Report, dated Jul. 16, 1998, that was received in EPC counterpart application EP 94 917899, filed on Apr. 25, 1994.

* cited by examiner

FMLV Clone 57

Bacterial Expressions Vectors

Mitochondrial DNA

2 LTR

Early LTR

Gag

| | T30175 | T30177 | T30038 |
|---|---|---|---|
| IC$_{50}$ (Mn$^{2+}$) | 115 | 50 | 90 |
| IC$_{50}$ (Mg$^{2+}$) | 21 | 12 | 75 |
| RATIO (IC$_{50}$ Mn$^{2+}$/ IC$_{50}$ Mg$^{2+}$) | 5.5 | 4.2 | 1.2 |

T30695 60/20

T30702 32/30

T30696 122/13

T30701 72/30

T30697 130/13

T30700 82/40

T30698 150/16

T30699 136/50

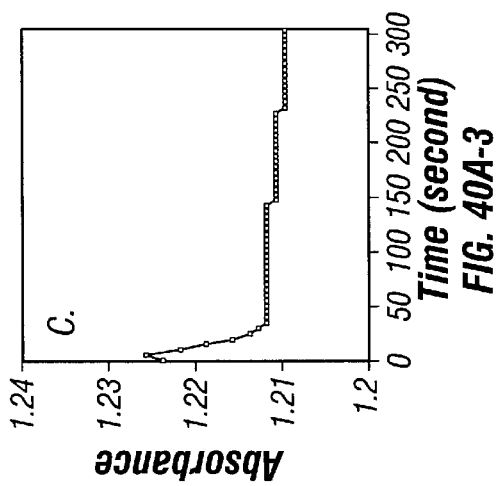
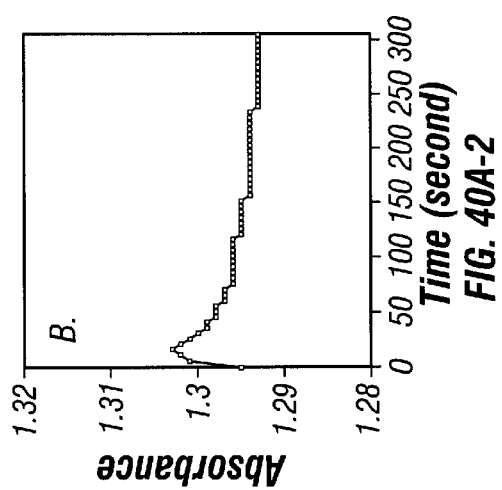
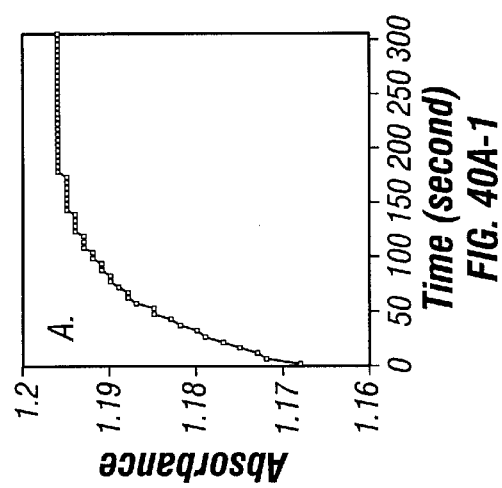
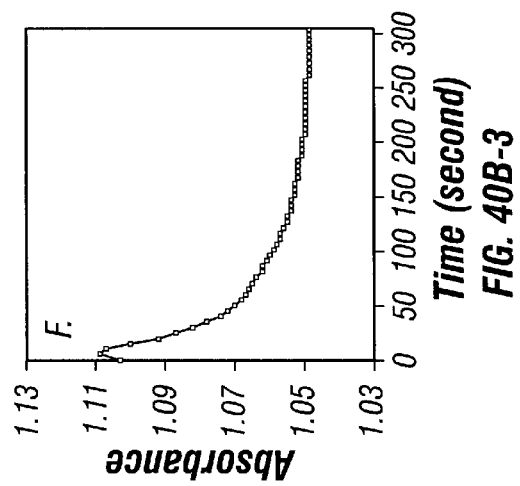
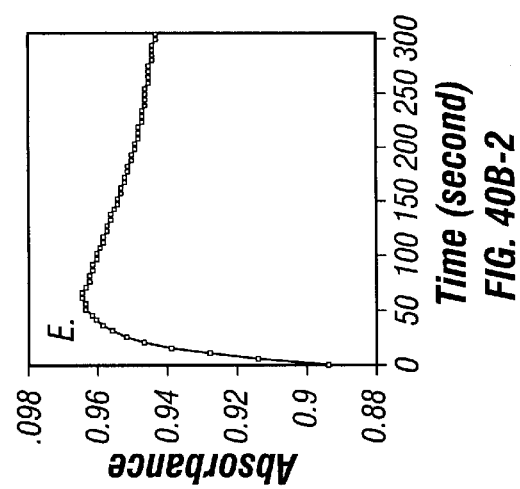
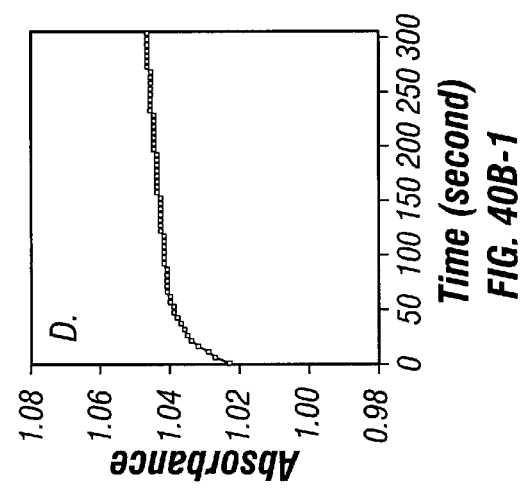
FIG. 40A-1   FIG. 40A-2   FIG. 40A-3
FIG. 40B-1   FIG. 40B-2   FIG. 40B-3

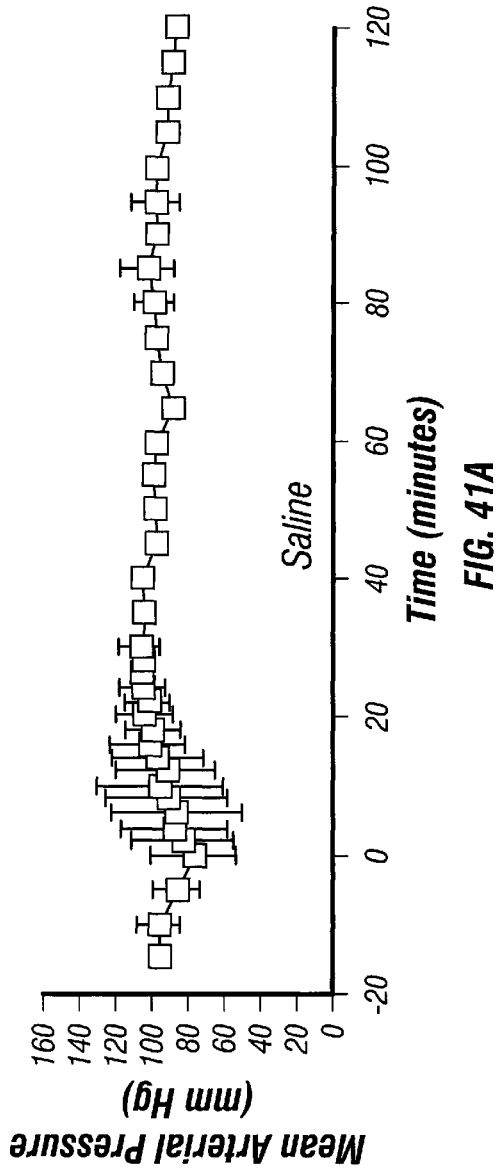
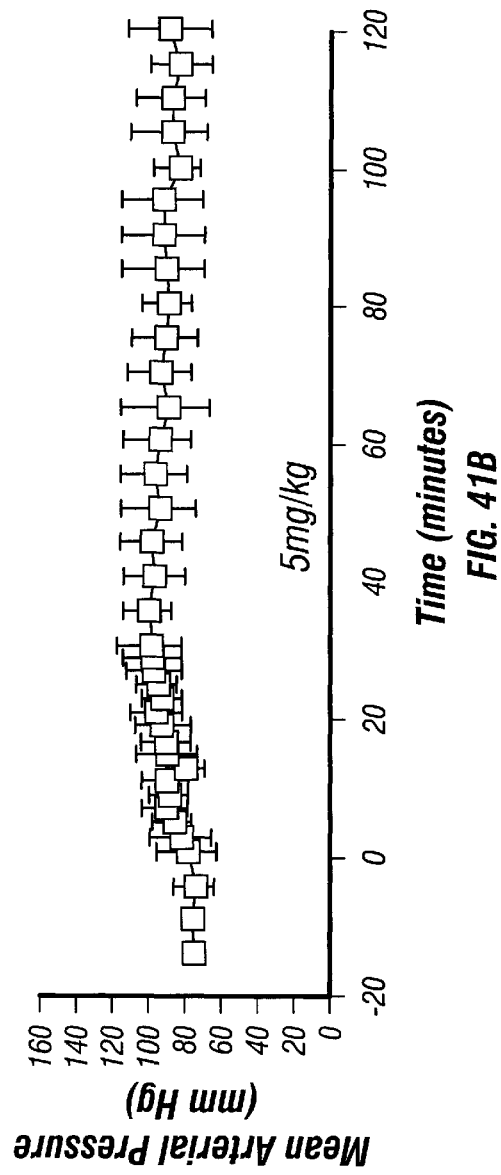
FIG. 41A
FIG. 41B

US 6,323,185 B1

ANTI-VIRAL GUANOSINE-RICH OLIGONUCLEOTIDES AND METHOD OF TREATING HIV

CROSS REFERENCE TO RELATED APPLICATIONS

The present application is a continuation-in-part of U.S. patent application Ser. No. 08/145,704 filed Oct. 28, 1993, now U.S. Pat. No. 5,567,604, which is a continuation-in-part of U.S. patent application Ser. No. 08/053,027 filed Apr. 23, 1993, now abandoned. This application is also a continuation-in-part of allowed U.S. patent application Ser. No. 08/535,168, filed Oct. 23, 1995, now U.S. Pat. No. 6,184,369, which is the U.S. national stage of PCT/US94/04529 filed Apr. 25, 1994. The present application also claims the benefit of the following 35 U.S.C §111(b) provisional applications: Ser. Nos. 60/001,505, filed Jul. 19, 1995, 60/013,688, filed Mar. 19, 1996, 60/014,007, filed Mar. 25, 1996, 60/015,714, filed Apr. 17, 1996, and 60/016,271, filed Apr. 23, 1996.

STATEMENT REGARDING FEDERALLY SPONSORED RESEARCH OR DEVELOPMENT

Research leading to this invention was supported in part by a grant from the United States Government through the National Institute of Health under a CRADA agreement. The U.S. Government has certain rights in this invention.

BACKGROUND OF THE INVENTION

1. Field of the Invention

The present invention relates generally to the field of oligonucleotide chemistry and anti-viral pharmacotherapy. More specifically, the present invention relates to novel guanosine-rich oligonucleotides and their use as novel anti-viral agents.

2. Description of the Related Art

General In Vitro Studies

Previously, it was believed that "antisense" oligonucleotides inhibit viruses by interfering with protein translation via an RNA:DNA duplex structure. More recent research, however, indicates a variety of possible mechanisms by which oligo-nucleotides inhibit viral infections. For example, oligodeoxycytidine (poly SdC) inhibits HIV-1. Marshall et al., PNAS (1992) 89:6265–6269, discussed the potential mechanism (competitive inhibition) by which oligodeoxycytidine directly inhibits viral reverse transcriptase. Poly SdC also inhibited AMV reverse transcriptase and Pol I (Klenow fragment) and polymerase α, β and γ. Previously, Matsukura et al., PNAS (1987) 84:7706–7710, used a similar phosphorothioate derivative of oligo-deoxycytidine to demonstrate inhibition of HIV-1 in culture. Marshall and Caruthers, Science (1993) 259:1564–1569, reported the use of diphosphorothioate oligo-nucleotides, e.g., antisense-specific, random nucleotide combinations and oligodeoxycytidine against HIV-1. In all cases, the mechanism of action was attributed to a direct inhibition of HIV-1 reverse transcriptase. Other potential mechanisms of anti-viral action of oligonucleotides were postulated by Boiziau et al., PNAS (1992) 89:768–772, e.g., promotion of RNAse H activity and inhibition of reverse transcriptase initiating cDNA synthesis. In addition, Goa et al., Molecular Pharmacology (1992) 41:223–229 reported that phosphorothioate oligo-nucleotides inhibit human DNA polymerases and RNAse H, and the adsorption or penetration of the virus into cells. Iyer et al., Nucleic Acids Research (1990) 18:2855–2859 reported that if a base was removed from an anti-sense polynucleotide forming an abasic site, the compound did not lose its activity which argues against the need for the formation of an RNA:DNA antisense mediated hybrid for anti-viral activity. Stein et al. have characterized the interaction of poly SdC with the V3 loop of HIV-1 gp120, and postulated that the specific interaction of poly SdC with the HIV-1 V3 loop may be a mechanism by which an oligonucleotide could inhibit HIV-1 in vivo.

It is known that synthetic oligonucleotides may be designed which are capable of binding to duplex DNA to form triplex DNA. See U.S. Pat. No. 5,176,996 Hogan & Kessler issued Jan. 5, 1993. That patent discloses a method for making synthetic guanosine-rich oligonucleotides which are targeted to specific sequences in duplex DNA and which form collinear triplexes by binding to the major groove of the DNA duplex.

Specific In Vitro Studies/In Vitro HIV Inhibition With T30177

Infection with the human immunodeficiency virus type 1 (HIV-1) and the subsequent development of acquired immunodeficiency syndrome (AIDS), has become a threat to public health on a global scale. Preventing further spread of this disease is a major health priority worldwide. Although HIV-1 was confirmed to be the causative agent of AIDS as early as 1984, few drugs and no vaccines are effective at preventing the ultimate onset of AIDS in HIV-1 seropositive individuals. This is due, in large part, to the complexity of the causative agent itself, the dynamics of virus production and the speed at which drug-resistant mutants can arise. Ho, et al., Nature 373:123–126 (1995); Wei, et al., Nature 373:117–122 (1995).

Infection of T-cells by HIV-1 results in the insertion of proviral (double-stranded) DNA into the host cell genome. Goff, S. P., Annu. Rev. Genet. 26:527–544 (1992). The integration process involves both the sequence-specific and sequence independent endonucleolytic and strand transfer activities of the virally encoded integrase enzyme. Katz, et al., Ann. Rev. Biochem. 63:133–173 (1994); Vink, et al., Trends in Genetics 9:433–438 (1993). Once the proviral state is established, the infection may manifest itself in several ways including a latent infection in which viral replication is not measurable until the cell becomes activated or through a chronic infection in which dividing or non-dividing cells persistently release virus in the absence of any cytopathic effect. In addition, recent reports on the kinetics of virus production (and clearance) indicate a dynamic process in which virtually a complete replacement of wild-type virus by drug-resistant virus in plasma can occur after only two to four weeks of drug therapy. Ho, et al., Nature 373:123–126 (1995); Wei, et al., Nature 373:117–122 (1995). For this reason it is of utmost importance to develop new anti-HIV-1 agents which can complement, by additive or synergistic activity, current therapies.

One relatively new approach used in the development of antiviral therapeutics for HIV-1 is the use of oligonucleotides designed as antisense agents. Letsinger, et al., Proc. Natl. Acad. Sci. USA 86:6553–6556 (1989); Lisziewicz, et al., Proc. Natl. Acad. Sci. USA 90:3860–3864 (1993); Milligan, et al., J. Med. Chem. 36:1923–1937 (1993). While much effort is being spent on rationally designed oligonucleotides such as antisense agents there have also been recent findings of multiple alternative mechanisms by which oligonucleotides can inhibit viral infections. Gao, et al., J.B.C. 264:11521–11526 (1989); Marshall, et al., Proc. Natl. Acad. Sci. USA 89:6265–6269 (1992); Ojwang, et al., J. AIDS 7:560–570 (1994); Rando, et al, J. Biol. Chem.

270:1754–1760 (1995). For example, Stein et al. (Stein, et al., *Antisense Research and Development* 3:19–31 (1993)) have characterized the interaction of oligodeoxycytidine, containing a phosphorothioate (PT) backbone (poly (SdC)) with the v3 loop of HIV-1 gp 120. It was determined that poly $(SdC)_{28}$ specifically interacted with the positively charged V3 loop with a Kd of approximately $5 \times 10^{-7}$M. Stein et al. (*Antisense Research and Development* 3:19–31 (1993)) then postulated that the interaction of poly (SdC) with the HIV-1 v3 loop may be a mechanism by which poly (SdC) could inhibit HIV-1 in vivo. More recently, Wyatt et. al. (Wyatt, et al., *Proc. Natl. Acad. Sci. USA* 91:1356–1360 (1994)) have described the interaction of a short G-rich oligonucleotide, synthesized with a total PT backbone, which also interacts with the v3 loop of HIV-1 gp 120. In addition, we have previously reported that oligonucleotides containing only deoxyguanosine (G) and thymidine (T), synthesized with natural phosphodiester (PD) internucleoside linkages, were capable of inhibiting HIV-1 in culture. Ojwang, et al., *J. AIDS* 7:560–570 (1994). The most efficacious member of he G22 this dG-rich class of oligonucleotides, I100-15, was found capable of folding upon itself to form a structure stabilized by the formation of two stacked guanosine-tetrads which yielded a guanosine-octet. Rando, et al, *J. Biol. Chem.* 270:1754–1760 (1995). Furthermore, it was observed that the positions of the guanosine bases in the I100-15 sequence, found in both the tetrads and connecting loops in that structure, were extremely important to the overall anti-HIV-1 activity of the oligonucleotide. Rando, et al, *J. Biol. Chem.* 270:1754–1760 (1995).

Site of Activity Studies-Viral Integrase Inhibition

Two events which are characteristic of the life cycle of retroviruses can be utilized for therapeutic intervention. One is reverse transcription, whereby the single-stranded RNA genome of the retrovirus is reverse transcribed into singled-stranded cDNA and then copied into double-stranded DNA. The next event is integration, whereby the double-stranded viral DNA generated by reverse transcriptase is inserted into a chromosome of the host cell, establishing the proviral state. Integration is catalyzed by the retroviral enzyme integrase which is encoded at the 3'-end of the pol gene. Varmus, et al. Mobile DNA, pp. 53–108, Am. Soc. Microbiol, Washington, D.C. (1989). Integrase first catalyzes the excision of the last two nucleotides from each 3'-end of the linear viral DNA, leaving the terminal conserved dinucleotide CA-3'-OH at these recessed 3' ends (FIG. 23A). This activity is referred to as the 3'-processing or dinucleotide cleavage. After transport to the nucleus as a nucleoprotein complex, Varmus, et al. *Mobile DNA*, pp. 53–108, Am. Soc. Microbiol, Washington, D.C. (1989), integrase catalyzes a concerted DNA strand transfer reaction by nucleophilic attack of the two viral ends onto a host chromosome. This reaction generates a recombination intermediate resembling an X structure, analogous to a Holliday junction intermediate. [For recent reviews see Katz and Skalka, Katz, et al.,*Ann. Rev. Biochem.* 63, 133–173 (1994), and Vink and Plasterk, Vink, et al., *Trends Genet.* 9, 433–437 (1993)]. Mutation analyses of the viral integrase gene demonstrate that integration is required for effective retroviral replication and that it is a legitimate target for the design of antiretroviral drugs (Engleman, et al., *J. Virol.* 69, 2729–2736 (1995); Englund, et al, *J. Virol.* 69, 3216–3218 (1995)).

It is known that AZT nucleotides can inhibit HIV-1 integrase, Mazumder, et al., *Proc. Natl. Acad. Sci.* 91, 5771–5775 (1994), and that substitution or unsaturation at the 3'-position of the deoxyribose confers potency against HIV-1 integrase. These results suggested that the enzyme's nucleotide binding site could serve as a potential drug target. It has been shown that the potential stacking interactions gained from the heterocyclic rings can further enhance potency against HIV-1 integrase.

Recently, oligonucleotides composed of deoxyguanosine and thymidine have been reported to inhibit HIV-1 replication. Rando, et al., *J. Biol. Chem.* 270, 1754–1760 (1995); Wyatt, et al., *Proc. Natl. Acad. Sci. U.S.A.* 91, 1356–1360 (1994). Oligonucleotides forming intramolecular G4s did not block virus adsorption but rather inhibited viral-specific transcripts. Rando, et al., *J. Biol. Chem.* 270, 1754–1760 (1995); Ojwang et al. *J. Aids* 7:560–570 (1994).

Structure-Function Studies

It is known that G-rich nucleic acid sequences can fold, in the presence of $Na^+$ or $K^+$ ion, to form orderly structures stabilized by guanosine tetrads. Depending on sequence, intramolecular folds, Rando et al. *J. Biol. Chem.* 270: 1754–1760, 1995), dimers (Smith, F. W., & Feigon, J. (1992) *Nature (London)* 344, 410–414, Sundquist, W. I. & Klug, A. (1989) *Nature (London)* 334, 364–366; Kang, et al. (1992) *Nature (London)* 356, 126131; Balaguumoorthy, P. & Brahmachari, S. K. (1994) *J. Biol. Chem.* 269, 21858–21869), tetrameres (Son, D. & Gilbert, W. (1990) *Nature (London)* 344, 410–414; Jin, et al. (1990) *Science* 250, 543–546; Jin, et al. (1992) *Proc. Natl. Acad. Sci. USA* 89, 8832–8836; Lu et al., (1992) *Biochemistry* 31, 2455–2459), and higher order associations have been detected. Such tetrad based structures have been postulated to serve as the structural basis for telomere function (Sen, D. & Gilbert, W. (1988) *Nature (London)* 334, 364–366), and have been hypothesized to play a role in retroviral replication (Bock et al. (1992) *Nature (London)* 355, 564–566), and transcription regulation (Marshall et al. (1992) *Proc. Nalt. Acid. Sci. USA* 8,9, 6265–6269; Wyatt et al. (1994) *Proc. Natl. Acad. Sci. USA* 91, 1356–60).

Recently, several groups have shown that compounds which contain tetrad-based folds may have activity as potential drug compounds. Bock and colleagues have shown that an intramolecular fold, obtained by a SELEX procedure can bind tightly to thrombin, so as to inhibit clotting (Bock et al. (1992) *Nature (London)* 355, 564–566). Additionally Wyatt et al. (Wyatt et al. (1994) *Proc. Natl. Acad. Sci. USA* 91, 1356–60) has shown that a dimer-wise pairing of phosphorothioate oligomers with the sequence T2G4T2 (four stranded intermolecular tetrads) gives rise to anti-HIV activity, by inhibition of viral adsorption to the cell surface.

The present inventors have also obtained evidence for sequence-selective inhibition of HIV-1 by simple phosphodiester oligonucleotides which form G-tetrad based structures. The highest activity was obtained with a 17 mer, referred to as T30177, with composition G12-T5 (Rando et al., (1994) *J. Biol. Chem.* 270, 1754–1760; Ojwang, J. et al. (1995) *J. Aids* 7, 560–570), with 2 phosphorothioate linkages (1 at each end) to block cellular exonuclease activity (Bishop et al. (1996) *J. Biol. Chem.* 271, 5698–5703). NMR evidence was obtained (Rando et al., (1995) *J. Biol. Chem.* 270, 1754–1760) to suggest that, by reference to similar oligomers (Smith, F. W., & Feigon, J. (1992) *Nature (London)* 344, 410–414), T30177 forms a stable intramolecular fold which is stabilized by a pair of G-tetrads, connected by three singlestranded loops and a 1–2 base long tail to either side of the fold. Those preliminary studies suggested that oligomer folding was coupled to $K^+$ ion binding (Rando et al., (1995) *J. Biol. Chem.* 270, 1754–1760). Additional studies have suggested that T30177 and related derivatives are potent inhibitors of HIV-1 integrase, in vitro (Ojwang et al. (1995) *Antimicrob. Agent Chemotherepy* 39, 2426–35).

Pharmacokinetic Studies-Single Dose

Antisense, triple-helix, duplex decoy, and protein-binding (aptamer) oligonucleotides have been shown to have potential as drugs for the treatment of a variety of human clinical disorders (Stein and Cheng, 1993; Marshall and Caruthers, 1993, *Science* 259: 1564–1570; Chubb and Hogan, 1992, *Trends in Biotechnology* 10: 132–136; Stull and Szoka, 1995, *Pharm. Res.* 12: 465–483. A number of oligonucleotides have undergone pre-clinical testing, and several are in human clinical trials. One finding that has aroused some concern (Black et al., 1994, *Antisense Res. Dev.* 4: 299–301) is the observation that total phosphorothioate oligonucleotides cause hemodynamic changes following rapid intravenous administration. Severe hypotension, leukopenia, complement activation, and death have been reported to occur in primates after rapid infusions of total phosphorothioate oligonucleotides (Cornish et al., 1993, *Pharmacol. Commun.* 3: 239–247; Galbraith et al., 1994, *Antisense Res. Dev.* 4: 201–206). These findings have raised the question of whether the cardiovascular toxicity is a property of phosphorothioate oligonucleotides, or of all oligonucleotides. On the basis of these findings, an FDA commentary has recommended that cardiovascular screening be performed for the pre-clinical safety assessment of oligonucleotides (Black et al., 1994).

Pharmacokinetic Studies-Repeat Dose

Oligonucleotides have advanced to the stage that they are now considered as potential therapeutics for the treatment of a variety of human diseases, and several are presently in clinical trials. Pre-clinical studies have generally shown that doses up to approximately 50 mg/kg are safe, but that higher doses can cause kidney and liver damage, and death (Srinivasan and Iversen, 1995, *J. Clin. Lab. Analysis* 9:129–137) Bolus intravenous administration has posed a particular concern since it has been shown to sometimes result in serious hypotensive events in primates (Cornish et al., 1993; Galbraith et al., 1994; Black et al., 1995). However, because the number of oligonucleotides that have been studied has been small, it is difficult to conclude at the time of making the invention whether all oligonucleotides share similar toxicities. In particular, given the various ways of modifying the backbone of oligonucleotides (Wu-Pong, 1994, *BioPharm* 7:20–33) and their ability to fold into distinct three-dimensional structures (Stull and Szoka, 1995, *Pharm. Res.* 12:465–483), Rando et al. *J. Biol. Chem.* 270; 1754–1760, 1995, the safety profile of different oligonucleotides may be quite distinct.

Human Clinical Trials

In addition to toxicological studies, efficacy studies should be carried out for oligonucleotide drugs. In the past, the preferred method of testing drug efficacy, especially in HIV-1 infected patients, was to monitor survival of treated patients. However, recent statistical studies have shown that a good indicator of anti-HIV drug efficacy is the reduction in the numbers of copies of viral genome per unit of patient serum (viral load). Mellors et al. (1996) *Science* 272:1167–1170. Reductions in viral load of 90%, or more preferably 99% are desired. However, reductions of viral load of lesser percentages can be useful, especially where the trend of the overall treatment regime is consistently downward.

Thus, there is a substantial need for antiviral drugs with novel chemistry and with sites of activity distinct from drugs presently used. Most highly desired would be antiviral drugs whose efficacy in humans is known.

SUMMARY OF THE INVENTION

In one embodiment of the present invention, there are provided methods and compositions useful in treating pathophysiological states caused by viruses, comprising administering a pharmacological dose of an oligonucleotide, the dose being sufficient to inhibit production of the virus, wherein the oligonucleotide contains a high percentage of guanosine bases. In preferred embodiments, the oligonucleotide has a three dimensional structure and this structure is stabilized by guanosine tetrads. In a further embodiment, the oligonucleotide compositions of the invention have two or more runs of two contiguous deoxyguanosines. In certain embodiments of the present invention, the target virus is either herpes simplex virus, human immunodeficiency virus, human papilloma virus, human cytomegalovirus, adenovirus, and hepatitis B virus.

In still yet another embodiment of the present invention, there is provided a guanosine-rich oligonucleotide having a three dimensional structure, wherein the three dimensional structure is stabilized by guanosine tetrads or at least two runs of two contiguous deoxyguanosines and wherein these oligonucleotides exhibit anti-viral activity. In a further embodiment, the oligonucleotides of the present invention have partially (pPT) or fully (PT) phosphorothioated internucleoside linkages (backbones) or other chemical modifications. In a further embodiment, the oligonucleotides of the present invention have chemically modified or unnatural (synthetic) bases.

BRIEF DESCRIPTION OF THE DRAWINGS

Figures for Section A

FIG. 5A shows that the reduction in full length transcripts directed by the T7 and T3 promoter when I100-51 (SEQ. ID. NO. 29) (anti-parallel triple helix forming oligonucleotide; FMLV2ap) was added. Samples in which no oligonucleotide was added were counted and used as 100% transcription reference points. In all other reactions $4 \times 10^{-6}$M of G101-50 (SEQ. ID. NO. 12) (4e-6) was added and where indicated G101-50 plus I100-51 at concentrations ranging from $2 \times 10^{-9}$ to $2 \times 10^{-6}$M (2e-9 to 2e-6). FIG. 5B shows the reduction in full length transcript by I100-01 (SEQ. ID. NO. 21) (FMLV2p). T7 directed transcripts were treated as in FIG. 5A. G101-50 was added to each reaction except the control (no oligo) with or without various concentration of I100-01 or I100-11 (SEQ. ID. NO. 26) (26% G-ctl). FIG. 5C shows the analysis of truncated (63 base pair) transcript.

FIG. 11 shows a schematic diagram of the HIV-1 genome not drawn to scale.

Figures for Section B

Figure 16:
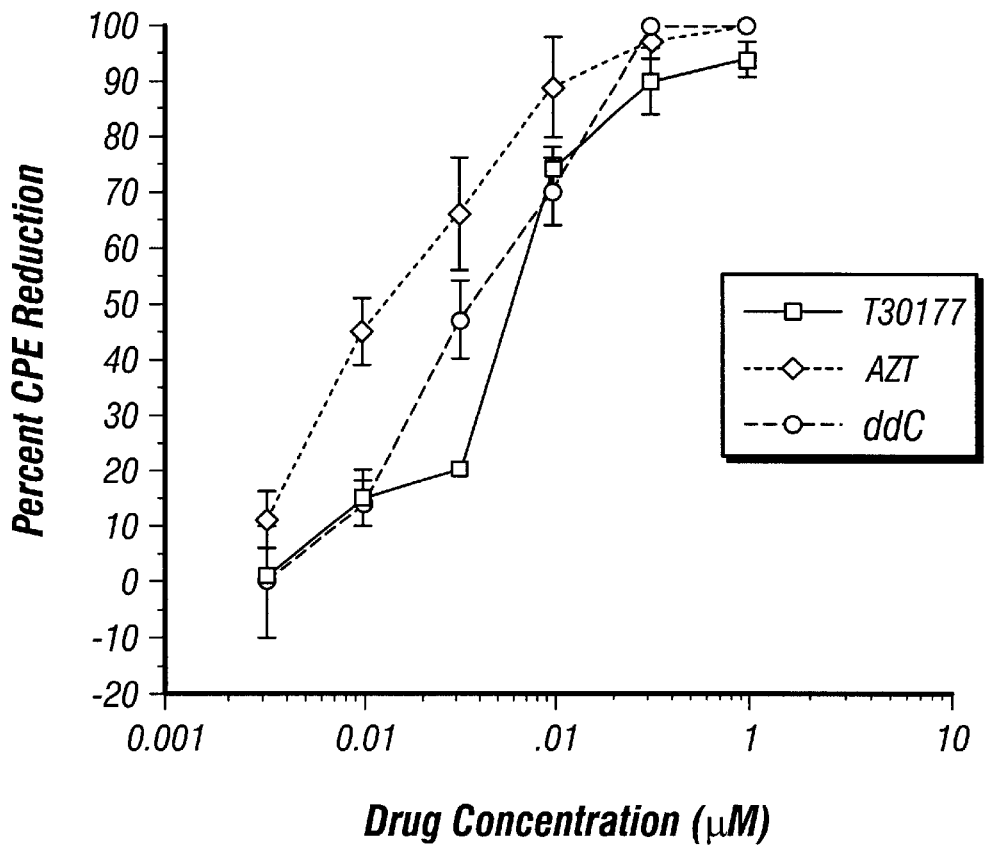

FIG. 16. Dose responsive profile for T30177, AZT and ddC. CEM-SS cells were infected with HIV-1$_{RF}$(0.01 MOI) and treated with various concentrations of each drug for six days at which time the degree of HIV-1 -induced syncytium formation (cytopathic effect, cpe) was addressed. The results shown are the averages of three or more experiments with the standard deviations indicated.

Figure 17:
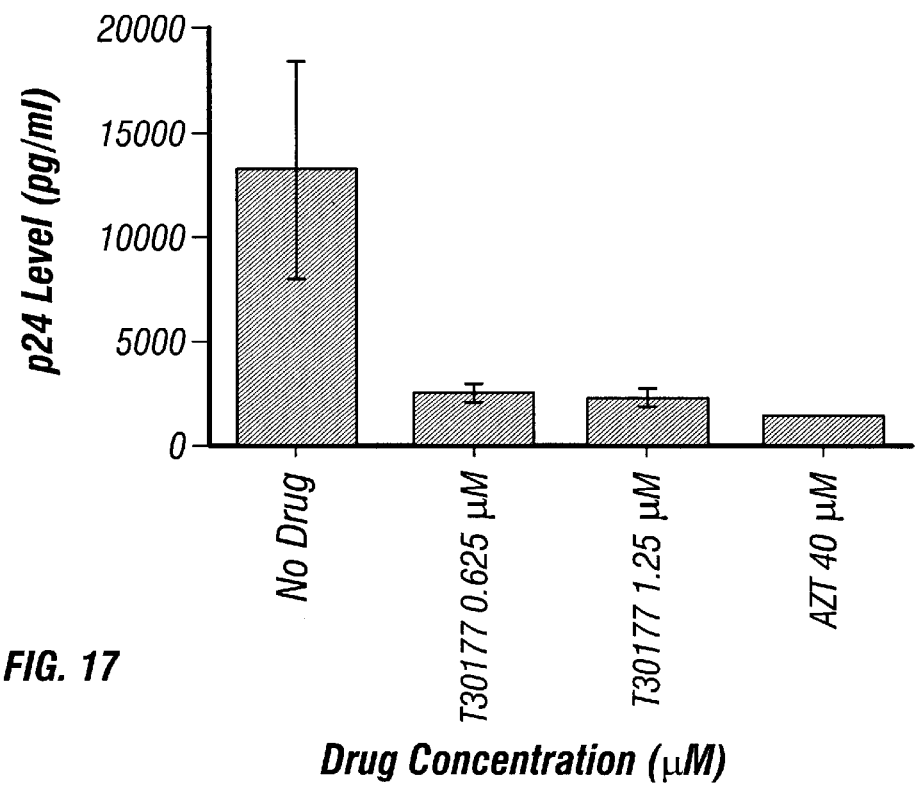

FIG. 17. Effect of T30177 on HIV-1 replication in primary macrophages. Primary macrophages were obtained from PBMC preparations and infected with HIV-$1_{DV}$ for 24 hours in the presence of the indicated amount of drug. Seven days post-infection the intracellular levels of p24 were quantitated using the Coulter p24 antigen capture ELISA kit. The results shown are the averages of three or more experiments.

Figure 18:
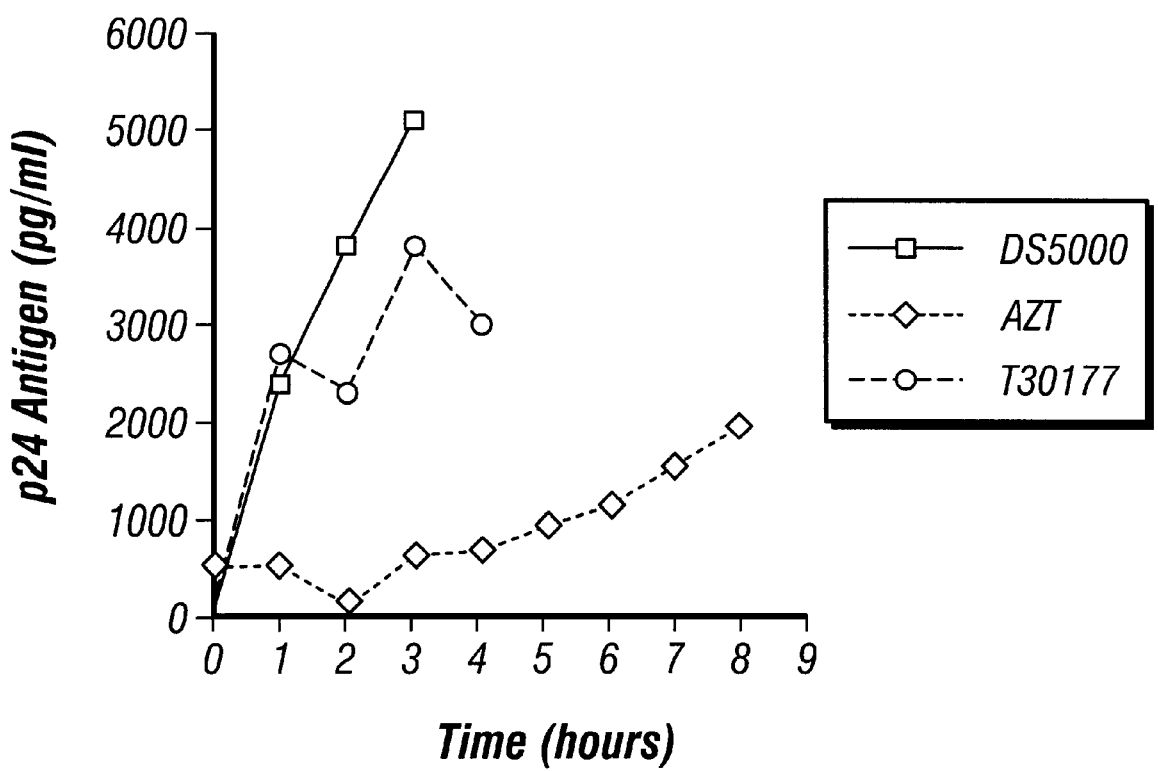

FIG. 18. Effect of time of drug addition on the inhibition profile of T30177, AZT, and DS5000. MT4 cells, infected with HIV-$1_{IIIB}$ at a MOI of 1, were treated at various times during (time 0) or post-virus-infection with the test compounds at a concentration 100-fold higher than their respective $IC_{50}$ values. Viral p24 levels in the culture medium were monitored 29 hour post-infection. The results shown are the averages of three or more experiments.

Figure 19A:
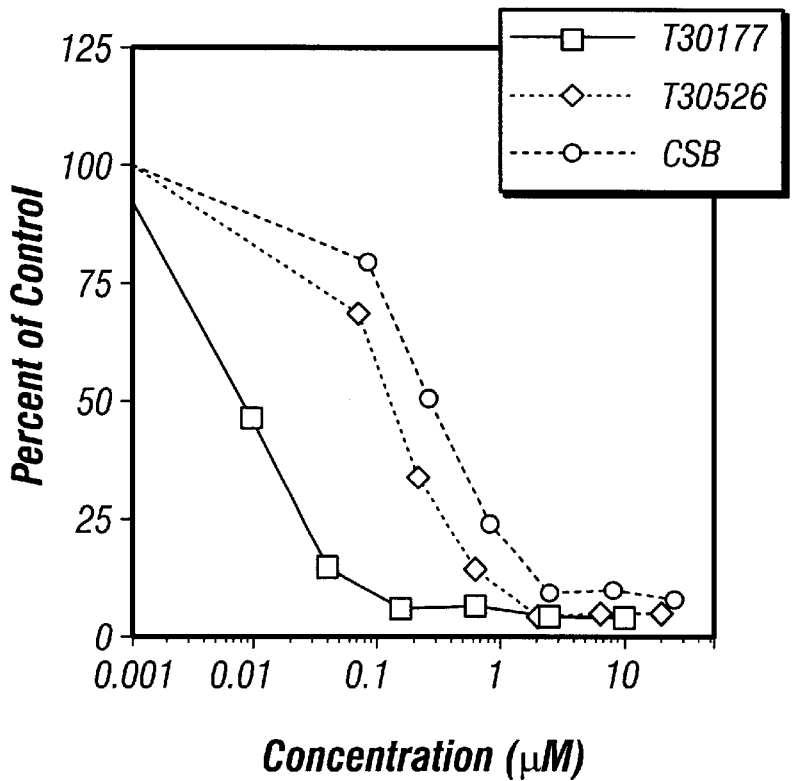
Figure 19B:
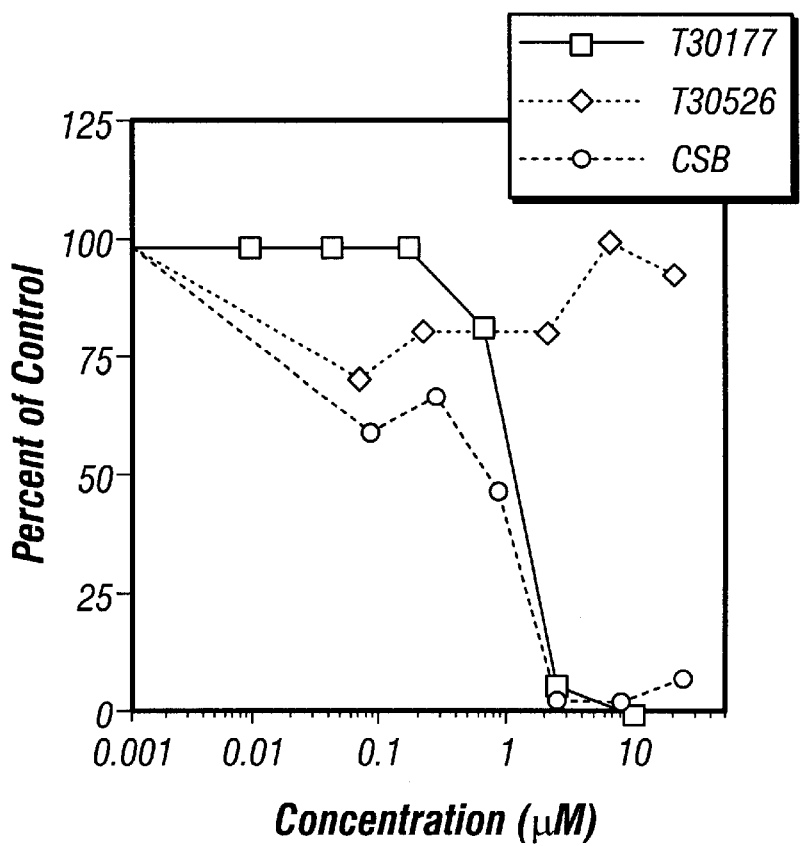

FIG. 19. HeLa-CD4-β-galactosidase cell assays. (FIG. 19A). HeLa-CD4-β-galactosidase cells were incubated in medium containing drug for one hour before virus was added to the culture medium. One hour after the addition of virus the cells were washed extensively to remove unbound virus and extracellular test material. Forty-eight hours post-infection the cells were fixed and stained with X-gal. Blue multinuclear cells were then counted under an inverted microscope (5). (FIG. 19B). HeLa-CD4-β-galactosidase cells were incubated for 1 hour in the presence of test compound at which time an equal number of HL2/3 cells were added to each well. Cells were incubated for 48 hours at which time they were fixed, stained with X-gal and counted under an inverted microscope.

Figure 20:
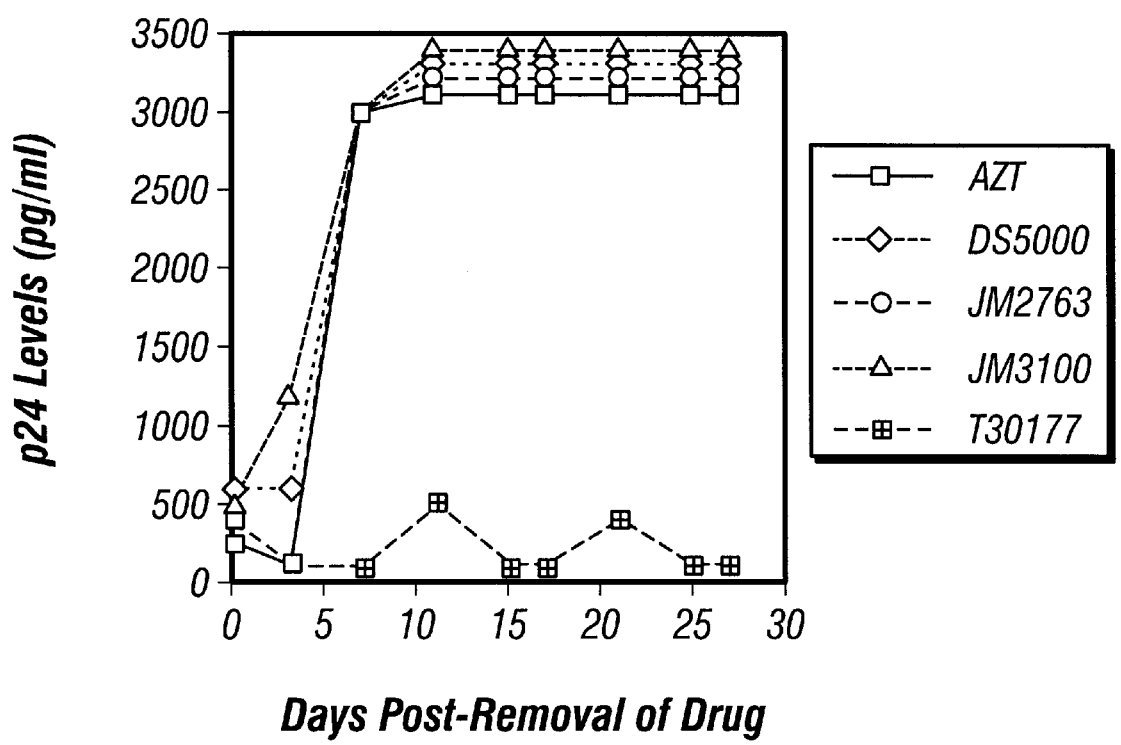

FIG. 20. Long term suppression of HIV-$1_{IIIB}$ after treatment of infected cell cultures with T30177. (A) MT4 cells were infected with 0.01 MOI of HIV-$1_{IIIB}$ and then cultured for 4 days in the presence of T30177, AZT, DS5000, JM2763 or JM3100 using a concentration of drug equivalent to 100fold over the respective $IC_{50}$ value. After 4 days the cells were washed extensively and further incubated in drug free medium. The level of viral p24 antigen in the culture medium was monitored at various times after removal of drug from the infected cell cultures. The values given are the averages of three or more experiments.

Figure 21A:
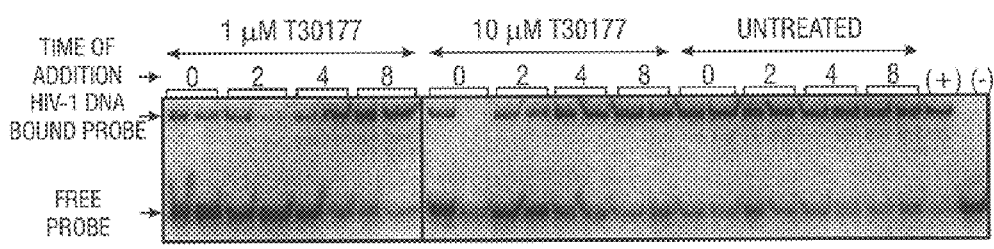
Figure 21B:
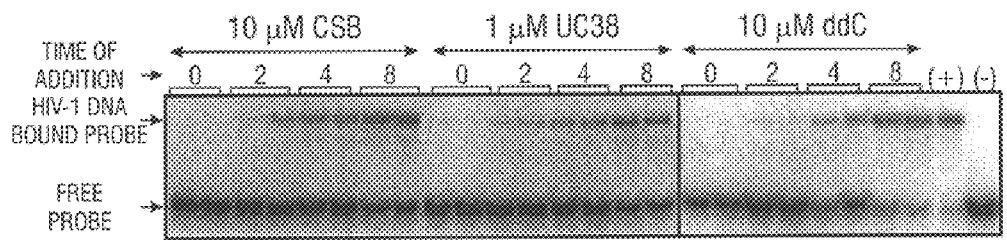

FIGS. 21A–B. Single cycle analysis of viral DNA. CEM-SS cells infected with HIV-$1_{SKI}$ at an MOI of 1, were treated with T30177, UC38, CSB or ddC at the indicated time post-viral infection. Time 0 indicates the treatment of cell cultures with drug during virus infection. After 12 hours the DNA was extracted from the infected cells and used as a template for PCR. The concentration of drug used in each assay is equivalent to 10 to 100-fold over their respective $IC2_{50}$ values.

Figure 22A:
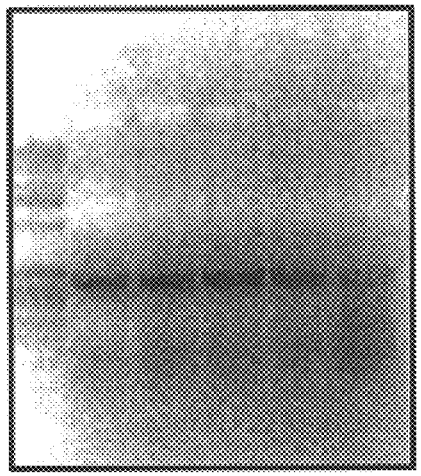
Figure 22B:
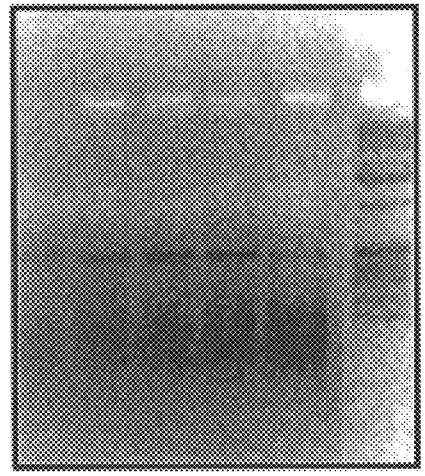
Figure 22C:
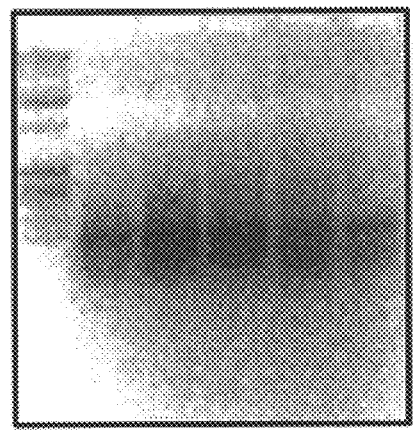
Figure 22D:
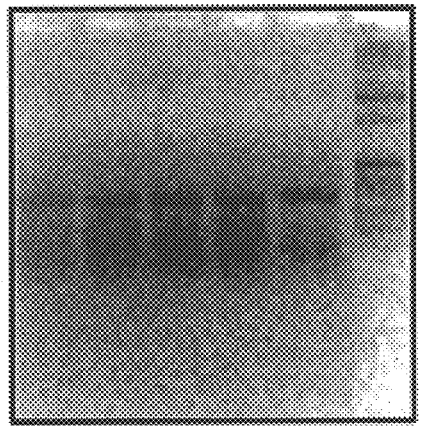

FIGS. 22A–D. Analysis of replicated viral DNA. CEM-SS cells were infected with HIV-$1_{SKI}$ at an MOI of 1 and then treated with T30177. Eighteen to 20 hour post-infection the low molecular weight Hirt DNA was analyzed using PCR primers which would amplify mitochondrial DNA (FIG. 22A), early viral synthesized cDNA (FIG. 22C), viral gag cDNA (FIG. 22D) and viral 2-LTR circles (FIG. 22B). The drug concentrations used were 0.0, 0.01, 0.1, 1 and 10 μM corresponding to lanes 1 to 5 respectively. The unlabeled lane in each panel contains molecular size marker control DNA.

Figures for Section C

Figure 23A:
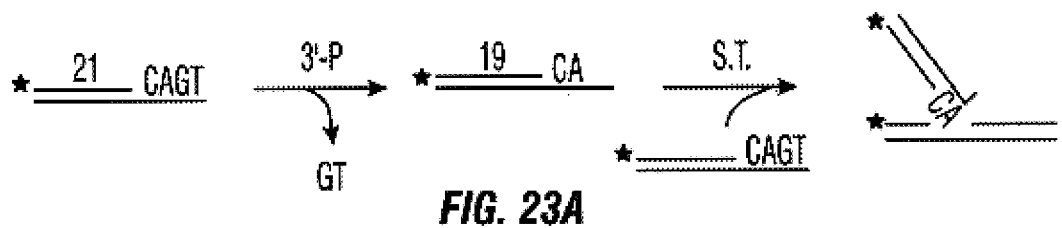
Figure 23B:
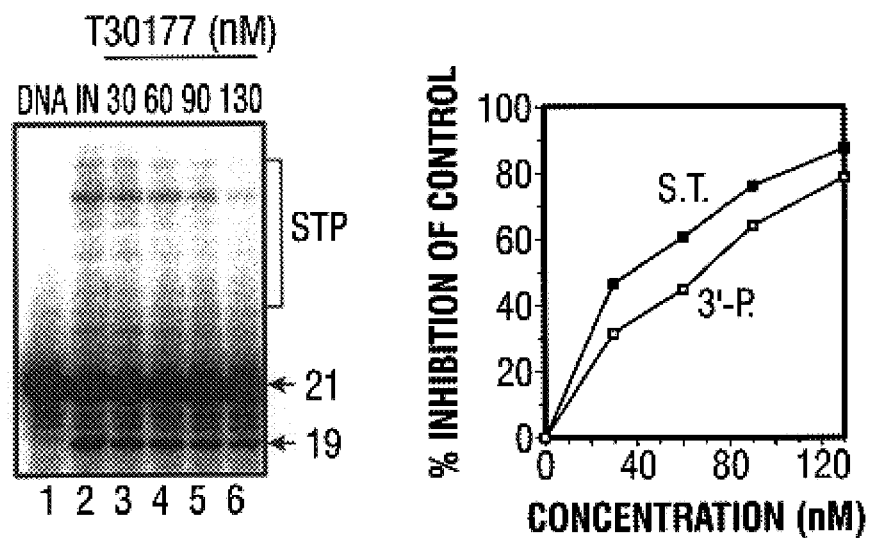
Figures 23C, 23D:
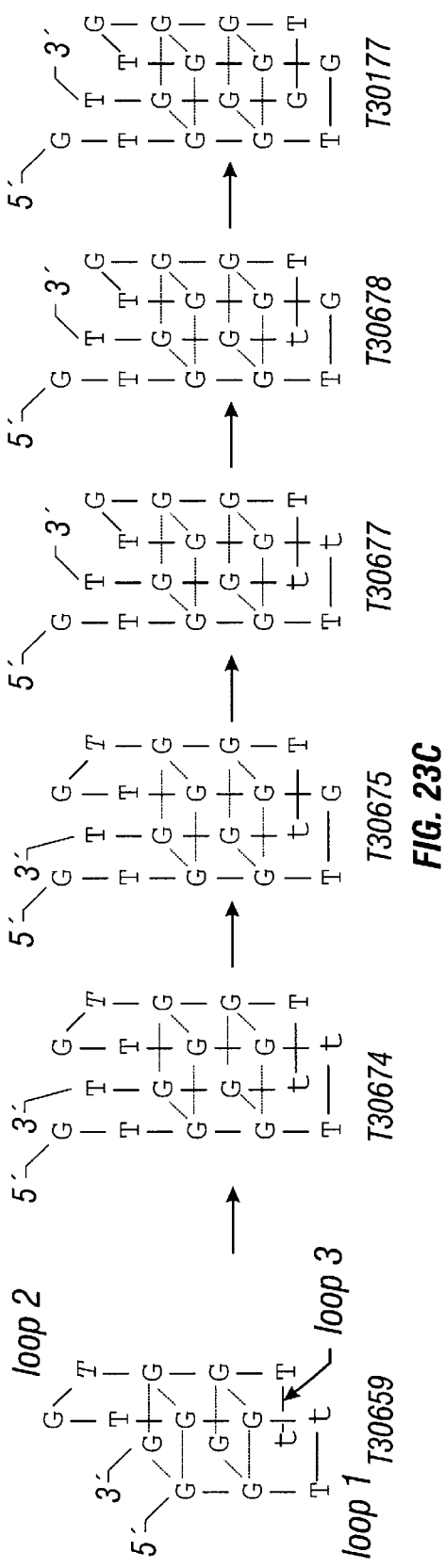

FIG. 23. Inhibition of HIV-1 integrase 3'-processing and strand transfer and HIV-$1_{RF}$ cytopathicity by guanosine quartets. (FIG. 23A) Schematic diagram showing 3'-processing (3'P, which liberates a GT dinucleotide) and strand transfer (S.T., which results in the insertion of one 3'-processed oligonucleotide into another target DNA), with 5'-end labeled (asterisk), blunt-ended oligonucleotide. (FIG. 23B) Left panel, concentration-response obtained from a typical experiment. The DNA substrate (21 mer), 3'-processing product (19 mer), and strand transfer products (STP) are shown. Lane 1, DNA along; lane 2, with integrase; lanes 3–6, with integrase in the presence of the indicated concentrations of T30177. Right panel, graph derived from quantitation (see Materials and Methods) of the dose response in the left panel showing inhibition of integrase-catalyzed 3'-processing (open squares) and strand transfer (filled squares). (FIG. 23C) Structures of guanosine quartets oligonucleotides. (FIG. 23D) $IC_{50}$ values for several G4 oligonucleotides against both activities of HIV integrase and HIV-$1_{RF}$ in cell culture. Insertions into the parent compound T30177 are shown by an italicized and underlined nucleotide while mutations are designated by a lower case nucleotide. The guanosines involved in the quartets are shaded and the loops are designated by the corresponding numbers (see FIG. 23D).

Figure 24A:
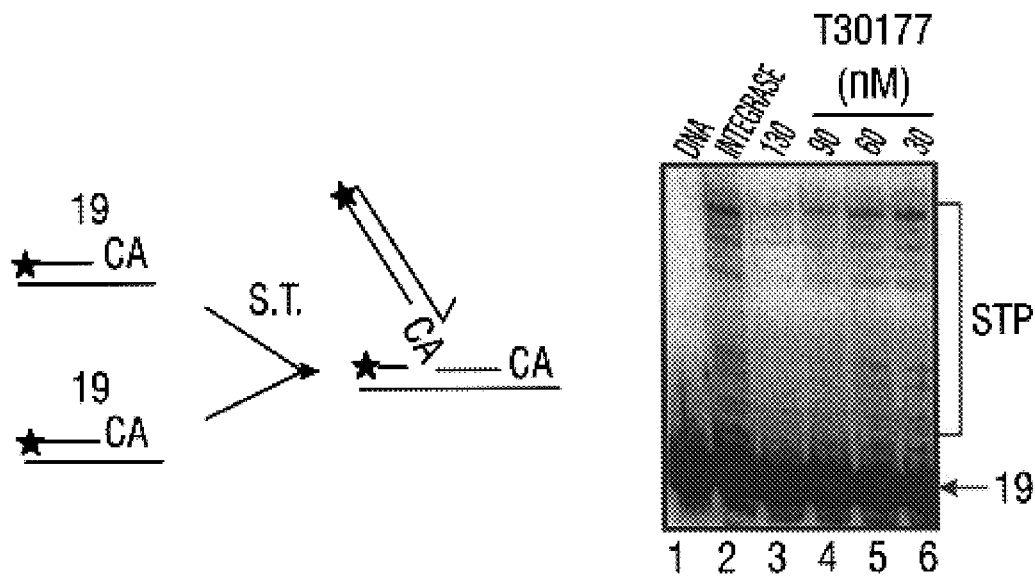
Figure 24B:
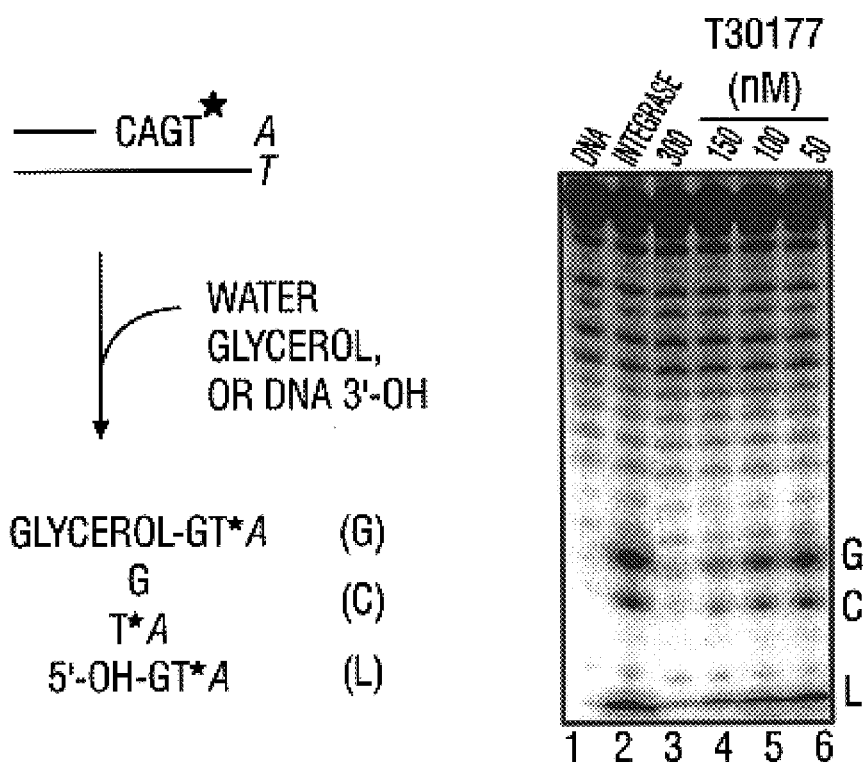

FIGS. 24A–B. Inhibition of strand transfer and 3'-processing activities of HIV-1 integrase by the guanosine quartet T30177. (FIG. 24A) Left, schematic diagram depicting the strand transfer assay using the precleaved oligonucleotide (19 mer substrate). Right Phosphorimager picture showing inhibition of strand transfer with T30177. The DNA substrate (19 mer) and strand transfer products (STP) are shown. Lane 1, DNA alone; lane 2, plus integrase; lanes 3–6, plus integrase in the presence of the indicated concentrations of T30177. (FIG. 24B) Left, schematic diagram depicting the 3'-processing assay using the oligonucleotide labeled at the 3'-end with $^{32}$P-cordycepin (*A) (22 mer substrate). Right, phosphorimager picture showing inhibition of HIV-1 integrase-catalyzed 3'-processing with T30177. Lane 1, DNA alone; lane 2, with integrase; lanes 3–6, in the presence of the indicated concentrations of T30177.

Figure 25A:
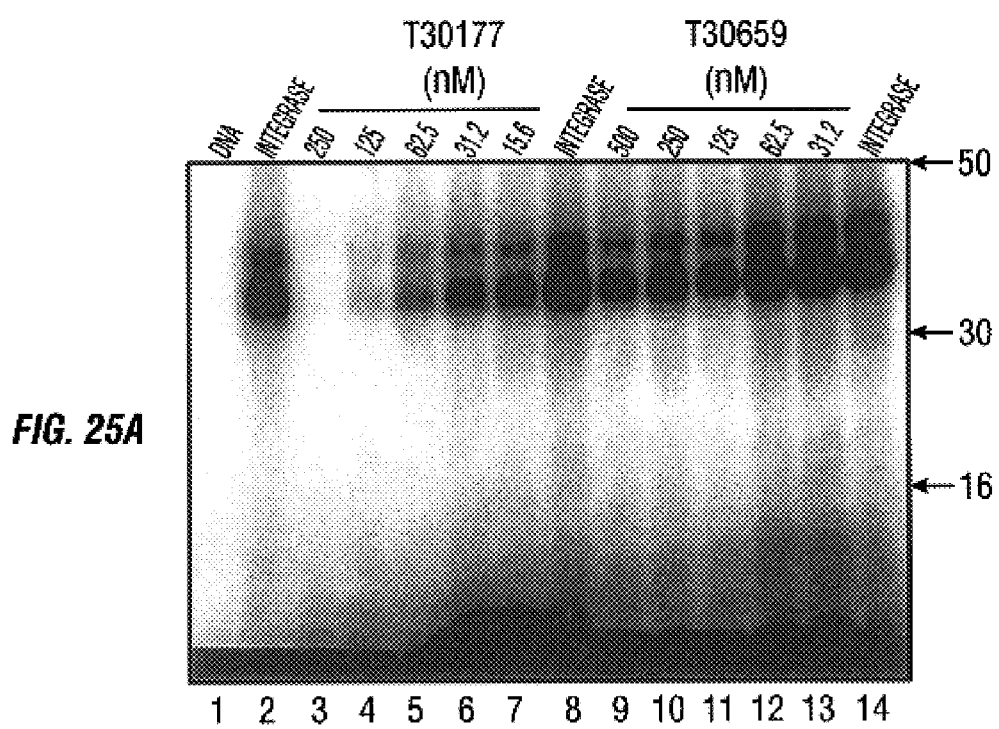
Figure 25B:
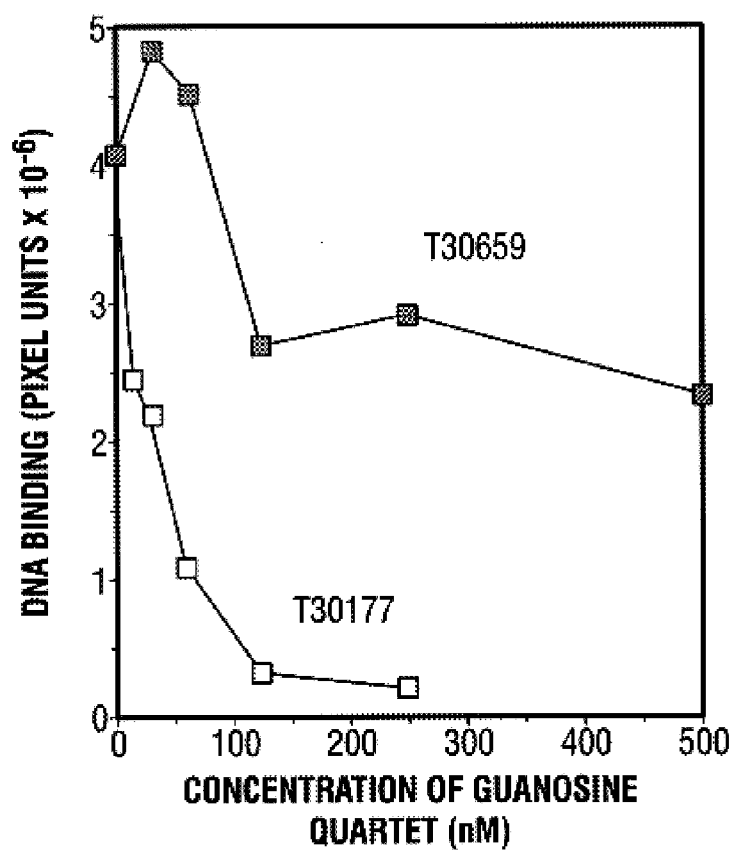

FIGS. 25A–B. Inhibition of the DNA binding activity of HIV-1 integrase by guanosine quartets. DNA binding was measured after UV crosslinking of reactions in which integrase was preincubated for 30 minutes at 30° C. with the guanosine quartet prior to addition of the DNA substrate. (FIG. 25A) Phosphorimager picture showing differential inhibition of DNA binding with T30177 and T30659. Lane 1, DNA alone (20 nM); lanes 2, 8, and 14, with integrase (200 nM); lanes 3–7, in the presence of the indicated concentrations of T30177; lanes 9–13, in the presence of the indicated concentrations of T30659. The mitigations of proteins of known molecular weight are shown to the right of the gel. (FIG. 25B) Graph derived from quantitation of the does response in (FIG. 25A) showing inhibition of integrase binding by T30177 (open squares) but not by T30659 (filled squares).

Figure 26A:
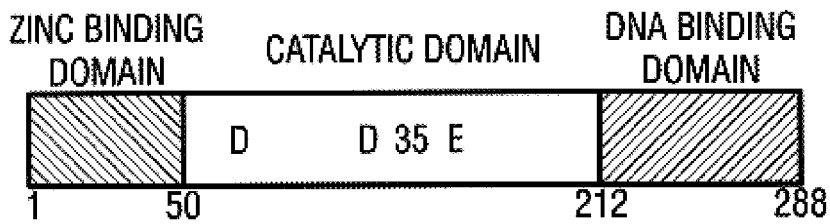
Figure 26B:
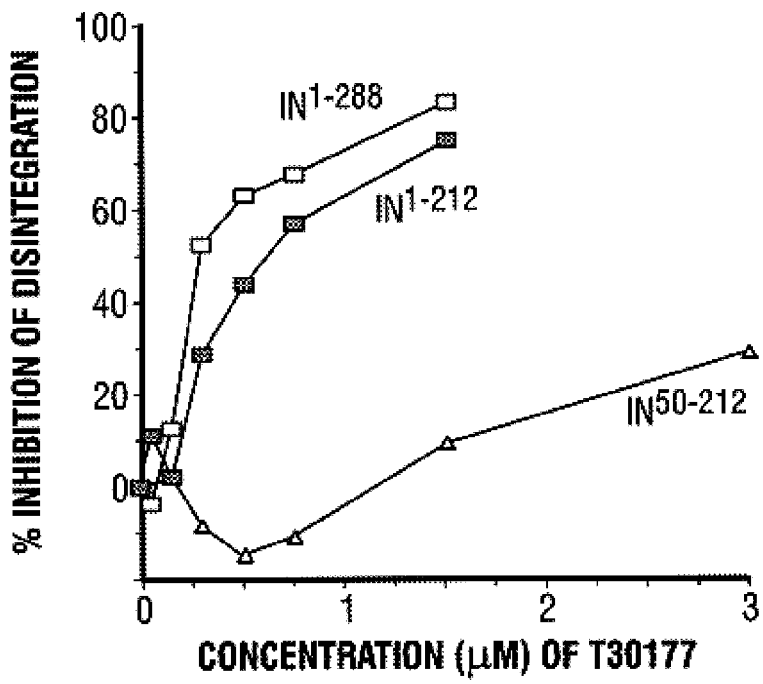
Figure 26C:
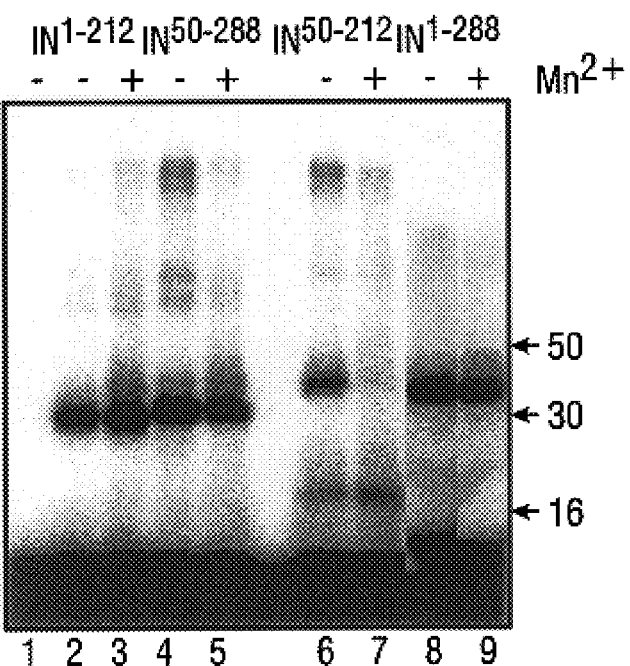

FIG. 26. Differential activities of T30177 on wild-type and deletion mutants of HIV integrase. (FIG. 26A) Schematic diagram showing the three domains of HIV-1 integrase. (B) Inhibition of wild-type $IN^{1-288}$ (open squares), $IN^{1-212}$ (closed squares), and $IN^{50-212}$ (open triangles) in the disintegration assay. (FIG. 26C) Binding of HIV-1 integrase wild-type ($IN^{1-288}$) and deletion mutants at a final concentration of 1 μM to $^{32}$P-end labeled guanosine quartet T30177 at a final concentration of 250 nM. The mobility of proteins of known molecular weight (in KDa) are shown to the right of each figure. Lane 1, T30177 alone; lanes 8–9, binding to wild-type, full-length HIV-1 integrase ($IN^{1-288}$) in the presence of the indicted metal; lanes 2–3, binding to $IN^{1-212}$ in the presence of the indicated metal; lanes 6–7, binding to $IN^{50-212}$ in the presence of the indicated metal are lanes 4–5, binding to $IN^{50-288}$.

Figure 27A:
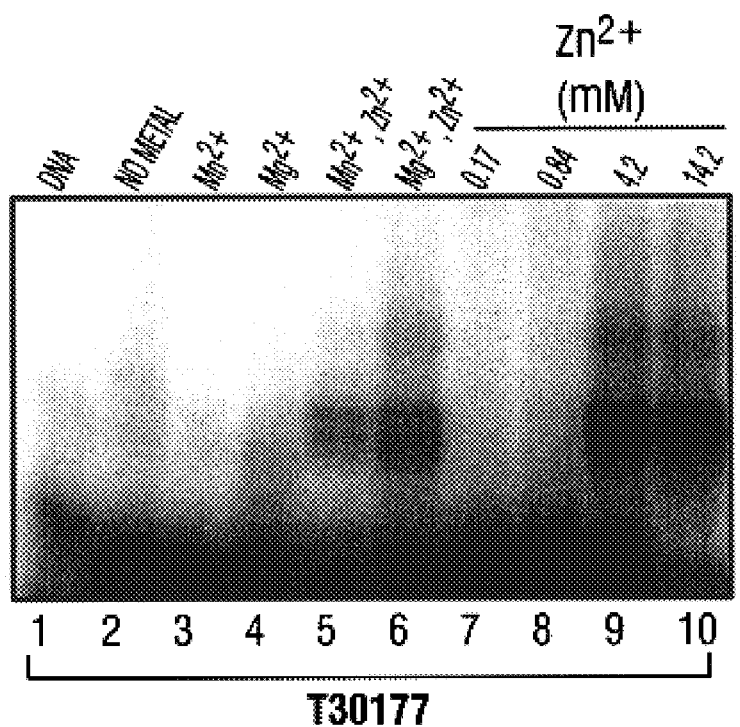
Figure 27B:
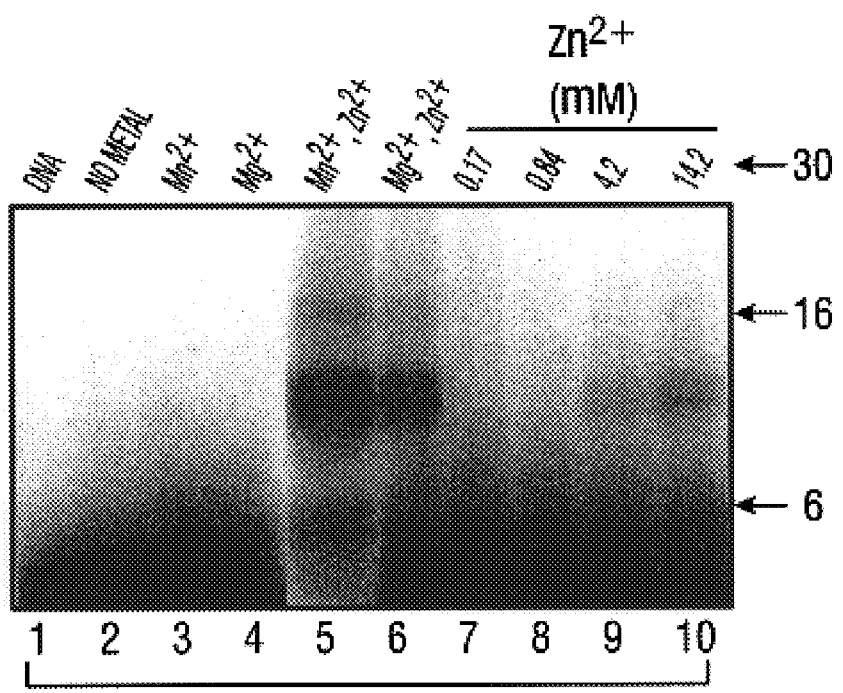

FIGS. 27A–B. DNA binding activity of the zinc finger domain of HIV-1 integrase. Binding of $IN^{1-55}$ to T30177 or the viral DNA substrate (see FIG. 23A, 21 mer). Lanes 1, DNA alone (50 nM); lanes 2, $IN^{1-55}$ (2 $\mu$M) with no metal; lanes 3, $IN^{1-55}$ with manganese (7.5 mM); lanes 4, $IN^{1-55}$ with magnesium (7.5 mM); lanes 5, $IN^{1-55}$ with manganese (7.5 mM) and zinc (4.2 mM); lanes 6, $IN^{1-55}$ with magnesium (7.5 mM) and zinc (4.2 mM); lanes 7–10, $IN^{1-55}$ in the presence of the indicated concentration of zinc alone.

FIGS. 28A–D. Increased binding to and inhibition by guanosine quartets in magnesium versus manganese. (FIG. 28A) Phosphorimager picture showing DNA binding of wild-type integrase to radiolabeled T30177. Lane 1, DNA alone (27 nM); lanes 2–5; binding of integrase (200 nM) in manganese buffer to the indicated concentration of T30177; lanes 6–9, binding of integrase (200 nM) in magnesium buffer to the indicated concentration of T30177. The migrations of proteins of known molecular weight are shown to the right of the gel. (FIG. 28B) Structures of T30177 and two analogs in which the internucleotidic linkages have been changed. (FIG. 28C) graph derived from quantitation (see Materials and Methods) of the inhibition of integrase-catalyzed 3'-processing in the presence of T30177 and analogs in either magnesium or manganese. Inhibition by T30177 (triangles), T30175 (squares), and T30038 (circles is shown either containing magnesium (filled symbols) or manganese (open symbols). (FIG. 28D) Table showing $IC_{50}$ values for 3'-processing for the guanosine quartets in buffer containing manganese and magnesium and the ratio of these values.

Figures 29A, 29B:
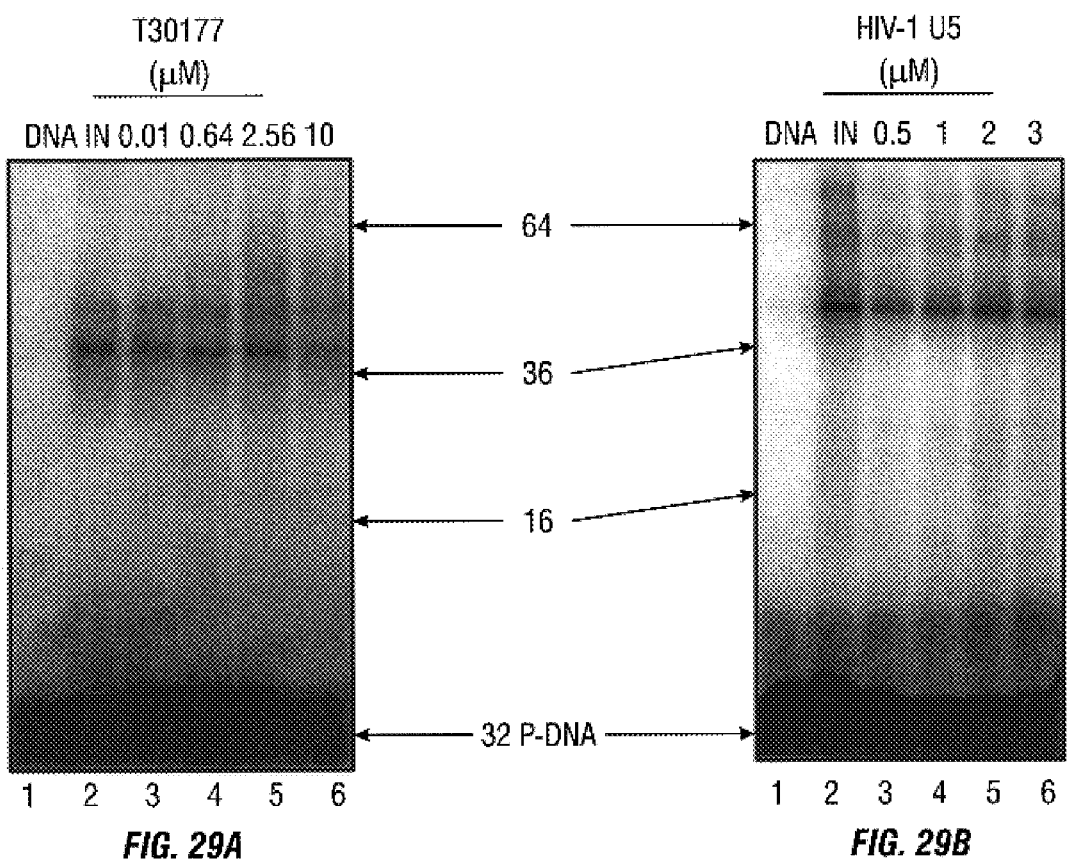

FIGS. 29A–B. Competition of binding to either U5 viral oligonucleotide (see FIG. 23A, 21 mer) (FIG. 29A) or guanosine quartet T30177. (FIG. 29B) Lanes 1, DAN alone; lanes 2, with wildtype, full-length HIV-1 integrase. Lanes 3–6 in panel (FIG. 29A), with integrase in the presence of the indicated concentrations of T30177 added after a 5 minute preincubation with the U5 viral DNA oligonucleotide. Lanes 3–6 in panel (FIG. 29B), with integrase in the presence of the indicated concentrations of viral U5 DNA oligonucleotide added after a 5 minute preincubation with the guanosine quartet T30177.

Figure 30A:
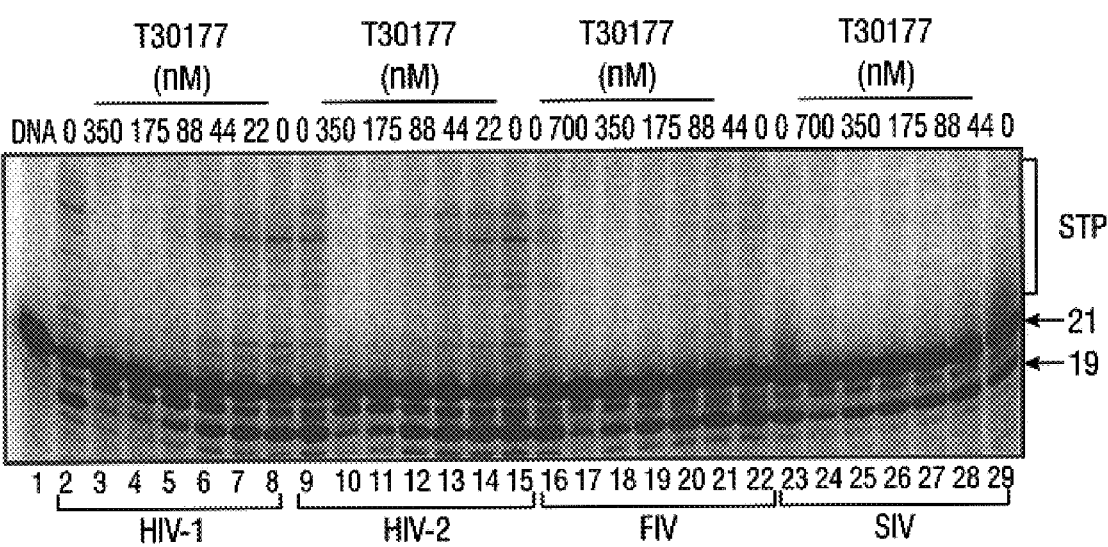
Figure 30B:
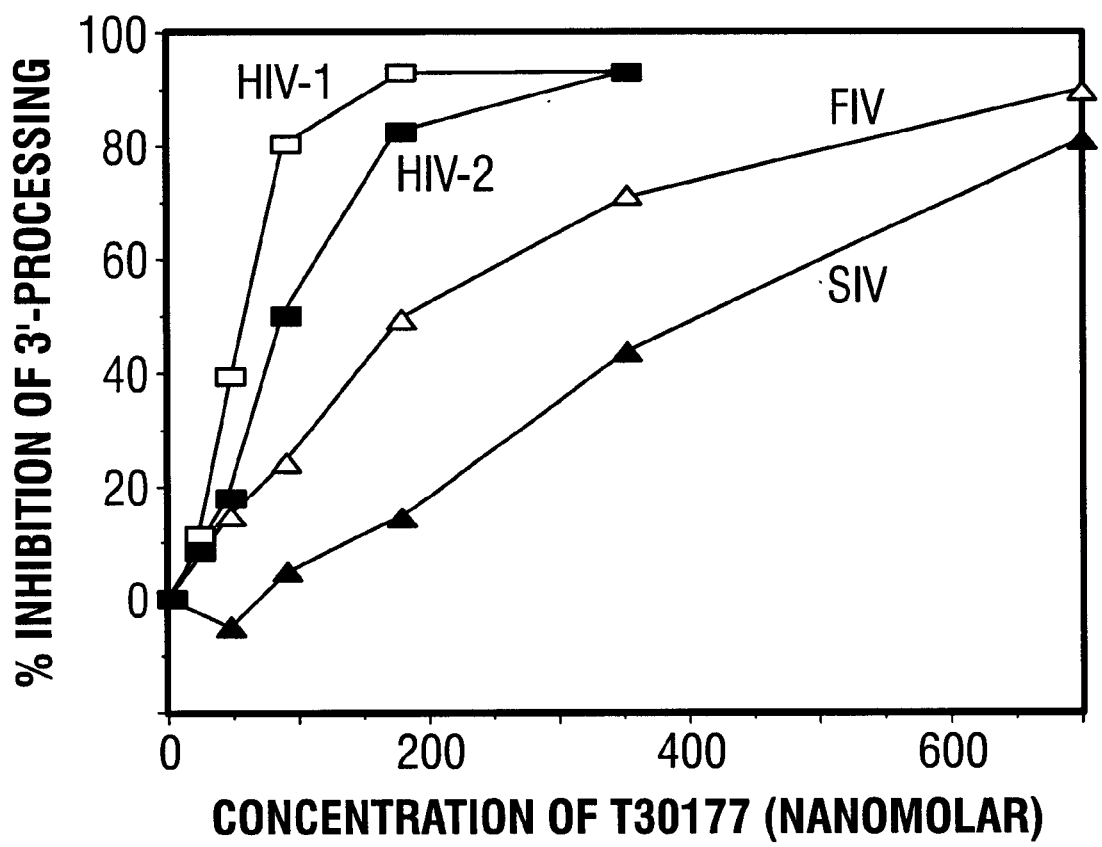

FIGS. 30A–B. Inhibition of the related retroviral integrases. (FIG. 30A) Inhibition of 3'-processing and strand transfer catalyzed by HIV-1 (lanes 2–8), HIV-2 (lanes 9–15), FIV (lanes 16–22), and SIV (lanes 23–29) integrases in the presence of T30177. Lane 1, DNA alone; lanes 2, 8, 9, 15, 16, 22, 23, and 29, with integrase; lanes 3–7, 10–14, 17–21, and 24–28, with integrase in the presence of the indicated concentrations of T30177. (FIG. 30B) Graph derived from quantitation (see Materials and Methods) of the dose responses in (FIG. 30A) showing inhibition of HIV-1 (open rectangles), HIV-2 (filled rectangles), FIV (open triangles), or SIV (filled triangles) integrase-catalyzed 3'-processing.

Figure 31:
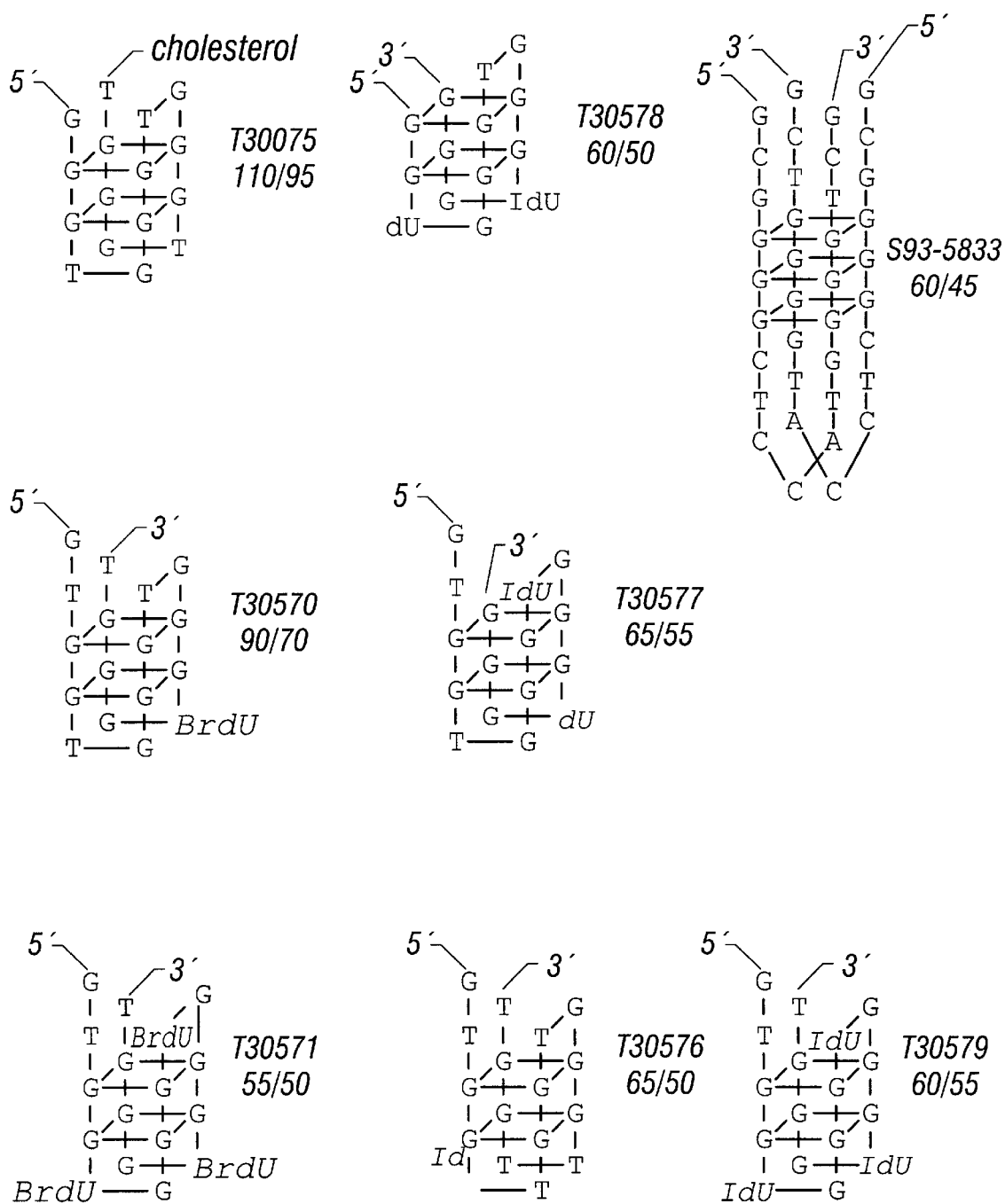

FIG. 31. Three-dimensional drawings of certain guanosine tetrad forming oligonucleotides referred to in Tables C-1 and C-2. Halosubstituted, end modified, and intermolecular guanosine quartets are shown.

Figure 32:
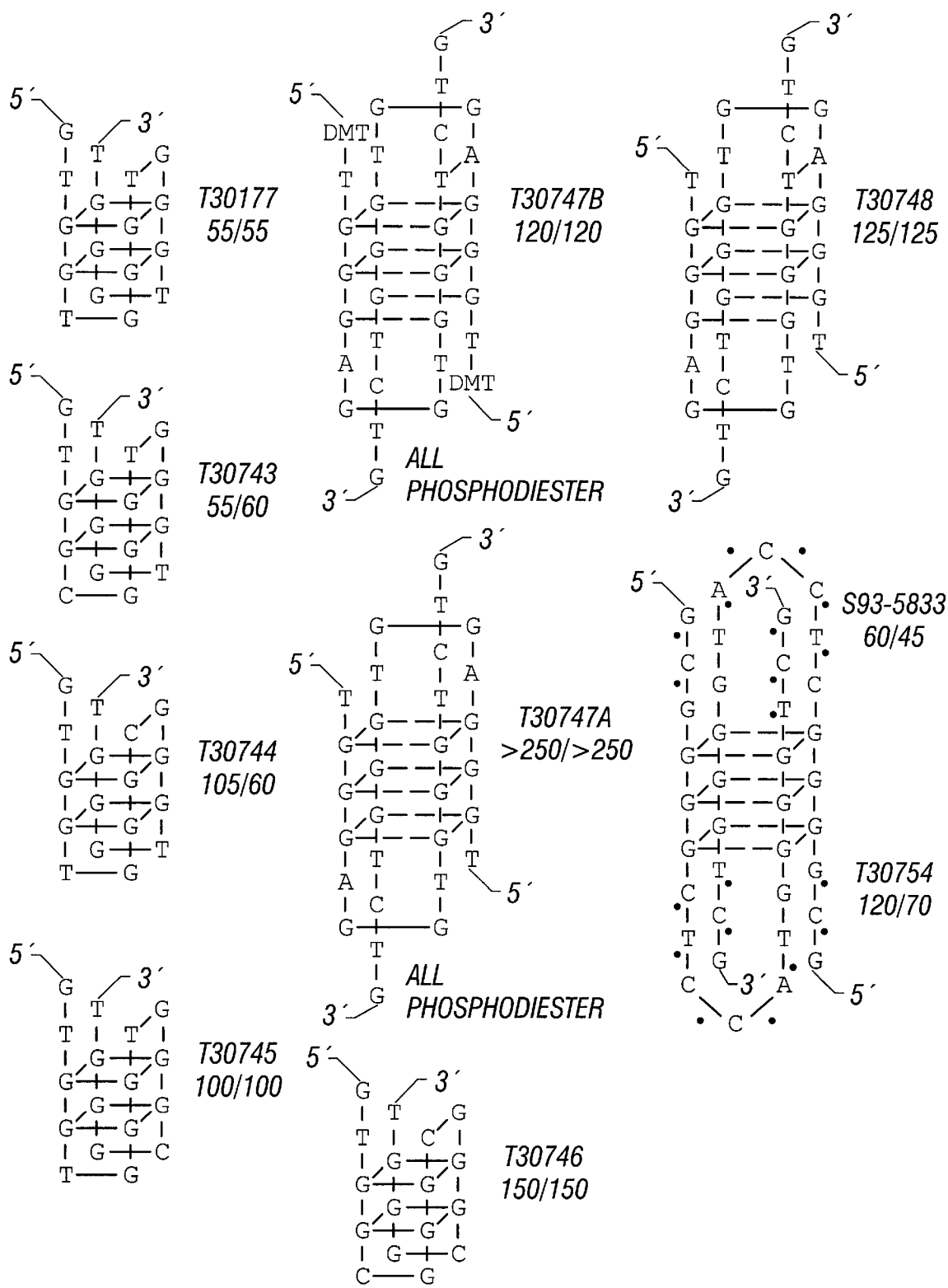

FIG. 32. Three-dimensional drawings of certain guanosine tetrad forming oligonucleotides referred to in Tables C-1 and C-2. Unless otherwise specified, all oligonucleotides have phosphorothiodiester linkages between the ultimate and penultimate bases at both the 5' and 3' ends. (*) denotes the position of the phosphorothiodiester linkages.

FIG. 33. Percentage inhibition of 3' processing by certain oligonucleotides in Table C-1.

Figure 34:
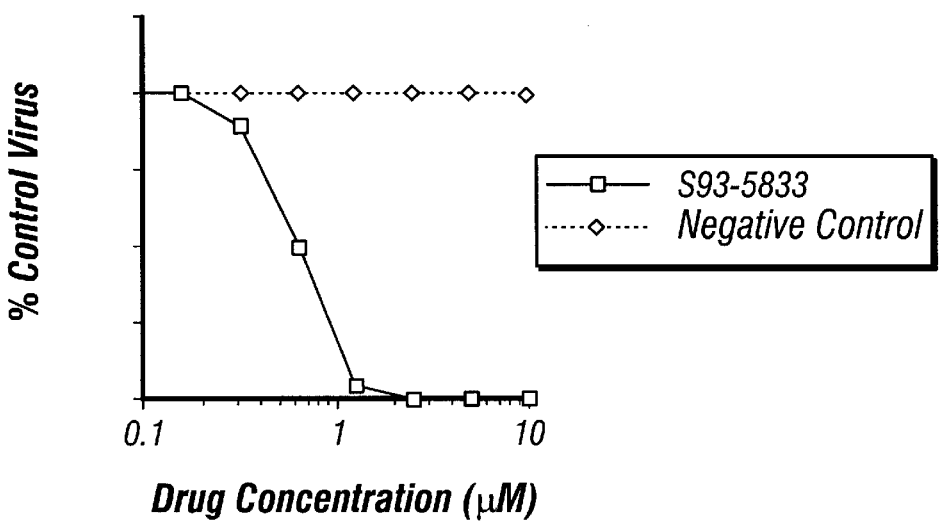

FIG. 34. Inhibition of syncytium formation by certain oligonucleotides in Table C-1.

Figure 35:
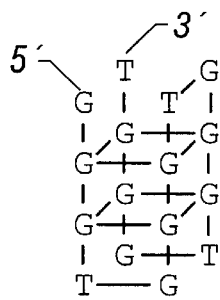
Figure 35:
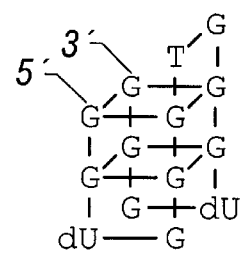
Figure 35:
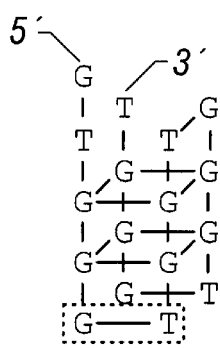
Figure 35:
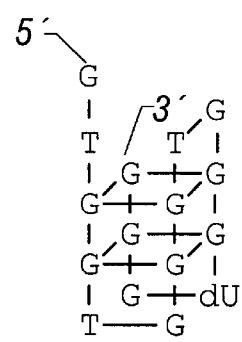
Figure 35:
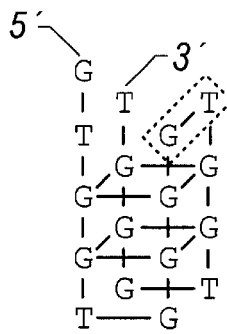
Figure 35:
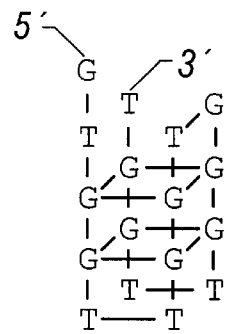
Figure 35:
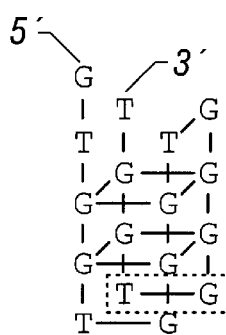
Figure 35:
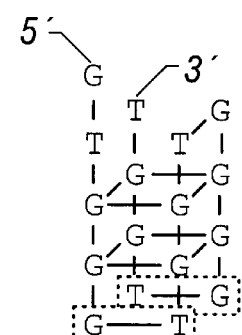

FIG. 35. Mutations in the loops of T30177. Three-dimensional drawings of certain guanosine tetrad forming oligonucleotides referred to in Tables C-1 and C-2.

Figure 36:
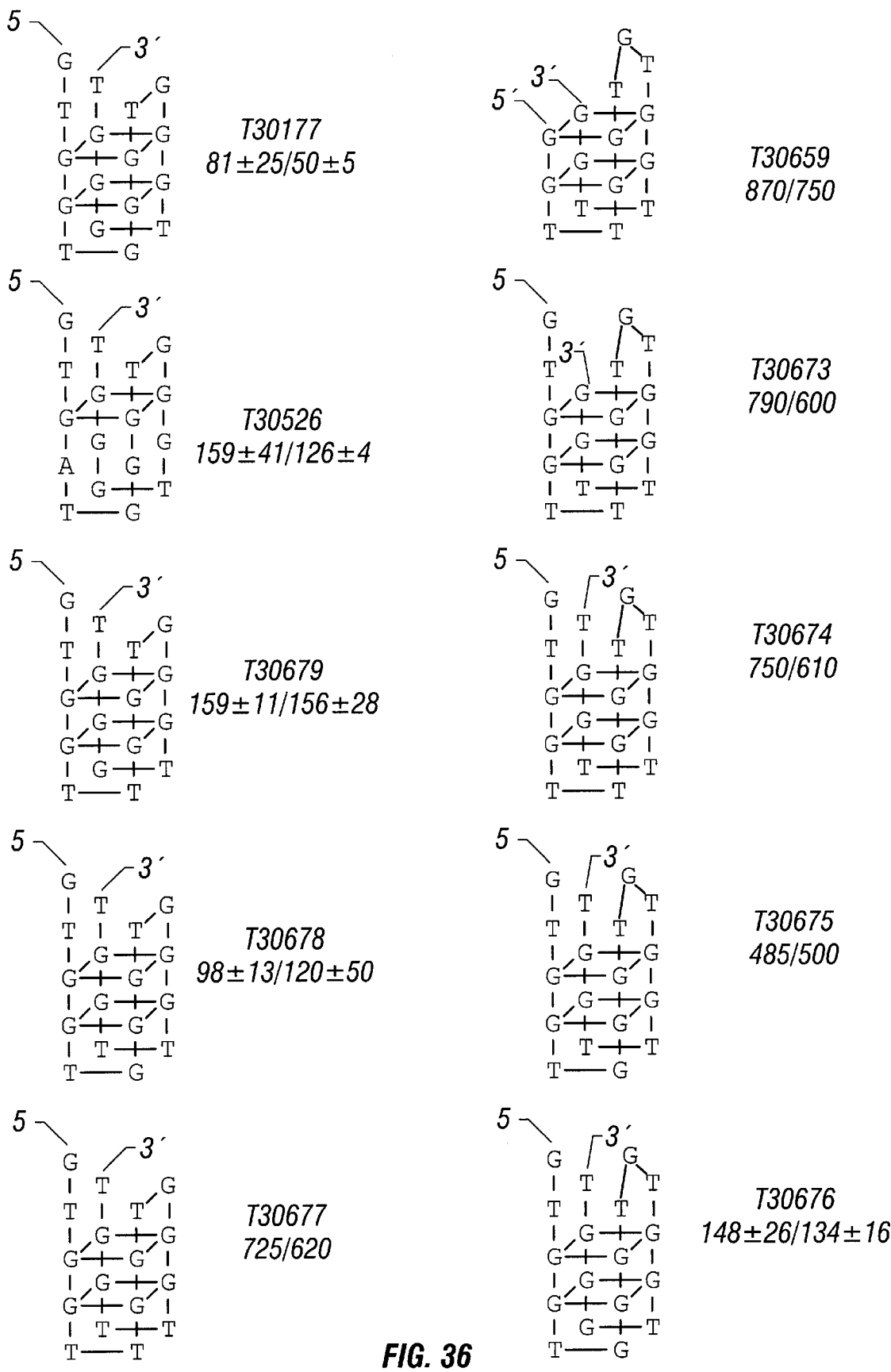

FIG. 36. Mutations, deletions and insertions in G quartets. Three-dimensional drawings of certain guanosine tetrad forming oligonucleotides referred to in Tables C-1 and C-2. $IC_{50}$ for 3' proc./str. tra. is indicated to the right of each tetrad.

Figures for Section D

Figure 37A:
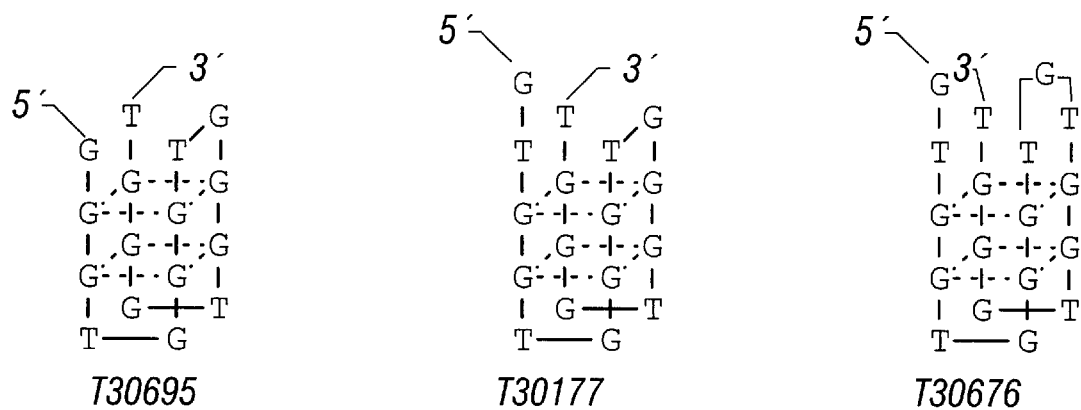
Figure 37B:
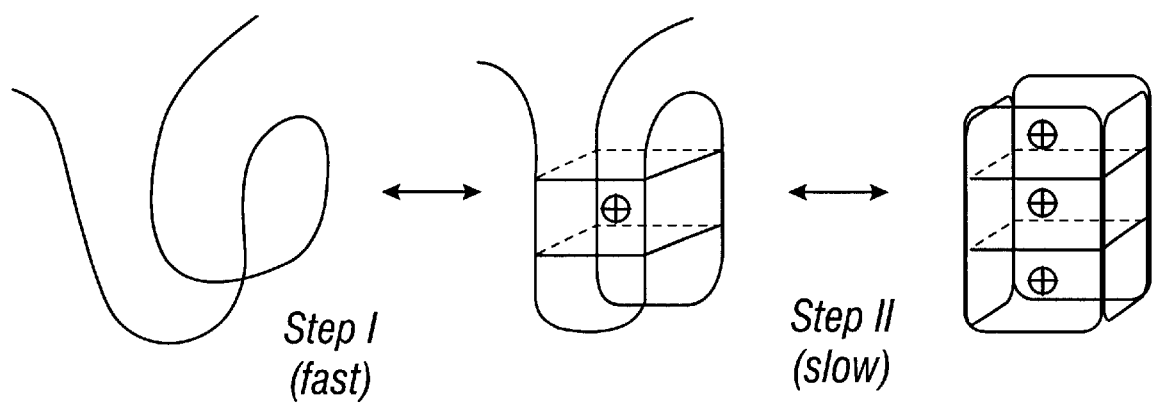

FIGS. 37A–B. Structure Models. FIG. 37A. The sequence and a structure model for oligonucleotides used in this study presented All four oligomers have been modified so as to include a single phosphorothioate linkage at the 5' and 3' terminus. Proposed sites of G-quartet formation have been identified by dotted lines. The continuity of the phosphodiester backbone is identified by solid lines. FIG. 37B. A two step kinetic model for ion induced folding of oligomers in this study. It is proposed that binding a first $K^+$ or $Rb^+$ ion equivalent, marked as a (+), occurs within the central G-octet, which has been identified by dotted lines. This first step is relatively fast, and is associated with higher apparent ion binding affinity. It is also associated with formation of unstacked loop domains, and the resultant net loss of UV hypochromism, as compared to the initial random coil state. The second step in the process involves as many as two additional $K^+$ or $Rb^+$ ion equivalents, (+), at the junction between the core octet and flanking loop regions. This second step requires significant ordering of the flanking loop domains, and is therefor associated with an increase of base stacking interaction, and a generally high activation energy.

Figure 38A:
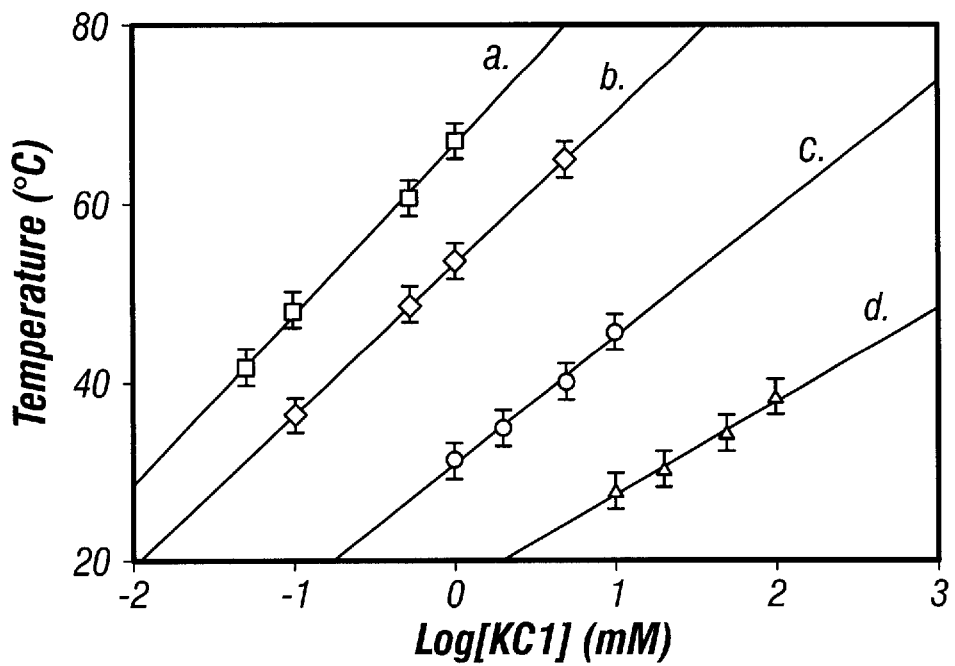
Figure 38B:
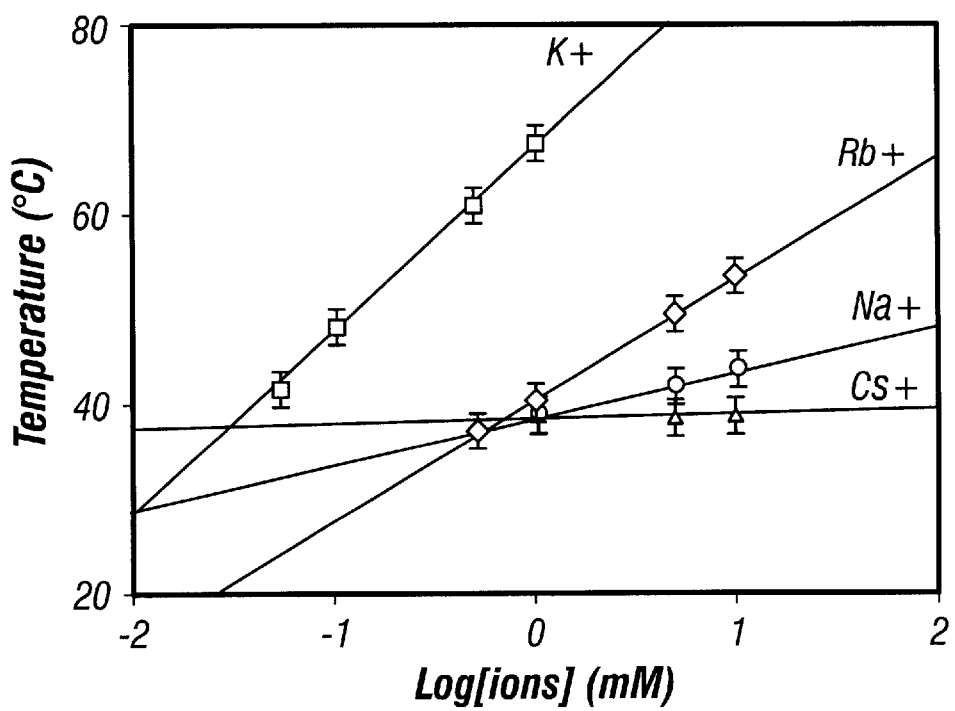
Figure 38C:
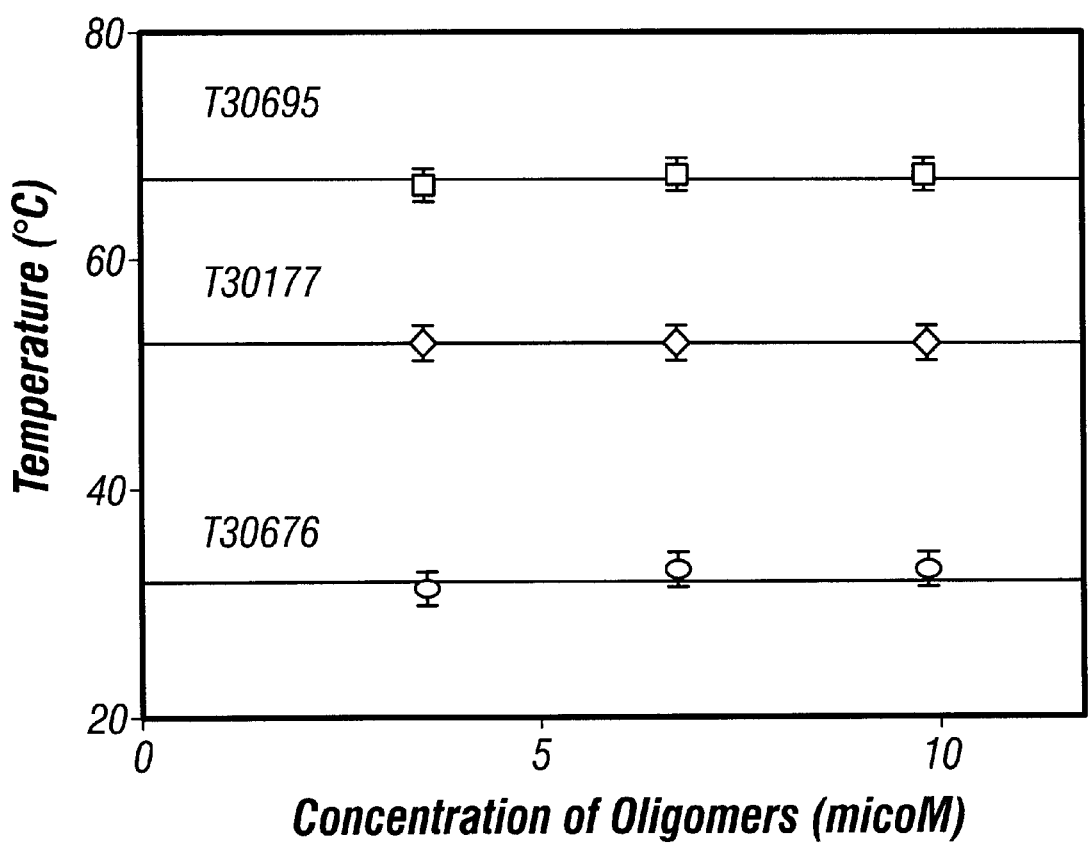

FIGS. 38A–C. Thermal Stability of Oligomer Folding. Thermal denaturation of oligomers has been measured as a function of ion type, ion concentration and strand concentration. Data have been obtained at 240 nm, in 20 mM Li3PO4, pH 7, as the supporting buffer. Tm values were calculated from the first derivative of a plot of absorbance vs. temperature, but similar values were obtained by using the midpoint of the overall absorbance change. FIG. 38A. Tm values for T30695 (curve a), T30177 (curve b), T30376 (curve c), and T30677 (curve d) obtained as a function of added 12 KCl concentration. FIG. 38B. The Tm Of T30695 obtained as a function of KCl, RbCl, NaCl or CsCl concentration. FIG. 38C. The strand concentration dependence of Tm has been measured at 1 mM of added KCl.

Figure 39A:
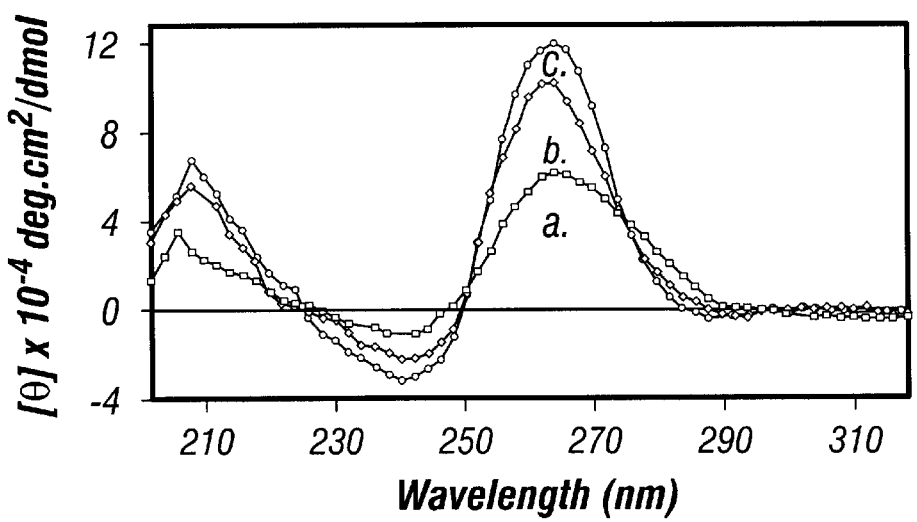
Figure 39B:
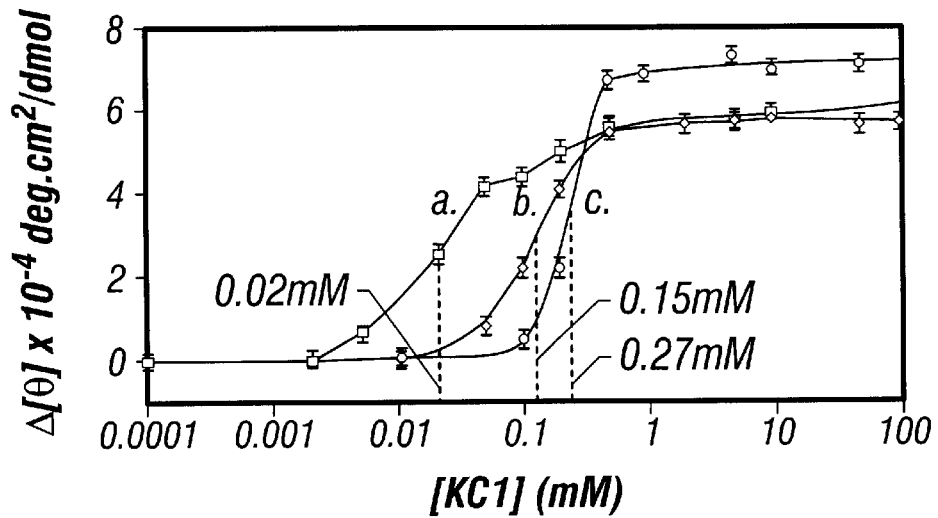
Figure 39C:
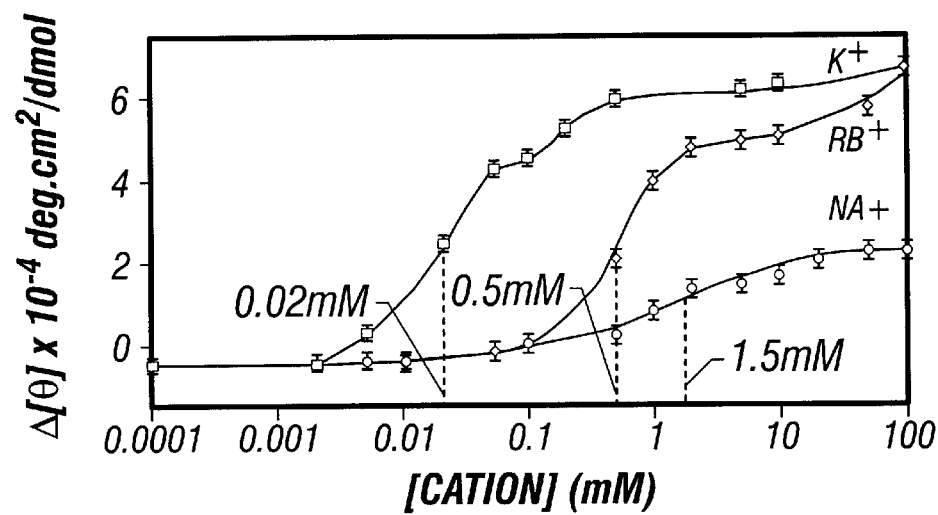
Figure 41C:
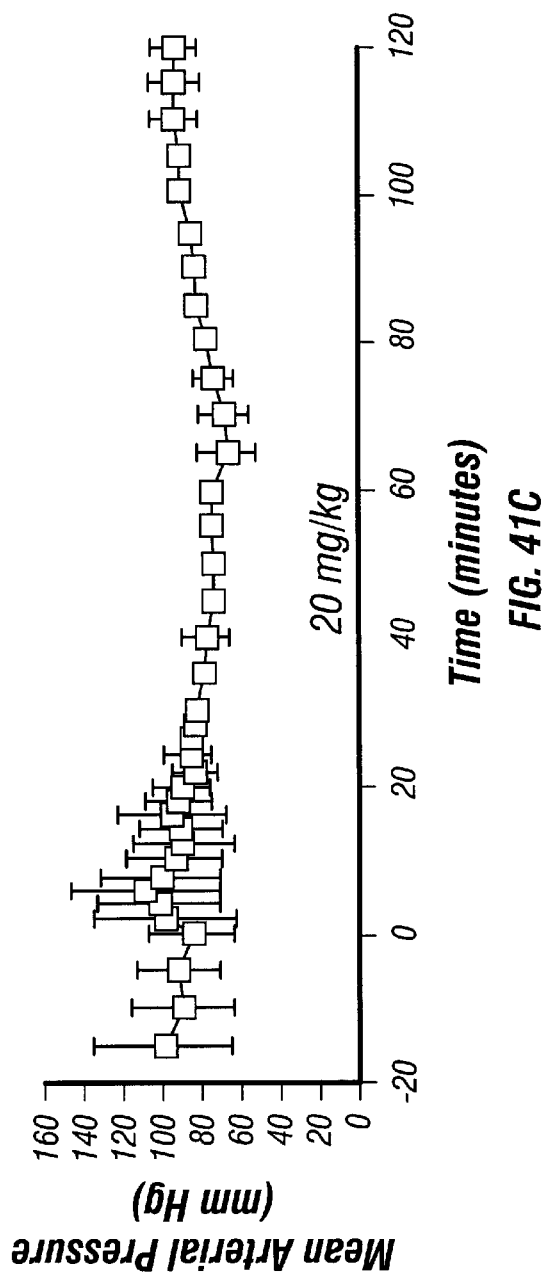
Figure 41D:
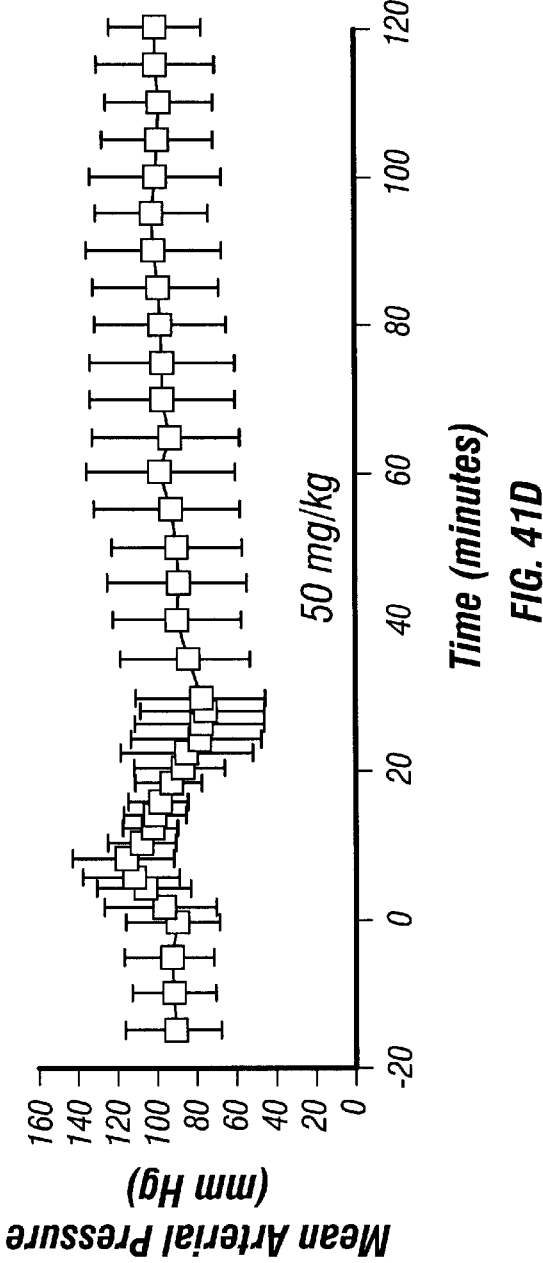
Figure 42A:
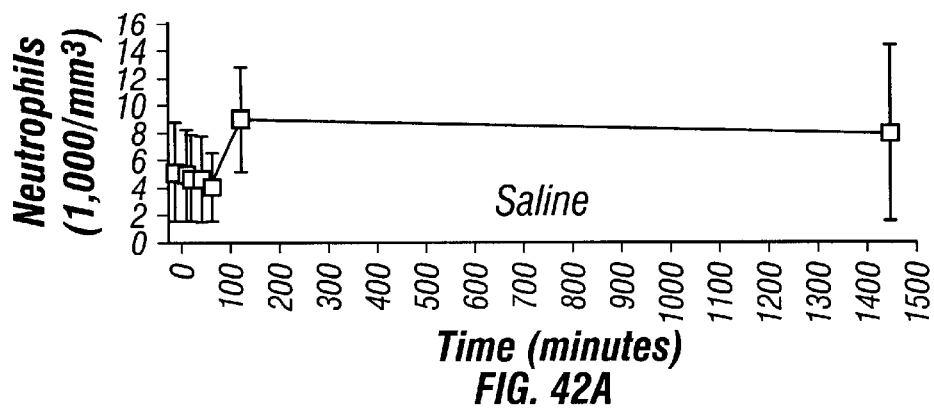
Figure 42B:
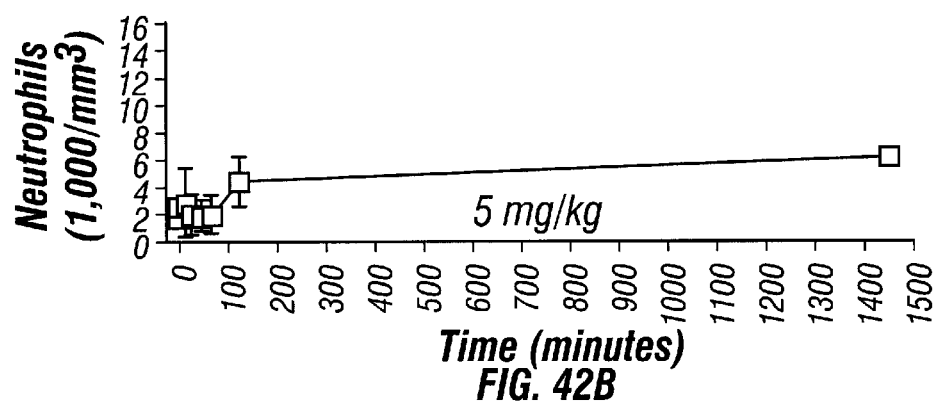
Figure 42C:
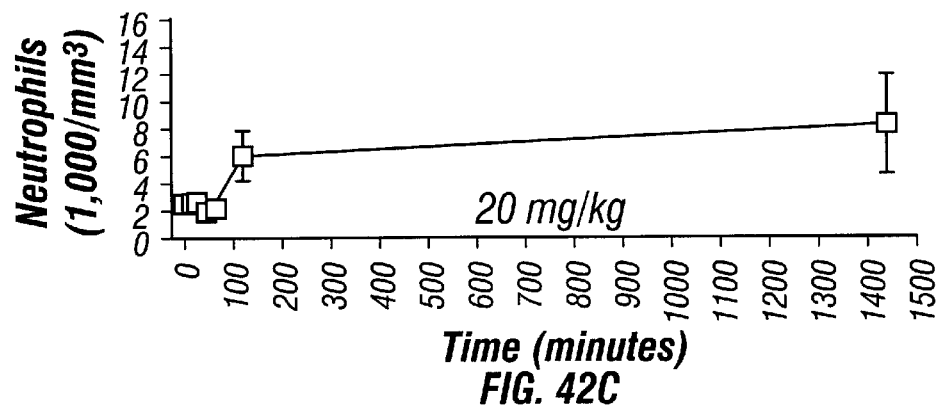
Figure 42D:
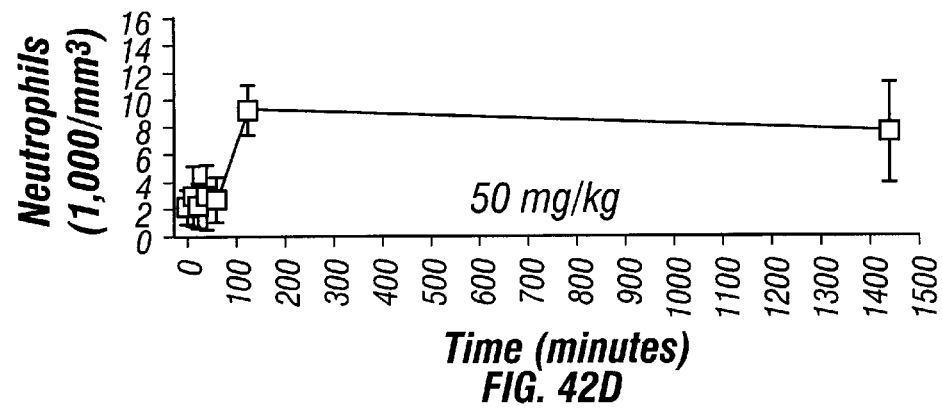

FIGS. 39A–C. Oligomer Folding Monitored by Circular dichroism (CD). CD data have been obtained at 25° C. in 20 mM Li3PO4 as a function of added ion concentration. Data have been presented as molar ellipticity in units of dmole bases. FIG. 39A. The CD spectrum of T30695 in the presence of 0 mM (curve a), 0.05 mM (curve b), or 10 mM (curve e) of added KCl. FIG. 39B. The change in ellipticity at 264 nm, relative to that measured in the absence of added ion is presented as a function of added KCl concentration for T30695 (curve a), T30177 (curve b) and T30676 (curve c). The overall midpoint of the measured KCl induced transition has been plotted for each oligomer: 0.02 mM, 0.15 mM and 0.27 mM, respectively. FIG. 39C. T30695 has been treated with increasing concentration of several different cations. The change in ellipticity at 264 nm was then measured as described in part B as a function of added KCl (curve a), RbCl (curve b) or NaCl (curve e).

FIGS. 40A1–3,B1–3. The Kinetics of Ion Induced Folding. Ion was added to oligomers at time zero in the standard 20 mM Li3PO4 assay buffer. Data have been presented as absorbance (A) vs. time after addition of metal ion. FIG. 40A. Kinetics for T30177 were measured at three added KCl concentrations: 0.2 mM (curve a); 1.0 mM (curve b); and 10 mM (curve e). FIG. 40B. Kinetics for T30695 were measured at three added RbCl concentrations: 1.0 mM (curve a), 5.0 mM (curve b) and 10 mM (curve e). For both, the data has been fit to a sum of two exponentials, i.e. $A(\tau)=A_1\exp(-\tau/T_1)+A_2\exp(-\tau/T_2)$.

Figures for Section E

FIGS. 41A–D. Mean arterial pressure of cynomolgus monkeys pAor to, during and following intravenous administration of AR177 over ten minutes. Blood pressure was continuously monitored via an indwelling femoral artery catheter. The values are the mean±s.d. of three monkeys at each dose.

FIGS. 42A–D. Neutrophil levels in blood of cynomolgus monkeys prior to, during and following intravenous administration of AR177 over ten minutes. Neutrophil levels were determined pre-dose (−10 minutes), and at 10, 20, 40, 60,120 and 1440 minutes following the initiation of the ten-minute infusion of AR177 into cynomolgus monkeys. The values are the mean±s.d. of three monkeys at each dose.

Figure 43:
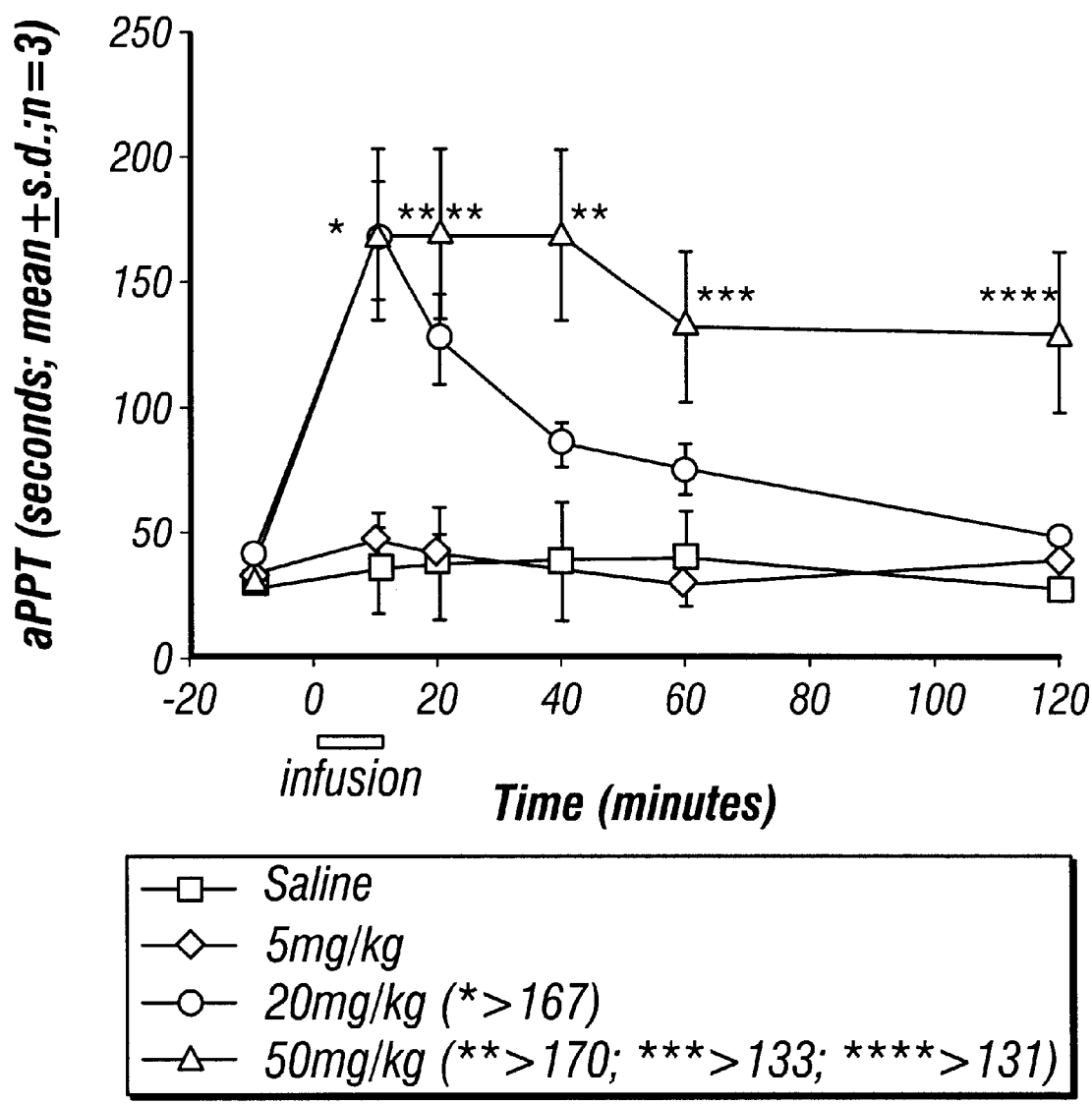

FIG. 43. aPTT versus time profile following a ten-minute infusion of AR177 to cynomolgus monkeys. aPTT was determined before and at various time after intravenous infusion of AR177 as described in the Methods section. aPTT levels returned to baseline by 24 hours in all groups. Certain aPTT values in monkeys at the 20 and 50 mg/kg dose time points, denoted by asterisks, exceeded the upper limit of the assay.

Figure 44:
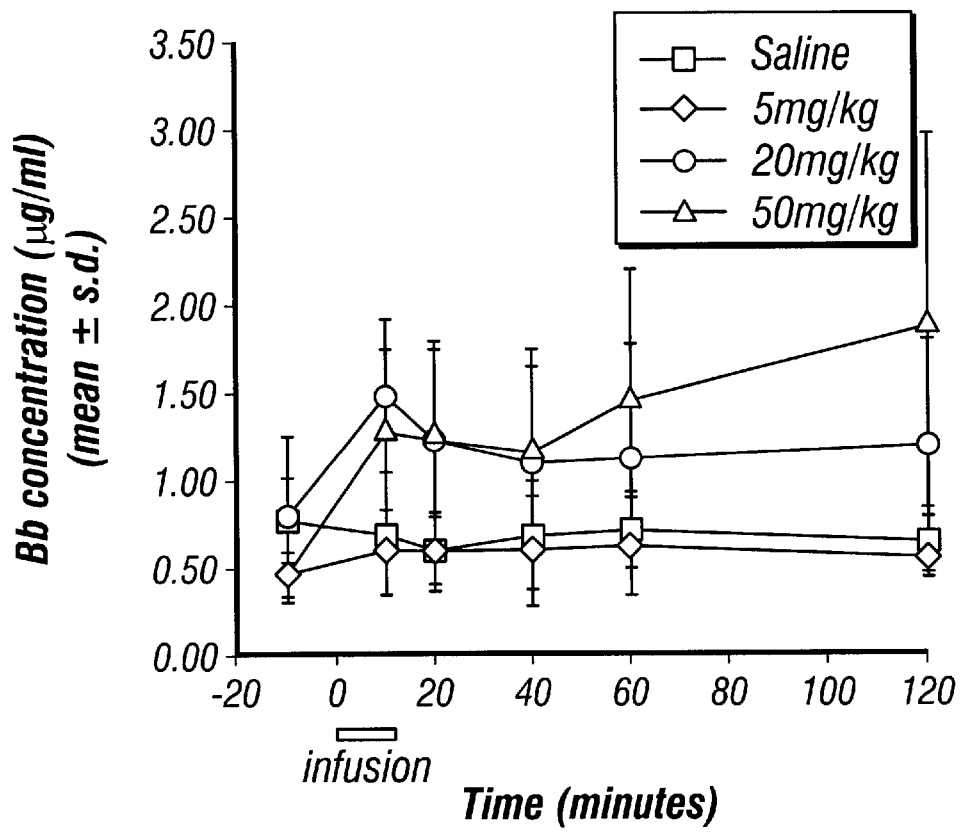

FIG. 44. Complement factor Bb concentration versus time profile following a ten minute infusion of AR177 to cynomolgus monkeys. Bb was determined before and at various times after intravenous infusion of AR177 as described in the Methods section. Bb levels returned to baseline by 24 hours in all groups.

Figure 45:
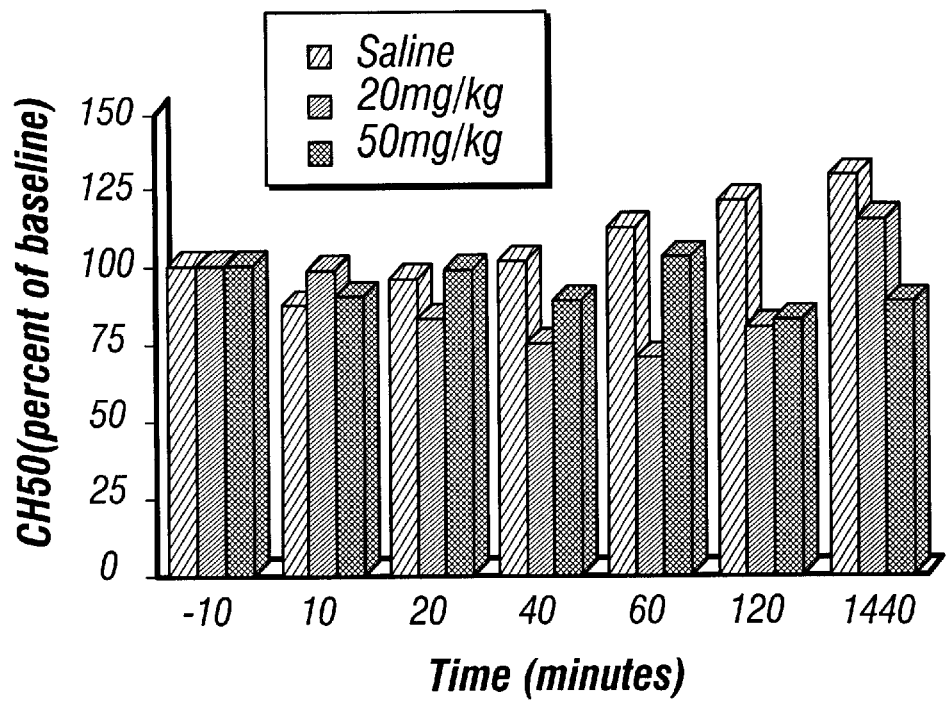

FIG. 45. CH50 levels in blood of cynomolgus monkeys prior to, during and following intravenous administration of AR177 over ten minutes. CH50 levels were determined pre-dose (−10 minutes), and at 10, 20, 40, 60,120 and 1440 minutes following the initiation of the ten-minute infusion of AR177 into cynomolgus monkeys. The values are the mean of two monkeys in the saline and 50 mg/kg groups, and three monkeys in the 20 mg/kg group. Data for the third monkey in the saline and 50 mg/kg groups, and for all of the 5 mg/kg group was not available.

Figure 46:
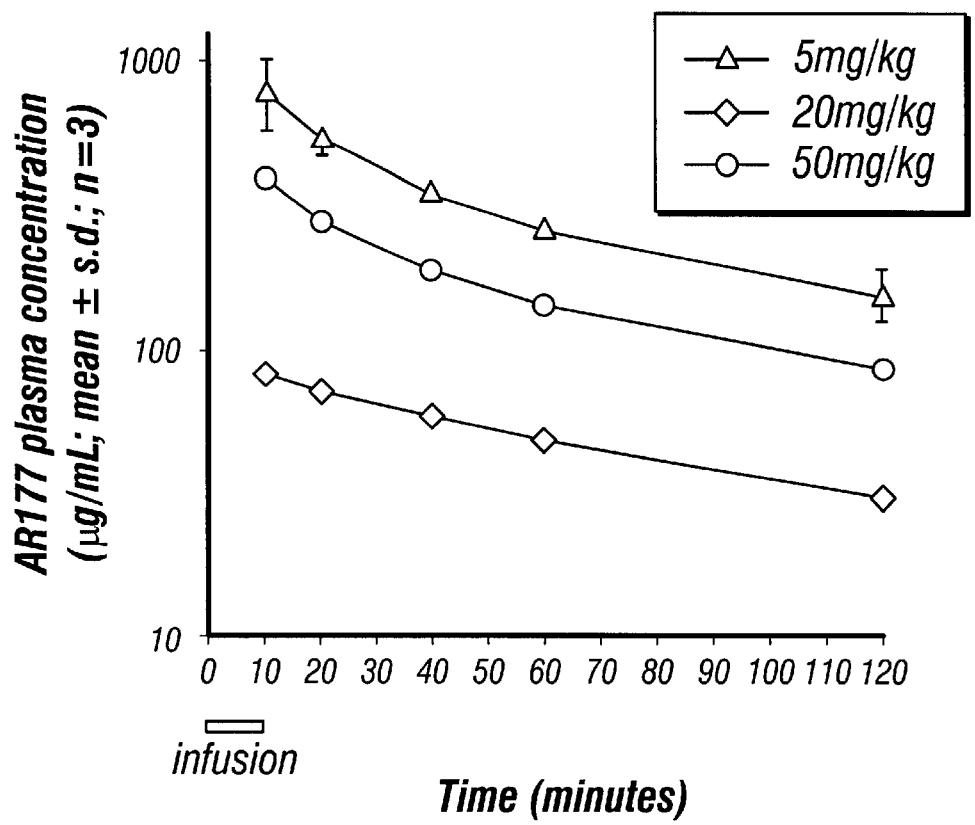

FIG. 46. Plasma $C_{max}$ of AR177 in cynomolgus monkeys administered AR177 as a ten-minute intravenous infusion. The plasma concentration of AR177 was determined by anion-exchange HPLC as described in the Methods section.

Figure 47:
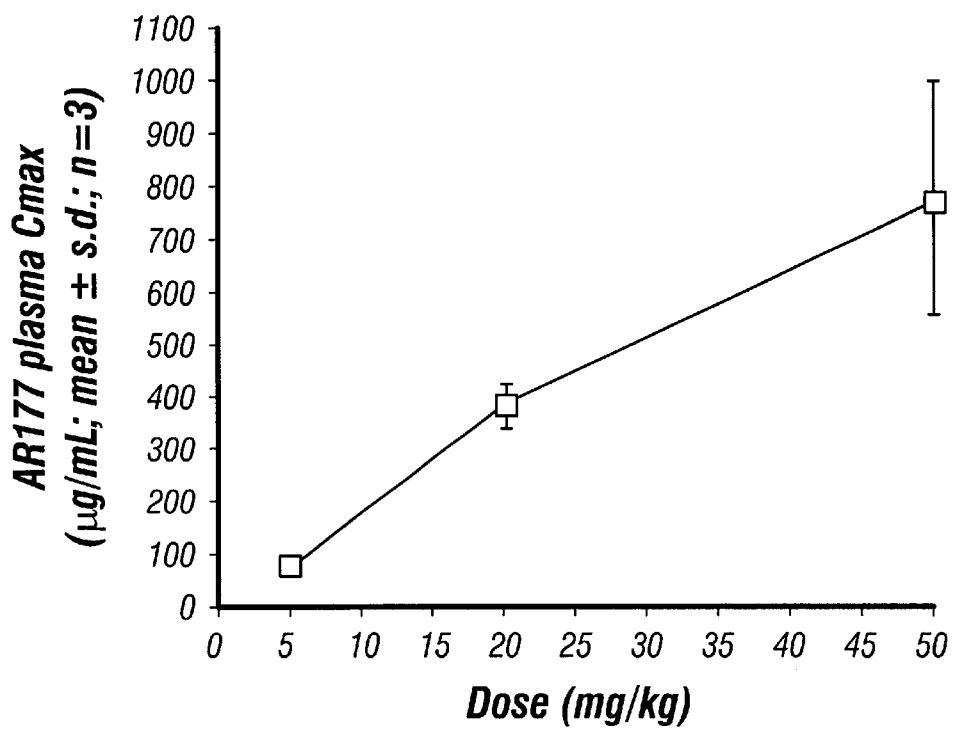

FIG. 47. AR177 plasma concentration versus time profiles following a ten-minute intravenous infusion to cynomolgus monkeys. The plasma concentration of AR177 was determined by anion-exchange HPLC as described in the Methods section. The plasma AR177 concentration at 24 hours for the 5, 20 and 50 mg/kg groups were <0.020 g/mL for the 5 and 20 mg/kg groups, and 0.24±0.42 µ/mL for the 50 mg/kg group.

Figure 48:
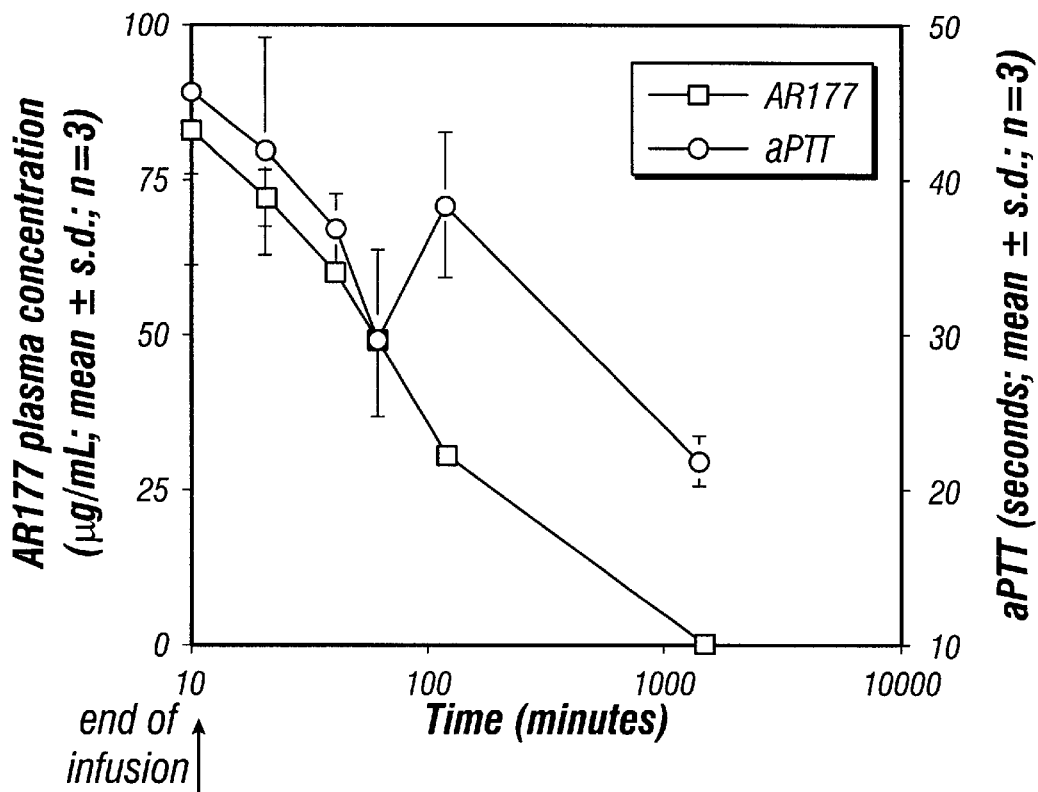

FIG. 48. The relationship between plasma AR177 and aPTT in cynomolgus monkeys following a ten-minute intravenous infusion of 5 mg AR177/kg. The plasma concentration of AR177 was determined by anion-exchange HPLC as described in the Methods section. The baseline aPTT level (at 10 minutes prior to dosing) was 32.1±4.4 seconds (mean±s.d.).

Figure 49:
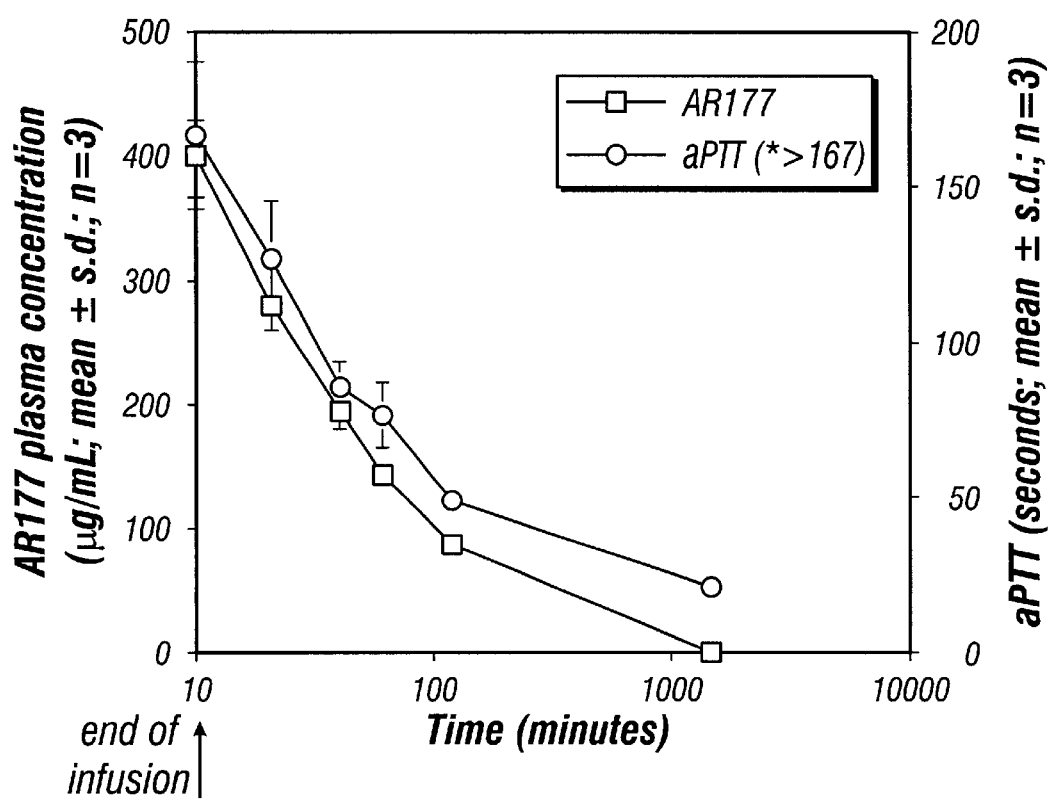

FIG. 49. The relationship between plasma AR177 and aPTT in cynomolgus monkeys following a ten-minute intravenous infusion of 20 mg AR177/kg. The plasma concentration of AR177 was determined by anion-exchange HPLC as described in the Methods section. The baseline aPTT level (at 10 minutes prior to dosing) was 41.6±6.7 seconds (mean±s.d.). The aPTT value in monkeys at the 10 minute time point, denoted by an asterisk, exceeded the upper limit of the assay.

Figure 50:
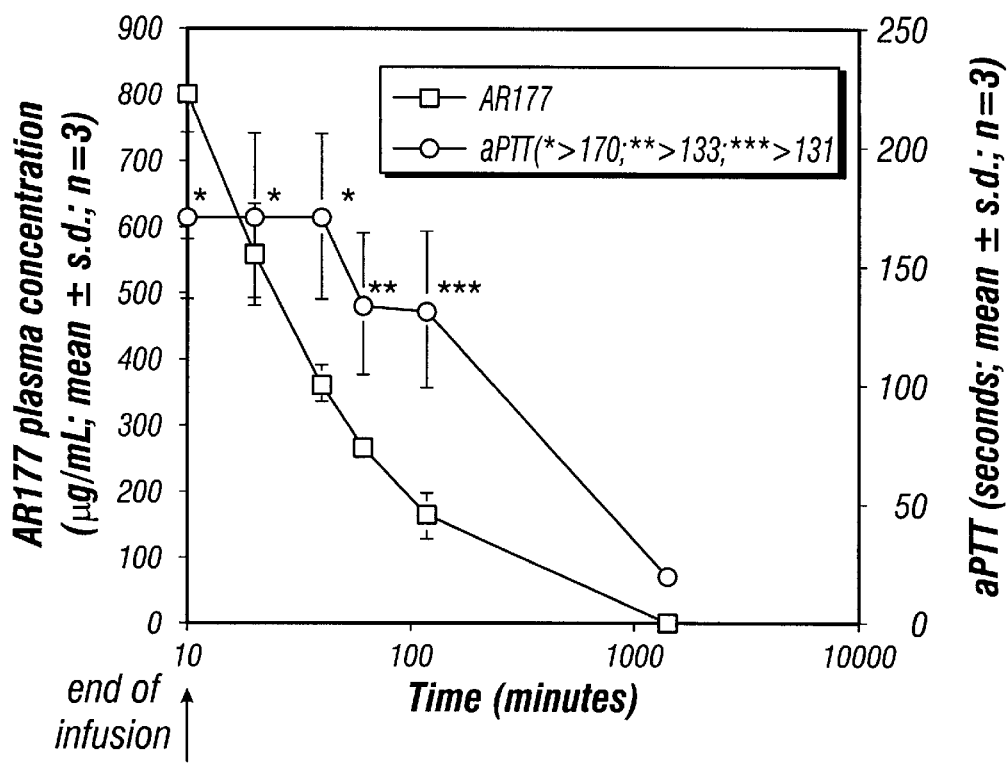

FIG. 50. The relationship between plasma AR177 and aPTT in cynomolgus monkeys following a ten-minute intravenous infusion of 50 mg AR177/kg. The plasma concentration of AR177 was determined by anion-exchange HPLC as described in the Methods section. The baseline aPU level (at 10 minutes prior to dosing) was 33.2±4.8 seconds (mean±s.d.). Certain aPTT values in monkeys at the 10 to 120 time points, denoted by asterisks, exceeded the upper limit of the assay.

Figures for Section F

Figure 51:
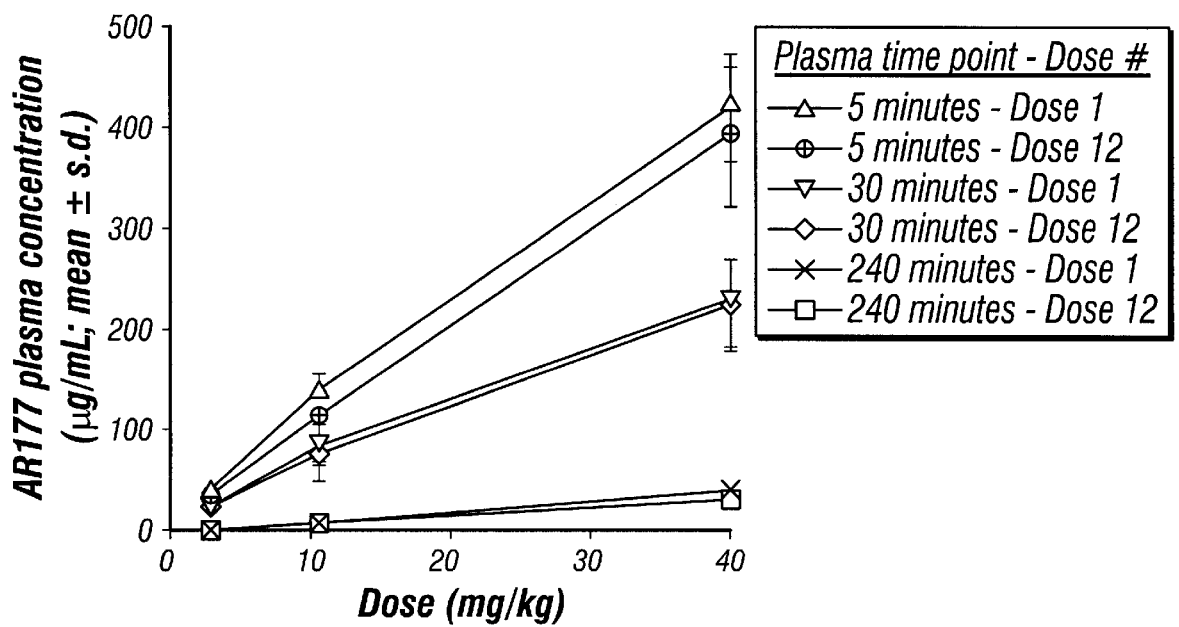

FIG. 51. AR177 plasma concentration after bolus IV dose 1 or 12 versus dose amount in Cynomolgus monkeys. Cynomolgus monkeys were given intravenous doses of 2.5, 10 or 40 mg/kg/day every other day for a total of 12 doses. Blood was obtained 5, 30 and 240 minutes following doses 1 and 12. The concentration of AR177 in the plasma of every monkey was determined by anion-exchange HPLC as described in the Methods section. There were six monkeys in the 10 and 40 mg/kg groups, and eight monkeys in the 40 mg/kg group. There was a linear relationship between each dose and the plasma concentration that was achieved at each of the sampling times.

Figure 52:
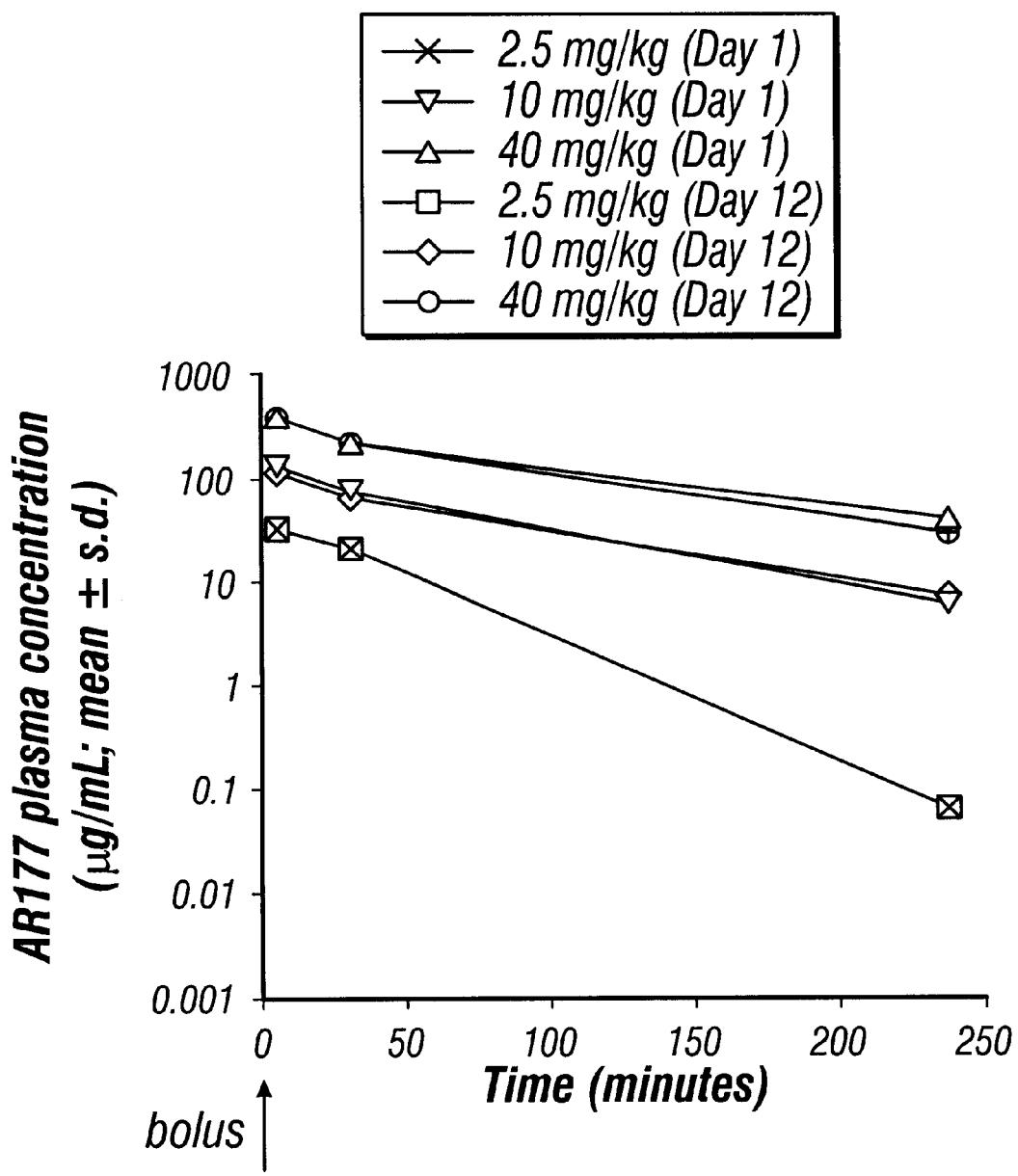

FIG. 52. AR177 plasma concentration versus time profile following a bolus IV injection (dose 12) to Cynomolgus monkeys. Cynomolgus monkeys were given intravenous doses of 2.5, 10 or 40 mg/kg/day every other day for a total of 12 doses. This figure shows the concentration of AR177 in the plasma 5, 30 and 240 minutes following dose 12. The concentration of AR177 in the plasma was determined in every monkey by anion-exchange HPLC as described in the Methods section. There were six monkeys in the 2.5 and 10 mg/kg groups, and eight monkeys in the 40 mg/kg group. There were no apparent difference between the disappearance of AR177 from the plasma following the 1st (FIG. F-3) and 12th doses.

Figure 53:
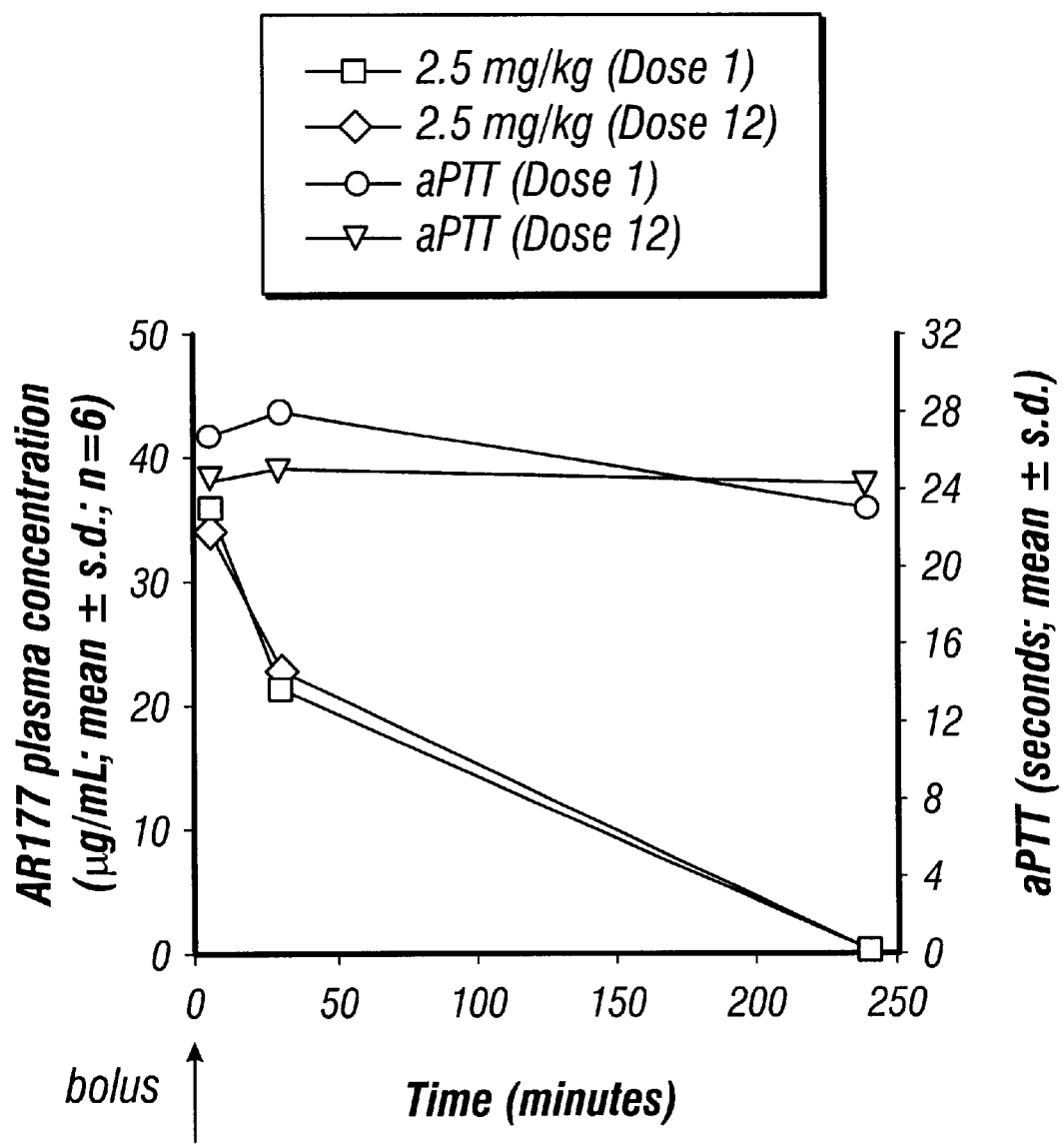

FIG. 53. The relationship between the plasma AR177 concentration and aPTT in Cynomolgus monkeys following a bolus IV injection of 2.5 mg AR177/kg. Cynomolgus monkeys were given intravenous doses of 2.5 mg/kg/day every other day for a total of 12 doses. This figure shows the plasma AR177 concentration versus aPTT levels 5, 30 and 240 minutes following doses 1 and 12. The concentration of AR177 in the plasma was determined in every monkey by anion-exchange HPLC as described in the Methods section. There were six monkeys in the 2.5 mg/kg group. The baseline aPTT levels just prior to (pre-dose) doses 1 and 12 were 24.1±3.4 seconds and 22.1±2.2. There was no change in the aPTT levels at any of the time points after the 1st or 12th doses of AR177 at 2.5 mg/kg.

Figure 54:
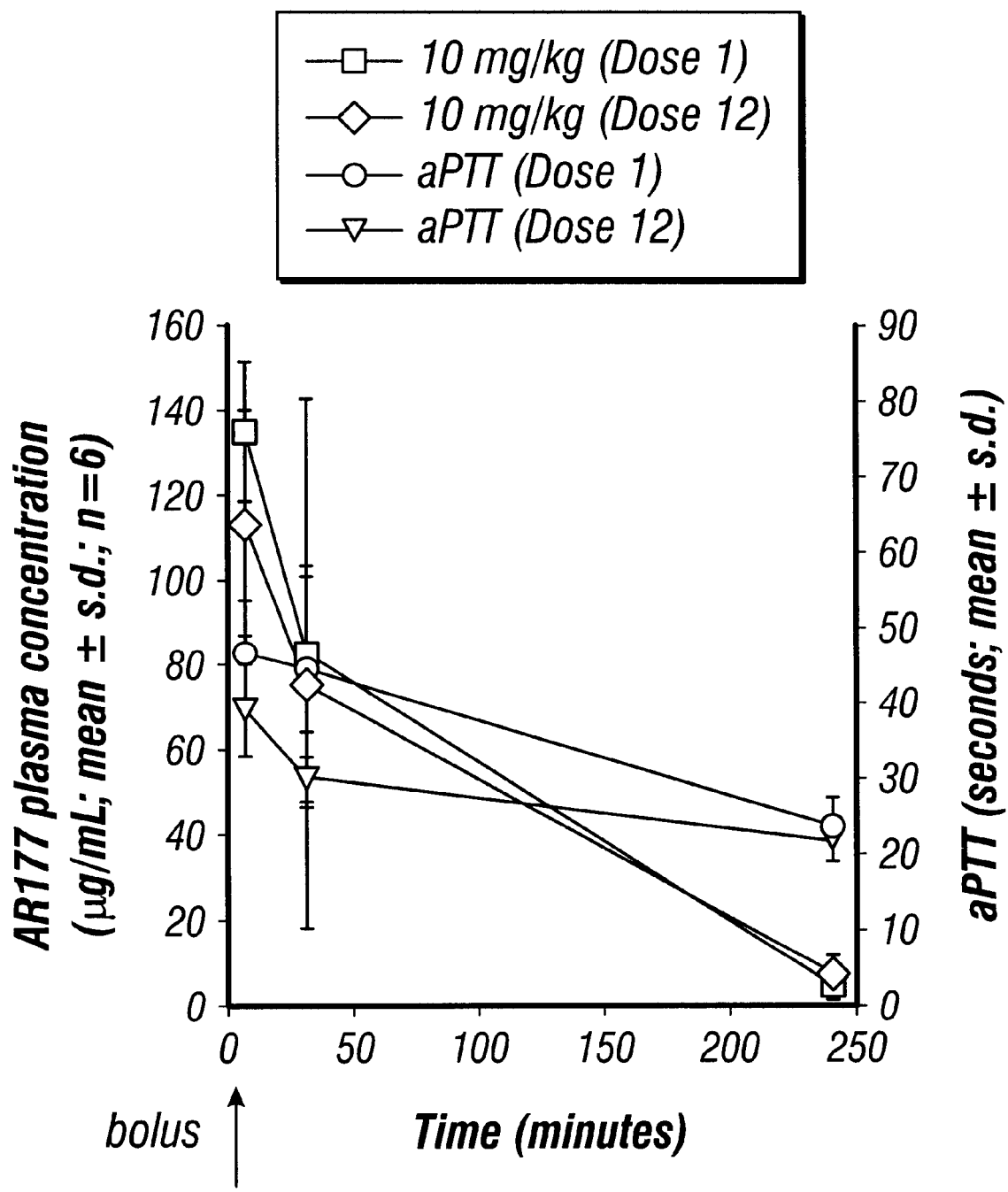

FIG. 54. The relationship between the plasma AR177 concentration and APTT in cynomolgus monkeys following a bolus IV injection of 10 mg AR177/kg. Cynomolgus monkeys were given intravenous doses of 10 mg/kg/day every other day for a total of 12 doses. This figure shows the plasma AR177 concentration versus aPTT levels 5, 30 and 240 minutes following doses 1 and 12. The concentration of AR177 in the plasma was determined in every monkey by anion-exchange HPLC as described in the Methods section. There were six monkeys in the 10 mg/kg group. The baseline aPTT levels just prior to (pre-dose) doses 1 and 12 were 23.3±1.8 seconds and 21.6±2.2. There was a close correlation between the aPTT] levels after the 1st or 12th doses of AR177 at 10 mg/kg and the aPTT levels.

Figure 55:
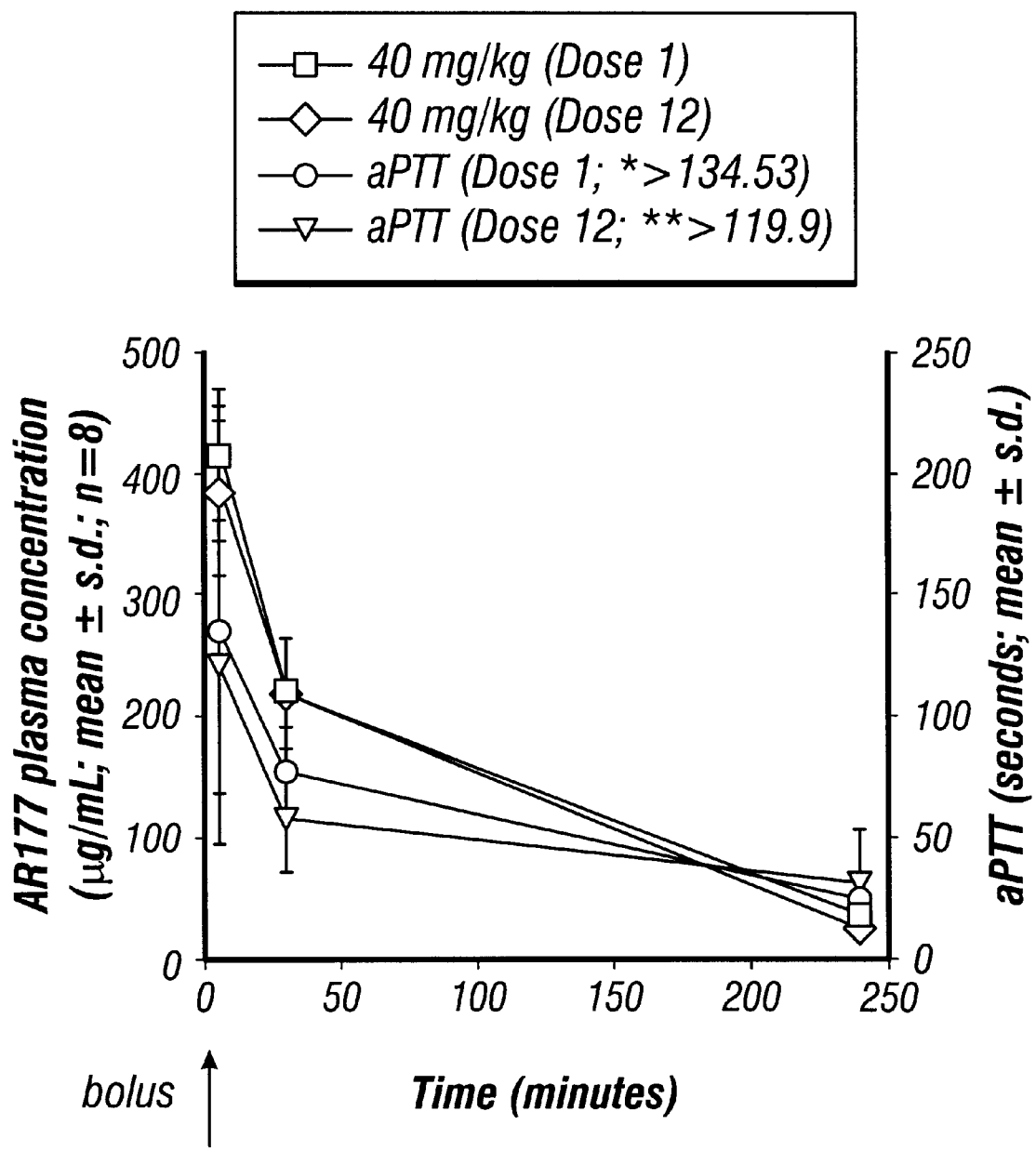

FIG. 55. The relationship between the plasma AR177 concentration and aPTT in cynomolgus monkeys following abolus IV injection of 40 mg AR177/kg. Cynomolgus monkeys were given intravenous doses of 10 mg/kg/day every other day for a total of 12 doses. This figure shows the plasma AR177 concentration versus aPTT levels 5, 30 and 240 minutes following doses 1 and 12. The concentration of AR177 in the plasma was determined in every monkey by anion-exchange HPLC as described in the Methods section. There were eight monkeys in the 40 mg/kg group. The baseline aPTT levels just prior to (pre-dose) doses 1 and 12 were 24.8±3.3 seconds and 22.5±2.5. Certain aPTT] values in monkeys at the 20 and 50 mg/kg dose time points at five minutes following doses 1 or 12, denoted by asterisks, exceeded the upper limit of the assay. There was a close correlation between the aPTT levels after the 1st or 12th doses of AR177 at 40 mg/kg and the aPTT levels.

Figures for Section G

Figure 56:
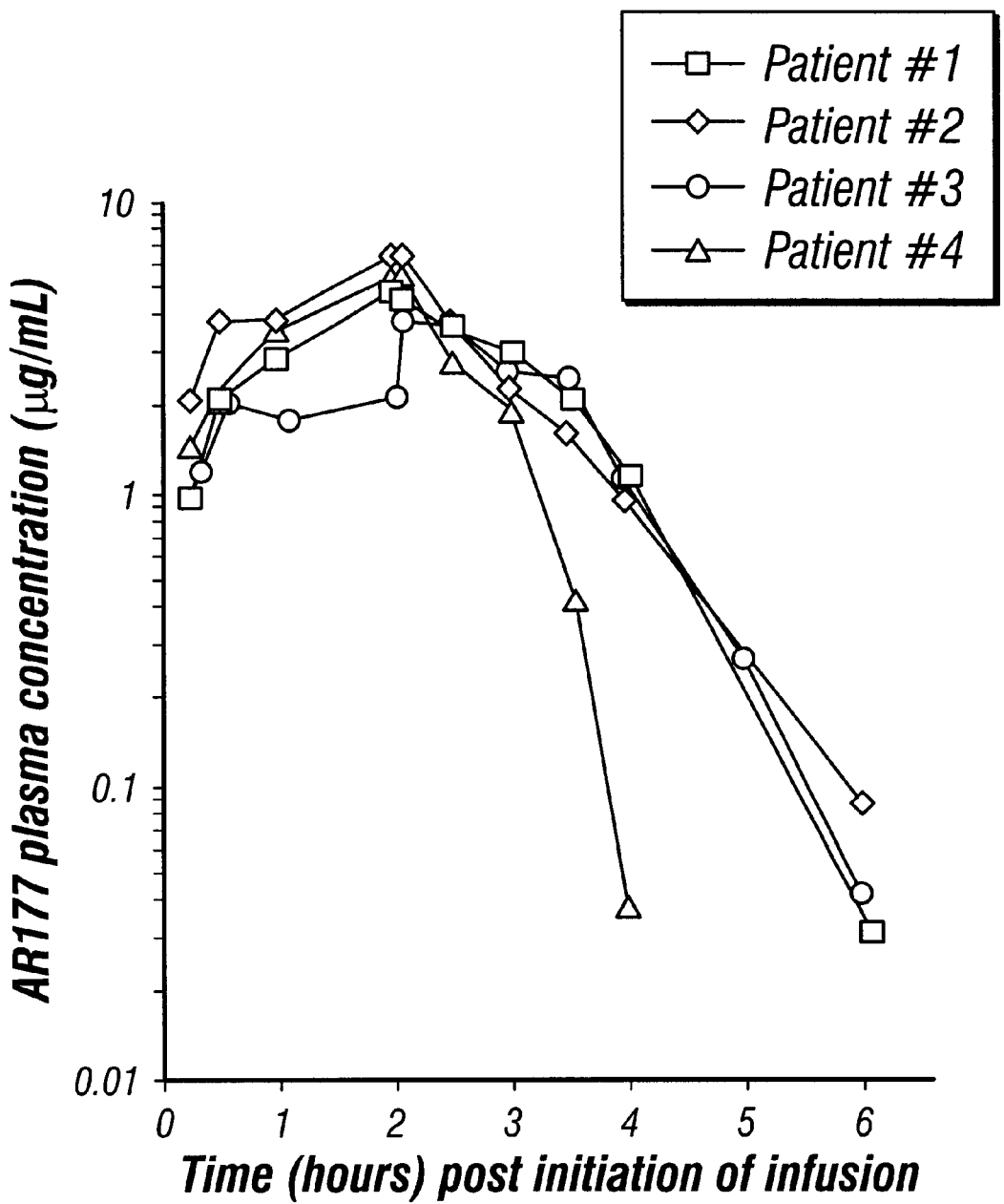

FIG. 56. AR177 pharmacokinetics following a single IV dose of 0.75 mg/kg to humans. Four HIV-positive human patients were administered AR 177 at 0.75 mg/kg as a two-hour intravenous (IV) infusion. Blood samples were collected in EDTA-coated tubes at various time points during and following the IV infusion. Plasma was obtained following low speed centriguation of the blood. The concentration of AR177 in the plasma was determined using a validated anion-exchange HPLC method.

Figure 57:
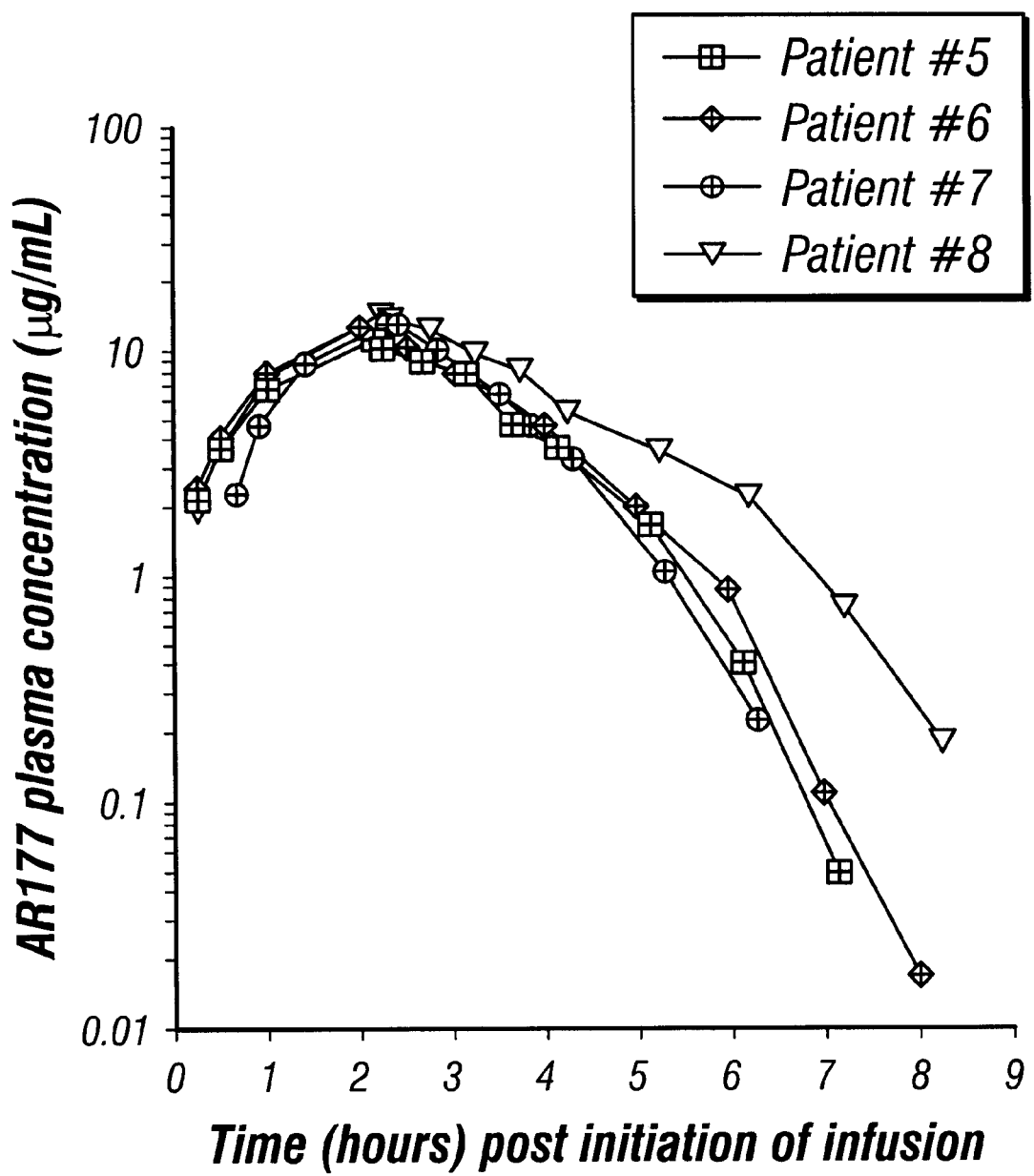

FIG. 57. AR177 pharmacokinetics following a single IV dose of 1.5 mg/kg to humans. Four HIV-positive human patients were administered AR177 at 1.5 mg/kg as a two-hour intravenous (IV) infusion. Blood samples were collected in EDTA-coated tubes at various time points during and following the IV infusion. Plasma was obtained following low speed centriguation of the blood. The concentration of AR177 in the plasma was determined using a validated anion-exchange HPLC method.

Figure 58:
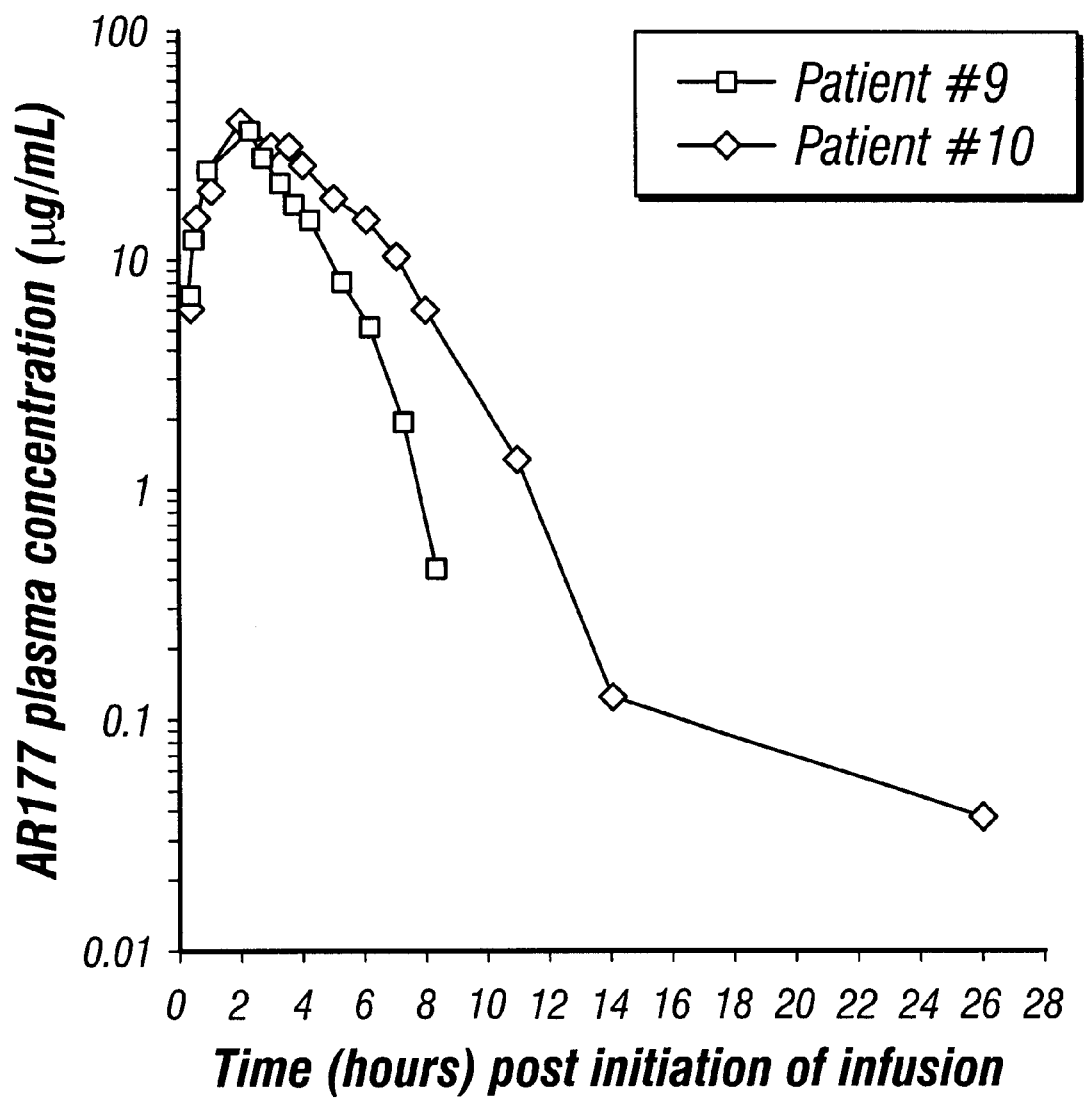

FIG. 58. AR177 pharmacokinetics following a single IV dose o 3.0 mg/kg to humans. Two HIV-positive human patients were administered AR177 at 3.0 mg/kg as a two-hour intravenous (IV) infusion. Blood samples were collected in EDTA-coated tubes at various time points during and following the IV infusion. Plasma was obtained following low speed centriguation of the blood. The concentration of AR177 in the plasma was determined using a validated anion-exchange HPLC method.

Figure 59:
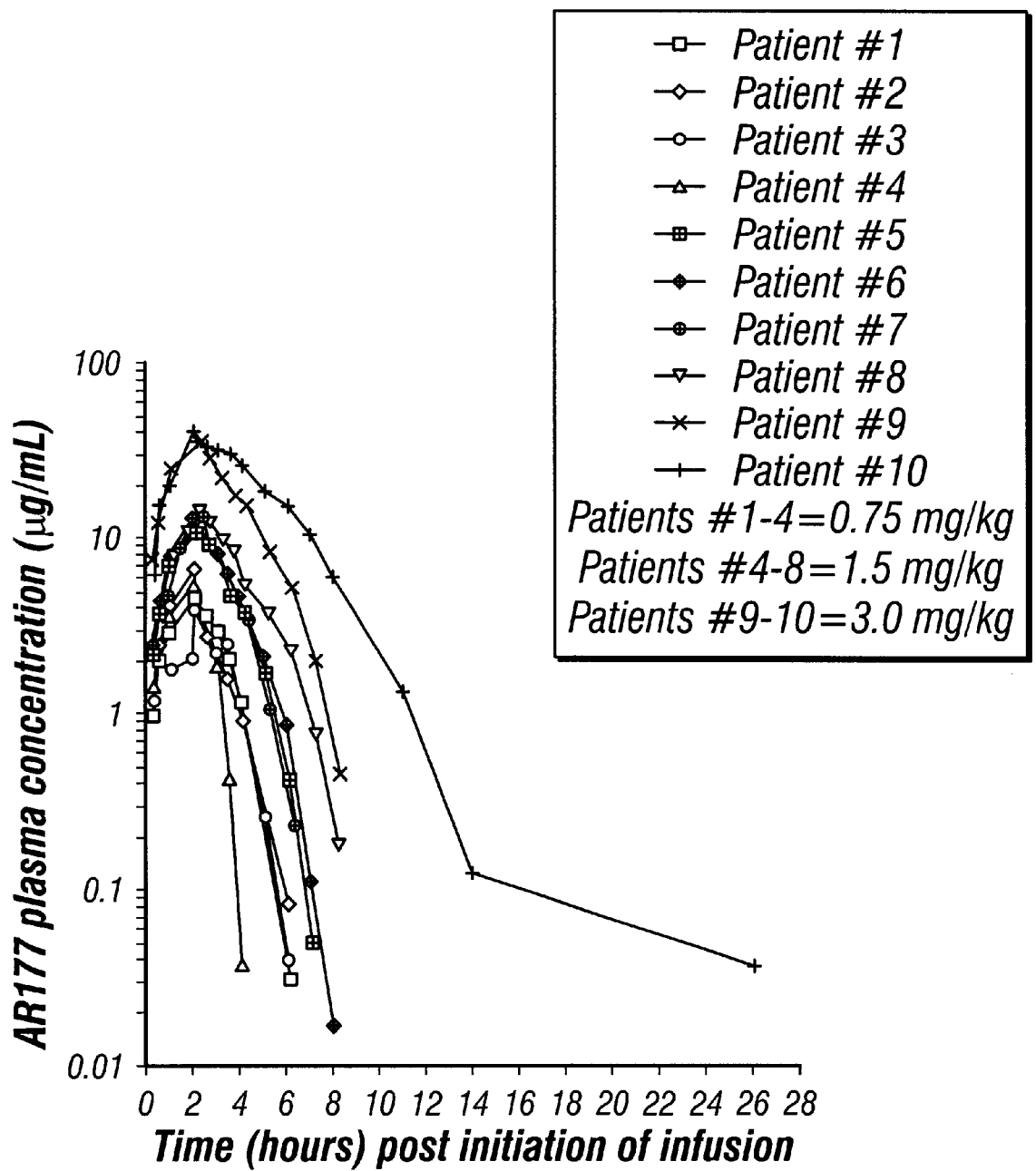

FIG. 59. AR177 pharmacokinetics following a single IV dose of 0.75, 1.5 or 3.0 mg/kg to humans. Ten HIV-positive human patients were administered AR177 at 0.75, 1.5 or 3.0 mg/kg as a two-hour intravenous (IV) infusion. Blood samples were collected in EDTa-coated tubes at various time points during and following the IV infusion. Plasma was obtained following low speed centriguation of the blood. The concentration of AR177 in the plasma was determined using a validated anion-exchange HPLC method.

Figure 60:
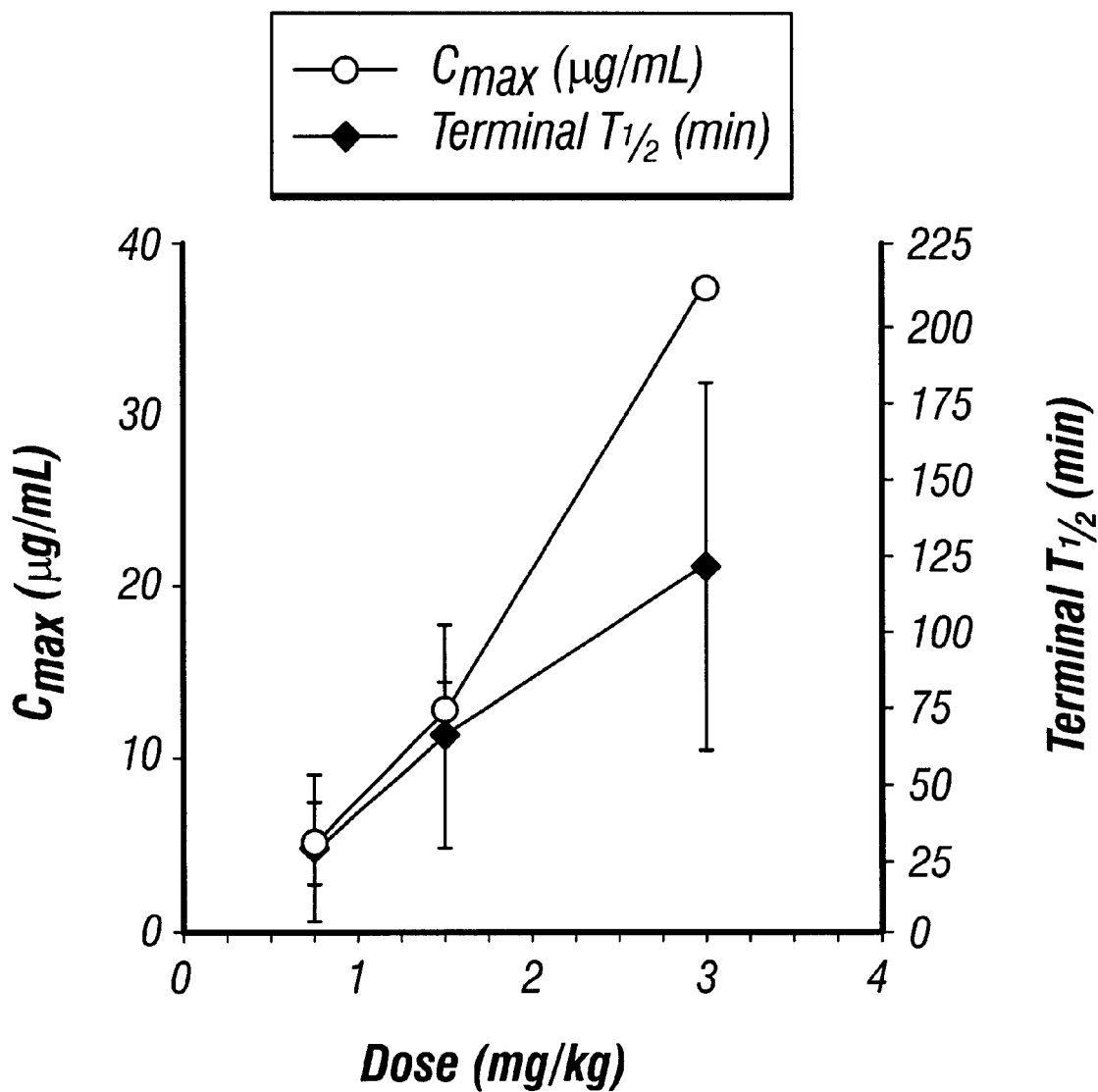

FIG. 60. AR177 T½ and $C_{MAX}$ following single doses to humans. HIV-positive human patients were administered AR177 at 0.75, 1.5 or 3.0 mg/kg as a two-hour intravenous infusion. The concentration of AR177 was determined in the plasma using a validated anion-exchange HPLC method. The $C_{MAX}$ (maximal plasma concentration of AR177) and plasma T½ (half-life of AR177 in plasma) were determined using PKAnalyst software (Micro Math, Salt Lake City, Utah).

PD. The term "PD" indicates phosphodiester internucleotide linkages in an oligonucleotide.

PT. The term "PT" indicates phosphorothioate internucleotide linkages in an oligonucleotide.

pPT. The term "pPT" indicates both phosphoroyhioate and phosphodiester internucleotide linkages in an oligonucleotide.

Figure 61:
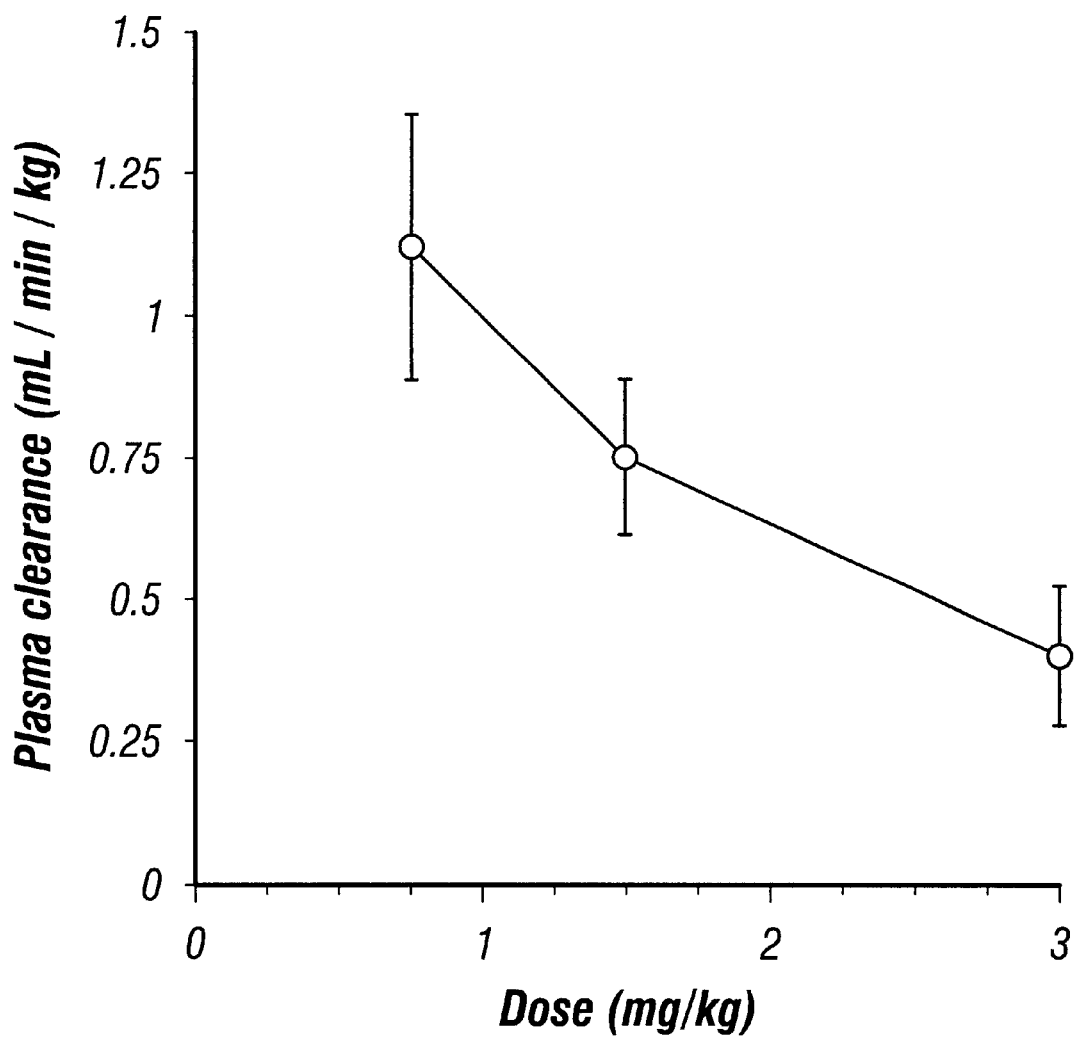

FIG. 61. AR177 clearance following single doses to humans. HIV-positive human patients were administered AR177 at 0.75, 1.5 or 3.0 mg/kg as a two-hour intravenous infusion. The concentration of AR177 was determined in the plasma using a validated anion-exchange HPLC method. The plasma clearance was determined using PKAnalyst software (Micro Math, Salt Lake City, Utah).

DETAILED DESCRIPTION OF THE INVENTION

INDEX TO DETAILED DESCRIPTION OF THE INVENTION

Definitions
A. General In Vitro Studies
B. Specific In Vitro Studies and In Vitro HIV Inhibition Using T30177
C. Site of Activity Studies-Viral Integrase Inhibition
D. Structure-Function Studies
E. Single Dose Pharmacokinetic Studies
F. Repeat Dose Pharmacokinetic Studies
G. Human Clinical Trials Definitions The following terms as defined will be used in the description of the invention:

OLIGONUCLEOTIDE

The term "oligonucleotide" as used herein is defined as a molecule comprised of two or more deoxyribonucleotides or ribonucleotides, preferably more than ten. Its exact size will depend on many factors including the specificity and antiviral activity of the oligonucleotide for various viruses. In addition, bases can refer to unnatural (synthetic) bases used in place of an A, C, T or G.

BASE

In referring to "bases" herein, the term includes both the deoxyribonucleic acids and ribonucleic acids. The following abbreviations are used. "A" refers to adenine as well as to its deoxyribose derivative, "T" refers to thymine, "U" refers to uridine, "G" refers to guanine as well as its deoxyribose derivative, "C" refers to cytosine as well as its deoxyribose derivative. A person having ordinary skill would readily recognize that these bases may be modified or derivatized to optimize the methods of the present invention. In addition, bases can refer to unnatural (synthetic) bases used in place of an A, C, T, or G.

INHIBITION

The term "inhibition" of viral replication is meant to include partial and total inhibition of viral replication as well as decreases in the rate of viral replication. The inhibitory dose or "therapeutic dose" of the compounds in the present invention may be determined by assessing the effects of the oligonucleotide on viral replication in tissue culture or viral growth in an animal. The amount of oligonucleotide administered in a therapeutic dose is dependent upon the age, weight, kind of concurrent treatment and nature of the viral condition being treated.

PHARMACOLOGICAL DOSE

The term "pharmacological dose" as used herein refers to the dose of an oligonucleotide which causes a pharmacological effect when given to an animal or human. The pharmacological dose introduced into the animal or human to be treated, will provide a sufficient quantity of oligonucleotide to provide a specific effect, e.g., (1) inhibition of viral protein or enzymes, (2) inhibition of viral-specific replication, (3) preventing the target site from functioning or (4) damaging the duplex DNA at the specific site or (5) ablating the DNA at the site or (6) inhibiting the transcription/translation of the gene under the regulation of the site being bound or (7) internal inhibition of transcription or translation of the gene containing the sequence. One skilled in the art will readily recognize that the dose will be dependent upon a variety of parameters, including the age, sex, height and weight of the human or animal to be treated, the organism or gene location which is to be attacked and the location of the target sequence within the organism. Given any set of parameters, one skilled in the art will be able to readily determine the appropriate dose.

PATHOPHYSIOLOGICAL STATE

The term "pathophysiological state" as used herein refers to any abnormal, undesirable or life-threatening condition caused directly or indirectly by a virus.

GTO

The term "GTOs" means an oligonucleotide in which there is a high percentage of deoxyguanosine, or contains two or more segments (runs) of two or more deoxyguanosine residues per segment.

GUANOSINE TETRAD

As used herein, the term "guanosine tetrads" refers to the structure that is formed of eight hydrogen bonds by coordination of the four $O^6$ atoms of guanine with alkali cations believed to bind to the center of a quadruplex, and by strong stacking interactions. Of particular interest to the I100-15 class of GTO is the structure of the telomere sequence repeat $T_4G_4$, first detected in Oxytricha. The oxytricha repeat has been studied in oligonucleotides by NMR and by crystallographic methods. See Smith et al., *Nature*, 1992, 356:164–68, and Kang et al., *Nature*, 1992 356:126–31. As predicted from numerous previous physical and biochemical studies, both the NMR and crystallographic studies suggest that folding is mediated by square planar Hoogsteen H-bonding among G-residues, with overall antiparallel orientation of the four strand equivalents comprising the tetrad fold. As expected, the crystallography has shown that the structure is selectively stabilized by tight binding of a small monovalent cation to the $O^6$ oxygen of guanosine.

The following examples are offered by way of illustration and are not intended to limit the invention in any manner.
A. General In Vitro Studies The present invention provides methods and compositions for treating a pathophysiological state caused by a virus, comprising the step of administering a pharmacological dose of an oligonucleotide, the dose being sufficient to inhibit the replication of the virus, wherein the oligonucleotide contains sufficient contiguous guanosines so that a guanosine tetrad (inter- or intra-molecular) can form, and the three dimensional structure of the oligonucleotide is stabilized by guanosine tetrads formed at strategic locations. Generally, this method of treating a virus-induced pathophysiological state may be useful against any virus. More preferably, the methods of the present invention may be useful in treating pathophysiological states caused by viruses such as herpes simplex virus, human papilloma virus, Epstein Barr virus, human immunodeficiency virus, adenovirus, respiratory syncytial virus, hepatitis B virus, human cytomegalovirus and HTLV I and II.

Generally, the oligonucleotides of the present invention contain a percentage of guanosine bases high enough to ensure anti-viral efficacy. The guanosine is important in forming tetrads which stabilize the three dimensional structure of the oligonucleotides. Thus, the oligonucleotides of the present invention may have any percentage of guanosine bases which will allow for tetrad formation provided that the oligonucleotide exhibits anti-viral activity. Preferably, the oligonucleotides of the present invention contain two or more segments of two or more guanosine bases, and an overall high percentage of G in order to enable the oligonucleotide to form at least one quanosine tetrad.

Generally, the oligonucleotides of the present invention may be capped at either the 3' or the 5' terminus with a modifier. Preferably, the modifier is selected from the group consisting of polyamine or similar compounds that confer a net positive charge to the end of the molecule, poly-L-lysine or other similar compounds that enhance uptake of the oligonucleotide, cholesterol or similar lipophilic compounds that enhance uptake of the oligonucleotide and propanol amine or similar amine groups that enhance stability of the molecule.

The phosphodiester linkage of the oligonucleotides of the present invention may be modified to improve the stability or increase the anti-viral activity. For example, a phosphodiester linkage of the oligonucleotide may be modified to a phosphorothioate linkage. Other such modifications to the oligonucleotide backbone will be obvious to those having ordinary skill in this art.

The present invention also provides specific methods of treating viral states. For example, the present invention provides a method of treating a pathophysiological state caused by a virus (in preferred embodiments, as specific virus such as, herpes simplex virus, human papilloma virus, Epstein Barr virus, human immunodeficiency virus, adenovirus, respiratory syncytial virus, hepatitis B virus, human cytomegalovirus and HTLV I and II), comprising the step of administering a pharmacological dose of an oligonucleotide, the dose being sufficient to inhibit the replication of the virus, wherein the three dimensional structure of the oligonucleotide is stabilized by the formation of guanosine tetrads.

This invention discloses a novel anti-viral technology. The total number of antiviral mechanisms by which oligonucleotides, and especially G-rich oligonucleotides, work is not completely known, although the inventors have at least narrowed the sites of action as to certain oligonucleotide drugs as will be seen below. However, in the different virus culture systems listed above, G-rich oligonucleotides were able to significantly reduce virus production in each. More importantly, actual human clinical studies have demonstrated the efficacy of the drug in reducing viral replicons in AIDS patients. The present invention is also drawn to oligonucleotides that have three dimensional structures stabilized by the formation of guanosine tetrads.

The present invention demonstrates poly and/or oligonucleotides inhibit growth of HIV-1, HSV1, HSV2, FMLV and HCMV and other viruses if the molecule contains a high percentage of ribo- or deoxyriboguanosine. The rest of the molecule is composed of thymine, cytosine, xanthosine or adenine nucleotides (ribo- or deoxyribo-), their derivatives, or other natural or synthetic bases. The 5' and 3' termini of the oligonucleotide can have any attachment which may enhance stability, uptake into cells (and cell nuclei) or anti-viral activity. The backbone which connects the nucleotides can be the standard phosphodiester linkage or any modification of this linkage which may improve stability of the molecule or anti-viral activity of the molecule (such as a phosphorothioate linkage).

Structural formulas for representative G-rich oligonucleotides disclosed in the instant invention are listed below in Table A-1.

TABLE A-1

| | |
|---|---|
| SEQ ID NO 5(B106-62) | 5'-gtggtggtggtgttggtggtggtttgggggtgggg-3' |
| SEQ ID NO 6(B106-71) | 5'-gtggttggtggtggtgtgtgggtttgggtgggggg-3' |
| SEQ ID NO 21(I100-01) | 5'-tggtgggtgtgtgggggtgttgggggttgttggtggggtggtgg-3' |
| SEQ ID NO 24(I100-07) | 5'-gtggtgggtgggtgggtggtgggtggtggttgtgggtgggtggtg-3' |
| SEQ ID NO 28(I100-50) | 5'-ggtggtggggtggttgttgggggttg-3' |
| SEQ ID NO 29(I100-51) | 5'-ggtggtggggtggttgttgggggttgttgggggtgtgtgggtggt-3' |
| SEQ ID NO 26(I100-11) | 5'-gatccatgtcagtgacactgcgtagatccgatgatccagtcgatg-3' |
| SEQ ID NO 12(Gl01-50) | 5'-ggtgggtggtttgtgtggttggtgggttt-3' |
| SEQ ID NO 13(G105-50) | 5'-gggggggggtgtgggggggggttgtggtgg-3' |
| SEQ ID NO 14(G106-50) | 5'-ggtgggtgggttgggggtgggtgggg-3' |
| SEQ ID NO 15(G109-50) | 5'-ggggtttggtgggggggttgggtggttg-3' |
| SEQ ID NO 16(G110-50) | 5'-gggtggtggtgttggtgttgtgtg-3' |
| SEQ ID NO 17(G113-50) | 5'-ggtgggggggttggtgtgtttg-3' |
| SEQ ID NO 1(A100-00) | 5'-tgggtggggtggggtgggggggtgtgggtgtggggtg-3' |
| SEQ ID NO 2(A100-50) | 3'-tgggtggggtggggtgggggggtgtgggtgtggggtg-5' |
| SEQ ID NO 4(A101-00) | 5'-ggtggtgggggggggtgggtggtggtgggggtgg-3' |
| SEQ ID NO 18(HIV26ap) | 5'-gtgtgggggggtggggtggggtggt-3' |
| SEQ ID NO 19(HIV26ctl) | 5'-gggtgggtgggtgggtgggtgggtgg-3' |
| SEQ ID NO 9(B107-51) | 5'-ggtggggtggtggtggttgggggggggggt-3' |
| SEQ ID NO 10(B133-54) | 5'-ggtggttgggggtgggggg-3' |
| SEQ ID NO 11(B133-55) | 5'-gggtgggtggtgggtggggg-3' |
| SEQ ID NO 20(I100-00) | 5'-gttgggggttgttggtggggtggtgg-3' |
| SEQ ID NO 27(I100- 12,PT) | 5'-gttgggggttgttggtggggtggtgg-3' |
| SEQ ID NO 22(I100-05) | 5'-tggtgggtgtgtgggggtgttgggggttgttggtggggtggtg-CHOL |
| SEQ ID NO 23(I100-06) | 5'-gtggtgggtgggtgggtggtgggtggtggttgtgggtgggtggtg-CHOL |
| SEQ ID NO 25(I100-08) | 5'-gttgggggttgttggtggggtggtgg-CHOL |
| SEQ ID NO 3 | 5'-gggtggtgggtgggtgg-3' |
| SEQ ID NO 30 | 5'-gggtggttgggtggttgg-3' |
| SEQ ID NO 31(1173) | 5'-gggtgggtgggtgggtgg-3' |
| SEQ ID NO 32(1174,PT) | 5'-gggtgggtgggtgggtgg-3' |
| SEQ ID NO 33(I100-15) | 5'-gtggtgggtgggtgggt-3' |
| SEQ ID NO 34(I100-16) | 5'-gtggtgggtgggtgggtggtgggtggt-3' |
| SEQ ID NO 35(I100-17) | 5'-gtggtgggtgggtgggtggtgggtggtggttgtgggt-3' |
| SEQ ID NO 36(I100-18) | 5'-ttgtgggtgggtggtg-3' |
| SEQ ID NO 37(I100-19) | 5'-tggtgggtggtggttgtgggtgggtggtg-3' |
| SEQ ID NO 38(I100-20) | 5'-gtgggtgggtggtgggtggtggttgtgggtgggtggtg-3' |
| SEQ ID NO 39(I100-21,PT) | 5'-gtggtgggtgggtgggtggtgggtggtggttgtgggtgggtggtg-3' |
| SEQ ID NO 40(1231) | 5'-gatccatgtcagtgacac-3' |
| SEQ ID NO 41(1232,PT) | 5'-gatccatgtcagtgacac-3' |
| SEQ ID NO 42(1229) | 5'-cccccccccccccccccc-3' |

TABLE A-1-continued

| | |
|---|---|
| SEQ ID NO 43(1230,PT) | 5'-cccccccccccccccccc-3' |
| SEQ ID NO 44(1198) | 5'-ttcatttgggaaaccccttggaacctgactgactggccgtcgttttac-3' |
| SEQ ID NO 45(1200) | 5'-gtaaaacgacggcca-3' |
| SEQ ID NO 46(I100-25) | 5'-gtggtgggtgggtgggg-3' |
| SEQ ID NO 47(I100-26) | 5'-gtggtgggtgggtggg-3' |
| SEQ ID NO 48(I100-35) | 5'-ggtgggtgggtgggt-3' |
| SEQ ID NO 49(I100-27) | 5'-gtggtgggtgggt-3' |
| SEQ ID NO 50(I100-28) | 5'-gtggtgggt-3' |
| SEQ ID NO 51(I100-30) | 5'-gtgggtgggtgggt-3' |
| SEQ ID NO 52(I100-29) | 5'-gtgggtgggt-3' |

HSV-2 CULTURE ASSAY

In viral yield reduction assays, Vero cells ($4 \times 10^4$ cells/tissue culture well) were incubated with oligonucleotide(s) for 14 hours before the oligonucleotide was removed and virus (HSV-2 strain HG52) was added to the cells at a multiplicity of infection (m.o.i.) of 0.1 to 1.0 ($4 \times 10^3$ to $4 \times 10^4$ PFU). The infection was allowed to proceed for 10 minutes after which the cells are washed and fresh media, containing the same oligonucleotide was added for an additional 14 hours. Then, the cells were subjected to a freeze/thaw lysis after which the released virus was titered.

HIV-1 CULTURE ASSAY

The SUP T1 T lymphoma cell line was infected with HIV-1 strain DV at a multiplicity of infection (m.o.i.) of 0.1 for one hour at 37° C. After the infection, free virus was washed off and the newly infected cells were plated ($5 \times 10^4$ cells) in quadruplicate in 96 well plates that had been prepared with various dilutions of oligonucleotide. The final concentration of drug varied between 0.1 and 20 uM. After 3 days of incubation at 37° C., the plates were scored for the presence of multinucleated giant cells (syncytia).

In assays designed to inhibit syncytia formation, a number of oligonucleotides exhibited anti-HIV-1 activity. The oligonucleotides and their IC50 are listed in Table A-2. I100-05 is the same as I100-01 with a cholesterol group attached to the 3' end via a triglycyl-linker. I100-08 is the same as I100-00 with a cholesterol group attached to the 3' end via a triglycyl-linker. I100-07 was designed as a sequence isomer to I100-01 and I100-06 is the cholesterol derivative of I100-07. A100-00 is the same sequence in the opposite orientation to HIB38p (A100-50). I100-07, originally designed as a control for I100-01 to be used in anti-FMLV experiments, was the most efficacious oligonucleotide tested against HIV-1.

Figure 3:
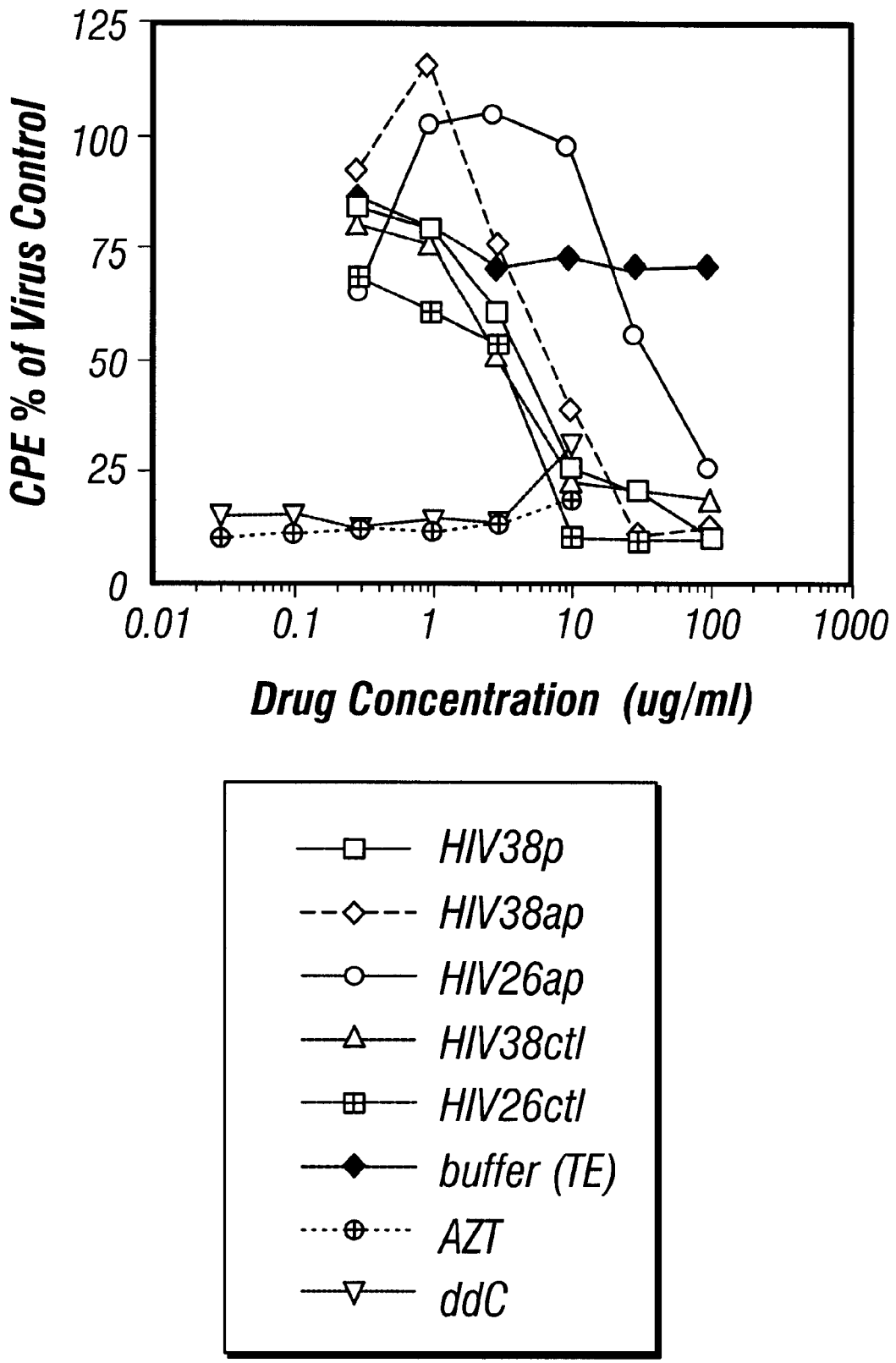
FIG. 3 shows MT-2 cells infected with 0.01 m.o.i. of HIV-1 and then treated with various concentrations of oligonucleotide or AZT or ddC. The data represents the number of viable cells remaining in the culture dish, i.e., not undergoing virus induced cytopathic effects (CPE). In this graph, 100% is the level of CPE occurring in cultures infected with virus but not treated with any drug.

In other experiments, the HIV-1 strain LAV was used to infect MT-2 cells at an m.o.i of 0.01. After 7 days, these cells were scored for cytopathic effects (CPE). In anti-HIV-1 assays in which MT-2 cells were infected at an m.o.i. of 0.01, several G-Rich oligonucleotides were able to inhibit viral-induced cytopathic effects with effective dose 50's (IC50s) in the 0.5–1.0 uM range (FIG. 3). The oligonucleotides shown in FIG. 3 were effective in the 0.5 to 1.0 uM range, including A100-00 (HIV38p) and A100-50 (HIV38ap), A101-00 (HIV38ctl), HIV-26ctl. The oligonucleotide HIV-26ap exhibited less efficacy in this assay with an IC50 in the 5 to 10 uM range. In FIG. 3, TE represents buffer alone, i.e., no drug, while AZT and ddC are control drugs.

TABLE A-2

$IC_{50}$ for oligonucleotides in an anti-HIV-1 syncytia formation assay.

| G-Rich oligonucleotide | IC50 |
|---|---|
| I100-00 | 3.75 µM |
| I100-01 | 4.50 µM |
| I100-05 | 3.25 µM |
| I100-08 | 3.25 µM |
| 1100-06 | 0.70 µM |
| I100-07 | 0.25 µM |
| A100-00 | 3.25 µM |

FMLV CULTURE ASSAY

Friend Murine Leukemia Virus (FMLV) was grown in a chronically infected murine fibroblast cell line (pLRB215) or was propagated in an acute assay system by infection of NIH3T3 cells. When the chronically infected cell line was used, pLRB215 cells were split (1×10hu 5) into 24 well culture dishes and incubated 16 to 20 hours at 37° C. The media was then removed and replaced with media containing various concentrations of oligonucleotide. After 1, 3 or 5 days, culture media was assayed for the presence of the viral reverse transcriptase enzyme.

In acute assays, NIH3T3 cells were split ($1 \times 10^4$) into 96 well dishes and allowed to incubate for 16–20 hours. After incubation, culture media was removed and concentrated virus stock (10 ul) was added to each well in 100 ul of completed media containing 2 ug/ml polybrene. The virus infection was allowed to proceed for 18 hours at which time the virus containing media was removed and complete media containing various concentrations of oligonucleotide was added. After 4 to 7 days, the culture media was assayed for the presence of viral reverse transcriptase.

HCMV CULTURE ASSAY

Human cytomegalovirus was cultured in the human diploid lung fibroblast cell line MRC-5. These cells were split and placed into 24 well culture dishes and preincubated for 24 hours with various concentrations of oligonucleotide (0.5 to 20 uM) in complete media. The oligonucleotide was then washed off and virus was added to the cells (approximately 0.1 m.o.i.) for 2 hours at 37° C. The virus was then removed and complete media containing the same concentration of oligonucleotide was added. Cells were then placed at 37° C. for 10–12 days at which time virus in the culture media was titered using a standard agar overlay procedure.

BACTERIAL T3 AND T7 ASSAYS

In this assay system, a 2 kb fragment (HindIII to EcoR1) of the FMLV virus (clone 57) was molecularly cloned between the HindIII/EcoR1 sites 10 bp downstream of the bacterial T7 promoter (p275A) or 50 bp downstream of the bacterial T3 promoter (pBSFMLV2). A shematic representation of these two recombinant plasmids can be seen in FIG. 1. Isolated recombinant DNA was then digested with DdeI. Oligonucleotides were then incubated with the digested DNA and the mixture was subjected to in-vitro transcription using either the T7 or T3 bacterial enzymes.

REVERSE TRANSCRIPTASE ASSAY

In this assay, reverse transcriptase (either MMLV or FMLV from pLRB215 culture media) was incubated with various concentrations of oligonucleotide and then assayed using the enzyme linked oligonucleotide sorbent assay ELOSA), the ELOSA kit which is commercially available from New England Nuclear.

EUKARYOTIC IN VITRO TRANSCRIPTION

In this assay, a recombinant plasmid containing the HSV-1 IE175 promoter fused to the bacterial chloramphenicol acetyltransferase gene (CAT) was linearized and used as a template for run off transcription studies. Commercially available HeLa cell nuclear extracts or prepared nuclear extracts of HSV-2 infected VERO cell were used.

INHIBITION OF HSV-2 ACTIVITY

Figure 1A:
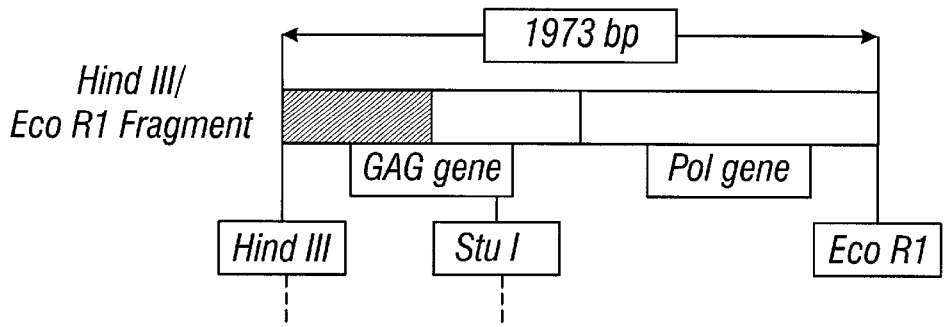
FIG. 1A shows a 1973 base pair Hind III to Eco R1 sub fragment of the Friend Murine Leukemia Virus (FMLV) clone 57 genome.
Figure 1B:
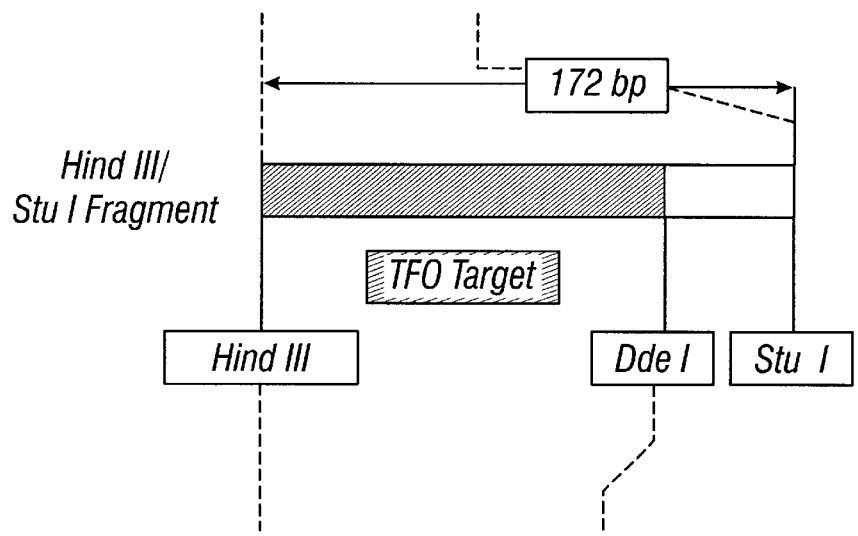
FIG. 1B shows a 172 base pair (HindIII to StuI) fragment which is an expanded portion of the 1973 base pair fragment. Within this fragment is the purine rich target to which triple helix forming oligonucleotides are directed.
Figure 1C:
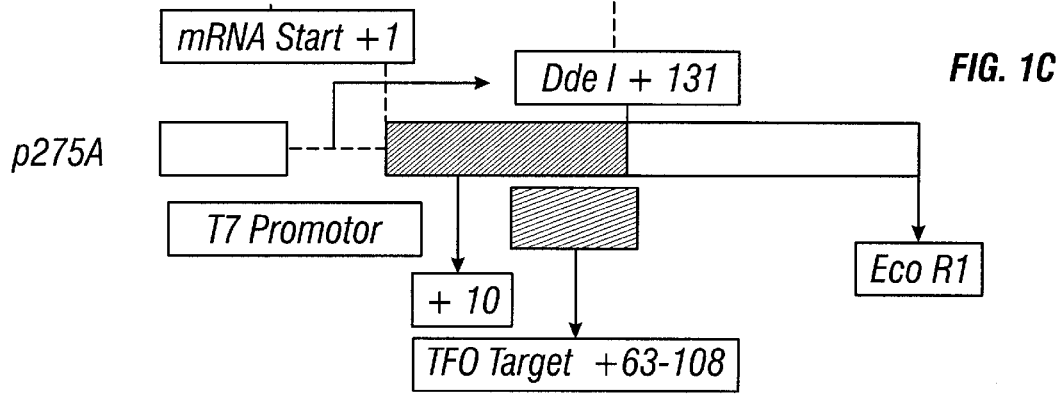
FIG. 1C shows the entire Hind III/Eco R1 FMLV fragment cloned into the pT7-2 plasmid (United States Biochemical Corporation) yielding p275A. In this recombinant the Hind III site is 10 base pairs downstream of the T7 MRNA start site. The 5' portion of the triple helix target region is 63 base pairs downstream of the mRNA start and the Dde I site is 131 base pairs downstream of the mRNA start site.
Figure 1D:
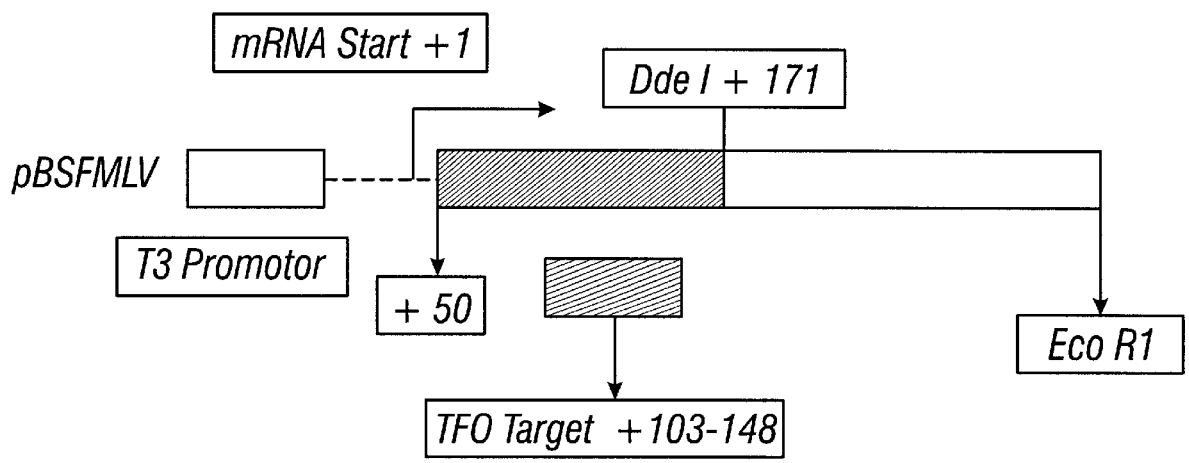
FIG. 1D shows the Hind III/Eco R1 FMLV fragment was cloned into pBS (Stratagene) yielding pBSFMLV. The Hind III site, triple helix target site and Dde I site are respectively 50, 103 and 171 base pairs downstream from the mRNA start site.
Figure 2:
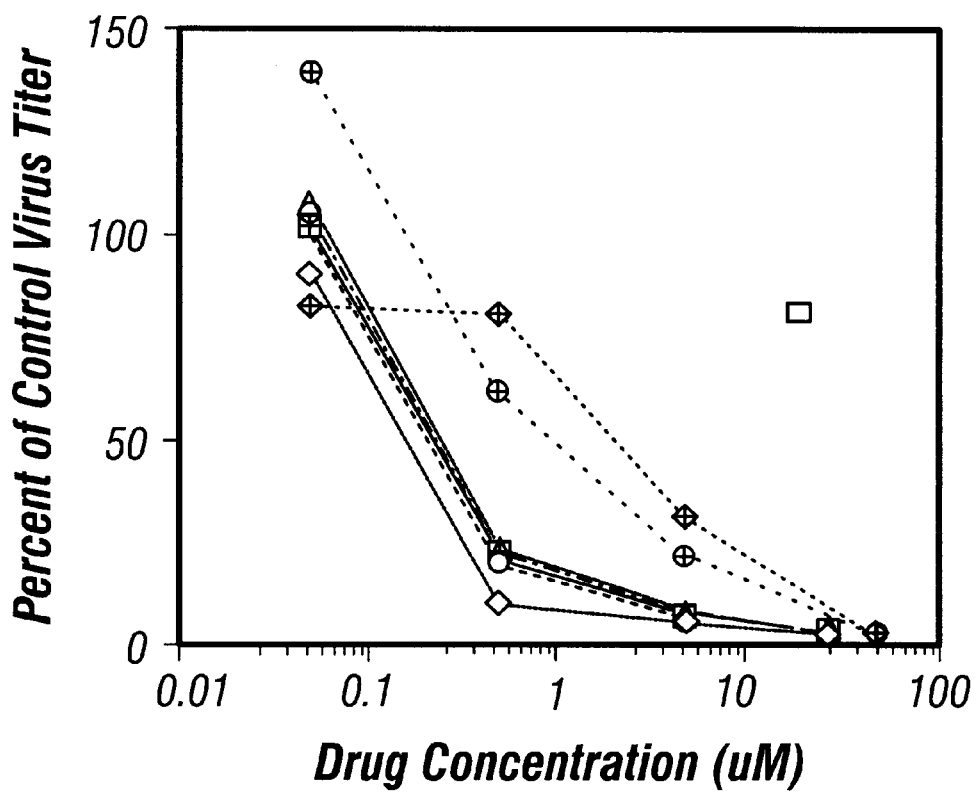
FIG. 2 shows that G-Rich phosphorothioated-oligonucleotides induced reduction in HSV-2 viral titer. VERO cells infected with HSV-2 were treated with various concentrations of the indicated drug. The results are plotted as percent virus yield relative to VERO cells infected with virus but not treated with drug (titer=1). The filled square (B106-62) (SEQ. ID. NO. 5) represents a single concentration point (20 $\mu$M) for this oligonucleotide. B106-96 is the fully phosphorothioated version of B106-62 (SEQ. ID. NO. 5). B106-97 is the fully phosphorothioated version of B106-71 (SEQ. ID. NO. 6). ACV (4a and 4b) is acyclovir tested against two different stock concentrations of HSV-2 strain HG52. In two experiments, after virus infection and before reapplication of oligonucleotide (BIO-96 or BIO-97), the cells were rinsed with a pH 3 buffer in order to remove all virus not yet internalized (96p3 and 97p3).
Figure 2:
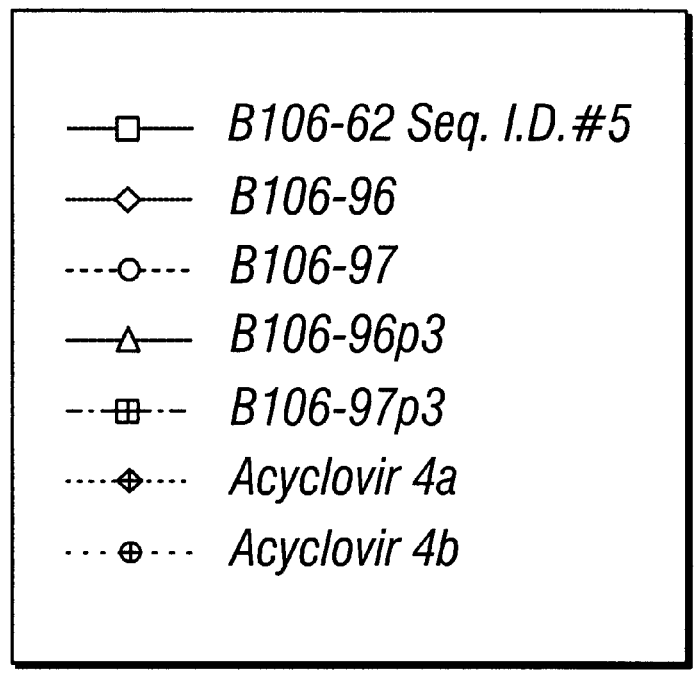

The oligonucleotide B106-62 was originally designed to form a triple helix structure with a portion of the promoter region of the major immediate early protein of HSV-2 (IE175). The phosphorothioate derivative of two oligonucleotides were synthesized and tested for anti-viral activity against HSV-2. FIG. 2 shows that the B106-62 oligonucleotide at 20 μM was able to reduce viral titers by approximately 20% whereas the phosphorothioate version (B106-96) reduced virus by 50% in the submicromolar concentration range. The control oligonucleotide (106-97), the phosphorothioate backbone derivative of B106-71, was also able to inhibit virus at the same levels as B106-96. Even when an extensive washing procedure at a pH of 3.0 was employed to remove excess virus not internalized during the infection, incubation with both B106-96 and B106-97 was able to significantly reduce virus yield. Thus, the inventors concluded that the mechanism of anti-viral activity was not merely a blocking of the adsorption of HSV-2 virions to cells.

Figure 4:
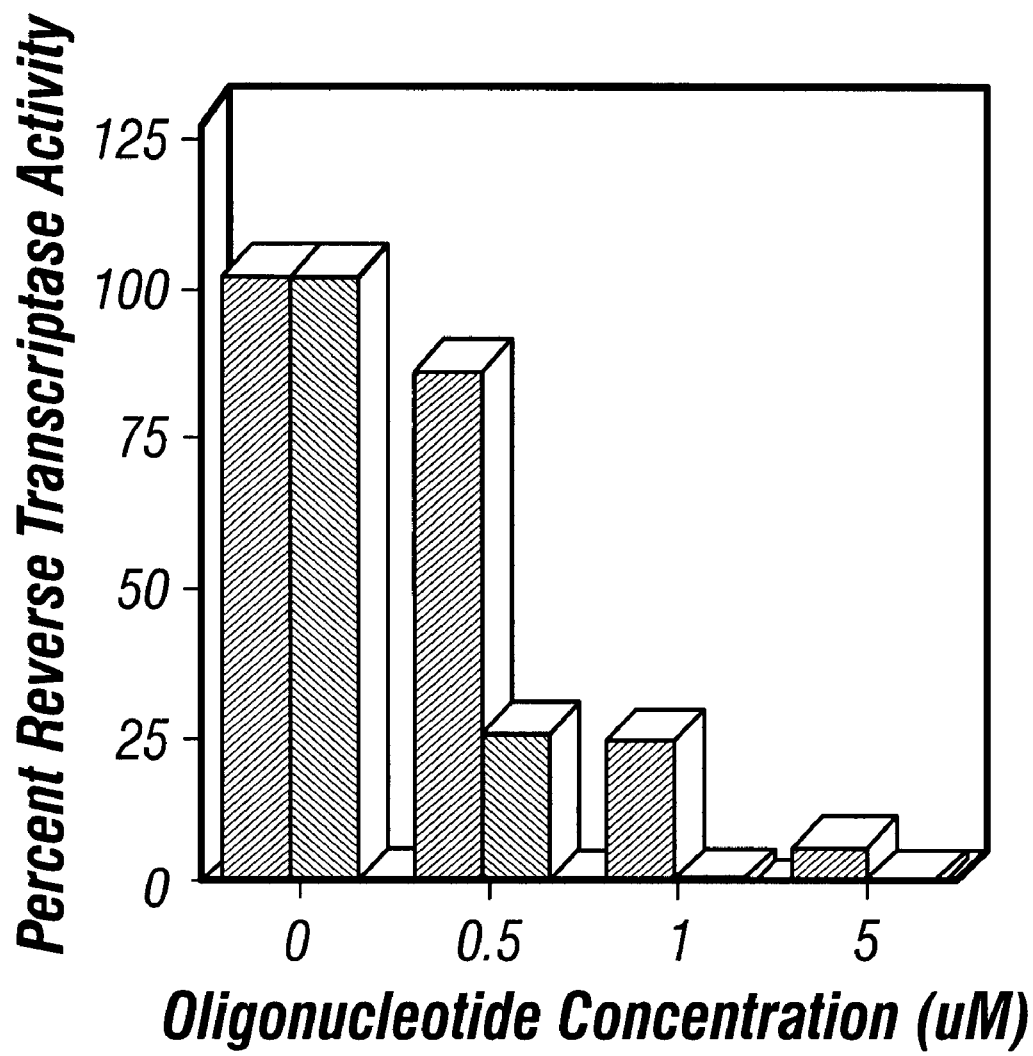
FIG. 4 shows the culture media taken from NIH3T3 cells chronically infected with FMLV was mixed with various concentrations of I100-51 (SEQ. ID. NO. 29) or I100-12 (SEQ. ID. NO. 27) (fully phosphorothioate version of I100-00 (SEQ. ID. NO. 20)). The mixtures were then assayed for the presence of viral reverse transcriptase. The data is presented as a percent of measurable reverse transcriptase in culture medium not treated with oligonucleotide.

FIG. 2 also shows the results of acyclovir in the same molar range as the oligonucleotides. Acyclovir was tested against two different stocks of HSV-2 strain HG52, as illustrated in FIG. 4.

OLIGONUCLEOTIDE SYNTHESIS

All oligonucleotides used in these examples were synthesized on a DNA synthesizer (Applied Biosystems, Inc., model 380B or 394), using standard phosphoramidite methods. All oligonucleotides were synthesize with an amino modified 3'-terminal, which resulted in the covalent attachment of a propanolamine group to the 3'-hydroxyl group or resulted in a cholesterol moiety attached to the 3'-terminal via a triglycyl-linker. Oligonucleotides used in this example were capped at their 3'-terminal with either a propanolamine or a cholesterol moiety to reduce degradation by cellular exonucleases. Phosphorothioate containing oligonucleotides were prepared using the sulfurizing agent TETD or beaucauge reagent. The 3'-cholesterol modified oligonucleotides were prepared and purified as described by Vu et al. (in *Second International Symposium on Nucleic Acids Chemistry,* Sapporo, Japan, 1993).

STABILITY AND TOXICITY

Guanosine-rich oligonucleotides with either full length phosphodiester (PD) or full length phosphorothioate (PT) backbones were stable in the culture media for 4 days, while oligonucleotides consisting of a more random composition of nucleotides were rapidly degraded. This indicates that the 3'-modified G-rich oligonucleotides with PD backbones were stable against both endonuclease and exonuclease digestion over a defined four day incubation in culture. The concentration of oligonucleotide needed to reduce cell proliferation by 50% ($TC_{50}$) of selected compounds, based on the dye metabolism assay was approximately 40 to 50 μM for oligonucleotides with PD backbones and 15 to 40 μM for those compounds containing a PT backbone. The $TC_{50}$ for selected oligonucleotides are presented in Table A-3. Stability and toxicity tests were replaced as described below

TABLE A-3

Guanosine/Thymidine and Control Oligonucleotide Sequences

| Oligo[a] | Length | 3'-Modification[b] | Sequence | $TC_{50}$ [c] |
|---|---|---|---|---|
| I100-07 | 45 mer | amine | 5'-gtggtgggtgggtgggtggtgggtggtggttgtgggtgggtggtg-3' | >50 μM |
| I100-06 | 45 mer | cholesterol | 5'-gtggtgggtgggtgggtggtgggtggtggttgtgggtgggtggtg-3' | |
| I100-00 | 26 mer | amine | 5'-          gttgggggttgttggtggggtggtgg-3' | 37 μM |
| I100-08 | 26 mer | cholesterol | 5'-          gttgggggttgttggtggggtggtgg-3' | |
| I100-12 | 26 mer | amine(PT) | 5'-          gttgggggttgttggtggggtggtgg-3' | 18 μM |
| I100-01 | 45 mer | amine | 5'-tggtgggtgtgtgggggggtgttgggggttgttggtggggtggtgg-3' | |
| I100-05 | 45 mer | cholesterol | 5'-ggtgggtgtgtgggggggtgttgggggttgttggtggggtggtgg-3' | |
| A100-00 | 38 mer | amine | 5'-tgggtggggtggggtgggggggtgtggggtgtggggtg          -3' | |
| 1173 | 18 mer | amine | 5'-gggtgggtgggtgggtgg                              -3' | |

TABLE A-3-continued

Guanosine/Thymidine and Control Oligonucleotide Sequences

| Oligo[a] | Length | 3'-Modification[b] | Sequence | $TC_{50}$ [c] |
|---|---|---|---|---|
| I100-11 | 45 mer | amine | 5'-gatccatgtcagtgacactgcgtagatccgatgatccagtcgatg-3' | 46.5 μM |
| 1231 | 18 mer | amine | 5'-gatccatgtcagtgacac    -3' | |
| 1229 | 18 mer | amine | 5'-cccccccccccccccccc    -3' | |

[a]All oligonucleotides listed were synthesized with phosphodiester backbones except I100-12 which had phosphorothioate (PT) linkages.
[b]The capping group at the 3'-end of the oligonucleotides was either a propanolamine or cholestrol moiety.
[c]Median inhibitory (toxic) concentration in tissue culture.

A. Cytotoxicity and Stability Assays.

The cytotoxicity of selected oligonucleotides was assayed using the CellTiter 96™ Aqueous Non-Radioactivity Cell Proliferation Assay (Promega). This is a colormetric method for determining the number of viable cells in proliferation or chemosensitive assays using a solution if MTS. Dehydrogenase enzymes found in metabolically active cells convert MTS into a formazan product. The SUP T1 cells used in the cytotoxicity assays were in log phase growth at the time of the assay. Cytotoxicity profiles for GTOs with PD backbones such as I100-15 (SEQ. ID. NO. 33) had $TC_{50}$s (50% cytotoxic concentration) in the range of 30 to 50 μM while GTOs with PT backbones such as I100-15 had $TC_5$s in the 10 to 30 μM range. The $TC_{50}$ for AZT in this assay format was approximately 10 μM.

Blockage of the hydroxyl terminus of oligonucleotides has been shown by many investigators to greatly reduce degradation by cellular exonucleases. Therefore, all oligonucleotides used in these studies were modified at their 3'-end with either a propanolamine group or a cholesterol group. For stability studies, 10 μM of GTOs were incubated in MEM (GIBCO) supplemented with 10% FBS. Aliquots were taken after 10 min, 1 day, 2 days, 3 days and 4 days. The aliquots at each time point were immediately extracted twice with 50:50 phenol-chloroform solution and then precipitated by the addition of ethanol. The recovered oligonucleotides were 5'-end-labeled using [γ-$^{32}$P]ATP and polynucleotide kinase. The integrity of the oligonucleotides was then analyzed on a 20% polyacrylamide gel with 7 M urea. The results indicated that a portion of each GTO with a PD backbone was present in the culture medium for three to four days while oligonucleotides composed of a more random assortment of all four nucleotides were rapidly degraded. In addition, positions within PD GTOs where there existed two or more contiguous pyrimidines were more susceptible to endonuclease digestion than regions containing purines or alternating purines and pyrimidines.

INHIBITION OF HIV-1 PRODUCTION IN CULTURE ASSAYS

B. Long Term Suppression of Acute HIV-1 Infections in SUP T1 cells

The anti-HIV-1 activity of a series of guanosine/thymidine oligonucleotides (GTOs), with PD backbones, containing different sequences motifs was tested. As seen in Table A-2, one of the sequence motifs tested (oligonucleotide I100-07) was 10 fold more active at inhibiting HIV-1 induced syncytium formation than the other motifs tested (e.g. I100-00 shown in Table A-1). I100-07 and its derivatives (length and chemical modifications) were further tested for their ability to inhibit virus in a dose-dependent fashion by measurement of syncytium formation and viral p24 production.

Briefly, HIV-1$_{DV}$ was used to infect the SUP T1 lymphoblastoid cell line at an m.o.i. of 0.1 $TCID_{50}$ for one hour at 37° C. prior to washing and resuspension in increasing concentrations of GTOs. The cells (2×10$^4$ cells/well) were inoculated in triplicate in 200 ul of RPMI 1640 containing 10% fetal calf serum. Four days later, the number of syncytia per well or the level of p24 in the medium was determined. The results of these assays are presented in Table A-4. which results indicated that GTOs with simple PD linkages were capable of inhibiting HIV-1 syncytia formation and p24 production in culture.

TABLE A4.

Guanosine/Thymidine Oligonucleotide Sequences

| Oligo | Length | linkage[a] | Sequence | | $IC50$[b] (μM) Syn | p24 | T.I.[c] |
|---|---|---|---|---|---|---|---|
| I100 | | | | | | | |
| -07 | 45 mer | PD | 5'- | gtggtgggtgggtgggtggtgggtggtggttgtgggtgggtggtg | 0.25 | 0.55 | |
| -21 | 45 mer | PT | 5'- | gtggtgggtgggtgggtggtgggtggtggttgtgggtgggtggtg | 0.225 | <0.20 | >100 |
| -20 | 38 mer | PD | 5'- | gtgggtgggtggtgggtggtggttgtgggtgggtggtg | 1.00 | 1.00 | |
| -19 | 29 mer | PD | 5'- | tggtgggtggtggttgtgggtgggtggtg | 3.75 | 2.00 | |
| -18 | 16 mer | PD | 5'- | tgtgggtgggtggtg | 3.75 | 3.00 | |

TABLE A4.-continued

Guanosine/Thymidine Oligonucleotide Sequences

| Oligo | Length | linkage[a] | Sequence | | IC50[b] (μM) Syn | p24 | T.I.[c] |
|---|---|---|---|---|---|---|---|
| -17 | 37 mer | PD | 5'- | gtggtgggtgggtgggtggtgggtggtggttgtgggt | 0.30 | 0.20 | |
| -16 | 27 mer | PD | 5'- | gtggtgggtgggtgggtggtgggtggt | 0.25 | 0.15 | >200 |
| -15 | 17 mer | PD | 5'- | gtggtgggtgggtgggt | 0.125 | 0.08 | >200 |
| -00 | 26 mer | PD | 5'- | gttgggggttgttggtggggtggtgg | 3.25 | ND | |
| -12 | 26 mer | PT | 5'- | gttgggggttgttggtggggtggtgg | 0.225 | >0.20 | |
| AZT | | | | | 0.04 | 0.40 | >200 |

[a]The internucleotide backbone linkages are denoted as PD for phosphodiester and PT for phosphorothioate.
[b]The IC50 valur for the syncytium p24 inhibition assays in uM concentration.
[c]T.I. = therapeutic index.

In order to determine the effect of backbone modification on GTO anti-viral activity, the PD backbone in two oligonucleotides sequences motifs was replaced with a PT backbone. The phosphorothioate containing oligonucleotides (I100-12 (SEQ. ID. NO. 27)) and I100-21 (SEQ. ID. NO. 24)) were then tested for their ability to inhibit HIV-1 induced syncytium formation and production of HIV-1 p24 in the SUP T1 acute assay system (Table A-4). The results from these assays indicated that the presence of phosphorothioate for phosphodiester substitutions in the oligonucleotide backbone molecules in the oligonucleotide backbone greatly enhanced the anti-viral activity of I100-00 (SEQ. ID. NO. 20) (I100-12 (SEQ. ID. NO. 27) but had little if any effect on I100-07 (SEQ. ID. NO. 24) (I100-21 (SEQ. ID. NO. 39) (Table A-4).

It was apparent from the studies that the anti-viral activity of I100-07 (SEQ. ID. NO. 24) was maintained when steps were taken to reduce the length of the molecule to 17 by deleting segments from the 3'-end (I100-15, -16, -17) (SEQ. ID. NOS. 33, 34, 35) but not by deletions from the 5'-end (I100-18, -19, -20) (SEQ. ID. NOS. 36, 37, 38). To further determine to optimal size of the PD oligonucleotide needed for maximal anti-HIV-1 activity, the I100-15 (SEQ. ID. NO. 33) size variants listed in Table A-5 were synthesized and assayed for antiviral activity.

TABLE A-5

Inhibition of HIV-1 Induced Syncytia Using Size variants of 1100-15.

| oligo | Sequence | | | IC50 Syn.(uM) |
|---|---|---|---|---|
| I100-15* | 5' | gtggtgggtgggtgggt | -3' | 0.16 |
| I100-25 | 5' | gtggtgggtgggtgggg | -3' | 0.25 |
| I100-26* | 5' | gtggtgggtgggtggg | -3' | 0. 12 |
| I100-35 | 5' | tggtgggtgggtgggt | -3' | 1.75 |
| I100-27 | 5' | gtggtgggtgggt | -3' | 4.50 |
| I100-28 | 5' | gtggtgggt | -3' | 4.50 |

TABLE A-5-continued

Inhibition of HIV-1 Induced Syncytia Using Size variants of 1100-15.

| oligo | Sequence | | | IC50 Syn.(uM) |
|---|---|---|---|---|
| I100-30 | 5' | gtgggtgggtgggt | -3' | 4.50 |
| I100-29 | 5' | gtgggtgggt | -3' | >10.00 |
| AZT | | | | 0.02 |

*At 5 uM these compounds suppressed virus at least 7 days post-removal of drug. All other compounds at 5 uM were the same AZT 7 days after removal of drug.

The duration of the viral suppression was assayed by changing the medium in HIV-1 infected cultures containing 2.5 uM of various oligonucleotides to complete media without added oligonucleotide on day 4 post-viral infection. The production of viral p24 antigen was then assayed on day 7 and day 11 post-infection. The results of this experiment indicated that the shorter variants of I100-07 (SEQ. ID. NO. 24) (I100-15 (SEQ. ID. NO. 33) and I100-16 (SEQ. ID. NO. 34)) as well as the PT version of this molecule (I100-21) (SEQ. ID. NO. 39), were capable of totally suppressing HIV-1 p24 production for at least 7 days after removal of the drug from the culture medium (table A-6). This substantial level of prolonged inhibition was >99% for I100-15 (SEQ. ID. NO. 33), I100-16 (SEQ. ID. NO. 34) and I100-21 (SEQ. ID. NO. 39) when compared to the p24 antigen levels obtained for untreated HIV-1 infected cells (Table A-6). The quantitation of p24 production relative to untreated HIV-1 infected SUP T1 cells for all oligonucleotides tested is presented in Table A-6. The presence of sulfur molecules in the backbone of oligonucleotide I100-7 (SEQ. ID. NO. 24) (I100-21 (SEQ. ID. NO. 39)) had a more marked effect on the reduction of virus seven days after removal of compound from the culture medium than was observed at the four day post-infection assay point (Table A-5).

TABLE A-6

Detection of HIV-1 p24 Antigen in the
Culture Media of GTO-Treated SUP T1 Cells.

| Oligonucleotide (2.5 uM) | Percent p24[a] | | |
|---|---|---|---|
| | Day 4[b] | Day 7 | Day 11 |
| Control SUP T1 cells | 100.0% | 100.0% | 100.0% |
| I100-07 | 6.0% | 15.9% | 8.6% |
| I100-21 (PT)[d] | 0.0% | 0.0% | 0.0% |
| I100-15 | 0.0% | 0.0% | 0.0% |
| I100-16 | 0.0% | 0.0% | 0.0% |
| I100-18 | 144.5% | 9.7% | 5.3% |
| I100-19 | 208.0% | 21.8% | 15.0% |
| 1100-12 (PT) | 0.0% | 0.0% | 0.0% |

[a]Level of detectable p24 in culture medium relative to control (infected but untreated SUP T1 cells after subtraction of background values.
[b]Day 4 post-infection culture medium was replaced with fresh medium without oligonucleotide.
[c]SUP T1 cells infected with HIV-1 but not treated with oligonucleotides or AZT were used as positive control cells in this experiment.
[d]1100-21 and 1100-12 contain phosphorothioate backbone linkages (PT).

In control experiments, the culture medium from HIV-1 infected SUP T1 cells treated with AZT (4 μM) was also replaced on day 4 post-infection with drug free media. In these experiments, two days after removal of AZT from the culture medium the presence of syncytium was observed in the HIV-1 infected cell cultures and by day 4 all cells were visibly infected with HIV-1.

To determine whether the prolonged suppression of HIV-1 was due to toxicity of the oligonucleotides, SUP T1 cells were counted for all treated samples 7 days after removal of the oligonucleotides from the infected cell cultures. The results indicated that for cells treated with 2.5 μM of drug there was no difference in the number of cells when compared with control cultures (uninfected, untreated) of SUP T1 cells.

C. Inhibition of HIV expression in patient derived peripheral blood mononuclear cells (PBMCs)

Figure 9A:
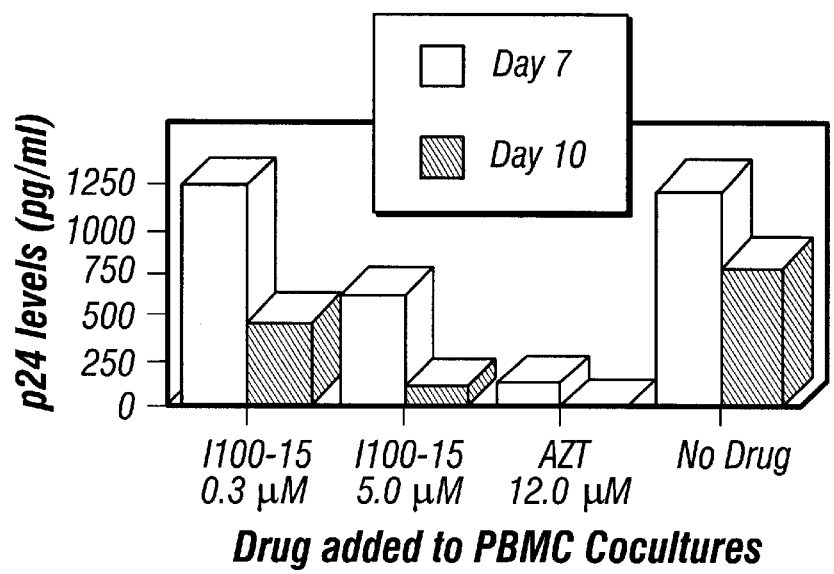
FIG. 9A reveals PBMCs derived from HIV-1 positive patients were mixed with HIV-1 negative PBMCs in culture medium containing drug I100-15 (SEQ. ID. NO. 33). On day 7 the cocultures were washed and resuspended in fresh medium containing drug. The p24 levels in medium collected on day 7 (before medium change) and day 10 were assayed for p24.
Figure 9B:
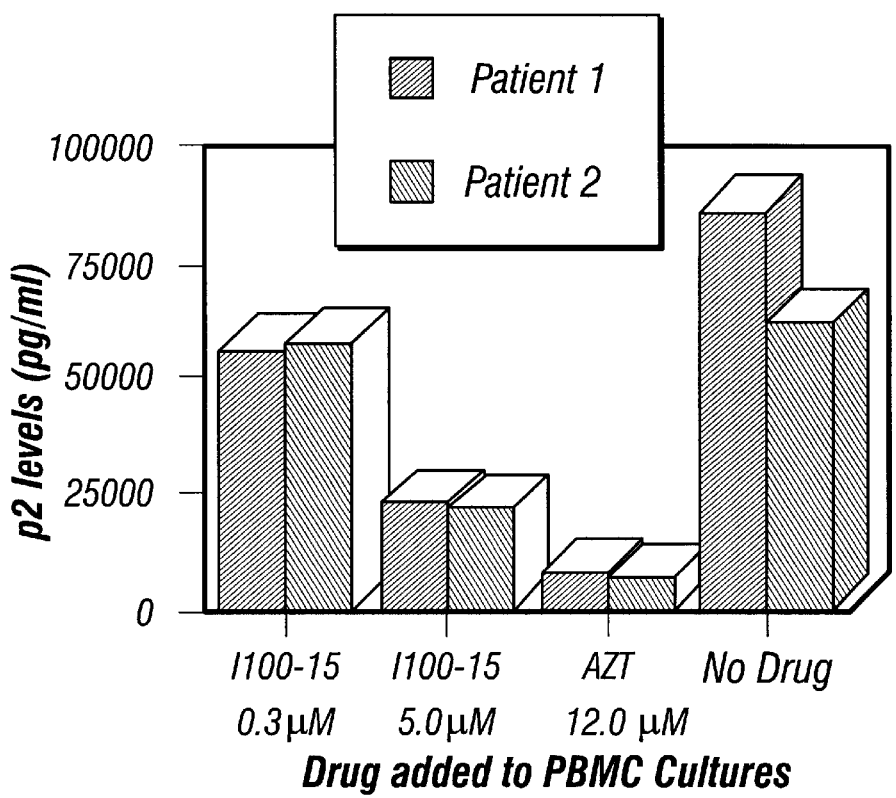
FIG. 9B HIV-1 negative PBMCs from two different donors were infected with HIV-1$_{DV}$ and then incubated in the presence of drug for 10 days at which time the culture medium was assayed for the presence of p24 antigen.

I100-15 was assessed for activity in PBMC cultures derived from AIDS patients. Briefly, PHA activated uninfected PBMC's were added to 4PBMC's derived from patients with HIV infection in the presence of varying concentrations of oligonucleotide. Anti-HIV activity was assessed by analyzing supernatants, collected every three days from these mixed cultures, for the presence of HIV p24. The PHA activated PBMC's were grown in the presence of 10 units/ml of IL-1 and medium was exchanged every three days for a period of three weeks. HIV p24 antigen production was assayed in drug-treated as compared to untreated control specimens. It should be noted that the results in these experiments (FIGS. 9A–B) observed for AZT were obtained when AZT was used at 12 uM which is roughly 300 fold greater than the $IC_{50}$ for this compound.

D. In-Vitro inhibition of HIV-1 reverse transcriptase (RT)

The ability of oligonucleotides to inhibit HIV-1 RT in vitro has been well documented. Marshall et al. *PNAS* 1992 89:6265–6269 have described a competitive interaction at the active site as the mechanism by which mono- or diphosphorothioate containing oligonucleotides inhibit HIV-1 RT independent of whether the molecule tested was antisense, a random sequence or poly SdC.

In order to determine whether I100-15 or its parent molecule, I100-07 (or the PT version I100-21), was interacting with HIV-1 RT, the activity of this enzyme was assayed in the presence of various concentrations of oligonucleotides. A kinetic analysis of the resultant enzyme inhibition was conducted to determine the mechanism of inhibition. The GTOs appeared to be inhibiting the RNA dependent DNA polymerase activity of the RT enzyme by competitive inhibition at the active site of the enzyme.

The $K_i$ value for all of the oligonucleotides tested is presented in Table A-7. The data indicate that for all oligonucleotides tested the presence of the sulfur group in the backbone greatly enhanced the interaction between the oligonucleotides and the enzymes. The median inhibitory dose ($ID_{50}$) for these oligonucleotides were also calculated (Table A-7). The $ID_{50}$ results are based on the ability of these compounds to inhibit 10 nM of HIV RT.

Short oligonucleotides (18 mers) with PD or PT backbones were assayed to determine whether the nature of the nucleotide sequence contributed to inhibition of HIV-1 RT in this assay system. Comparison of the effects of the PD versions of a GTO (1173 or I100-15), poly dC (1229) or a random nucleotide sequence (1231) suggested that at this length none of the sequence motifs inhibited RT (Table A-7). Other 18 mer PD GTO sequence motifs tested yielded similar results. Enzyme inhibition monitored by both $K_1$ and $ID_{50}$ was observed for the PT versions of these same 18 mer oligonucleotides (Table A-7). The degree of enhancement of observed enzyme inhibition for all oligonucleotides tested when the sulfur group was present in the backbone, was between one to three orders of magnitude (Table A-7).

TABLE A-7

In Vitro Inhibition of HIV-1 RT by PD and PT Oligonucleotides.

| Oligonucleotides | Length | Linkage[b] | Ki (μM) | ID50 (μM) |
|---|---|---|---|---|
| I 100-00 | 26 | PD | 0.37 | 5.0 |
| I 100-12 | 26 | PT | 0.005 | 0.015 |
| I 100-07 | 45 | PD | 0.137 | 2.5 |
| I 100-21 | 45 | PT | 0.001 | 0.004 |
| I 100-15 | 17 | PD | >5.0 | >5.0 |
| 1173 | 18 | PD | >5.0 | >5.0 |
| 1174 | 18 | PT | 0.015 | 0.0154 |
| 1229 (poly dC) | 18 | PD | >5.0 | >5.0 |
| 1230 (poly dC) | 18 | PT | 0.044 | 0.033 |
| 1231 (GATC) | 18 | PD | >5.0 | >5.0 |
| 1232 (GATC) | 18 | PT | 0.56 | 0.045 |

[a]Each pair of oligonucleotides contain the same sequence and differ only in the nature of their backbone linkage. Oligonucleotides 1229 and 1230 were poly dC while the 1231 and 1232 oligonucleotides were a random sequence of all four bases (GATC).
[b]The backbone modifications are denoted as PD for phosphodiester and PT for phosphorothioate.

The results from this set of experiments demonstrated that I100-15 is minimally inhibitory to the RNA dependent DNA polymerase activity of HIV-1 RT. The data also indicated that chemically modifying GTOs, poly dC or a random sequence oligonucleotide greatly enhanced the in vitro inhibitory activity of the molecule. Therefore, chemically modified oligonucleotides such as the antiviral G-rich molecule describe by Wyatt et al. [112] has, by nature, a different set of characteristics from oligonucleotides with natural PD backbones.

E. Inhibition of the interaction of HIV-1 gp120 with cellular CD4

The outer envelope glycoprotein gp120 of HIV-1 mediates viral attachment to the cell surface glycoprotein CD4 in the initial phase of HIV-1 infection. The effects of both PD and PT modified oligonucleotides on this interaction were examined using a gp120 capture ELISA kit.

The concentration of the gp120 used in these studies (125 ng/ml) was determined to be within the linear range of the detection assay. The ability of oligonucleotides to inhibit gp120/CD4 interactions by binding to gp120 was determined by preincubation of the test compounds with soluble gp120 before addition to the immobilized CD4. The results of this experiment (Table A-8) are presented as the concentration of oligonucleotide needed to reduce by 50% CD4 bound gp120 ($ID_{50}$ [gp120]). The reciprocal experiment was then performed to measure the ability of the oligonucleotides to inhibit these interactions by binding to immobilized CD4. In this set of experiments I100-00 (SEQ. ID. NO. 20), I100-07 (SEQ. ID. NO. 24) and the PT versions of these two oligonucleotides were capable of preventing the interaction of gp120 with immobilized CD4 ($ID_{50}$ [CD4], Table A-8). For both sequences tested, the PT version of the oligonucleotide had $ID_{50}$ values which were 50 to 100 fold lower than that of the PD version.

A fixed length (18 mer) set of oligonucleotides with either PD or PT backbones were assayed to determine whether the nature of the nucleotide sequence contributed to inhibition of gp120/CD4 interactions. As was observed for the inhibition of HIV-1 RT, the PD versions of these molecules had little or no measurable effects on the binding of gp120 with CD4. However, the PT versions of these oligonucleotides did yield measurable inhibitory activity. The 18 mer GTO (1174) interrupted gp120/CD4 interactions at approximately 10 fold lower concentrations than poly $(SdC)_{18}$ (1230) while the random sequence 18 mer (1232) had no measurable activity (Table A-7).

TABLE A-8

In Vitro Inhibition or HIV-1 gp120 Interaction with CD4 by PD and PT Oligonucleotides.

| Oligonucleotide | Linkage[a] | ID50 [gp 120]($\mu$M) | ID50[CD4]($\mu$M) |
|---|---|---|---|
| I 100-00 | PD | 3.50 | 18 |
| I 100-12 | PT | 0.08 | 0.475 |
| I 100-07 | PD | 0.80 | 4.25 |
| I 100-21 | PT | 0.07 | 0.048 |
| 1173 | PD | >100 | >100 |
| 1174 | PT | 0.09 | 0.45 |
| 1229 (poly dC) | PD | >100 | >100 |
| 1230 (poly dC) | PT | 1.00 | 3.25 |
| 1231 (GATC) | PD | >100 | >50 |
| 1232 (GATC) | PT | >10 | >10 |

[a]Each pair of oligonucleotides contain the same sequence and differ only in the nature of their backbone linkage.
[b]The backbone modifications are denoted as PD for phosphodiester and PT for phosphorothioate.

F. Oligonucleotide interactions with the v3 loop of HIV-1 gp120

It had been reported previously that poly SdC oligonucleotides were able to bind to the third variable loop domain of HIV-1 gp120 (v3 loop). The degree of interaction was reported to be dependent on the length of the oligonucleotide studied, with a rapid decrease in binding affinity observed for compounds shorter than 18 nucleotides.

It was noted that the detection antibody used to monitor inhibition of gp120/CD4 interactions in the capture gp120 ELISA KIT (HRP-$\alpha$-GP120) as described above (Table A-8) recognized an epitope in the gp120 v3 loop (manufacturer's information). For this reason, control experiments were performed to determine whether the observed inhibition of gp120/CD4 interactions was due in part, or in whole, to interference with the HRP-$\alpha$-gp120 detection antibody. The results indicated that I100-07 (SEQ. ID. NO. 24) and I173 (SEQ. ID. NO. 31) (PD backbones) did not inhibit the detection of immobilized gp120. However, the PT oligonucleotides tested (I100-21 (SEQ. ID. NO. 39) and 1174 (SEQ. ID. NO. 32)) were able to slightly inhibit the detection of gp120 at oligonucleotide concentrations above 5 $\mu$M. This level of inhibition was too small to account for the $ID_{50}$ [gp120] values presented for I100-21(SEQ. ID. NO. 39) and 1174 (SEQ. ID. NO. 32) in Table A-8.

Figure 10A:
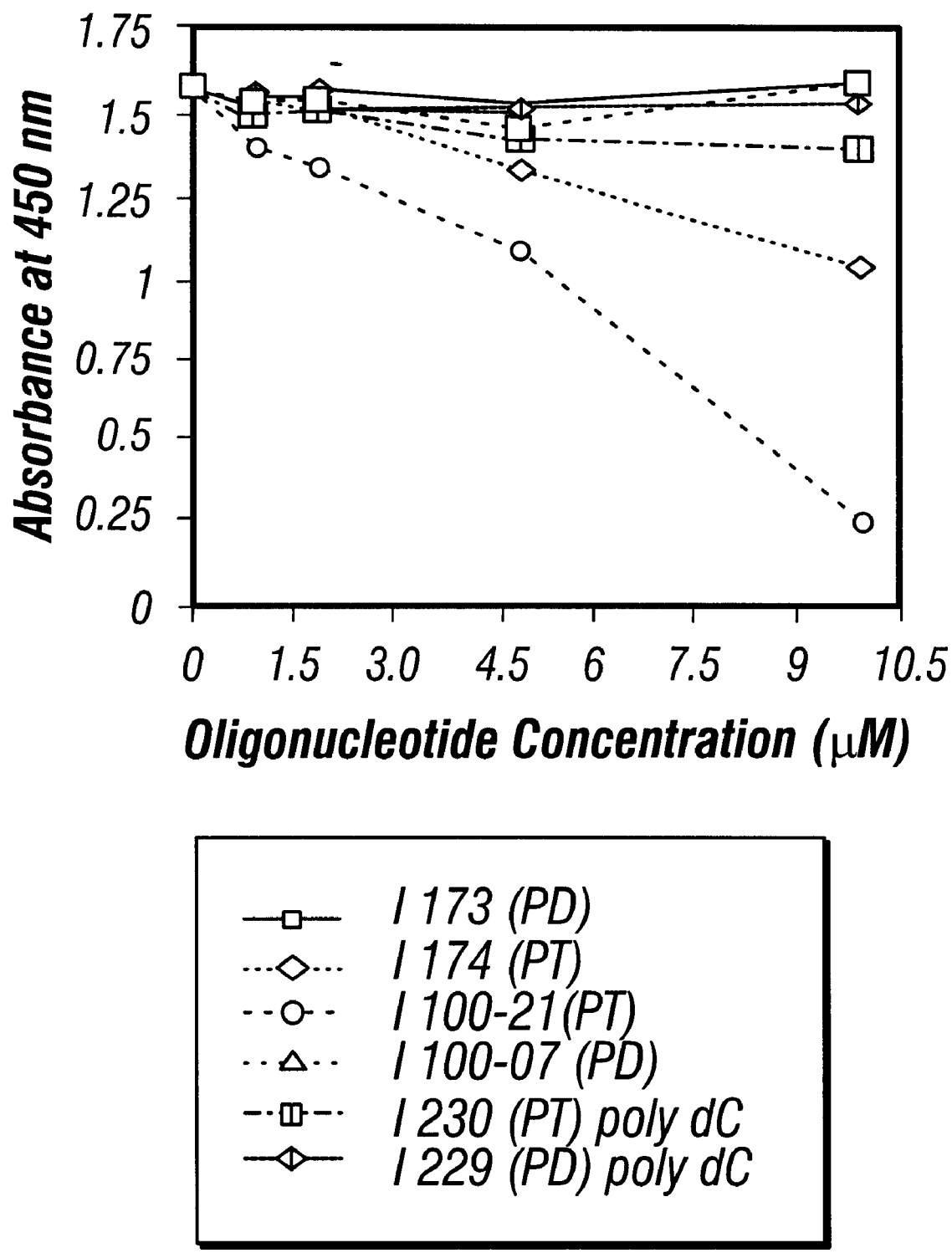
FIGS. 10A and 10B show inhibition of binding of V3 loop specific Mabs to HIV-1 gp120 by phosphorothioate containing oligonucleotides. Matched sequence oligonucleotides with either phosphodiester (PD) or phosphorothioate (PT) backbones were assayed for their ability to inhibit the interaction of V3 loop specific Mabs with the gp120 molecule: SEQ. ID. NOS. 31 (1173) and 32 (1174); SEQ ID. NOS. 24 (I100-07) and 39 (I100-21); or SEQ. ID. NOS. 42 (1229) and 43 (1230). To do this, immobilized gp120 was preincubated with oligonucleotides before washing and the addition of Mab NEA 9284 (FIG. 10A) or Mab NEA 9301 (FIG. 10B).
Figure 10B:
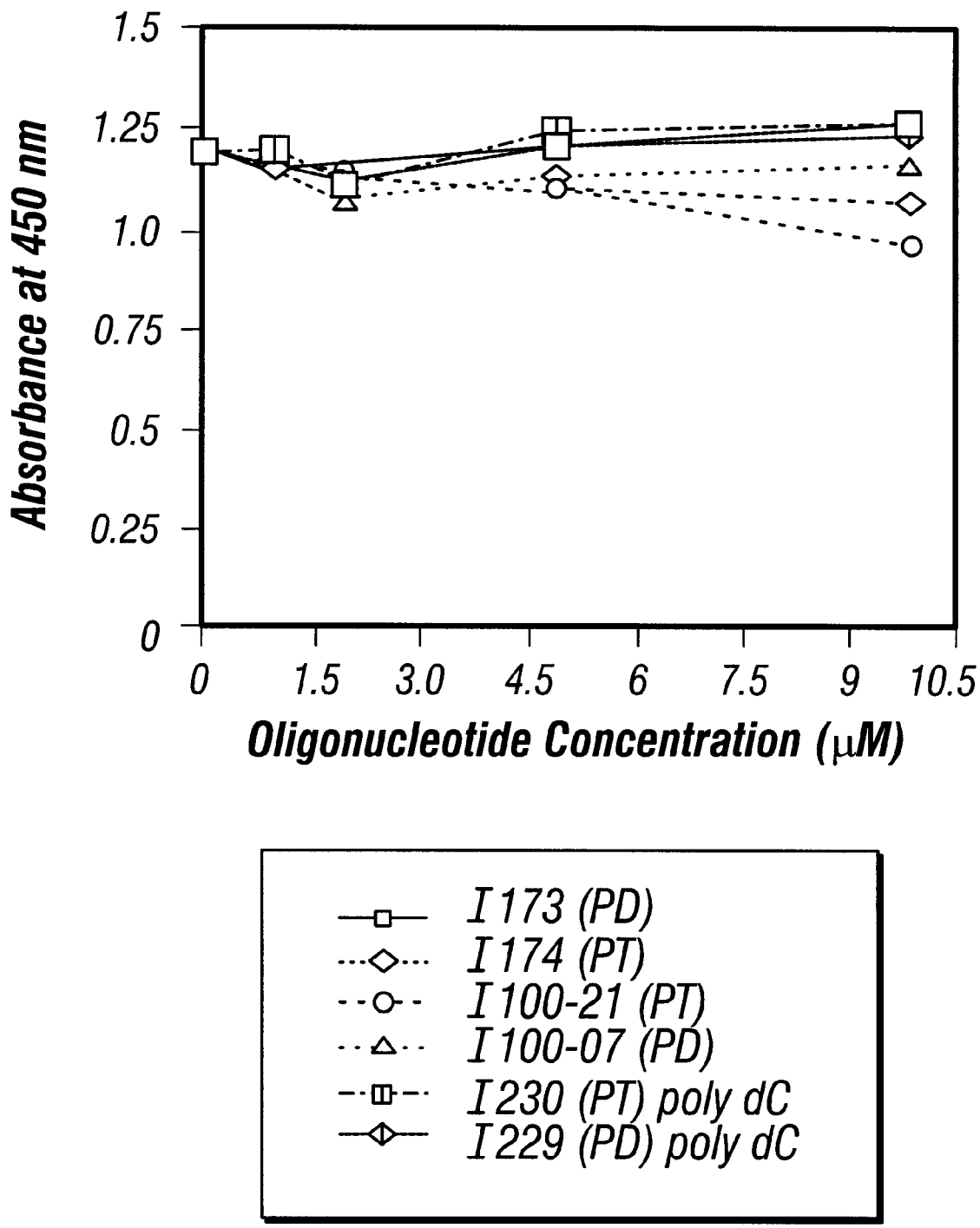

Further analysis of oligonucleotide interactions with the v3 loop was conducted using a v3 loop specific murine Mab, NEA-9284 (FIG. 10). PT oligonucleotides were able to inhibit binding of NEA-9284 to gp120. The presence of bound gp120 specific Mab was determined using a HRP-labeled goat-$\alpha$-mouse antibody. The results of these experiments indicated that PT oligonucleotides were able to inhibit binding of NEA -9284 to gp120. The $ID_{50}$ for the most active oligonucleotide (1100-21) (SEQ. ID. NO. 39) was approximately 4 to 7 $\mu$M. This concentration is approximately 10 to 30 fold higher than the $IC_{50}$ for this oligonucleotide against HIV-1 in culture (Table A-8). The PD oligonucleotides tested did not inhibit the binding of any Mab to gp120. Therefore, it was determined to be unlikely that this was the mechanism by which the PD GTOs such as I100-07 (and hence I100-15) (SEQ. ID. NO. 33) were inhibiting HIV-1.

G. Analysis of HIV-1 RNA and DNA in single cycle assays

Figures 11A, 11B:
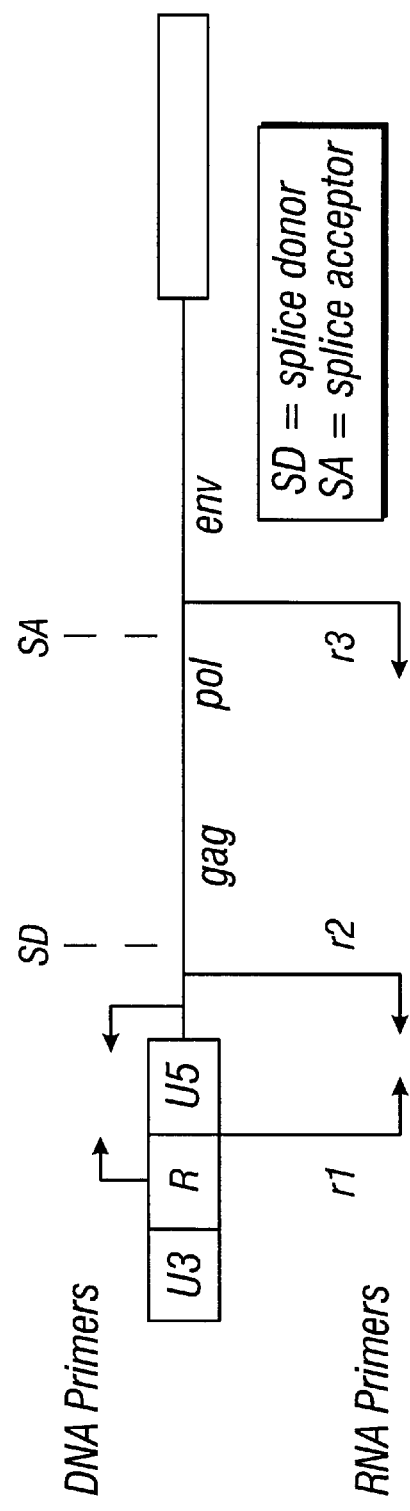
FIG. 11A shows DNA primers.
FIG. 11B shows RNA primers.

Total RNA and DNA were extracted from SUP T1 cells 36 hours after infection with 0.1 m.o.i of HIV-$1_{DV}$. In this assay, the infected cells were treated with I100-15 (SEQ. ID. NO. 33) or AZT at various time points before, during or after infection. Harvesting of the infected cells at 36 hr post-infection allowed for the analysis of approximately one round of viral replication. A schematic diagram of the positions of the PCR primers used in the DNA and RNA analysis is shown in FIG. 11.

Total extracted DNA was analyzed using a PCR primer set which would amplify a 200 bp portion of the viral genome spanning the repeat element (R) into the gag gene. The primer set detected full-length or nearly completely synthesized viral DNA. This is the last region of the minus strand of viral DNA that is synthesized. Thus, for DNA to be detected by this primer set, two template-switching events have occurred and contiguous 5'LTR to gag sequences must be present on either the minus or plus strand of DNA.

Figure 12:
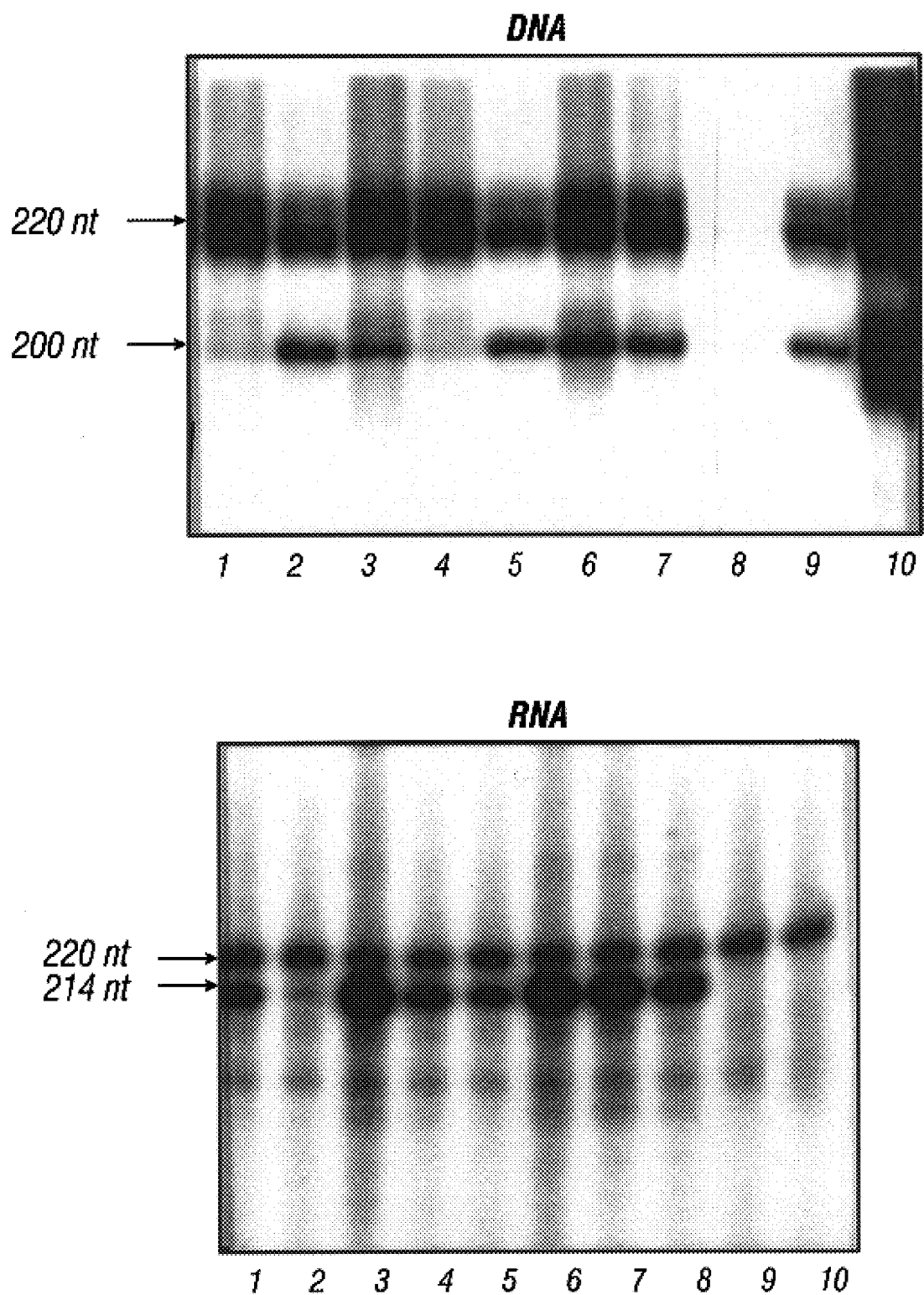
FIG. 12 shows analysis of DNA (PCR) and RNA (RT-PCR) extracted from SUP T1 cells three days post-infection with HIV-1. (Top Panel). PCR analysis of HIV-1 infected drug treated SUP T1 cell DNA used 0.1 µg of total extracted DNA for each reaction. In this experiment either AZT, at 0.3 µM which is 10 fold over the IC$_{50}$ value (lane 1) or I100-15 (SEQ. ID. NO. 33) at 5.0 (lane 2) or 0.3 µM (lane 3) were added to SUP T1 cells at the same time as HIV-1. Lanes 4 (AZT), 5 (5.0 µM I100-15 (SEQ. ID. NO. 33)) and 6 (0.3 µM I100-15) are the results of DNA samples obtained from cells in which drug was added 8 hours post-infection. Lanes 8 to 10 contain 10, 100 or 1000 ng of DNA extracted from HIV-1 infected control SUP T1 cells. The band corresponding to 220 bp is the predicted size of the internal β-actin control and the 200 bp fragment is the predicted size for the amplified portion of the HIV-1 genome. The bottom panel contains RT-PCR analysis of extracted RNA (1 µg/reaction) obtained from cells treated in an identical fashion as those described in lanes 1–6 of the top panel. Lanes 7 and 8 are control HIV-1 infected cell mRNA and lanes 9 and 10 are the results obtained using uninfected untreated SUP T1 cell mRNA.

In the same reaction mixture, a PCR primer set which would amplify a 220 bp region of the human $\beta$-actin gene was used. The results indicated that in cells treated with AZT there was a marked decrease in viral DNA synthesis when the drug was added up to 4 hrs post-infection (data in FIG. 12 shows zero hour and 8 hour time of addition studies). The effects of I100-15 on the early rounds of viral DNA synthesis was minimal.

The results of this experiment indicated that I100-15 did not inhibit virus entry into the cells because of the detectable levels of viral DNA even in samples treated with I100-15 (SEQ. ID. NO. 33) at the same time as virus infection (zero hour addition). Furthermore, it suggested that I100-15 (SEQ. ID. NO. 33) had a different mechanism of action compared to AZT.

Additional experiments using alternative PCR primers suggested that there may be alterations in the viral DNA synthesis caused by I100-15 (SEQ. ID. NO. 33). The observed amplification products, when primers clustered in the U3 region of the virus were used, yielded a banding pattern which was not predicted and obviously different from the infected cell control (untreated) and the AZT treated infected cell samples.

RNA extracted from HIV-1 infected cells was analyzed by RT-PCR. In this assay, the antisense primer of the PCR primer pairs was used with MMLV RT and extracted mRNA to synthesize cDNA strand. The resultant cDNA was then used as a template in PCR reactions. Two RNA primer sets were used to analyze unspliced (primers r1 and r2) and spliced (primers r1 and r3) HIV-1 transcripts. Predicted sizes of the amplified products were 101 bp and 214 bp for the unspliced and spliced species respectively. The same β-action primers used for the analysis of the DNA samples were used as controls in this experiment.

The results obtained using primer pair r1 and r3 are depicted in FIG. 12. The results of this experiment clearly indicated that a reduced level of HIV-1 specific transcript was observed in samples treated with I100-15 (SEQ. ID. NO. 33) in the samples treated with drug at the same time as virus infection (zero hours). It was also clear that while samples treated with AZT had reduced levels of viral cDNA, viral mRNA was still being produced. The same decrease in HIV-1 specific transcript was observed in viral infected cells treated with I100-15 (SEQ. ID. NO. 33) when the r1 and r2 primer pair was used (data not shown).

H. Structural analysis of I100-15 and I100-26

I100-07 (SEQ. ID. NO. 24), and its derivative products including I100-15 (SEQ. ID. NO. 33) and I100-26 (SEQ. ID. NO. 47), are composed entirely of deoxyguanosine (G) and deoxythymidine (T). These G-rich oligonucleotides were purified using anion exchange reverse phase HPLC. Using this procedure the oligonucleotide is purified in the presence of sodium ions. Monovalent cations are known to encourage self-associated structures for G-rich molecules, all of which involve formation of G-tetrads. The G-tetrad formation involves the formation of eight hydrogen bonds by coordination of the four $O^6$ atoms of guanine with alkali cations believed to bind to the center of a quadruplex, and by strong stacking interactions. The oligonucleotides purified using anion exchange chromatography then have an opportunity to form inter- or intra-molecular tetrads. The tetrad structure can be strengthened by replacing the sodium ion with potassium.

I. Nondenaturing gel analysis

Figure 13:
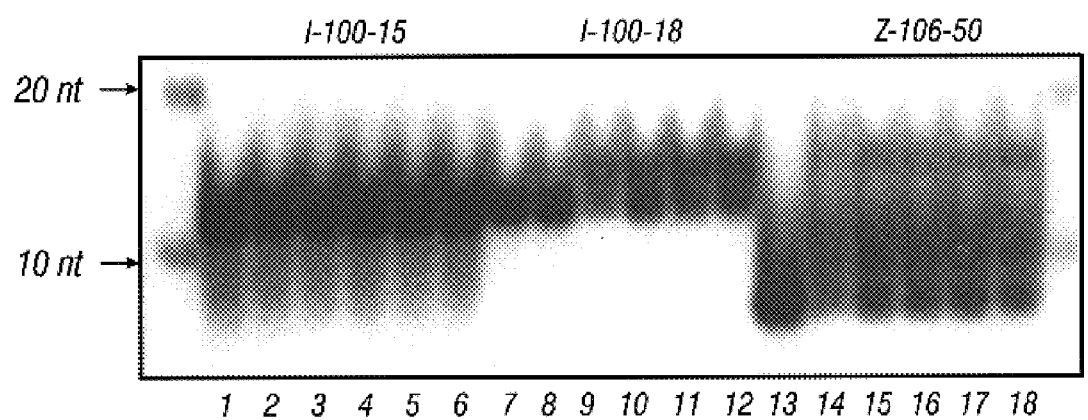
FIG. 13 shows the results of three oligonucleotides ($10^{-5}$ M) incubated with increasing concentrations (0, 7.5, 15, 30, 60 and 120 mM) of KCl (lanes 1–6 for I100-15 (SEQ. ID. NO. 33), 7–12 for I100-18 (SEQ. ID. NO. 36) and 13–18 for Z106-50). The nucleotide markers are poly dT.

I100-15 (SEQ. ID. NO. 33)(17 mer, Table A-5) was analyzed using nondenaturing polyacrylamide gel electrophoresis. In this experiment, trace concentrations of radiolabeled oligonucleotide ($10^{-7}$M) was incubated with increasing concentrations of cold oligonucleotide (up to $10_{-5}$M) before gel analysis in the presence of monovalent cation. Under the gel conditions used, I100-15 (SEQ. ID. NO. 33) migrated as a unique band faster than a random coiled (denatured) 17 mer oligonucleotide would and it was shown to do so in a concentration independent fashion (data not shown). This was in contrast to I100-18 (SEQ. ID. NO. 36)(16 mer, 10 fold less active than I100-15 (SEQ. ID. NO. 33)) which appeared to migrate as multiple species in a concentration dependent fashion under the same gel conditions (data not shown). The same phenomena was observed when $10^{-5}$ oligonucleotide (total cold and radiolabeled oligonucleotide) was incubated with increasing concentration of KCl (FIG. 13). I100-15 (SEQ. ID. NO. 33) migrated as a unique species at all concentrations of KCl while I100-18 (SEQ. ID. NO. 36) and Z106-50 (ggttggggttggg) migrated as multiple species.

The results from these assay suggested that I100-15 (SEQ. ID. NO. 33) folds into an intramolecular structure while other G-rich oligonucleotides such as I100-18 (SEQ. ID. NO. 36) and Z106-S50 aggregate into higher order intermolecular structures. It was noted that the total phosphorothioate oligonucleotide G-rich compound described by Wyatt et al., P.N.A.S. 1994 91:1356–66, with the sequence $T_2G_4T_2$, was claimed to fold into an intermolecular tetrad. Therefore, I100-15 (SEQ. ID. NO. 33) (PD backbone) is structurally and chemically different from the oligonucleotide reported (ISIS PT oligonucleotide).

J. Tetrad Structure. Principally due to its role in telomere formation, the structure of four stranded nucleic acid tetrads has been well studied Most eukaryotes possess a repeating G-rich sequence of the form T/C)nGm where n=1-4 and m=1-8. Of particular interest to the study of the I100-15 (SEQ. ID. NO. 33) class of GTO was the structure of the telomere sequence repeat $T_2G_4$, first detected in Oxytricha. The Oxytricha repeat has been studied in oligonucleotides by NMR, Smith et al., Nature 1992, 356:164–68, and by crystallographic methods, Kang et al. Nature, 1992, 356:126–31. As had been predicted from numerous previous physical and biochemical studies, both the NMR and crystallographic studies suggested that folding is mediated by square planar Hoogsteen H-bonding among G residues, with overall antiparallel orientation of the four strand equivalents comprising the tetrad fold. As expected, the crystallography has shown that the structure is selectively stabilized by tight binding of a small monovalent cation to the $O^6$ oxygen of guanosine. But surprisingly, both NMR and crystallography confirm that the folded structure possess alternating syn/anti glycosidic bond angles (as opposed to all anti for most duplex structures).

Feigon and colleagues have used NMR and modelling to deduce the structure of a 28 base-long oligonucleotide ($G_4T_4G_4T_4G_4T_4G_4$, Oxy 3.5) which is capable of forming a well-defined all-antiparallel intramolecular tetrad, Smith et al., Nature 1992, 356:164–68. The present inventors postulated that if the GTO I100-15 (SEQ. ID. NO. 33) were to fold to form a stable intramolecular tetrad, its NMR properties would be expected to be similar to those of the Oxy 3.5 molecule.

In the folded state, the salient NMR characteristics of the intramolecular Oxy 3.5 tetrad were as follows:

1. Narrow linewidths, indicative of monomer formation only.
2. Induction of well-defined guanosine N1 Hoogsteen imino resonances in the 11.2 to 11.7 ppm range. The chemical exchange rate of these protons is very slow, reflective of the high positive cooperativity of tetrad folding and dissociation.
3. Spectral simplicity, indicative of a single predominant folded structure, rather than an equilibrium among different folded structures.
4. Intrabase H8-C1' and interbase H7-C2" NOE connectivity which demands a pattern of alternating syn-anti glycosidic bond angle throughout the "tetrad stem" of the folded structure.

K. One dimensional NMR analysis

Figure 14:
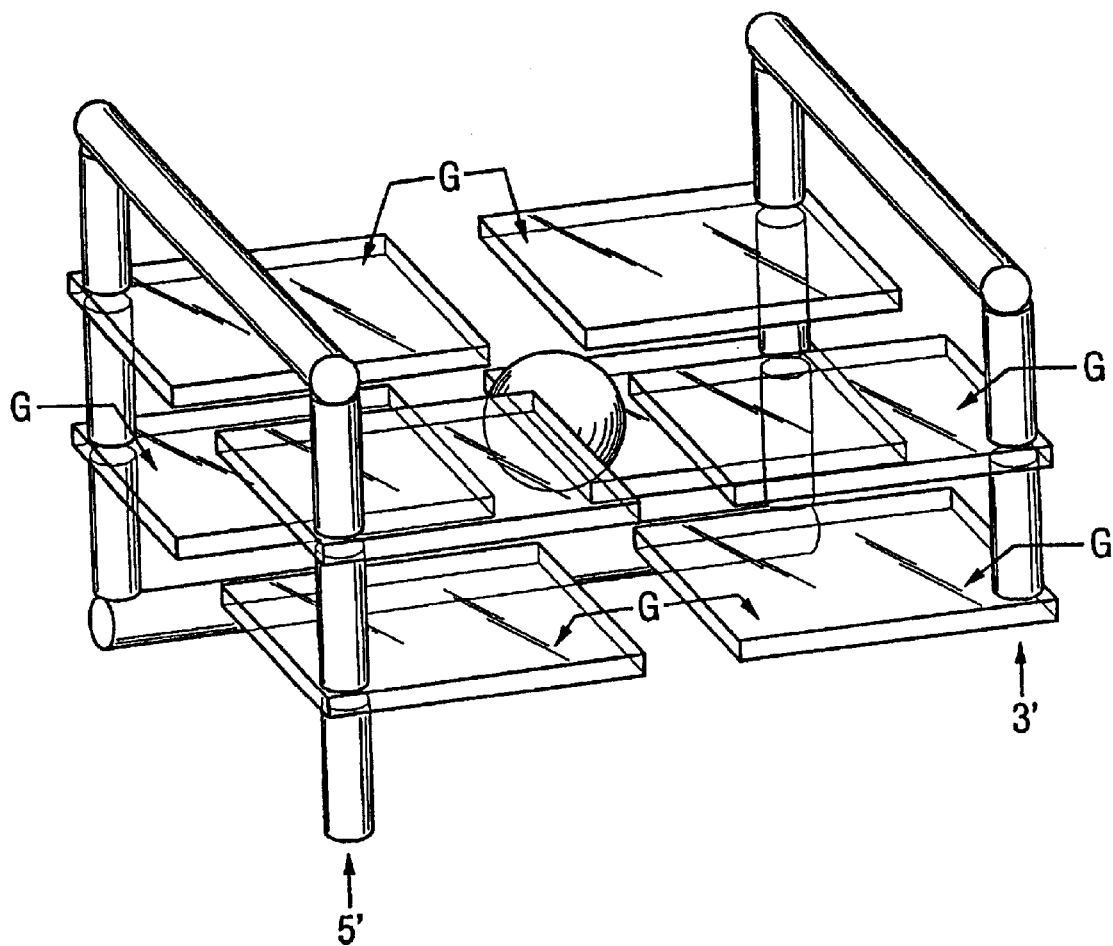
FIG. 14 shows a line model for I100-15 (SEQ. ID. NO. 33) folded into an intramolecular tetrad of the Oxytricha class is depicted. The 5'-end of the molecule is in the bottom left hand side. The bases (Gs) are stacked on top of each other with the 4 bases in each plane stabilized through their hydrogen bonding with each other and their interaction with the K$^+$ ion complex in the center of the tetrad.

Displayed in FIG. 14 is a line model for I100-15 (SEQ. ID. NO. 33), folded to form an intramolecular tetrad of the Oxytricha class. From a physical perspective, the possibility that an intramolecular tetrad structure might form in high KCl or NaCl is not surprising. What was surprising was the fact that this model proposed a stem region comprising a single G-octet and intervening loop regions which were only two bases long.

In order to test the general feasibility of this model, a detailed 3D molecular model for a I100-15 (SEQ. ID; NO. 33) was constructed. In so doing, the inventors assumed that the 8 G's comprising the octet core of the structure formed a standard square planar octet, and that glycosidic angles were as in the crystal and NMR structures of the antiparallel Oxytricha tetrads, Smith et al., Nature 1992, 356:164–68, and Kang et al., Nature 1992, 356:126–31. Additionally, a single $K^+$ ion was introduced into the center of the G-octet, with octahedral coordination to $GO_6$. Initially, 2 base loop structures were created so as to connect elements of the octet without disruption. Subsequent to this initial postulation, the structure was subjected to mechanical refinement with full electrostatics, employing Charmm parameters in Sybyl.

After refinement, it was observed that coordinates of the octet core were not significantly altered and that backbone parameters within the loop domains were within acceptable energetic limits.

First, the structure was very compact, nearly spherical, with the three loop regions and the 5' "GT tail" comprising the surface of the tetrad core. Based upon this structure, it appeared likely that interaction with cellular macromolecules would be heavily dominated by the structures of these surface loops. In that regard, the inventors believe that it may be inappropriate to think of such interactions as "tetrad binding." The inclusion of G-tetrads in such a structure may not be important as a recognition element per se, but instead provides a latticework upon which an orderly loop array is positioned.

Further, although the loop regions did not appear to be under mechanical stress, they were short enough so that they possessed very high configurational freedom. Because of those severe length constraints, it was found that all feasible loop models display a distinct "rabbit ears" structure, wherein the two base planes of the loop region are unstacked, and point outward from the center of the octet core. Such rigid, unstacked, single strand loop character was very distinctive as compared to other known folded nucleic acid structures. Therefore, varying the sequence or chemical structure of these loops, one at a time, was necessary to determine if bonding interactions between these loops and cellular macromolecules are important to the observed anti-HIV activity.

The structures described above possessed a single G-octet core, which was known to be the minimum structure required for nucleation of tetrad formation. Therefore, when paired with the observed short loop size, the intramolecular tetrad structure proposed for I100-15 (SEQ. ID. NO. 33) is best described as meta-stable, relative to other more robust tetrads which have been described in the literature. An increase of the core from 2 to 3 stacked tetrads, or an increase in the length of flexibility of one or more loops would be expected to increase the thermodynamic and/or kinetic stability of this structure significantly. Thus, the observed anti-HIV activity can be improved by sequence modification which enhances the stability of the underlying tetrad latticework.

Finally, it was observed that I100-15 (SEQ. ID. NO. 33) and homologues display profound resistance to cellular nucleases. One interesting aspect of the proposed structure was that, even in the loop domains, phosphodiester linkages are generally buried from interaction with large solutes, such as a nuclease. The structure analysis proposed defined local phosphodiester backbone structure at low resolution. When paired with explicit biochemical analysis of phosphodiester cleavage rate, it is possible to define sites for selective introduction of backbone modification in I100-15 (SEQ. ID. NO. 33) homologies, for the purpose of extending the biological half life in vivo.

The gel electrophoresis data described above suggested that I100-15 (SEQ. ID. NO. 33) spends very little time as a random coil at 25° C., under native salt conditions. Although the gel data rules out intermolecular associations, the data do not constrain the oligomer to any particular folded monomeric structure. Oligonucleotide folding in I100-15 (SEQ. ID. NO. 33) has been studied employing a combination of high resolution NMR and methods.

Stable formation of a discrete octet core, mediated by tight binding of a single monovalent ion is crucial to the model described above. Given that G-N1 imino protons give rise to sharp, characteristic $^1$H NMR signals in such a structure, focus has been on the potassium ion dependence and temperature dependence of I100-15 (SEQ. ID. NO. 33) folding, as assessed by $^1$H NMR at 500 mHz.

For these measurements, I100-15 (SEQ. ID. NO. 33) was synthesized at 15 uM scale employing fast deblocking "Expedite" chemistry on a Milligen synthesizer. Subsequent to purification by denaturing anion-exchange chromatography in base (10 mM LiOH, 0.2 to 0.7M NaCl), oligomer purity was confirmed by denaturing gel electrophoresis (7M urea, 65° C.). For NMR, the oligomer was desalted and transferred into 20 mM LiCl adjusted to pH 6.0, which minimizes folding to form tetrads. Oligonucleotide strand concentration was held constant at 2.7 mM. NMR was measured in $H_{20}$, employing a Redfield pulse sequence to saturate the water resonance, as described previously, Dittrich et al., *Biochemistry*, 1994 33:4111–4120.

Figure 15:
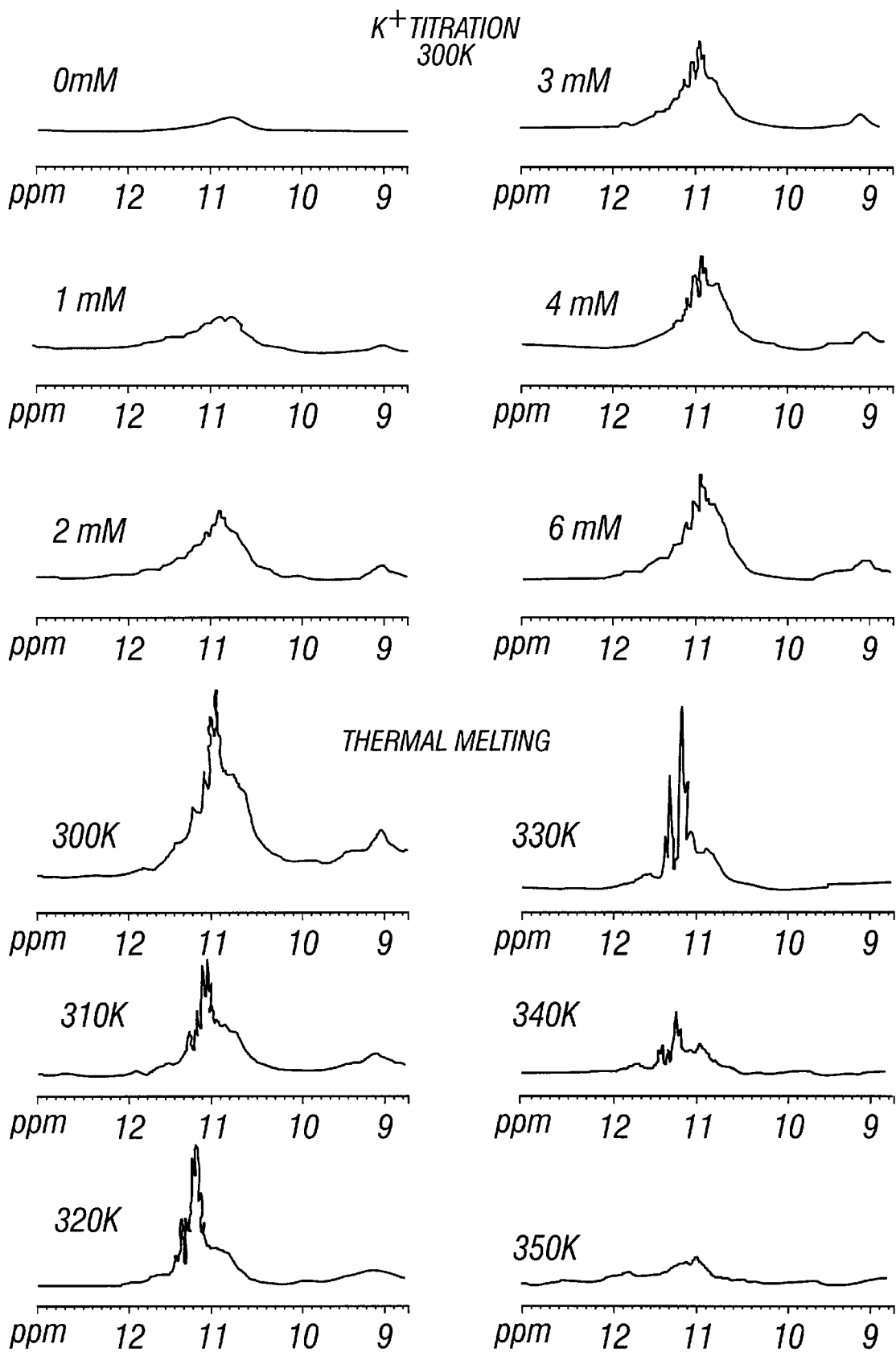
FIG. 15 displays a one dimensional NMR analysis of a KCl titration and thermal melting parameters for I100-15 (SEQ. ID. NO. 33).

In FIG. 15 a KCl titatation is displayed. At 300° K., in the absence of added K$^+$, imino proton signals cannot be resolved in the 10–12 ppm region. Subsequent to addition of KCl, substantial narrowing of imino signals was obtained, saturating at an added KCl concentration of 3 mM, which is very close to one added K$^+$ equivalent per octet. Above 4 mM, it can be seen that at least two classes of imino resonance can be detected in the 10–12 ppm range with roughly equal intensity: a broad envelope from 10–11 ppm, upon which several sharp resonances are superimposed in the 11–11.5 ppm region.

By analogy with chemical shifts of other G tetrad structures, the inventors tentatively ascribed the sharp imino signals to the 8 Hoogsteen H bonds of the core octet. The broad envelope was ascribed to the G and T imino resonances contributed by the loop and 5' terminal domains. Consistent with published tetrad NMR data, a broad envelop of signal was detected at 9 ppm, which most likely results from unusually slow exchange of guanosine N2 protons engaged in Hoogsteen pairing.

In order to better distinguish the two classes of imino$^1$H signal and, additionally, to investigate the gross stability characteristics of the folded I100-15 structure, thermal melting analysis, at 2.7 mM in strands, 6 mM KCl, 20 mM LiCl, pH 6.0 over the range from 300° K. to 345° K. was performed.

Substantial line narrowing of "Hoogsteen" imino proton signals was seen at 310° K., which appears to be accompanied by broadening of the poorly resolved imino envelope at 10.7 ppm. This caused a narrowing of the plateau above 310° K., giving rise to 7–8 well-resolved imino protons at 320° K. By reference to the NMR behavior of the Oxytricia tetrad and other tetrad structures, the formation of 7 to 8 narrow, well-resolved imino resonances at elevated temperatures strongly suggested that in the presence of one bound K$^+$ ion per octet equivalent, I100-15 folded into a discreet tetrad structure, stabilized by the 8 Hoogsteen H-bonds of the presumed octet.

In the range from 330 to 340° K., the imino proton spectrum undergoes an abrupt transition, which is likely to be representative of cooperative unfolding of the octet. Stability of this kind, accompanied by apparently high thermal cooperativity is very striking indeed, and is generally indicative of a single, well-defined folded oligonucleotide structure.

The origin of the shallow temperature dependence of the spectral parameters, leading to enhanced $^1$H resolution at 320° K., remains to be determined. It is likely to have resulted from weak intermolecular association which occur in the millimolar strand concentration range. This interpretation is born out by preliminary analysis of spectral parameters as a function of strand concentration (not shown). Independent of interpretation, the data suggested that high quality NMR data may be obtained for exchangeable and non-exchangeable I100-15 (SEQ. ID. NO. 33) protons at 35° C., 20 mM, LiCl, 6 mM KCl and 2 mM in strand equivalents.

INHIBITION OF HCMV ACTIVITY

Several different oligonucleotides reduced HCMV titers in tissue culture. Each of the oligonucleotides contained a different percentage of guanosine residues and a different number of total nucleotides in the polymer. The results of this assay are depicted in Table A-9. All oligonucleotides were capable of reducing viral titer in culture including G101-50 (SEQ. ID. NO. 12) which contained only 53% G residues (16 out of 30 total nucleotides). In Table A-9, the length and percent guanosine nucleotides is indicated for each oligonucleotide tested.

TABLE A-9

Oligonucleotide Inhibition of HCMV Activity
Viral Yield in plaque forming units (PFU)

| Oligo. Conc. | oligonucleotide (% G) | | | | |
|---|---|---|---|---|---|
| | G101-50 (53%) 30 mer | G105-50 (80%) 31 mer | G106-50 (78%) 29 mer | G109-50 (65%) 29 mer | G113-50 (64%) 24 mer |
| None | $4.5 \times 10^3$ PFU | $4.5 \times 10^3$ PFU | $4.5 \times 10^3$ PFU | $4.5 \times 10^3$ PFU | $4.5 \times 10^3$ PFU |
| 20.0 µM | Ø | $4.5 \times 10^1$ PFU | $2.5 \times 10^1$ PFU | $8.0 \times 10^1$ PFU | $3.5 \times 10^1$ PFU |
| 10.0 µM | $2.5 \times 10^1$ PFU | $1.8 \times 10^2$ PFU | $4.0 \times 10^1$ PFU | $4.5 \times 10^1$ PFU | $4.0 \times 10^1$ PFU |
| 1.0 µM | $7.0 \times 10^2$ PFU | $1.9 \times 10^2$ PFU | $6.0 \times 10^1$ PFU | $1.5 \times 10^2$ PFU | $5.0 \times 10^2$ PFU |
| 0.5 µM | $8.0 \times 10^2$ PFU | $2.7 \times 10^2$ PFU | $1.3 \times 10^2$ PFU | $3.0 \times 10^2$ PFU | $5.4 \times 10^2$ PFU |

In NIH3T3 cells chronically infected with FMLV, oligonucleotides (FIG. 1) were capable of inhibiting virus production. However, oligonucleotide controls in this experiment were capable of inhibiting virus production in culture.

IN VITRO ENZYMATIC ASSAYS

Culture media containing FMLV reverse transcriptase (RT) was mixed with various concentrations of I100-51 (SEQ. ID. NO. 29) or I100-12 (SEQ. ID. NO. 27), (the phosphodiester backbone of I100-51 (SEQ. ID. NO. 29) having been modified to a phosphorothioate backbone). Reverse transcriptase was measured as described in the section entitled "Reverse Transcriptase Assay" above. FIG. 4 shows that both oligonucleotides were capable of inhibiting the RT enzyme. Inhibitory concentrations for 50% reduction in RT activity was between 0.5 to 1 µM for I100-51 and less than 0.5 uM for I100-12 (SEQ. ID. NO. 27).

Figure 5A:
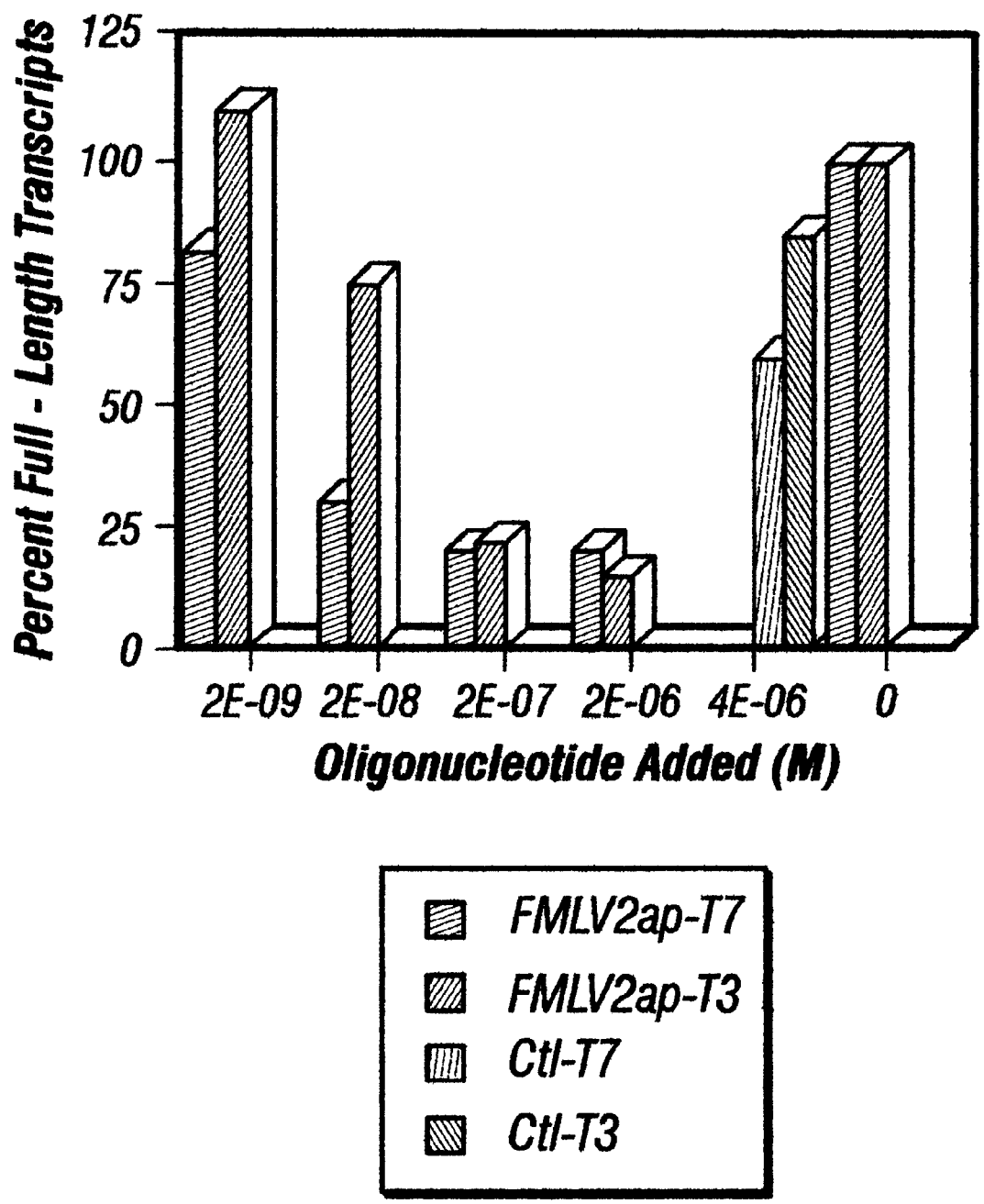
FIGS. 5A, 5B and 5C show the radioabelled ($^{32}$P) full-length or truncated mRNA transcripts were analyzed by polyacrylamide gel electrophoresis, and then quantitated by cutting out the specific transcript and measuring the radioactivity in a scintillation counter.
Figure 5B:
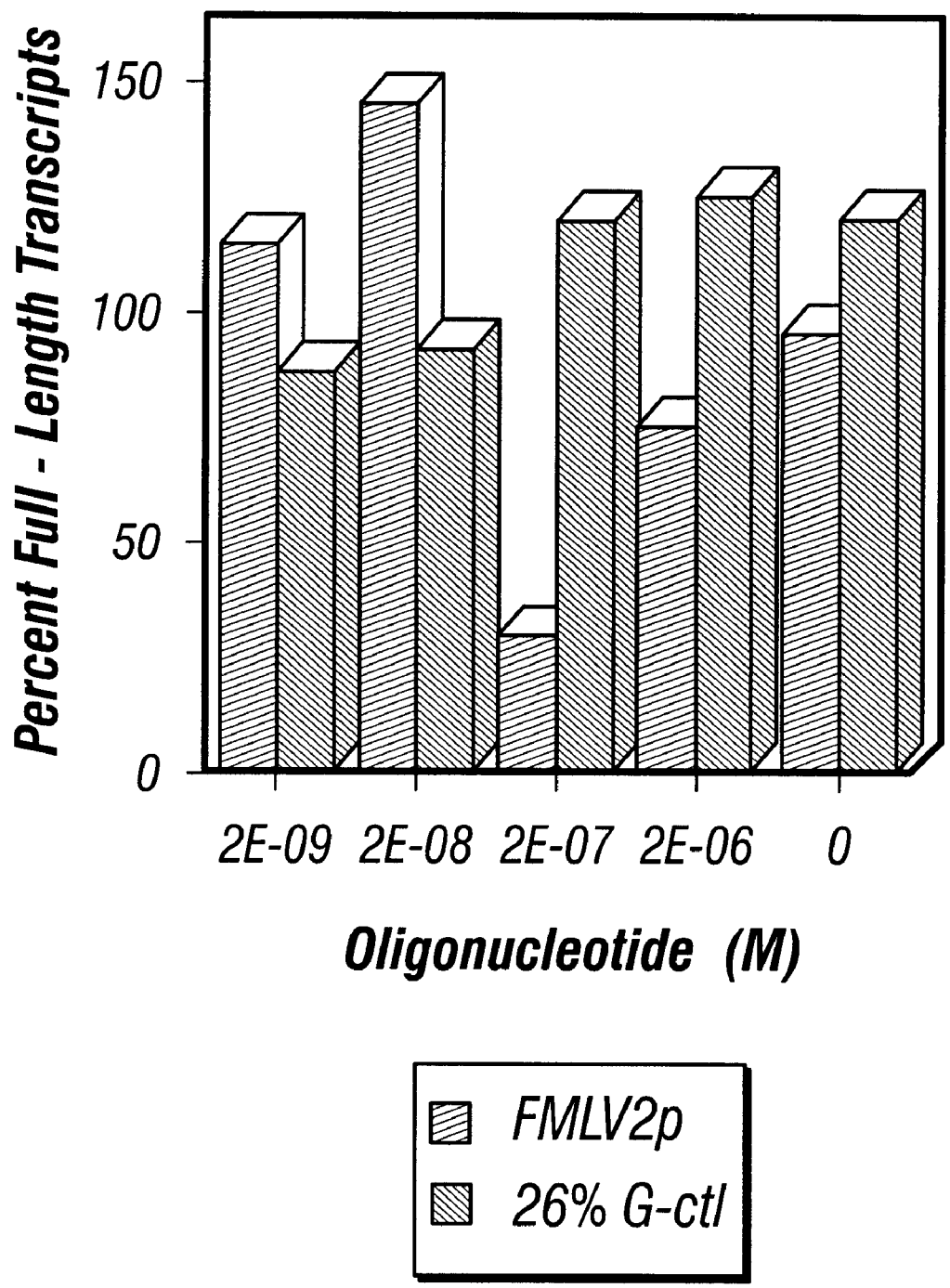
Figure 5C:
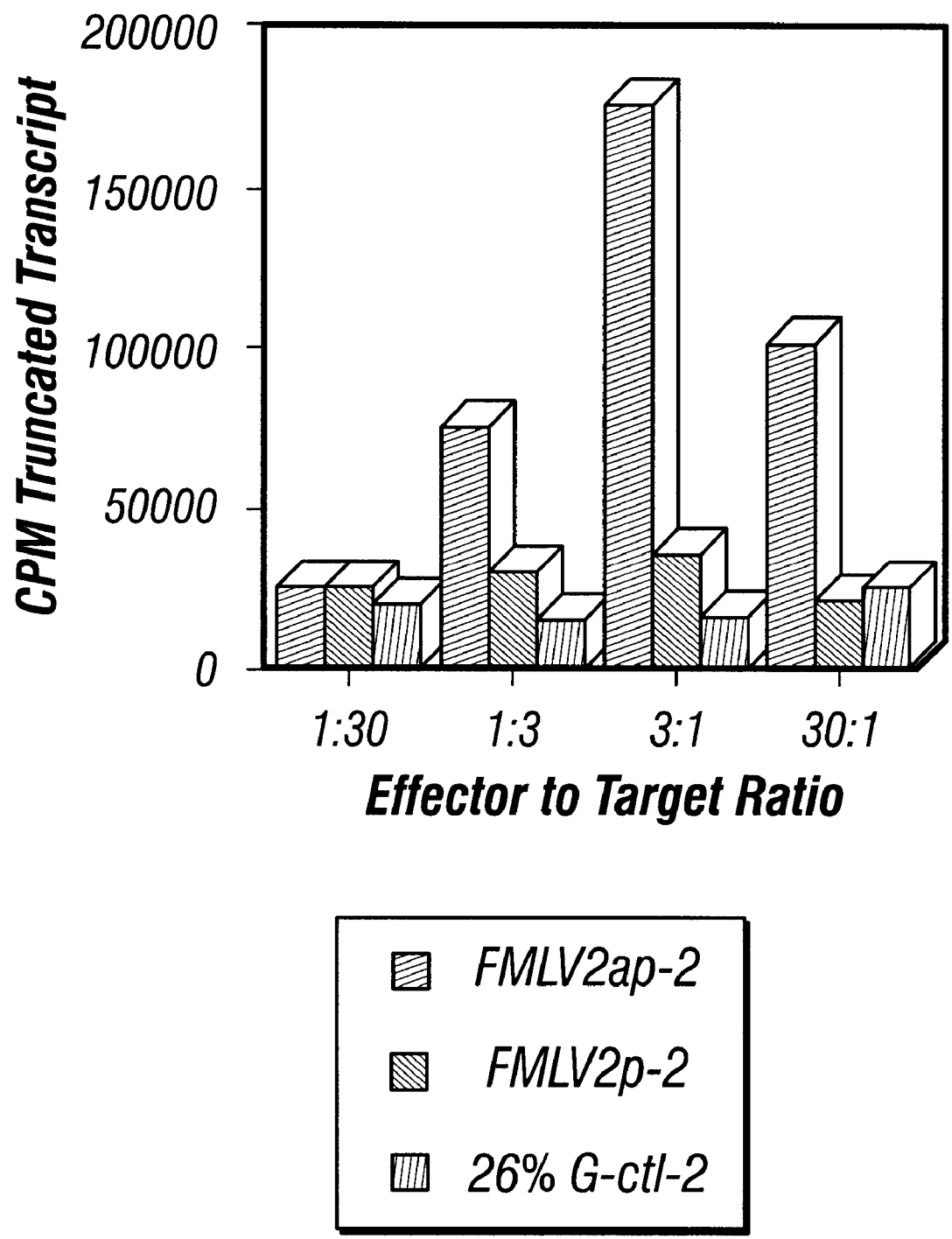
Figure 6:
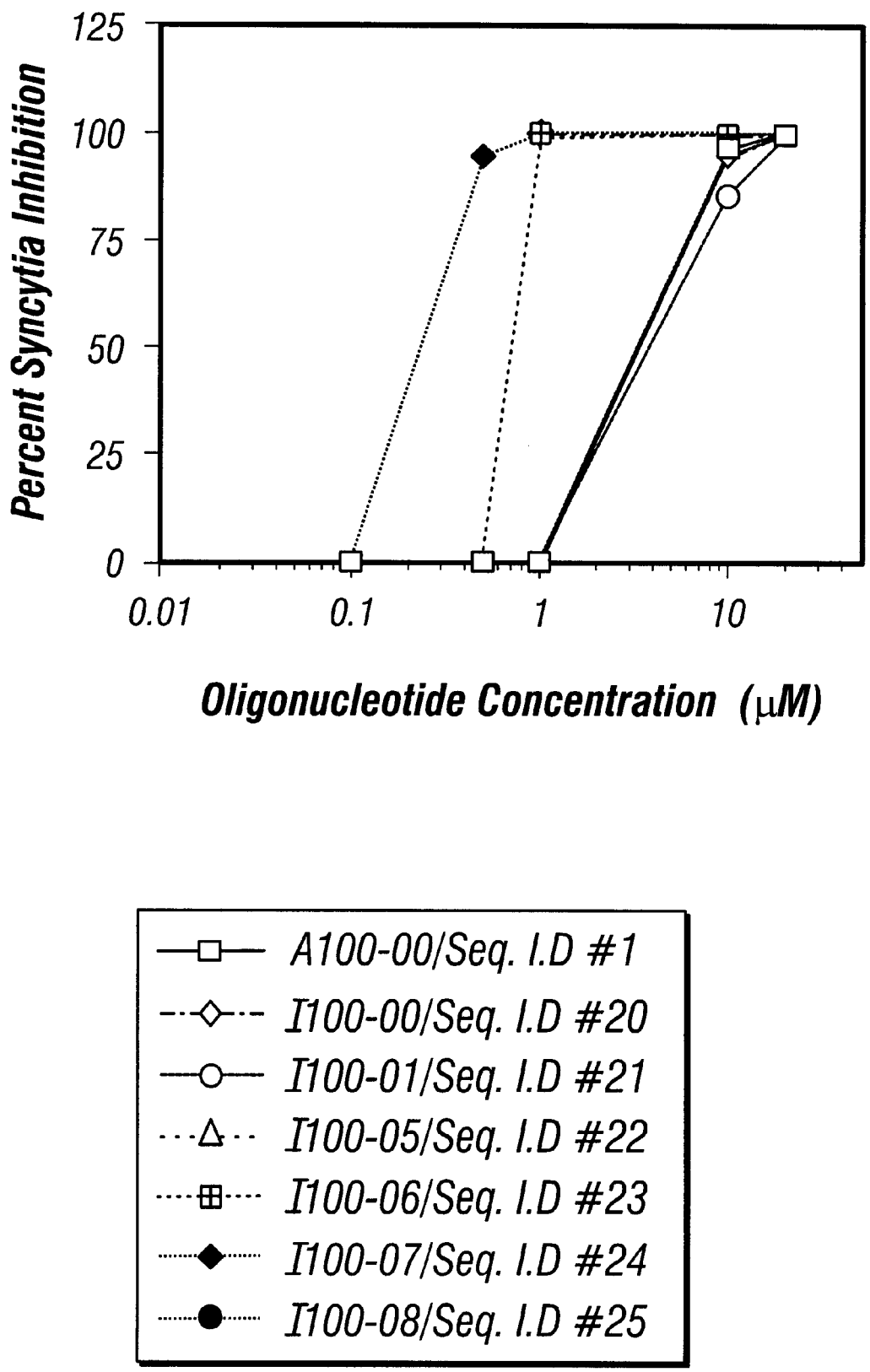
FIG. 6 shows inhibition of HIV-1 induced syncytia formation four days post-infection. SUP T1 cells were infected with HIV-1$_{DV}$ for four hours and then treated with various concentrations of oligonucleotides. Four days post-infection cells were scored for syncytium formation. All assays were performed in quadruplicate and the average values used to plot this graph. The legend to the right of the graph indicates the symbol used for each oligonucleotide tested.
Figure 7:
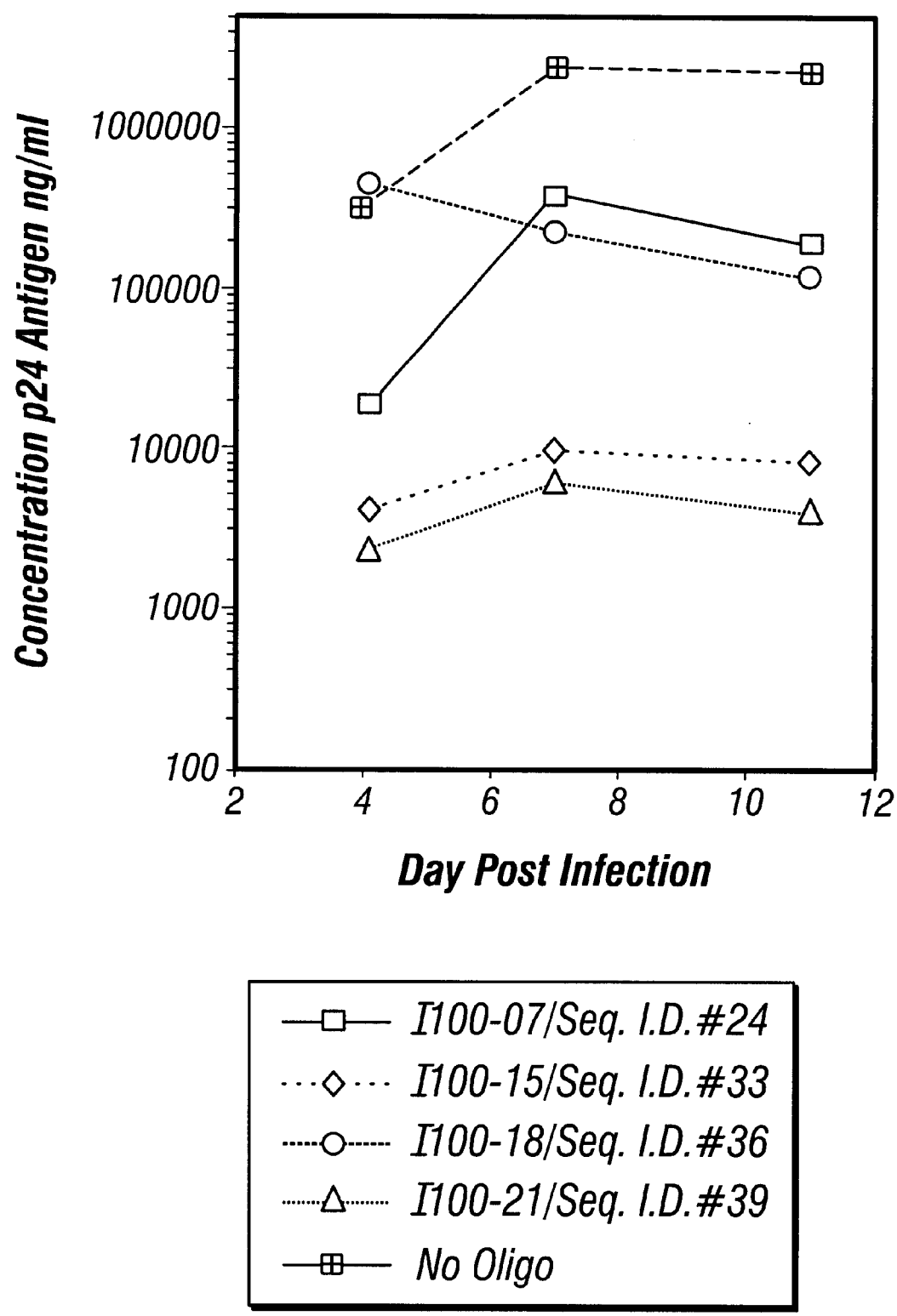
FIG. 7 shows continued suppression of HIV-1 p24 production seven days post removal of oligonucleotide. Four days post-infection with HIV-1$_{DV}$, the media from infected cells treated with oligonucleotides (2.5 µM) was removed and replaced with fresh media without oligonucleotide. The presence of viral p24 antigen was then assayed 7 and 11-days post infection. All samples were assayed in quadruplicate and the average values used to plot this graph. I100-07 (SEQ. ID. NO. 24); I100-15 (SEQ. ID. NO. 33); I100-18 (SEQ. ID. NO. 36); I10021 (SEQ. ID. NO. 39). The legend to the right of the graph indicates the symbol used for each oligonucleotide tested.
Figure 8:
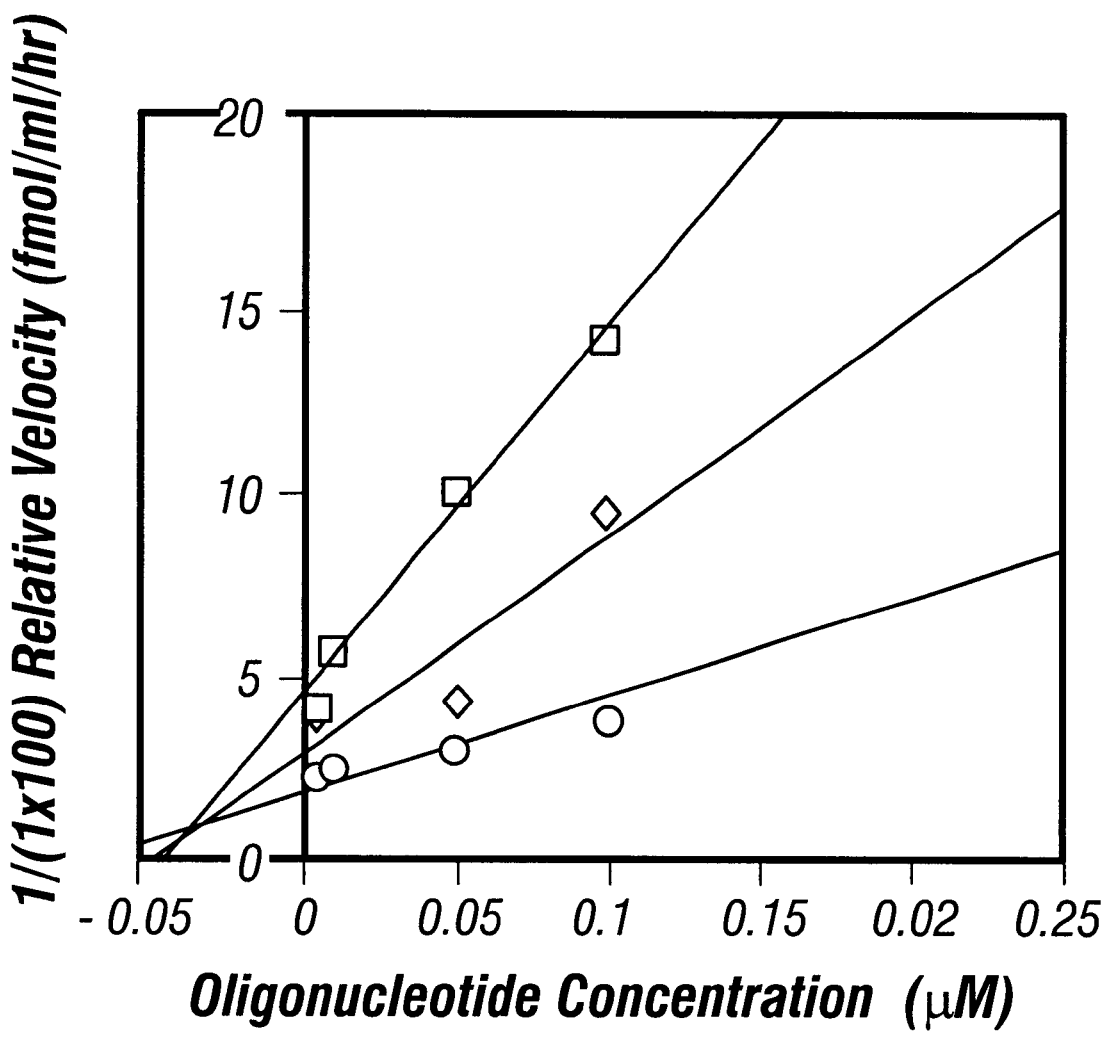
FIG. 8 shows a Dixon Plot of random oligonucleotide 1232 (SEQ. ID. NO. 41) obtained from kinetic analysis of inhibition of HIV-RT with respect to dNTP. The inhibition constant $K_i$ was determined by simultaneously varying dNTP (without dATP) concentrations at the same time as inhibitor (oligonucleotide 1232). The $K_i$ determination was performed at 0.125 mM, 0.25 mM and 0.5 mM dNTP concentrations with constant Primer-Template concentration of 0.2 pM. HIV-RT was used at 1 unit in each reaction. The reported values are the result of simultaneous independent duplicates determinations.
Figures 1, 33A:
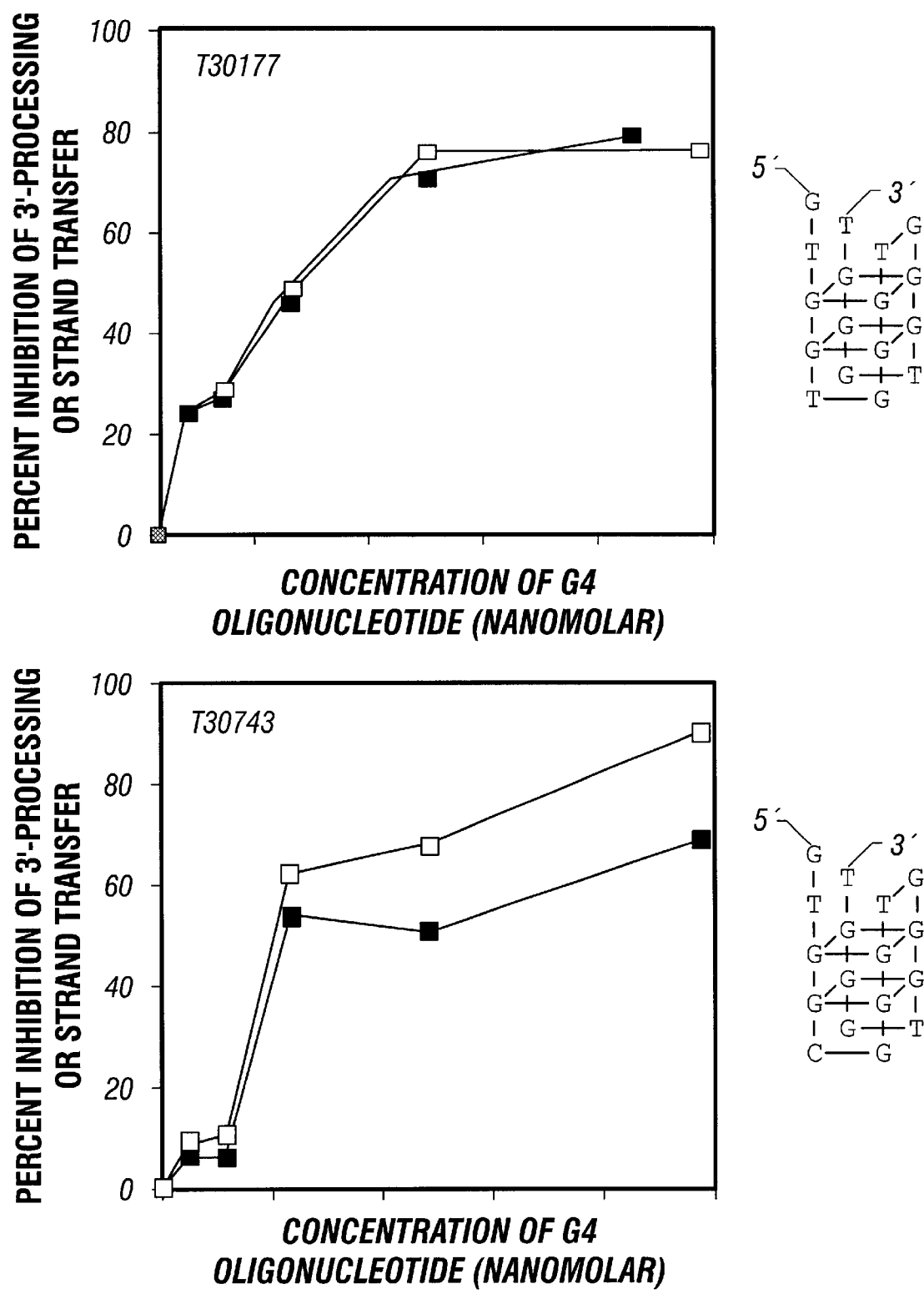
Figures 2, 33A:
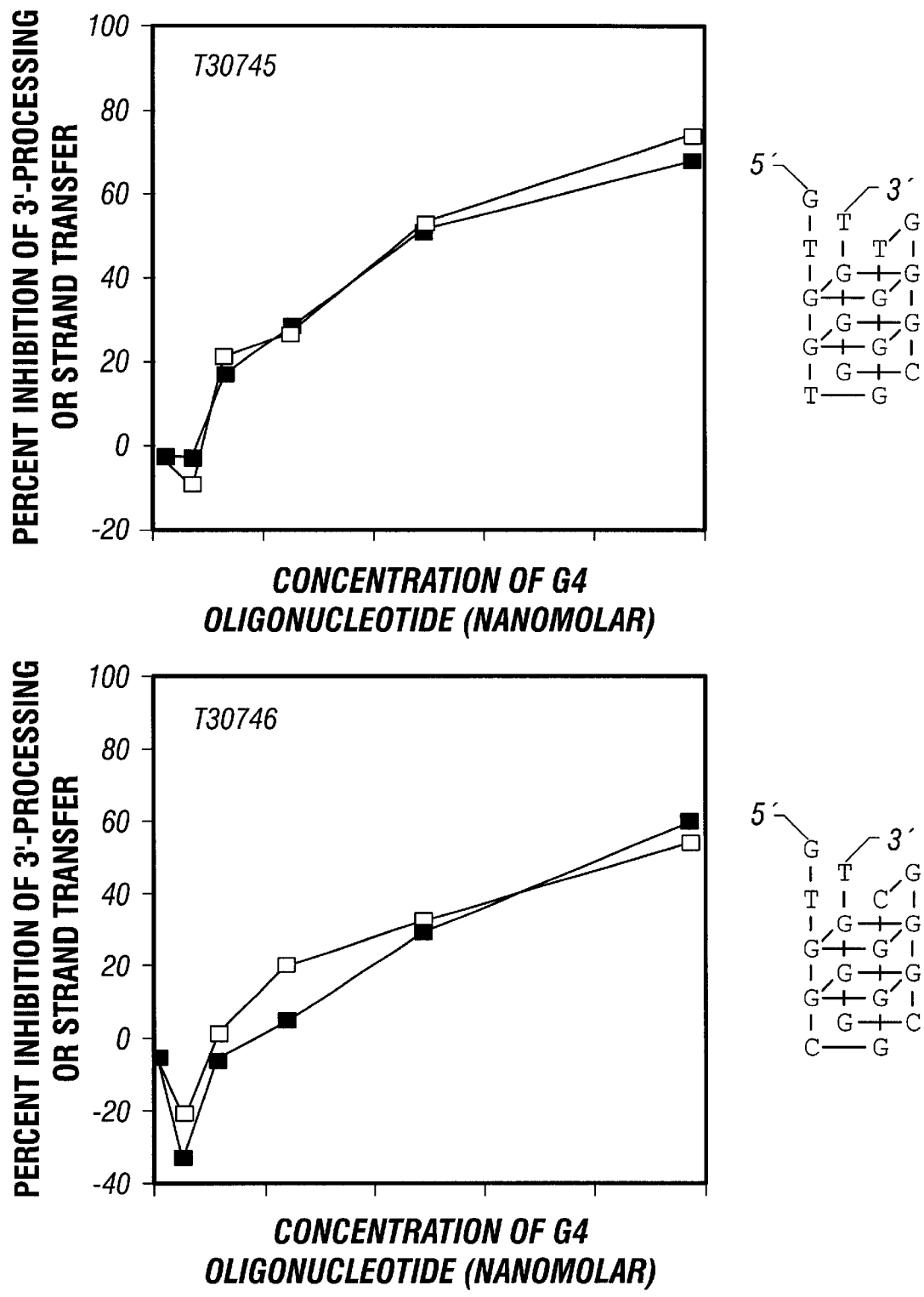
Figures 3, 33A:
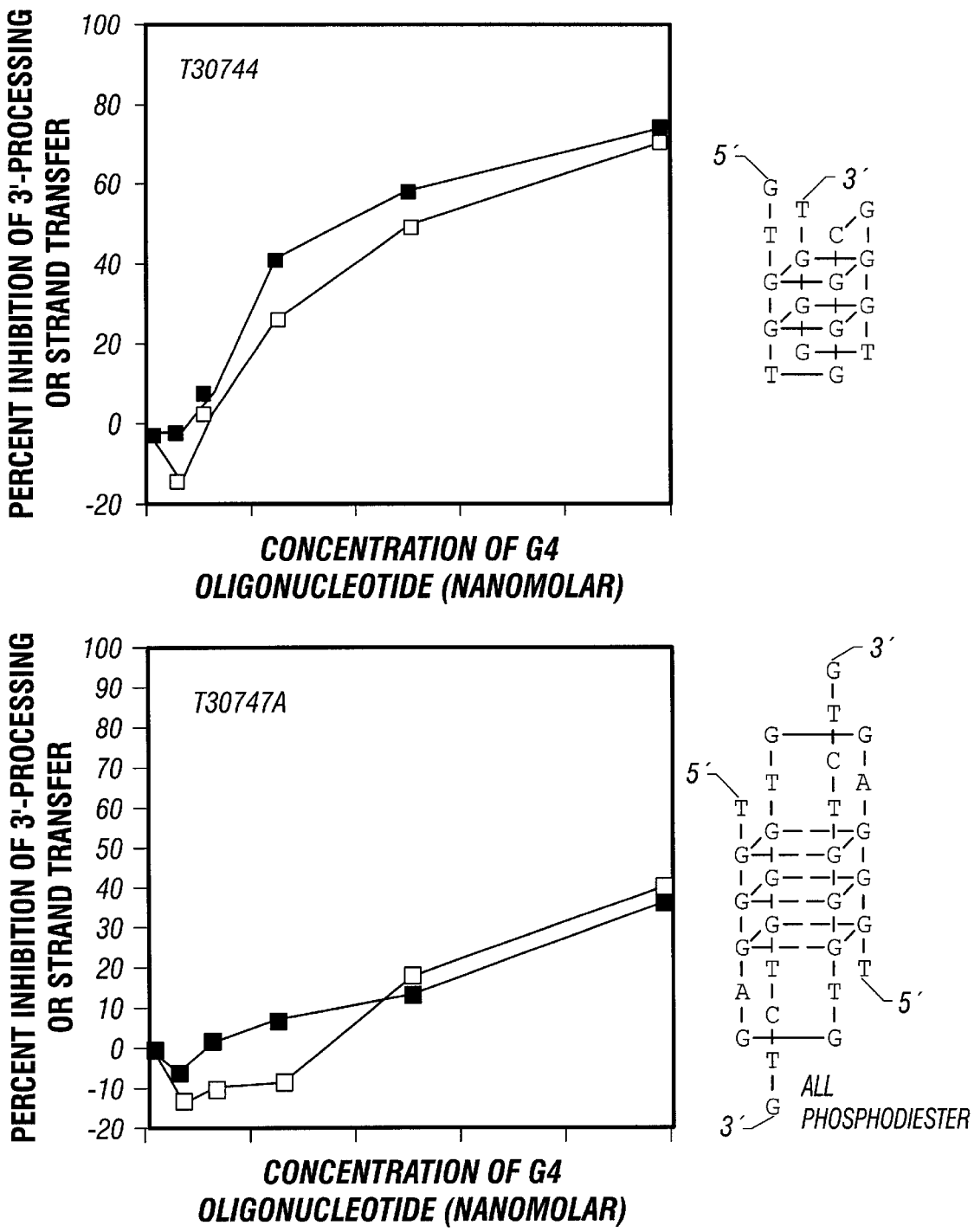
Figures 1, 33B:
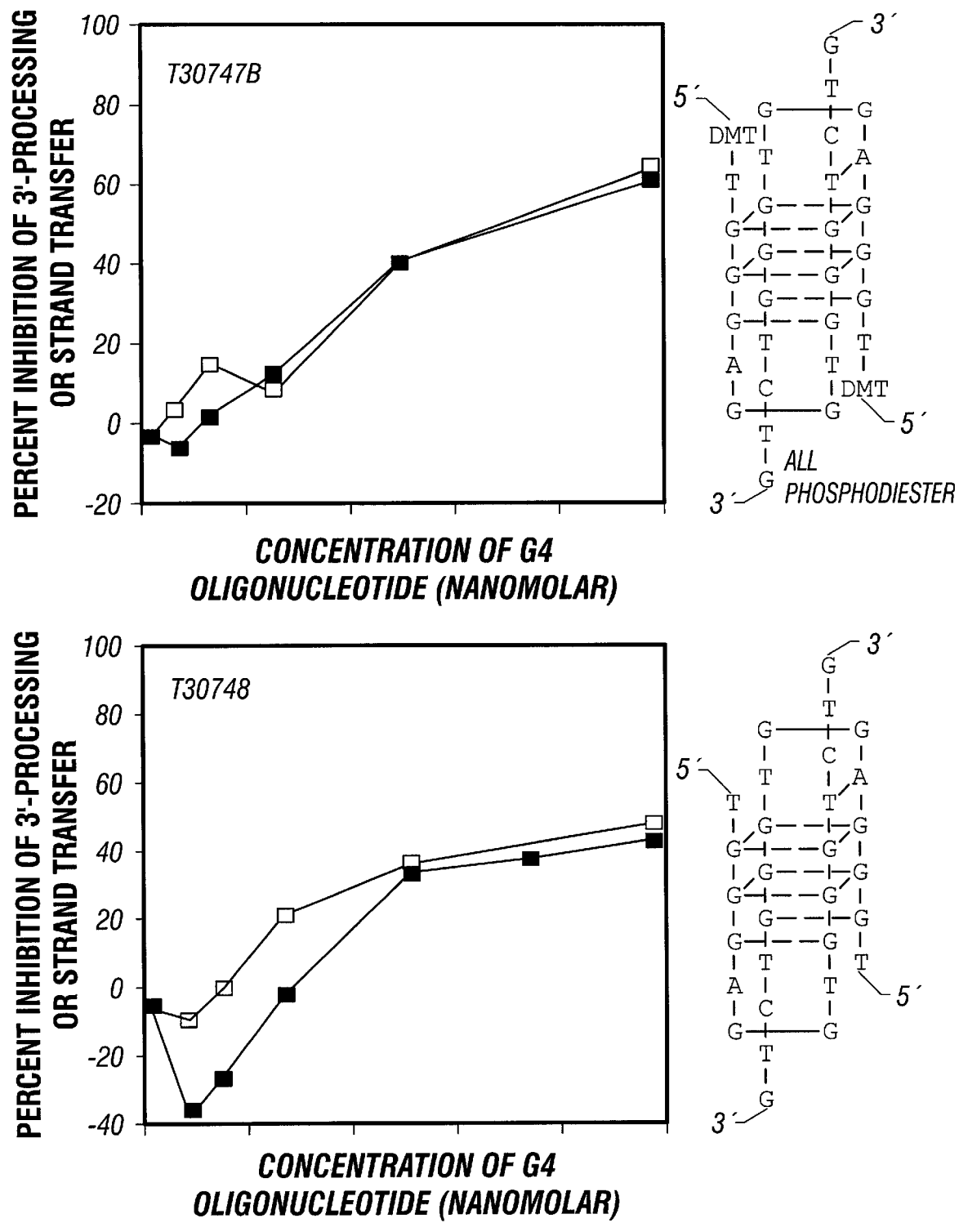
Figures 2, 33B:
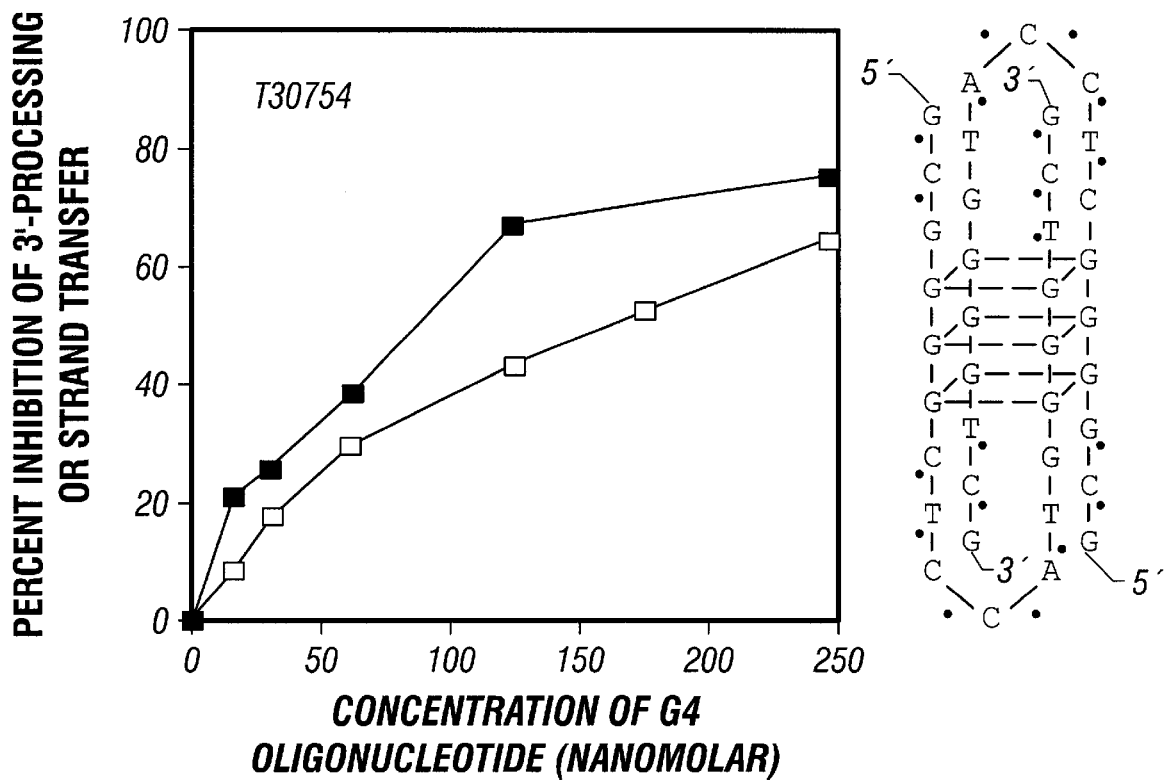

The I100-51 (SEQ. ID. NO. 29)(FMLV2ap), attenuated full length transcription directed by either the T7 or T3 polymerases (FIG. 5A). As can be seen in FIG. 1, full length transcripts directed by the T7 promoter would be 131 bases long while full length transcripts directed by the T3 promoter would be 171 bases long (position of the Dde I site relative to the mRNA start site). The sequence isomer of I100-51 (SEQ. ID. NO. 29)(I100-01 (SEQ. ID. NO. 21)= FMLV2p), designed parallel to the target strand was also capable of significantly inhibiting transcription from the T7 promoter (FIG. 5B). However, only the anti-parallel triple helix forming oligonucleotide FMLV2ap inhibited via attenuation of transcription as can be seen in the build up of a truncated transcript in the reaction mix (FIG. 5C). The truncated transcript analyzed in FIG. 5C was approximately 63 bases long and matched the predicted size fragment when p275A was used as a template (T7 promoter). G101-50 (SEQ. ID. NO. 12) (53% G) inhibited T7, but not T3 directed, transcription by a mechanism other than attenuation (FIG. 5A) since no truncated transcripts were observed when this oligonucleotide was used alone. I100-11 (SEQ. ID. NO. 26) (26% G) increased the level of specific transcripts directed by the T7 promoter (FIG. 4).

In experiments designed to monitor inhibition of transcription initiation of the HSV-1 IE175 promoter, using oligonucleotides, both specific and control G-Rich oligonucleotides were capable of inhibiting eukaryotic transcription when a HeLa cell extract system was used. The oligonucleotides used were B133-54 (SEQ. ID. NO. 10); B133-55 (SEQ. ID. NO. 11) and B107-51 (SEQ. ID. NO. 9) as specific inhibitors via potential triple helix mechanism of action and G101-50 (SEQ. ID. NO. 12) and I100-11 (SEQ. ID. NO. 26) as the low G-content control oligonucleotides.

The experiments described above clearly demonstrated the anti-viral activity in tissue culture assays for several G-Rich oligonucleotides against HSV-2, HIV-1, HCMV and FMLV. In addition, G-Rich oligonucleotides specifically inhibited the bacterial RNA polymerase enzymes T7 and T3, the FMLV and HIV-1 reverse transcriptase enzyme and eukaryotic RNA polymerase.

B. Specific In Vitro Studies and In Vitro HIV Inhibition Using T30177

As was demonstrated by the inventors in the studies initially conducted as described below, T30177 is an oligonucleotide composed of only deoxyguanosine and thymidine, it is 17 nucleotides in length is the same sequence as I10015 (SEQ. ID. NO. 33), and it contains single phosphorothioate internucleoside linkages at its 5' and 3' ends for stability. This oligonucleotide does not share significant primary sequence homology with, or possess any complementary (antisense) sequence motifs to the HIV-1 genome. As shown below, T30177 inhibited replication of multiple laboratory strains of HIV-1 in human T-cells lines, peripheral blood lymphocytes, and macrophages. T30177 was also shown to be capable of inhibiting multiple clinical isolates of HIV-1 and preventing the cytopathic effect of HIV-1 in primary CD4⁺T-lymphocytes. In assays using human peripheral blood lymphocytes there was no observable toxicity associated with T30177 at the highest concentration tested (100 µM), while the median inhibitory concentration IC$_{50}$) was determined to be in the 0.1 to 1.0 µM range for the clinical isolates tested, resulting in a high therapeutic index for this drug. In temporal studies, the kinetics of addition of T30177 to infected cell cultures indicated that like the known viral adsorption blocking agents dextran sulfate and Chicago sky blue, T30177 needed to be added to cells during, or very soon after, viral infection. However, analysis of nucleic acids extracted 12 hr-post infection from cells treated with T30177, at the time of virus infection, established the presence of unintegrated viral cDNA, including circular proviral DNA, in the treated cells. In vitro analysis of viral enzymes revealed that T30177 was a potent inhibitor of HIV-1 integrase reducing enzymatic activity by 50% at concentrations in the range of 0.01 to 0.10 µM. T30177 was also able to inhibit viral reverse transcriptase activity, however, the 50% inhibitory value obtained was in the range of 1–10 μM depending upon the template used in the enzymatic assay. No observable inhibition of viral protease was detected at the highest concentration of T30177 used (10 μM). In experiments in which T30177 was removed from infected cell cultures 4 days post-HIV-1 infection, total suppression of virus production was observed for more than 27 days. Polymerase chain reaction analysis of DNA extracted from cells treated in this fashion was unable to detect the presence of viral DNA 11 days after removal of drug from the infected cell cultures. The ability of T30177 to inhibit both laboratory and clinical isolates of HIV-1 and the experimental data suggested to the inventors that T30177 represented a novel class of integrase inhibitors, indicating that this compound was a viable candidate against evaluation as a therapeutic agent for HIV-1 in humans.

In the present study the inventors disclose the mechanism by which a variant of I100-15 (SEQ. ID. NO. 33) (T30177) was able to inhibit multiple HIV-1 laboratory strains in acute and long-term suppression assays. The data indicated that T30177 is a potent and selective inhibitor of HIV-1 via at least two mechanisms. One mechanism involves interfering with CD4- and gp120-mediated cell fusion events. However, T30177 is 100-fold less effective in inhibiting gp 120-induced cell fusion events than it is at inhibiting an early event in the viral life cycle, suggesting a specific point of interdiction distinct from that of blocking virus/cell interactions. The data also clearly showed that T30177 is a potent inhibitor of the HIV-1 integrase enzyme in vitro and that by blocking these events in the viral life cycle T30177 is able to suppress virus production for prolonged periods after an initial short treatment regimen with the drug.

Materials Used in In Vitro HIV Inhibition Studies

Oligonucleotides. The deoxyguanosine-rich and other oligodeoxynucleotides used in this study were synthesized, purified, and characterized as previously reported. Ojwang, et al., *J. AIDS* 7:560–570 (1994); Rando, et al, *J. Biol. Chem.* 270:1754–1760 (1995). The sequence and phosphorothioate (PT) pattern of the oligonucleotides used in antiviral assays is shown in Table B-7.

Materials. Zidovudine (3'-azido-3'-deoxythymidine, AZT) and the nucleoside analogs 2',3'-dideoxyionsine (ddI) and 2',3'-dideoxycytidine (ddC) were obtained from the AIDS Research and Reference Reagents Program, National Institute of Allergy and Infectious Diseases. Dextran sulfate (DS5000) was purchased from Sigma, and the bicyclam derivatives JM2763 and JM3100 (De Clereq, et al., *Antimicrob. Agents Chemother.* 38:668–674 (1994)) were obtained from Johnson Matthey (Westchester, Pa.). Chicago sky blue (CSB) was obtained from the Drug Synthesis and Chemistry Branch, National Cancer Institute.

Cytotoxicity Analysis. The cytotoxicity of T30177 was assayed as described above. The concentration of drug necessary to give one-quarter ($TC_{25}$), one-half ($TC_{50}$) or 95% ($TC_{95}$) of the maximum inhibition of growth response was then determined. The degree of cell proliferation was determined according to the manufacturer's instructions.

In other experiments the effect of T30177 on the viability of primary human PBMCs, PBLs and macrophages was determined using the trypan blue dye exclusion technique. Griffiths, B., *IRL Press,* p. 48 (1992), or by measuring the degree of [$^3$H]thymidine or [$^3$]leucine uptake in these cells (McGrath, M. S., et al. *Proc. Natl. Acad. Sci. USA* 86:2844–2848 (1989)).

Antiviral assays

HIV-1 infection assays using cell lines

Laboratory strains of HIV-1, HIV-2, simian immunodeficiency virus (SIV), or the low passage isolate HIV-1$_{DV}$ (Ojwang, et al., *J. AIDS* 7:560–570 (1994)), were used to infect established cell lines using the indicated multiplicity of infection (MOI) of virus, for one hour at 37° C. prior to washing and resuspension in medium containing increasing concentrations of drug. The infected cells ($2\times10^4$ cells/well) were inoculated in triplicate in 200 μl of complete medium which contains RPMI 1640 (Life Technologies) supplemented with 10% FBS, penicillin (50 U/mL), streptomycin (50 μg/mL) and L-glutamine, (2 mM). Four to 6 days post-infection, drug treated and control wells were analyzed for HIV-1 induced cytopathic effects, for the presence of viral reverse transcriptase (RT) or viral p24 antigen in the culture medium. Buckheit, et al., *AIDS Research and Human Retroviruses* 7:295–302 (1991); Ojwang, et al., *J. AIDS* 7:560–570 (1994); Rando, et al, *J. Biol. Chem.* 270:1754–1760 (1995). Cytopathic effects (CPE) were monitored by either direct counting of HIV-1 inducted syncytium formation or by staining cells with the tetrazolium dye XT or MTT. Buckheit, et al., *AIDS Research and Human Retroviruses* 7:295–302 (1991). The AZT resistant strain of HIV-1 (ADP/141) was kindly provided by Dr. Brendan Larder and the AIDS Directed Programme Reagent Project, Medical Research Council, England.

HIV-1 infection of PBMCs

Peripheral blood mononuclear cells (PBMCs) were isolated from blood of HIV-1 negative and hepatitis B virus (HBV) negative (healthy) donors by Ficoll/Hypaque density gradient centrifugation, cultured as described by Gartner and Popovic (Gartner et al., In Techniques in HIV Research, p. 59–63 (1990)), then activated with phytohemagglutinin (2 μg/mL) and cultured in RPMI 1640 medium supplemented with 15% fetal bovine serum (FBS) and human recombinant interleukin 2 (IL-2, 30 units/mL). After 3 days PBMCs ($2\times10^5$ cells/well) were infected with various isolates of HIV-1 at a multiplicity of infection (MOI) of 0.01. After 2 hours at 37° C. cells were washed and treated with various concentrations of T30177 or AZT, as described by Buckheit and Swanstrom, id. (1991). The medium was changed on day 3 or 4 post-infection and fresh drug was added at these times. Seven days after infection, HIV-1 replication was analyzed using the Coulter p24 antigen-capture assay. Assays were performed in triplicate. Data was obtained by spectrophotometric analysis at 40 nm using a Molecular Devices Vmax plate reader.

HIV-1 infection of PBLs

Human peripheral blood lymphocytes (PBLs) were isolated from blood drawn from HIV-1 and HBV seronegative donors. PBLs were isolated by Ficoll-Hypaque density gradient centrifugation. The PBLs were suspended in culture medium (RPMI 1640 medium supplemented with 2 mM L-glutamine, 20% FBS and 50 μg/mL gentamicin) and the cells counted using the trypan blue exclusion technique. After adjustment of cell density to $1\times10^7$ cells per mL with culture medium, the suspension was placed in a T-75 culture flask and incubated flat at 37° C. in a humidified atmosphere of 5% $CO_2$ for 2 hours. The non-adherent cell population was decanted into a sterile disposable flask. Phytohemagglutinin (PHA-P) was added to the PBL suspension at a concentration of 2 μg/mL and the PBl preparation was then further incubated at 37° C. for 48 hours. At this time an aliquot of the culture was used for virus infectivity studies. PBLs ($5\times10^5$ cells/well) were infected with HIV-1 isolates at an MOI of 0.2. This level of infection yielded a satisfactory virus control RT activity value result at day 7 post-infection (Buckheit, et al., id. (1991)). Two hours post-infection, the cells were separated from the virus by centriguation, washed twice with culture medium, and suspended in culture medium containing IL-2 at a concentration 30 units/mL and at a cell density $2 \times 10^5$ PHA-P-stimulated PBL cells/0.1 mL of culture medium. Seven day post-infection, HIV-1 replication was analyzed using either the RT or p24 assay systems. Data was obtained in the p24 assays by spectrophotometric analysis at 450 nm using a Molecular Devices Vmax plate reader.

Inhibition of acute infection of primary human macrophages

Human macrophage cultures were established as described by Crow et al. Crowe, et al., *AIDS Research and Human Retroviruses* 3(2):135–145 (1987). Briefly, PBMC's isolated from HIV-1 and HBV seronegative donors was allowed to adhere to glass at 37° C. for two hours in calcium and magnesium free PBS (pH 7.4). The non-adherent cells were aspirated and the adherent cells were washed three times with cold PBS. The adherent macrophages were scraped free from the plate, counted, and inoculated into 96 well plates at a concentration of $10^5$ cells/well in RPMI 1640 medium supplemented with 10% human serum. The macrophages were cultivated in RPMI 1640 with 10% human serum. After incubation overnight at 37° C. the macrophages were infected with HIV-$1_{DV}$ at a multiplicity of infection of 0.1 for 24 hours at 37° C. in the presence of the indicated amount of drug. Unabsorbed virus was then washed off and the cells were further incubated for 7 days at 37° C. in complete medium supplemented with the indicated amount of drug. On day 7 post-infection the adherent macrophages were washed extensively with PBS and lysed with detergent. Cytoplasmic HIV p24 levels were then quantitated and percent inhibition were calculated and compared to control infected but untreated cells.

Long term suppression studies

Long term suppression assays were performed in MT-4 cells infected with HIV-$1_{MB}$ (MOI of 0.01) using drug concentrations representing 1, 10 or 100-fold over the median $IC_{50}$ value for each compound. Four days post-infection, cells were washed twice with phosphate-buffered saline (PBS) and resuspended in complete medium without drug (day 0). Viral breakthrough was monitored at several time points by measurement of viral p24 antigen production in the culture medium or the presence of intracellular viral DNA as described previously, (Rando, et al, *J. Biol. Chem.* 270:1754–1760 (1995)).

Other viral assays

Respiratory syncytial virus (RSV strain A2), and influenza A (FLUA strain H3N2) virus assays were performed as described by Wyde et al. (Wyde, et al., Drug. Dev. Res. 28:467–472 (1993)) while Herpes Simplex viruses types 1 and 2 (HSV-1, HSV-2) plaque reduction assays were performed as previously described. Lewis, et al, *Antimicrob. Agents Chemother.* 38:2889–2895 (1994). Vesicular stomatitis virus (VSV), Vaccinia virus, Sindbis virus, Coxsackie virus B4, Polio virus-1, and Semliki forest virus assays were performed as described by De Clercq. De Clereq, E., *Antimicrob. Agents Chemother.* 28:84–89 (1985). The arenaviridae assays (Junin and Tacaribe viruses) were performed as described by Andrei and De Clercq. Andrei, et al., *Antiviral Res.* 14:287–299 (1990). Punta Toro virus (ATCC VR-559) and Yellow fever virus (vaccine strain 17D) assays were performed using Vero cells.

Flow cytometric analysis of HIV-1 infected lymphocytes

Seven days post-HIV-1 infection of PBMCs, the infected cell culture medium was analyzed for HIV-1 production using the p24 antigen-capture assay. In addition, cells from both the drug treated and control wells were analyzed for CD4 and CD8 antigens by cytofluorometry. Briefly, cells were washed and treated with fluorochrome-labeled monoclonal antibodies to CD4 or CD8 (Becton Dickinson). The cells were washed again and fixed with 2% paraformaldehyde before analysis. Crissman, et al., *Flow Cytometry and Sorting*, p. 229–230 (1990) and Crowe et al., *AIDS Res. Hum. Retroviruses* 3:135–145 (1987).

Single cycle analysis of mHV-1 cDNA

CEM-SS cells ($2 \times 10^6$ cells/well) in 0.5 mL of complete medium were infected with HIV-$1_{SKI}$ at a MOI of 1.0 for 45 minutes on ice at which time complete culture medium (10 mL) was added to the cells. The infected cells were then pelleted (1000 RPM for 10 min. at 4° C.), washed twice and aliquoted into a 24-well flat bottom plate ($2 \times 10^5$ cells/well). The indicated amount of drug was added to the infected cell cultures at various times during or post-infection. The cells were harvested 12 hours post-infection at which time cell pellets were lysed in 100 µL polymerase chain reaction (PCR) lysis buffer (50 mM KCl, 10 mM Tris-HCl (pH8.3), 2.5 mM $MgCl_2$, 0.1 mg/mL gelatin, 0.45% Nonidet P40, 0.45% Tween 20 and 75 µg/mL Proteinase K) at 50° C. for one hour followed by 95° C. for 10 minutes. The lysate was stored at −20° C. until use.

PCR analysis of viral cDNA was performed using 10 µL of total cell lysate in a 100 µL reaction buffer as previously described (Rando, et al, *J. Biol. Chem.* 270:1754–1760 (1995)). The primers used were 5'-ATAATCCACCTATCCCAG TAGGAGAAAT-3' and 5'-TTTGGTCCTTGTCTTATGTCCAGAATCG-3' which will amplify a 115 bp segment of the HIV-1 genome. The cycle conditions used were 95° C. for 10 minutes to denature the DNA, followed by 30 cycles of 95° C. for 75 seconds, 60° C. for 75 seconds, and a final extension step at 60° C. for 10 minutes. Thirty µL of the amplification reaction were mixed with 10 ul of $\tau$-$^{32}$P-labeled internal probe (5'-ATCCTGGGATTAAATAAAATAGTAAGAATGTATAG-CCCTAC-3'), placed at 95° C. for 7.5 minutes and then annealed at 55° C. for 15 minutes. The resultant products were separated by electrophoresis on a 10% polyacrylamide gel.

Analysis of viral replication

CEM-SS cells ($2 \times 10^7$) were infected with HIV-$1_{SKI}$ (MOI of I) for 45 minutes at 37° C. with gentle mixing. Following virus attachment, the cells were gently pelleted, washed twice and resuspended in complete tissue culture medium. The cells were then divided into aliquots, treated with various concentrations of drug and placed in T75 culture flasks. The cells were incubated at 37° C. for 18–20 hours and then harvested by centriguation. To extract nucleic acids for analysis of HIV-1 integration low- and high-molecular weight DNA were prepared from HIV-1 infected cells (untreated or treated with increasing concentrations of drug) according to the protocol originally described by Hirt (Hirt, B. J., *J. Mol. Biol.* 26:365–369 (1967)) and modified by Gowda et al. Gowda, et al., *J. Immunol.* 142:773–780 (1989).

DNA (300 ng), obtained from the low-molecular weight Hirt fractions, was used as the template in PCR analysis undergoing a 30 cycle amplification reaction using the conditions described by Steinkasserer et al. (Steinkasserer, et al., *J. Virol.* 69:814–824 (1995)). PCR primer sets included control primers for the amplification of mitochondrial DNA (sense, 5'-GAATGTCTGCACAGCCACTTT-3'; antisense, 5'-ATAGAAAGGCTAGGACCAAAC-3'; amplified product, 427 bp); primers for the detection of early viral transcription events (M667 and AA55 primers as described by Zack et al. (Zack, et al., *Cell* 61:213–222 (1990)), amplified product, 142 bp); primers for the detection of the viral gag gene (sense, 5'-AGTGGGGGGACATCAAGCAGCCATGCAAAT-3';

antisense, 5'-TTTGGTCCTTGTCTTATGTCCAGAATG-3', amplified product 300 bp); and primers for the detection of circular proviral DNA (sense, 5'-CCTTTTAGTCAGTGTGGAAAATCTCTAGCA-3'; antisense, 5'-CAG TGGGTTCCCTAGTTAGC-3', amplified product, 536 bp). PCR products were separated by agarose gel electrophoresis and visualized by ethidium bromide staining.

Reverse transcriptase enzyme inhibition assays

Purified recombinant RT (HIV-$1_{BH10}$) was obtained from the University of Alabama, Center for AIDS research. The enzyme assays utilized three different template:primer systems, primed ribosomal RNA, gapped duplex DNA, and poly(rA)p(dT)$_{12-18}$ to evaluate the inhibition of HIV-1 RT as described by White et al. (White, et al., *Antiviral Res.* 16:257–266 (1991), and Parker et al. (Parker, et al., *J. Biol. Chem.* 266:1754–1762 (1991)).

Integrase enzyme assays

Purified recombinant HIV-1 integrase enzyme (wild-type) was a generous gift from Dr. R. Craigie, Laboratory of Molecular Biology, National Institute of Diabetes and Digestive and Kidney Diseases. The enzyme (0.25 μM) was preincubated in reaction buffer at 30° C. for 30 minutes. All 3'-processing and strand-transfer reactions were performed as described previously by Fresen et al. (Fresen, et al., *Proc. Natl. Acad. Sci. USA* 90:2399–2403 (1993)) and Mazumder et al. (Mazumder, et al., *Proc. Natl. Acad. Sci. USA* 91:5771–5775 (1994)). Enzyme reactions were quenched by the addition of Maxam-Gilbert loading dye, and an aliquot was electrophoresed on a denaturing 20% polyacrylamide gel. Gels were then dried and subjected to autoradiography using Kodax XAR-2 film or exposed in a Molecular Dynamics Phospholmager cassette.

Protease assays

HIV-1 protease enzyme (Bachem) was diluted to 166 ug/mL in 50 mM NaOAc, 5 mM DTT, 2 mM EDTA, and 10% glycerol (pH 5.0) and stored as 10 ul aliquots at −20° C. HIV protease substrate I (Molecular Probes) was diluted to a working concentration of 0.32 nmol/μL. Enzyme (20 μL), substrate (20 μL) and drug (20 μL) were added to each well of a microtiter plate. Positive and negative controls were evaluated in parallel. Fluorescence was quantitated on a Labsystems Fluoroskan II using 355 nm for excitation and 460 nm emission wavelengths at 37° C. at time zero and at 30 minute intervals for 2 hours.

HeLa-CD4-β-galactosidase cell assays

Two different assays using genetically engineered HeLa cells were performed as described previously. Buckheit, et al., *AIDS Research and Human Retroviruses* 10: 1497–1506 (1994). These assays utilized the HeLa-CD4-LTR-β-galactosidase cell line (Kimpton, et al., *J. Virol.* 66:2232–2239 (1992)), which employ a tat protein-induced transactivation of the β-galactosidase gene driven by the HIV-1 long terminal repeat (LTR). One assay involved infecting the HeLa-CD4LTR-β-galactosidase cells with HIV-1 while the second assay monitored the expression of β-galactosidase after incubation of the HeLa-CD4-LTR-β-galactosidase cell with HL2/3 cells. Buckheit, et al., *AIDS Research and Human Retroviruses* 10:1497–1506 (1994); Ciminale, et al., *AIDS Research and Human Retroviruses* 6:1281–1287(1990). The HL2/3 cells express both the HIV-1 envelope glycoprotein and tat gene product so that co-cultivation of these cells with the HeLa-CD4-LTR-β-galactosidase cells would allow for CD4- and gp120-mediated cell fusion. The extent of cell fusion can then be monitored by the degree of tat transactivation of LTR-driven β-galactosidase expression. Buckheit, et al., *AIDS Research and Human Retroviruses* 10:1497–1506 (1994); Ciminale, et al., *AIDS Research and Human Retroviruses* 6:1281–1287 (1990).

Results of the In Vitro HIV Inhibition Studies

As described above, the anti-HIV-1 activity, in cell culture assays of the oligonucleotide (I100-15) (SEQ. ID. NO. 33) composed entirely of G and T was established by the inventors. See also, Ojwang, et al., *J. AIDS* 7:560–570 (1994); Rando, et al, *J. Biol. Chem.* 270:1754–1760 (1995). I100-15 (SEQ. ID. NO. 33) was found to inhibit HIV-$1_{DV}$ in SUP T1 cells with a median inhibitory concentration (IC$_{50}$) of 0.125 μM. I100-15 (SEQ. ID. NO. 33) was synthesized with an unmodified (natural) PD internucloeside linkage and a propanolamine group attached to the 3'-terminus to increase the stability of the oligonucleotide. T30177, a modified variant of I100-15 (SEQ. ID. NO. 33), has the same sequence as I100-15 (SEQ. ID. NO. 33) but contains an hydroxyl moiety at its 3'-terminus and a single PT internucleoside linkage at both the 5'- and 3'-ends.

Cytotoxidty Assays

The cytotoxicity of T30177 was determined using several different cell lines and primary human cells as described above. The TC$_{25}$, TC$_{50}$ and TC$_{95}$ values obtained are shown in Table B-1. The cytotoxicity profile obtained for log phase growing cells was variable depending upon the cell line used, while the slower growing PBMCs, PBLs, and macrophages all tolerated the compound at concentrations exceeding 100 μM as monitored using the trypan blue exclusion, [³H]thymidine uptake, or [³H]leucine uptake techniques.

TABLE B-1

Cytotoxicity of T30177 in established cell lines and primary cells.

| | | CYTOTOXICITY (μM)[a] | | |
|---|---|---|---|---|
| | Cell Type | TC$_{25}$ | TC$_{50}$ | TC$_{95}$ |
| Cell Lines[b] | CEM-SS | 50.8 ± 3.2 | 92.0 ± 3.0 | >100 |
| | MT4 | 34 ± 4.0 | 70 ± 7.1 | >100 |
| | CEMx174 | 10 ± 2.5 | 50 ± 5.2 | >100 |
| | MT2 | 27 ± 3.5 | 61.2 ± 5.5 | >100 |
| | AA5 | 45.66 ± 2.0 | 94.2 ± 3.1 | >100 |
| | U937 | >100 | >100 | >100 |
| | Vero | >100 | >100 | >100 |
| | NIH3T3 | >100 | >100 | >100 |
| Primary human cells[c] | PBLs | >100 | >100 | >100 |
| | PBMC | >100 | >100 | >100 |
| | Macrophages | >100 | >100 | >100 |

[a]TC$_{25}$, TC$_{50}$, and TC$_{95}$ values are the concentrations of T30177 required to inhibit 25%, 50% and 95% of growth (cell lines) or cell survival (primary human cells).
[b]The cytotoxicity of T30177 in human cell lines was determined using log phase growing cells.
[c]The cytotoxicity of T30177 in primary human cells was determined using trypan blue exclusion technique or by measuring the uptake of [³H] thymidine or [³H]leucine on slow growing primary cells.

Inhibition of Viral Replication in Cell Lines

CEM-SS cells were infected with HIV-$1_{RF}$ at an MOI of 0.01 and treated with T30177 (pPT variant of SEQ. ID. NO. 33, i.e., having part phosphorothiodiester linkages and part phosphodiester linkages, AZT or ddC for six days. In this assay system T30177 inhibited HIV-$1_{RF}$ replication in a dose-dependent manner with an IC$_{50}$ value of 0.075 μM while the control drugs, AZT and ddC, had IC$_{50}$ values of 0.007 and 0.057 μM respectively (FIG. 16). T30177 was then assayed against additional strains of HIV-1 in a variety of different cell lines. The results from these assays showed that the degree of inhibition observed for each strain of HIV-1 analyzed was greatly influenced by the cell line used (Table B-2). In addition, as observed for DS5000, T30177 was inhibitory for the AZT-resistant strain of HIV-1 tested (ADP/141) which has four mutations in its RT gene (67N, 70R, 215F and 219Q).

TABLE B-2

Inhibitory effects of T30177, AZT, and DS500 on viral replication.

| Virus | Cell Line | T30177 | IC$_{50}$($\mu$M)$^a$ AZT | DS5000$^b$ |
|---|---|---|---|---|
| HIV-1 strains$^c$ | | | | |
| SKI | CEM-SS | 0.025 ± 0.006 | 0.022 ± 0.0001 | — |
|  | MT2 | 0.06 ± 0.001 | 0.66 ± 0.005 | — |
| RF | CEM-SS | 0.075 ± 0.0002 | 0.007 ± 0.0002 | — |
|  | MT2 | 0.270 ± 0.04 | 0.03 ± 0.005 | — |
|  | MT4 | 0.037 ± 0.03 | — | 0.018 ± 0.02 |
| DV | SUP T1 | 0.06 ± 0.004 | 0.03 ± 0.005 | — |
| IIIB | CEM-SS | 2.83 ± 0.17 | 0.002 ± 0.0003 | — |
|  | MT2 | 1.94 ± 0.12 | 0.01 ± 0.004 | — |
|  | MT4 | 0.15 ± 0.02 | — | 0.034 ± 0.016 |
|  | SUP T1 | 0.6 ± 0.06 | 0.03 ± 0.006 | — |
|  | AA5 | <0.32 | <0.003 | — |
| ADP/141 | MT4 | 0.27 ± 0.05 | — | 0.032 ± 0.008 |
| HIV-2/SIV strains | | | | |
| HIV-2$_{ROD}$ | MT4 | 27.5 ± 11.6 | — | 0.082 ± 0.088 |
| HIV-2$_{EHO}$ | MT4 | 5.98 ± 1.05 | — | 0.084 ± 0.086 |
| SIV$_{MAC251}$ | MT4 | 1.5 ± 1.2 | — | 0.548 ± 0.48 |

$^a$The IC50 value is the concentration of drug required to inhibit virus production by 50%. The results presented are the averages of three or more experiments.
$^b$For DS5000 the $\mu$M units are an approximation based upon the average molecular weight (5000) of the material used in these studies.

T30177 was also tested for its ability to inhibit laboratory strains of HIV-2 and SIV. The results (Table B-2) from these assays indicate that T30177 is more active against the strains of HIV-1 and SIV tested than against the two strains of HIV-2 tested (ROD and EHO). In addition, T30177 was found to be inactive against a variety of enveloped and nonenveloped viruses tested (Table B-3) with IC$_{50}$ values found to be grater than the highest concentration of drug tested (200 $\mu$g/mL or 37 $\mu$M). This is in contrast to DS5000 which was found to be a potent inhibitor of all of the enveloped viruses tested except Vaccinia and Semliki forest viruses (Table B-3).

TABLE B-3

Inhibition of viral replication in cell lines treated with T30177 or DS5000.

| | IC$_{50}$($\mu$g/mL)$^a$ | | | |
|---|---|---|---|---|
| | T30177 | | T30177 | DS5000$^b$ |
| | DS5000 | | | |
| Envelope Viruses: | | | | |
| HSV-1 (KOS) | >200 | | 2 | 400 | >400 |
| HSV-2 (G) | >200 | | 2 | 400 | >400 |
| HSV-1 TK (B2006) | >200 | | 2 | 400 | >400 |
| HSV-1 TK (VMW1837) | >200 | | 2 | 400 | >400 |
| Sindbis virus | >200 | | 10 | ≧200 | >400 |
| Semliki forest virus | >200 | | >400 | ≧200 | >400 |
| Vesicular Stomatitis virus | >200 | | 20 | 400 | >400 |
| Vaccinia virus | >200 | | >400 | 400 | >400 |
| Punta Toro virus | >200 | | 10.9 | >200 | >400 |

TABLE B-3-continued

Inhibition of viral replication in cell lines treated with T30177 or DS5000.

| | IC$_{50}$($\mu$g/mL)$^a$ | | |
|---|---|---|---|
| | T30177 DS5000 | T30177 | DS5000$^b$ |
| Yellow Fever virus | >200 | 26 | >200 | >200 |
| RSV (A2) | >200 | 4 | >400 | >200 |
| Influenza A (H3N2) | >125 | — | >200 | >400 |
| Junin virus | >50 | 13 | >50 | >200 |
| Tacaribe | >50 | 13.5 | >50 | >200 |
| Non Enveloped Viruses: | | | | |
| Coxsackle virus (B4) | >200 | >400 | ≧400 | >400 |
| Polio virus-1 | >200 | >400 | ≧400 | >400 |

$^a$Concentration of drug required to reduce virus-induced cytopathogenicity by 50% (IC$_{50}$). The assay results are presented in $\mu$g/mL units. For T30177 5.4 $\mu$g/mL is equal to 1 $\mu$M and for DS5000 5 $\mu$g/mL is approximately equal to 1 $\mu$M.
$^b$The minimum concentration required to cause microscopically detectable alterations is normal cell morphology (MCC). The results presented are the averages of the three or more experiments.

Inhibition of HIV-1 Replication in Peripheral Blood Cells

The primary targets of HIV-1 infection in vivo are CD4$^+$ T lymphocytes and macrophages. Therefore in the following set of experiments the inventors tested the efficacy of T30177 on HIV-1 replication in PBMCs, PBLs and macrophages.

Activated PBMCs were infected with laboratory strains of HIV-1 and cultured in the presence of T30177, AZT or ddI. Treatment of infected PBMCs with T30177 inhibited the replication of the all four HIV-1 isolates tested with IC$_{50}$ values ranging from 0.12 to 1.35 $\mu$M (Table B-4). In this assay AZT was more efficacious against all HIV-1 isolates tested, on a molar scale, than T30177 while at the same time T30177 was more potent than ddI against the two HIV-1 strains tested. It is also interesting to note that HIV-1$_{IIIB}$ was more susceptible to T30177 in assays performed using PBMCs than in assays using T-cell lines (Tables B-2 and B-4).

TABLE B4

HIV-1 replication in primary human cells treated with T30177, ddI or AZT

| Virus Strains (Cells) | HIV-1 Isolate | T30177 | IC$_{50}$ $\mu$M$^a$ ddI | AZT |
|---|---|---|---|---|
| Laboratory Isolates$^b$ (PBMCs) | IIIB | 0.12 ± 0.006 | 0.74 ± 0.05 | 0.003 ± 0.0002 |
|  | JR$_{CSF}$ | 0.28 ± 0.04 | 2.0 ± 0.5 | 0.0025 ± 0.001 |
|  | RF | 0.75 ± 0.13 | ND$^c$ | 0.272 ± 0.003 |
|  | MN | 1.35 ± 0.10 | ND | 0.053 ± 0.001 |
| Clinical Isolates$^b$ (PBLs) | WEJO(SI) | 0.30 ± 0.01 | 2.18 ± 0.026 | 0.017 ± 0.0001 |
|  | BAKI(SI) | 0.23 ± 0.005 | 2.61 ± 0.003 | 0.020 ± 0.006 |
|  | WOME(SI) | 0.71 ± 0.002 | 0.41 ± 0.008 | 0.025 ± 0.0003 |
|  | ROJO(SI) | 3.9 ± 0.02 | 0.87 ± 0.001 | 0.052 ± 0.0004 |
|  | JOGA(NSI) | 0.33 ± 0.004 | ND | >1.0 |
|  | BLCH(NSI) | 3.08 ± 0.006 | ND | 0.022 ± 0.0008 |

TABLE B4-continued

HIV-1 replication in primary human cells treated with T30177, ddI or AZT

| Virus Strains (Cells) | HIV-1 Isolate | T30177 | IC$_{50}$ $\mu$M[a] ddI | AZT |
|---|---|---|---|---|
| | VIHU(NSI) | 1.3 ± 0.02 | 1.21 ± 0.009 | 0.036 ± 0.0007 |
| | S. E. Asia | 0.58 ± 0.003 | ND | 0.06 ± 0.005 |
| | N. Amer. #1 | 0.25 ± 0.003 | ND | 0.01 ± 0.004 |
| | N. Amer. #2 | 2.92 ± 0.005 | ND | 1.65 ± 0.007 |
| | 942716 | 0.86 ± 0.006 | ND | 0.002 ± 0.003 |
| | 942751 | 0.38 ± 0.003 | 2.2 ± 0.02 | 0.028 ± 0.0025 |

[a]Concentration of drug required to inhibit viral production by 50% (IC$_{50}$) was determined using the Coulter p24 antigen capture or RT assays.
[b]Antiviral assays were performed using laboratory strains of HIV-1 in peripheral blood mononuclear cells (PBMCs) or using syncytium inducing (SI) or non-syncytium inducing (NSI) clinical isolates of HIV-1 in PBLs.
[c]The value was not determined (ND).

The therapeutic potential of any anti-HIV drug is dependent upon its ability to inhibit clinical isolates of the virus obtained from different geographical locations. Therefore, the inventors evaluated the ability of T30177 to inhibit the infection of PBLs using a variety of clinical isolates of HIV-1 which were both syncytium inducing (SI) and non syncytium inducing (NSI) strains of HIV-1. In addition, the isolates used in this study had their origins in different geographic regions. After infection with HIV-1 the PBLs were cultured in the presence of T30177, AZT or ddI for seven days. T30177 inhibited the viral replication of all the HIV-1 isolates tested with IC$_{50}$ values ranging from 0.23 to 3.08 $\mu$M (Table B-4). In the same assay, AZT and ddI had IC$_{50}$ values ranging from 0.01 to 1.65 $\mu$M and 0.41 to 2.61 $\mu$M, respectively. It is important to note that T30177 was active against both NSI and SI isolates and was very active against he JOGA isolate which was obtained from a pediatric patient. The JOGA isolate was also observed to be relatively resistant to AZT treatment (Table B-4).

Another major target cell of HIV-1 infection is the macrophage. Fully differentiated macrophages were infected with HIV-1$_{DV}$ and treated with T30177 or AZT. T30177 significantly inhibited HIV-1 replication in macrophages (FIG. 17). However, due to the long exposure of cells to virus (24 hours), T30177 and AZT worked best when administered at concentrations above the IC$_{50}$ values obtained for these drugs in assays performed in established cell lines.

Variations in Viral MOI

To investigate the effect of variations in the MOI on the anti-HIV-1 activity of T30177, CEM-SS or MT4 cells were infected with various MOIs of HIV-1$_{RF}$ or HIV-1$_{IIIB}$ (Table B-5). Unlike AZT, T30177 was much less sensitive to changes in the viral MOI. For example in these assays when the MOI of HIV-1$_{RF}$ was changed from 0.01 to 1.28, T30177 only exhibited a 14-fold increase in its IC$_{50}$ value while at the same time the IC$_{50}$ value for AZT increased over 1000-fold (Table B-5).

TABLE B-5

Effect of changes in viral multiplicity of infection (MOI) on the anti-HIV-1 activity of T30177 and AZT.

| HIV-1[b] Isolate/ Cell | Multi- plicity of Infec- tion | IC50/IC90 in 23 $\mu$M$_a$ T30177 | AZT |
|---|---|---|---|
| RF (CEM- SS) | 0.01 | 0.20/0.50 ± 0.01/0.03 | 0.01/0.19 ± 0.001/0.001 |
| | 0.02 | 0.41/1.50 ± 0.03/0.04 | 0.02/0.47 ± 0.009/0.046 |
| | 0.04 | 0.60/1.56 ± 0.01/0.02 | 0.07/0.86 ± 0.005/0.03 |
| | 0.08 | 0.70/1.56 ± 0.01/0.08 | 0.50/1.0 ± 0.01/0.005 |
| | 0.16 | 0.87/1.6 ± 0.01/0.03 | 0.6/>10.0 ± 0.05 |
| | 0.32 | 1.25/4.7 ± 0.15/0.27 | 8.5/>10.0 |
| | 0.64 | 2.64/4.75 ± 0.05/0.16 | >10.0/>10.0 |
| | 1.28 | 2.81/4.77 ± 0.04/0.06 | >10.0/>10.0 |
| IIIB (MT4) | 0.02 | 3.1/6.6 ± 0.23/0.8 | 0.037/0.22 ± 0.003 |
| | 0.01 | 2.7/9.2 ± 0.03/0.25 | 0.01/0.03 ± 0.002 |
| | 0.3 | 3.38/7 ± 0.15/0.5 | 0.15/3.3 ± 0.01/0.05 |
| | 1 | 6.8/26 ± 0.53/5.1 | 0.42/3412 ± 0.1/10 |

[a]The concentration of drug needed to limit virus production by 50 (IC50) and 90 (IC90) percent as measured in the cpe assay
[b]The strain of HIV-1 and cell line used for each assay is indicated.

Effect of T30177 on CD4 and CD8 T-cell Subsets

One of the principal immunological markers correlated with progression to AIDS is the decline in T lymphocytes which express the CD4 cell determining marker (CD4). The change in CD4$^+$ T-lymphocytes is usually monitored by noting changes in the ratio of CD4$^+$ to CD8$^+$ lymphocytes in the blood. To determine the effect of T30177 treatment on the CD4/CD8 ratio, CD4 and CD8 antigen expression was analyzed on the surface of cultured PBMCs seven days post-infection with either laboratory strains or clinical isolates of HIV-1. In these experiments treatment with either AZT or T30177 increased the number of CD4$^+$ T-cells in the cell culture, relative to untreated infected cultures (Table B-6). The observed increase in CD4$^+$ cells was dependent on the drug concentration used and was inversely correlated with the level of virus production (FIGS. 16 and Tables B-2 and B-4). These results suggest that the blockage of HIV-1 replication parallels the suppression of the cytopathic effects of the virus in primary human lymphocytes.

TABLE B-6

Effect of T30177 or AZT on the ratio of CD4/CD8 lymphocytes in HIV-1 infected PBMCs[a].

| HIV-1 Strains | Drug Conc. | % CD4 | % CD8 | CD4/CD8 Ratio | HIV-1 Isolates | Drug Conc. | % CD4 | % CD8 | CD4/CD8 Ratio |
|---|---|---|---|---|---|---|---|---|---|
| No Virus | No Drug, Day 0 | 39% | 80% | 0.49 | No Virus | No Drug, Day 0 | 39% | 80% | 0.49 |
| | No Drug, Day 7 | 45% | 71% | 0.63 | | No Drug, Day 7 | 45% | 71% | .063 |
| IIIB | No Drug | 1% | 98% | 0.01 | SE Asia | No Drug | 2% | 99% | 0.02 |
| | 0.1 $\mu$M AZT | 31% | 79% | 0.39 | | 0.1 $\mu$M AZT | 29% | 82% | 0.35 |
| | 1.0 $\mu$M AZT | 30% | 81% | 0.37 | | 1.0 $\mu$M AZT | 31% | 82% | 0.38 |
| | 5.0 $\mu$M AZT | 27% | 86% | 0.31 | | 5.0 $\mu$M AZT | 29% | 86% | 0.34 |
| | 0.1 $\mu$M T30177 | 1% | 98% | 0.01 | | 0.1 $\mu$M T30177 | 2% | 99% | 0.02 |
| | 1.0 $\mu$M T30177 | 18% | 85% | 0.21 | | 1.0 $\mu$M T30177 | 12% | 90% | 0.13 |

TABLE B-6-continued

Effect of T30177 or AZT on the ratio of CD4/CD8 lymphocytes in HIV-1 infected PBMCs[a].

| HIV-1 Strains | Drug Conc. | % CD4 | % CD8 | CD4/CD8 Ratio | HIV-1 Isolates | Drug Conc. | % CD4 | % CD8 | CD4/CD8 Ratio |
|---|---|---|---|---|---|---|---|---|---|
|  | 5.0 μM T30177 | 27% | 83% | 0.33 |  | 5.0 μM T30177 | 29% | 82% | 0.35 |
|  | 10.0 μM T30177 | 27% | 83% | 0.33 |  | 10.0 μM T30177 | 29% | 82% | 0.35 |
| MN | No Drug | 6% | 96% | 0.06 | N. Amer. #1 | No Drug | 28% | 79% | 0.35 |
|  | 0.1 μM AZT | 25% | 82% | 0.30 |  | 0.1 μM AZT | 25% | 83% | 0.30 |
|  | 1.0 μM AZT | 35% | 79% | 0.44 |  | 1.0 μM AZT | 25% | 84% | 0.30 |
|  | 5.0 μM AZT | 36% | 78% | 0.46 |  | 5.0 μM AZT | 26% | 85% | 0.31 |
|  | 0.1 μM T30177 | 5% | 95% | 0.05 |  | 0.1 μM T30177 | 21% | 84% | 0.25 |
|  | 1.0 μM T30177 | 18% | 86% | 0.21 |  | 1.0 μM T30177 | 26% | 80% | 0.33 |
|  | 5.0 μM T30177 | 25% | 81% | 0.31 |  | 5.0 μM T30177 | 27% | 81% | 0.33 |
|  | 10.0 μM T30177 | 26% | 80% | 0.33 |  | 10.0 μM T30177 | 29% | 81% | 0.36 |
| RF | No Drug | 14% | 89% | 0.16 | N. Amer. #2 | No Drug | 4% | 97% | 0.04 |
|  | 0.1 μM AZT | 23% | 84% | 0.27 |  | 0.1 μM AZT | 6% | 95% | 0.06 |
|  | 1.0 μM AZT | 32% | 76% | 0.42 |  | 1.0 μM AZT | 13% | 89% | 0.15 |
|  | 5.0 μM AZT | 34% | 81% | 0.42 |  | 5.0 μM AZT | 25% | 85% | 0.29 |
|  | 0.1 μM T30177 | 10% | 92% | 0.11 |  | 0.1 μM T30177 | 4% | 98% | 0.04 |
|  | 1.0 μM T30177 | 26% | 82% | 0.32 |  | 1.0 μM T30177 | 5% | 95% | 0.05 |
|  | 5.0 μM T30177 | 31% | 83% | 0.37 |  | 5.0 μM T30177 | 28% | 82% | 0.34 |
|  | 10.0 μM T30177 | 29% | 85% | 0.34 |  | 10.0 μM T30177 | 27% | 84% | 0.32 |

[a]The percentage of CD4 and CD8 antigen bearing T-cells in the HIV-1 infected PBMC population was determined by flow cytometric analysis of cells treated with fluorescein labeled a-CD4 or a-CD8 monoclonal antibodies.

In vitro some HIV-1 isolates infect CD4+ lymphocytes, shed infectious virus into the culture medium but do not cause destruction of the infected cells. Garry, R. F., AIDS 3:683–694 (1989). This may explain results obtained when the inventors used the North American isolate number 1 (N. Amer. #1, Table B-5). When this virus was used to infect PBMC's, in the absence of drug, a CD4/CD8 ratio of 0.35 was observed 7 days post-infection. At the same time analysis of the culture medium from cells infected with this isolate revealed the presence of viral p24 antigen (Table B-4) which suggested that a productive viral infection had occurred.

Time of drug addition studies

T30177, DS5000 or AZT was added to MT-4 cells infected with HIV-1$_{IIIB}$ (MOI of 1) at various times post-infection. Test compounds were added at a concentration 100-fold higher than the determined IC$_{50}$ value for each drug in the standard assay performed using MT-4 cells and the IIIB strain of HIV-1 (Table B-2). Viral p24 antigen levels were monitored 29 hour post-infection. The results of this assay indicate that postponing the addition of T30177 for one hour was enough to dramatically reduce the inhibitory effects of this compound in a fashion similar to that of DS5000 and clearly different from AZT which lost its protective capacity when added to the cell culture medium 3 or 4 hours post-infection (FIG. 18). A similar result was obtained when comparing T30177 with CSB, a known inhibitor of both virus binding to cells and fusion related events (Clanton, et al., J. Aids 5:771–781 (1992)), in that the antiviral activity of both T30177 and CSB was greatly reduced if added to infected cell cultures one hour post-virus infection (data not shown).

HeLa-CD4β-galactosidase cell studies

To differentiate the effects of T30177 on early events in the viral life cycle, through integration and subsequent production of the tat gene product, from the inhibition of HIV-1 gp 120-mediated cell fusion two experimental protocols were employed. The first protocol monitored the effects of the drug on the ability of HIV-1$_{RF}$ to infect and/or replicate within HeLa-CD4-LTR-β-galactosidase cells and was performed as described in Methods. In this experiment drug interdiction at any step in the viral life cycle through the production of the tat gene product would cause a decrease in expression of the β-galactosidase gene, the transcription of which is regulated by the HIV-1 LTR. The results show that T30177 is a potent inhibitor of β-galactosidase production in this assay with an IC$_{50}$ value of 0.009 μM, while the IC$_{50}$ value obtained for CSB in the same experiment was 0.26 μM (FIG. 19A). In control experiments T30177 had no observable direct effect on β-galactosidase enzyme activity at concentrations up to 10 μM (data not shown).

The second protocol used was a virus-free assay designed to monitor CD4- and gp120-mediated cell fusion events. In this assay T30177 was able to interfere with the fusion process (FIG. 19B). However, the observed IC$_{50}$ value (1 μM) was approximately 100-fold higher than that needed to interfere with β-galactosidase production in the virus infection assay (FIG. 19A). In the same assay system the IC$_{50}$ value observed for CSB increased approximately 3-fold to 0.8 μM over the concentration needed to interrupt β-galactosidase production in the virus infection assay (FIG. 19).

The three-dimensional structure of an oligonucleotide with the sequence of T30177 is stabilized by the formation of an intramolecular G-octet, (Rando, et al, J. Biol. Chem. 270:1754–1760 (1995)). Previously the inventors have reported how the replacement of one of the Gs involved with tetrad formation with a deoxyadenosine (A) reduced the anti-HIV-1 activity of the resultant molecule. Rando, et al, J. Biol Chem. 270:1754–1760 (1995). To determine the effects of intramolecular tetrad formation in T30177 on the observed inhibition of β-galactosidase production in the two assays presented in FIG. 19, the inventors tested T30526, an oligonucleotide in which a dA has been substituted for a dG at a position that would interrupt the formation of one of the two tetrads involved in the G-octet. T30526 has the same partial PT patterns as T30177 (Table B-7). T30526 has the same partial PT pattern as T30177 (Table B-7). T30526 was found to be approximately 100-fold less potent that T30177 in inhibiting HIV-1$_{RF}$ production in culture assays (Table B-7), 10–15-fold less potent at inhibiting virus-infected cell β-galactosidase production (FIG. 19A) and did not inhibit cell fusion at the highest concentration of drug tested (20 μM, FIG. 19B).

TABLE B-7

Inhibition of various HIV-1 strains in culture assays and the HIV-1 integrase enzyme in vitro.

| Compound | nucleotide sequence | backbone[c] | Antiviral Assay[a] $IC_{50}(\mu M)$ RF | SKI | IIIB | Anti-Integrase Assay[b] $IC_{50}\mu M)$ 3'-proc | strand tran. |
|---|---|---|---|---|---|---|---|
| G-Octet anti-HIV-1: | | | | | | | |
| T30175 | 5'-GTGGTGGGTGGGTGGGT-3' | PD | 6.58 | — | — | 0.170 | 0.125 |
| T30177 | 5'-GTGGTGGGTGGGTGGGT-3' | pPT | 0.075 | 0.025 | 2.83 | 0.092 | 0.046 |
| T30038 | 5'-GTGGTGGGTGGGTGGGT-3' | PT | 0.030 | — | — | 0.090 | 0.070 |
| T30526 | 5'-GTGATGGGTGGGTGGGT-3' | pPT | 11.7 | — | — | 0.200 | 0.123 |
| G-Octet thrombin binding: | | | | | | | |
| T30340 | 5'-GGTTGGTGTGGTTGG-3' | PD | > | — | — | >0.50 | >0.5 |
| T30659 | 5'-GGTTGGTGTGGTTGG-3' | pPT | 100.0 | 2.81. | >20.0 | >0.50 | >0.5 |
| T30341 | 5'-GGTTGGTGTGGTTGG-3' | PT | >20.0 | — | — | 0.042 | 0.023 |
| | | | 4.76 | | | | |
| Antisense, Anti-HIV-1: | | | | | | | |
| T30658 | 5'-TCTTCCTCTCTCTACCCACGCTCIC-3' | PD | >20.0 | >20.0 | >20.0 | >0.5 | >0.5 |
| T30662 | | pPT | >20.0 | >20.0 | >20.0 | >0.5 | >0.5 |
| T30531 | 5'-TCTTCCTCTCTCTACCCACGCTCIC-3' | PT | 0.17 | — | — | 0.030 | 0.036 |
| | 5'-TCTTCCTCTCTCTACCCACGCTCIC-3' | | | | | | |
| Control Compounds: | | | | 0.007 | 0.022 | 0.002 | >1.0 | >1.0 |
| AZT | | | 0.016 | — | 0.031 | 0.07 | 0.06 |
| DS500[d] | | | 0.057 | 0.26 | 0.078 | >1.0 | >1.0 |
| ddC | | | 0.02 | 0.09 | 0.09 | — | — |
| UC38 | | | 1.7 | 1.6 | 0.6 | — | — |
| CSB | | | | | | | |

[a]Antiviral assay results were obtained from infection of CEM-SS or MT4 cells with the indicated virus strain. The results are the averages of three or more experiments.
[b]Anti-integrase results were obtained from experiments designed to monitor the 3'-processing or strand-transfer activities of the enzyme, the results presented are the averages of three or more experiments.
[c]Oligonucleotides were synthesized with either total phosphodiester (PD) backbone, total phosphorothioate (PT) backbone, or partial phosphorothioate (pPT) backbone, in which the 5'-and 3'-penultimate internucleoside linkages were phosphorothioate.
[d]For DS5000 the μM units are an approximation based upon the average molecular weight (5000) of the material used in these studies.

Long term suppression of HIV-1

In separate experiments, HIV-1$_{IIIB}$ infected MT-4 cells were treated with T30177, AZT, DS5000, or the bicyclam compounds JM2763 or JM3100 for four days using drug concentrations equivalent to 1, 10 or 100-fold over their respective IC$_{50}$ values (Table B-7). The IC$_{50}$ values used for JM2763 and JM3100 were from previously reported results, (De Clereq, et al., Antimicrob. Agents Chemother. 38:668–674 (1994)). After four days in culture the cells were washed and then further cultured in complete medium without drug. The cells were monitored daily for the appearance of viral-induced syncytium formation and every second or third day for viral p24 antigen in the culture medium. In cells treated with T30177, at 100-fold over the IC$_{50}$ value (approximately 10 μM), suppression of virus P24 production was observed for at 1st 27 days after removal of drug from the infected cell culture (FIG. 20). Furthermore, there was no detectable viral cDNA (by PCR analysis) in cells examined up to 11 days after the removal of T30177 from the infected cell culture (data not shown). Cells treated in the same fashion with AZT, DS5000, JM2763, or JM31000 had measurable levels of viral p24 antigen in the culture medium within 3 days after removal of the drug (FIG. 20). The degree of continued suppression was contingent upon the concentration of T30177 used in the assay and the duration of the drug treatment regimen (data not shown). The concentration and duration of treatment regimen data are consistent with those previously reported for 1100–15, (Rando, et al, J. Biol. Chem. 270:1754–1760 (1995)).

To determine if exposure of cells to T30177 protects them for subsequent infection with HIV-1, cultures of HIV-1 infected MT-4 cells treated for 4 days with T30177 (100-fold over the IC$_{50}$ value) were washed and then reinfected with HIV-1$_{IIIB}$ before resuspension in fresh culture medium without drug. In these assays there was no protection of cells from the second round of viral infection (data not shown).

Single cycle analysis of viral cDNA

Total DNA from HIV-1$_{SKI}$ infected CEM-SS cells was isolated 12 hour post-infection and analyzed for the presence of viral cDNA as described in Methods. In this experiment viral cDNA was detected in cells treated with 1 or 10 μM T30177 (approximately 10- to 100-fold over the $IC_{50}$ value) even when the drug was added to the cell culture at the time of virus infection (FIG. 21). This is in contrast to the results obtained when the adsorption blocking drug CSB (10 μM), the nucleoside RT inhibitor ddC (10 μM), or the nonnucleoside RT inhibitor UC38 (1 μM) were used as control drugs. UC38 is an analog of oxathiincarboxanilide. Bader, et al., *Proc. Natl. Acad. Sci. U.S.A.* 88:6740–6744 (1991); McMahon, et al., *Proc. Natl. Acad. Sci. USA* (1995). As expected there was no detectable viral DNA in cells treated during, or very soon after, virus infection with any of the three control drugs when used at concentrations 10- to 100-fold over their reported $IC_{50}$ values (Table B-7, FIG. 21).

Analysis of replicated viral DNA

The inventors have previously reported on the presence of viral cDNA in T30177 treated SUP T1 cells 36 hour post infection with a lower MOI (multiplicity of infection of virus) of HIV-$1_{DV}$. Rando, et al, *J. Biol. Chem.* 270:1754–1760 (1995). As described above, viral cDNA was also detected in T30177 treated cells 12 hour post-infection with a high MOI of virus (FIG. 21). To determine the extent of viral replication within these cells PCR primers were used which would differentiate between the different stages of viral replication through the production of circular proviral DNA (2-LTR circles). The results of these experiments indicate that viral replication has occurred in the T30177 treated cells up to an including the production of 2-LTR circles (FIGS. 22A–D).

Inhibition of viral enzymes

Oligonucleotides with PT backbones have been reported to be much more potent inhibitors of HIV-1 reverse transcriptase (RT) than the same molecules with PD backbones. Ojwang, et al., *J. AIDS* 7:560–570 (1994). T30177 was able to inhibit HIV-1 RT however, the concentration needed to inhibit the enzyme by 50% was above 5 μM when gapped duplex DNA or RNA:DNA templates were used (Table B-8). It is interesting to note that when the primed ribosomal RNA template was used the $IC_{50}$ value for T30177 was in the 1 μM range (Table B-8).

TABLE B-8

Inhibition of recombinant HIV-1 Reverse Transcriptase.

| | $IC_{50}$(μM) | |
|---|---|---|
| Template | T30177 | AZT 5'-triphosphate |
| poly(rA) · p(dT) 12-18 | 11.0 | 0.59 |
| | 4.2 | 0.6 |
| gapped duplex DNA | 8.0 | 0.47 |
| | 10.0 | 0.40 |
| ribosomal RNA | 1.2 | 0.019 |
| | 0.36 | 0.008 |

[a]The concentration required to inhibit enzyme activity by 50% ($IC_{50}$) is given for duplicate experiments in μM units.

T30177 was also tested for its ability to inhibit HIV-1 protease and integrase enzymes. When concentrations of T30177 up to 10 μM were used in protease inhibition assays no effect on the viral enzyme was observed (data not shown). However, when assayed for its effect on HIV-1 integrase, T30177 was able to reduce both the 3'-processing and strand transfer activities of the integrase enzyme with $IC_{50}$ values of 0.092 and 0.046 μM, respectively (Table B-7).

To determine if the sequence, three dimensional structure, chemical composition of the backbone or a combination of these parameters contributed to the observed anti-integrase activity of T30177, the inventors synthesized and tested for enzyme inhibitory activity the oligonucleotides shown in Table B-7. T30038, T30175, and T30526 are variations of T30177. T30340, T30341 and T30659 are variations of the thrombin-binding aptamer sequence reported by Bock et al. Bock, et al., *Nature* 355:564–566 (1992). Both the dG-rich sequence of the anti-HIV-1 oligonucleotide T30177 and the thrombin binding aptamer have been shown to fold upon themselves to form structures stabilized by intramolecular G-octets. Rando, et al, *J. Biol. Chem.* 270:1754–1760 (1995) .; Schultze, et al., *J. Mol. Biol.* 235:1532–1547 (1994); Wang, et al., *Biochem.* 32:1899–1904 (1993). Oligonucleotides T30531, T30658 and T30662 are variations of the antisense compound GEM91 reported to be a potent inhibitor of HIV-1. Agrawal et al., *Antisense Research and Development* 2:261–266 (1992).

The $IC_{50}$ values for each of these oligonucleotides tested in the integrase assay are shown in Table B-7. The results of this experiment indicate that any of the sequence motifs tested were potent inhibitors of the HIV-1 integrase enzyme when the oligonucleotides were synthesized with a PT backbone. When the number of PT linkages in the backbone was reduced to one linkage at each end of the molecule (pPT) the thrombin binding aptamer (T30559) and the antisense sequence (T30662) no longer displayed anti-integrase activity while the level of inhibition observed using T30177 was relatively the same as that observed using the total PT version of this molecule (T30038). For compounds with total PD backbones only the total PD version of T30177 sequence motif was able to inhibit viral integrase with $IC_{50}$ values of 170 and 125 nM for the 3' processing and strand transfer enzyme activities, respectively. T30526, the tetrad-disrupted mutant version of T30177, was still able to inhibit viral integrase protein in this assay, albeit at a concentration 2- to 3-fold higher than that observed using T30177.

Conclusions of the In Vitro HIV Inhibition Studies

The inventors expanded upon the earlier observations of their initial studies (see also, Ojwang, et al., *J. AIDS* 7:560–570 (1994); Rando, et al, *J. Biol. Chem.* 270:1754–1760 (1995)) on the anti-HIV-1 activity of dG-rich oligonucleotides by demonstrating the efficacy of T30177 against multiple laboratory strains and clinical isolates of HIV-1. Using the cytotoxicity (Table B-1) and the efficacy data (Tables B-2 and B-4), it was found T30177 to have a wide range of therapeutic indices TIs) depending upon the viral strain and cell line used in a given assay. For example, when T30177 was used to inhibit HIV-$1_{SKI}$ in CEM-SS cells a TI of 3680 was obtained. However, when measuring the effect on HIV-$1_{RF}$ in MT2 cells, the TI for T30177 was only 226.

The variability in efficacy of T30177 in PBMCs and PBLs, which depended upon the clinical isolate tested, was very similar to the variation in activity observed for the nucleoside analogs AZT and ddI. It is interesting to note that an approximately 20 fold variation in the $IC_{50}$ value was observed for T30177 when used to inhibit HIV-$1_{IIIB}$ in CEM-SS cells (2.8 μM) versus PBMSc (0.12 μM) (Tables B-2 and B-3). An explanation for this observation may be that when viruses are propagated continuously in homogeneous cell lines the "adapt" to those cells and begin to display phenotypes different from low passage clinical isolates. Therefore, results obtained using clinical isolates to infect heterogeneous populations of primary cells (PBMCs or PBLs) may be more predictive of in vivo efficacy than data generated using laboratory strains of HIV-1 in established cell lines. It is unlikely that HIV-$1_{IIIB}$ is a resistant strain of HIV-1 since T30177 was more effective against this virus in PBMCs than in cell lines. However, given the well documented ability of HIV-1 to mutate and thus develop resistance to known therapies, efforts are underway to determine if resistant mutants can arise after treatment of HIV-1 infected cells with T30177.

In mechanism of action studies it was found that T30177 displayed some antiviral activity which indicated a mechanism of action similar to the known blockers of virus adsorption or virus mediated cell fusion such as dextran sulfate and CSB (FIGS. 18 and 19). Like CSB and DS5000, T30177 needed to be added to cells at the time of or soon after virus infection. However, T30177 is 100-fold less effective in inhibiting gp 120-induced cell fusion events than it is at inhibiting early events in the viral life cycle, suggesting a specific point of interdiction with virus distinct at least from that of CSB. In addition, the antiviral profile of T30177 also displayed other characteristics which distinguished T30177 from DS5000 and CSB. For example, while DS5000 is active against a wide range of enveloped viruses, T30177 appears to be a more selective inhibitor of retroviruses with maximum efficacy displayed when used to inhibit strains of HIV-1 (Tables B-2 and B-3).

Experimental results presented in FIG. 21 show that unlike control drugs CSB, AZT, and UC38, when T30177 was added to cell cultures during virus infection it was unable to completely block viral infection even when used at concentrations 100-fold over the $IC_{50}$ value (~10 $\mu$M). Furthermore, analysis of viral DNA demonstrated that viral replicative intermediates including circular proviral DNA were present in infected cells treated with T30177 (FIGS. 21 and 22). This data, coupled with the ability of T30177 to completely suppress virus outbreak (FIG. 20), and possibly clear virus from infected cell cultures, after removal of drug from infected cells (a profile not observed for AZT, DS5000, JM2763 or JM3100), suggests that a second mechanism of action, distinct from inhibition of virus binding or inhibition of cell fusion events, is at work. One possible alternative mechanism is that T30177 interferes with the viral integration process. A combination of activities including inhibition of virus attachment or internalization, virus-mediated cell fusion events and viral integration could explain the loss of virus from infected cell cultures. This typothesis is supported by the observation that T30177 is a potent inhibitor of HIV-1 integrase function in vitro (Table B-7) and by the observed accumulation of circularized proviral DNA in the low-molecular weight Hirt DNA fractions (FIG. 22).

It is clear that highly charged molecules such as DS5000 and oligonucleotides with total PT backbones are excellent inhibitors of the integrase enzyme in vitro. However, since T30177, of all the pPT molecules tested maintained its level of enzyme inhibitory activity (Table B-7), it is unlikely that the mechanism of inhibition is totally based upon a polyanion effect as seen for compounds such as DS5000 and suramin. Carteau, et al., *Arch. Biochem. Biophys.* 305:606–610 (1993). It is unclear at this time whether the G-octet structure, with the two base long dG loops, found in T30177 is of paramount importance for inhibition of viral integrase since the G-octet sequence found in T30659 did not inhibit integrase activity while T30526 (tetrad disrupting mutant) was able to inhibit enzyme activity albeit at a reduced level.

While the time of drug addition studies would suggest interference with virus internalization as a key mechanism of action for T30177 it is also clear that readily detectable viral nucleic acids do enter the cells. It is quite possible that T30177 inhibits HIV-1 via several different mechanisms of action. Another possibility is that T30177 is carried into the cell along with the infecting virus or is slow to accumulate within cells (Bishop et al. 1996 *J. Biol. Chem.* 271:56988–5703) hence the need to add drug during virus infection. Experiments designed to address these possibilities are underway.

The recently reported emergence rate of drug-resistant virus to current approved therapies for HIV-1 ($T_{1/4}$ of approximately 2 days) suggests that single drug therapy for this virus cannot succeed (Ho, et al., *Nature* 373:123–126 (1995); Wei, et al., *Nature* 373:117–122 (1995), and therefore, a likely treatment regimen for any new drug candidate would be in combination with one or more other drugs which have differing antiviral mechanisms of action. Further experimentation might determine that the actual mechanism of action for T30177 may not be via either inhibition of virus binding/internalization or inhibition of viral integration, however, it is unlikely that this oligonucleotide is acting via the same mechanism as drugs currently in use for HIV-1. In additional studies the Applicants have determined that T30177 is stable in serum and within cells, with a half-life measured in days (Bishop, et al. *J. Biol. Chem.* 1996 271:5698–5703). This information taken together with the ability of T30177 to suppress HIV-1 for over four weeks after an initial treatment regimen, in culture, makes this class of compounds an attractive candidate for development of oligonucleotide-based therapeutic agents for HIV-1.

C. Site of Activity Studies-Viral Integrase Inhibition

Next the inventors undertook studies to demonstrate the potent inhibition of HIV-1 integrase by oligonucleotides containing intramolecular guanosine quartets or octets abbreviated (G4s) and to provide better understanding of the structure-activity results from a series of these structures and the site of molecular interactions with HIV-1 integrase. The relevance of these findings with respect to HIV-1 integrase binding to its DNA substrate and to dimerization of the retroviral genome was also reviewed.

Materials Used in Site of Activity Studies

Preparation of oligonucleotide substrates and inhibitors

The following HPLC purified oligonucleotides were purchased from Midland Certified Reagent Company (Midland, Tex.): AE117, 5'-ACTGCTAGAGATTTTCCACAC-3'; AE118, 5'-GTGTGGAAAATCTCTAGCAGT-3'; AE157, 5'-GAAAGCGACCGCGCC-3'; AE146, 5'-GGACGCCATAGCCCCGGCGCGGTCGCTTTC-3'; AE156, 5'-GTGTGGAAAATCTCTAGCAGGGGCTATGGCGTC-C-3'; AE118S, 5'-GTGTGGAAAATCTCTAGCA-3'; RM22M, 5'-TACTGCTAGAGATTTTCCACAC-3'. The AE117, AE118, and the first 19 nucleotides of AE156, correspond to the U5 end of the HIV-1 long terminal repeat (LTR).

To analyze the extents of 3'-processing and strand transfer using 5'-end labeled substrates, AE118 was 5'-end labeled using $T_4$ polynucleotide kinase (Gibco BRL) and y-[$^{32P}$]-ATP (Dupont-NEN). The kinase was heat-inactivated and AE117 was added to the same final concentration. The mixture was heated at 95° C., allowed to cool slowly to room temperature, and run on a G-25 Sephadex quick spin column (Boehringer Mannheim) to separate annealed double-stranded oligonucleotide from unincorporated label.

To analyze the extent of strand transfer using the "pre-cleaved" substrate, AEl118S was 5'-end labeled, annealed to AE117, and column purified as above.

To analyze the choice of nucleophile for the 3'-processing reaction, AE118 was 3'-end labeled using $\alpha$-[$^{32P}$]-crdycepin triphosphate (Dupont-NEN) and terminal transferase (Boehringer Manheim). Engleman, et al, *Cell* 67, 1211–1221 (1991); Vink, et al., *Nucleic Acids Res.* 19, 6691–6698 (1991). The transferase was heat-inactivated and RM22M was added to the same final concentration. The mixture was heated at 95° C., allowed to cool slowly to room temperature, and run on a G-25 spin column as before.

To determine the extent of 30 mer target strand generation during disintegration, Chow, et al., *Science* 255, 723–726 (1992), AE157 was 5'-end labeled, annealed to AE156, AE146, and AE117, annealed, and column purified as above.

Oligonucleotides composed of deoxyguanosine and thymidine were synthesized, purified, and incubated with potassium ion to generate the G4s. The guanosine quartet (G4) forming structures were then purified as previously described. Rando, et al., *J. Biol. Chem.* 270, 1754–1760 (1995).

Integrase proteins and assays

Purified recombinant wild-type HIV-1 integrase, deletion mutants $IN^{1-212}$, $IN^{50-288}$, $IN^{50-212}$, Bushman, et al., *Proc. Natl. Acad. Sci. U.S.A.* 90, 3428–3432 (1993), and $IN^{1-55}$ and site-directed mutants $INF^{F185K/C280S}$ and $IN^{F185K/C280S/H12N/H16N}$ were generous gift T. Jenkins and R. Craigie, Laboratory of Molecular Biology, NIDDK, NIH, Bethesda, Md. Dr. Craigie also provided the expression system for the wild-type HIV-1 integrase. A plasmid encoding the HIV-2 integrase was generously provided by Dr. R. H. A. Plasterk (Netherlands Cancer Institutes). Purified recombinant wild-type FIV and SIV integrases were generous gifts of Drs. S. Chow (UCLA) and R. Craigie (NIDDK), respectively.

Integrase was preincubated at a final concentration of 200 (for HIV-1 and HIV-2) or 600 nM (for FIV and SIV) with inhibitor in reaction buffer (50 mM Nacl, 1 mM HEPES, pH 7.5, 50 $\mu$M dithiothreitol, 10% glycerol (wt/vol), 7.5 mM $MnCl_2$ or $MgCL_2$ (when specified), 0.1 mg/mL bovine serum albumin, 20 mM 2-mercaptoethanol, 10% dimethyl sulfoxide, and 25 mM MOPS, pH 7.2) at 30° C. for 30 minutes. When magnesium was used as the divalent metal ion, polyethylene glycol was added at a final concentration of 5% to increase activity as previously described (Engelman & Craigie, 1995). Preincubation for 30 minutes of the enzyme with inhibitor was performed to optimize increases the inhibitory activity in the 3'-processing reaction (Fesen et al., 1994). Then, 30 nM of the 5'-end $^{32}$P-labeled linear oligonucleotide substrate was added, and incubation was continued for an additional 1 hr. The final reaction volume was 16 $\mu$L.

Disintegration reactions, Chow, et al., *Science* 255, 723–726 (1992), were performed as above with a Y oligonucleotide (i.e., the branched substrate in which the U5 end was "integratred" into target DNA) was used.

Electrophoresis and quantitation

Reactions were quenched by the addition of an equal volume (18 $\mu$L) of loading dye (98% deionized formamide, 10 mM EDTA, 0.025% xylene cyanol, 0.025% brornophenol blue). An aliquot (5 $\mu$L) was electrophoresed on a denaturing 20% polyacrylamide gel (0.09 M Tris-borate pH 8.3, 2 mM EDTA, 20% acrylamide, 8M urea). Gels were dried, exposed in a Molecular Dynamics Phosphorimager cassette, and analyzed using a Molecular Dynamics phosphorimager (Sunnyvale, Calif.). Percent inhibition was calculated using the following equation:

$$100\times[1-(D-C)/(N-C)],$$

where C, N, and D are the fractions of 21 mer substrate converted to 19 mer (3'-processing product) or strand transfer products for DNA alone, DNA plus integrase, and integrase plus drug, respectively. $IC_{50}$ was determined by plotting the drug concentration versus percent inhibition and determining the concentration which produced 50% inhibition.

UV crosslinking experiments

The method used has been described by Engleman et al. Engelman, et al., *J. Virol.* 68, 5911–5917 (1994). Briefly, integrase (at the indicated concentration) was incubated with substrate in reaction buffer as above for 5 minutes at 30° C. Reactions were then irradiated with a UV transilluminator (254 mm wavelength) from 3 cm above (2.4 mW/$cm_2$) at room temperature for 10 minutes. An equal volume (16 $\mu$L) of 2×SDS-PAGE buffer (100 mM Tris, pH 6.8, 4% 2-mercaptoethanol, 4% SDS, 0.2% bromophenol blue, 20% glycerol) was added to each reaction. Twenty $\mu$L aliquots were heated at 95° C. for 3 minutes prior to loading on a 12% or 18% SDS-polyacrylamnide gel. The gel was run at 120 V for 1.5 hours, dried, and exposed in a Phosphorimager cassette. For inhibition of DNA binding experiments (FIG. 21), integrase (200 nM) was preincubated with the guanosine quartet (at the indicated concentration) for 30 minutes at 30° C. prior to the subsequent addition of the radiolabeled viral DNA substrate (20 nM). For the competition experiments (FIG. 29), integrase (200 nM) was pre-incubated with either the radiolabeled viral DNA substrate (20 nM) or T30177 (20 nM) for 5 minutes at 30° C. prior to the addition of competitor DNA at the indicated concentration.

Results of the Site of Activity Studies

Guanosine quartet oligonucleotides inhibit HIV-1 integrase

The inhibition of HIV-1 integrase by a series of oligonucleotides which can form G4s is shown in FIG. 23. Oligonucleotides T30177 and T30659 (a variant of the thrombin binding optimer shown in Table C-1)(Ojwang, et al., *Antimicrob. Agents Chemother.* 39, 2426–2435 (1995)) fold upon themselves into structures stabilized by two G4s stacked upon each other to form a guanosine octet (Rando, et al., *J. Biol. Chem.* 270, 1754–1760 (1995); Schultze, et al., *J. Mol. Biol.* 235, 1532–1547 (1994)). Interestingly, T30177 (SEQ ID NO.87) is active against HIV-1 in cell culture and against purified HIV-1 integrase in vitro (Ojwang, et al., *Antimicrob. Agents Chemother.* 39, 2426–2435 (1995)) while T30659 (SEQ ID NO.53) is not. For example, inhibition of both the 3'-processing and strand transfer activities of HIV-1 integrase (FIGS. 23A) by T30177 was observed in the nanomolar range (see FIG. 23B).

In order to ascertain why T30177 was effective and T30659 was not, the inventors made a series of compounds to incrementally change one compound into the other. The structures of these compounds are shown in panels C and D of FIG. 23. The differences between T30177 and T30659 (i.e., the presence of additional bases at both ends, different sequences in all three loops, and extension of loop 2) manifest themselves in dramatic increases in the IC50 values (FIG. 23D). To distinguish the contributions of each of these changes, the inventors first added the same 5'- and 3'-nucleotides to T30659 as are present on T30177, yielding T30674 (a variant of SEQ. ID. NO. 33 shown in Table C-1) (FIG. 23C). These changes did not confer potency (FIG. 23D). Then it was undertaken to change either loop 1 to obtain T30675 (FIG. 23C) or the three bases in loop 2 into those found in T30177, yielding compound T30677 (FIG. 23C). Neither change by itself conferred potency (FIG. 23D). However, when the change was accomplished in two of the loops to resemble T30177, yielding T30676 or T30678 (variants of SEQ. ID. NO. 33 shown in Table C-1) (FIG. 23C), the inventors were able to significantly improve the activity over that of T30659. Interestingly, a two- to three-fold decrease in potency was also observed when a second quartet was unable to form, yielding T30526 (FIG. 23D). These data suggest not only that the octet structure is critical but also that the loops are important for interaction with HIV-1 integrase.

The activities of the oligonucleotides in the cellular assays did not strictly correlate with the in vitro anti-integrase activity (FIG. 23D). The correlation is complicated by the differential stabilities and susceptibilities to nuclease digestion of the oligonucleotides in vivo (Joshua O. Ojwang and Robert F. Rando, unpublished).

In FIG. 23, G4 oligonucleotides were initially tested in a dual assay which measures both 3'-processing and strand transfer. Craigie, et al., *Cell* 62, 829–837 (1990); Katz, et al., *Cell* 63, 87–95 (1990). A strand transfer assay using "pre-processed" (3'-recessed) substrate (19 mer in FIG. 24A, left panel) was also performed to determine whether the strand transfer reaction was truly being inhibited or whether the inhibition of the 3'-processing reaction caused the decrease in the subsequent strand transfer products. Inhibition of strand transfer using this substrate was observed in the same concentration range (FIG. 24A, right panel) as that seen with the blunt-ended, duplex oligonucleotide substrate (FIG. 23A, top). Therefore, G4 oligonucleotides inhibit both steps of the integrase reactions: 3'-processing and strand transfer.

Inhibition of 3'-processing was confirmed using DNA substrates labeled at the 3'-end, (Engleman, et al, *Cell* 67, 1211–1221 (1991); Vink, et al., *Nucleic Acids Res.* 19, 6691–6698 (1991)) (FIG. 24B, left panel), showed that all of the G4s tested inhibited glycerolysis, hydrolysis, and circular nucleotide formation to the same extent (FIG. 24B, right panel). Thus, G4 oligonucleotides exert a global inhibition of the three nucleophiles in the 3'-processing reaction (glycerol, water, or the hydroxyl group of the viral DNA terminus).

Having demonstrated that the catalytic activities of integrase could be inhibited by G4 oligonucleotides, the inventors next examined whether DNA binding was also affected, They performed UV crosslinking of integrase-DNA reactions to address this question. Crosslinking of substrate DNA to integrase followed by electrophoresis results in a product having a molecular weight of approximately 39 kDa (Engleman et al., 1994, Yoshinaga et al., 1994). As seen in FIGS. C-3A and C-3B, binding of HIV-1 integrase to radiolabeled U5 DNA substrate was inhibited by preincubation of the enzyme with T30177 in the same concentration range as its $IC_{50}$ value for strand transfer (lanes 3–7). In contrast, preincubation of the enzyme with T30659, which was poorly active in the 3'-processing/strand transfer assay (FIG. 23D), resulted in only modest inhibition of DNA binding even at a T30659 concentration of 500 nM (FIG. 25A, lanes 9–13).

Importance of the HIV-1 integrase zinc finger region for guanosine quartet oligonucleotide interactions Integrase can catalyze in vitro an apparent reversal of the DNA strand transfer reaction called disintegration. Chow, et al., *Science* 255, 723–726 (1992). In contrast to the 3'-processing and strand transfer reactions, disintegration requires neither the N-terminal zinc-finger region nor the C-terminal DNS-binding domain of integrase. Bushman, et al., *Proc. Natl. Acad. Sci. U.S.A.* 90, 3428–3432 (1993). For this reason, the HIV-1 integrase catalytic core domain, $In^{50-212}$ (FIG. 26A), can be use din the intramolecular disintegration assay and for testing the site of action of inhibitors. Mazumder, et al., *Proc. Natl. Acad. Sci.* 91, 5771–5775 (1994); Mazumder, et al., *AIDS Res. Hum. Retrov.* 11, 115–125 (1995).

In the disintegration assay, only the $In^{1-288}$ and $IN^{1-212}$ proteins (FIG. 26B) were inhibited by T30177 (with $IC_{50}$s of 270 and 600 nM, respectively) while neither $IN^{50-212}$ (FIG. 26B) nor $IN^{50-288}$ (data not shown) showed more than 30% inhibition at a 3 $\mu$M concentration of T30177. The concentration of T30177 required for inhibition of disintegration was higher than that required for inhibition of either 3'-processing or strand transfer. These results are consistent with those observed with other molecules (Fesen et al., 1994, Mazumder et al, 1994). This observation suggests that the active site of HIV-1 integrase may tolerate drug-induced protein or DNA distortion during the disintegration reaction, consistent with the relative tolerance of integrase to mutagenesis of either substrate features (Chow & Brown, 1994) or protein structural domains (Bushman et al., 1993) in this reaction. This is the first example of an HIV-1 integrase inhibitor requiring the enzyme zinc-finger region for inhibitory activity. These results suggest that the zinc-finger may assist in stabilizing binding to T30177.

This hypothesis was investigated further by monitoring binding of wild-type, full length integrase ($IN^{1-288}$) and of the deletion mutants to radiolabeled T30177. The concentration of T30177 required for DNA-protein complex formation was the same as that required for complex formation using the viral U5 DNA substrate (i.e., in the 20 nM range). UV crosslinking assays, Engelman, et al., *J. Virol.* 68, 5911–5917 (1994), showed that $INI^{1-288}$ formed a DNA-protein complex of the expected molecular weight in the absence or presence of added manganese (FIG. 26C, lanes 8 and 9). The $IN^{1-212}$ protein, which has previously been shown to bind to linear viral DNA only at high concentrations (approximately 2.56 $\mu$M) and only in the presence of divalent metal ion, (Engelman, et al.,*J. Virol.* 68, 5911–5917 (1994)), was able to crosslink to T30177 with the same efficiency as wild-type integrase in the absence or presence of added manganese (lanes 2 and 3). The $IN^{50-288}$ protein, which contains a nonspecific DNA-binding domain, was also able to crosslink to T30177 with the same efficiency as wild-type integrase in the absence or presence of added manganese (lanes 4 and 5), consistent with its ability to bind to viral U5 DNA (Engelman et al., 1994). The extent of crosslinking was significantly diminished in the case of the core mutant $IN^{50-212}$ compared to $IN^{1-212}$ in the absence or presence of manganese (compare lanes 2 and 3 with 6 and 7, faster migrating complex). The higher molecular weight species in lane 6, having the expected molecular weight of a dimer, has been reproducibly observed, but its density has not been confirmed. These data support the notion that the N-terminus of HIV-1 integrase assist in the formation or stabilization of an HIV-1 integrase-T30177 complex, perhaps by binding the oligonucleotide.

DNA-binding activities of the HIV-1 integrase zinc finger domain

To further analyze the binding of the N-terminal zinc finger region to T30177 and compare these results to the viral U5 substrate, UV crosslinking was performed with an $In^{1-55}$ deletion mutant (FIG. 26A) containing only this domain. As seen in FIGS. 27A–B, this mutant could not bind either the T30177 oligonucleotide or the viral DNA substrate when only manganese or magnesium was present left and right panels, lanes 3 and 4). However, the $IN^{1-55}$ protein could bind to both DNAs in the presence of zinc and either manganese or magnesium (left and right panels, lanes 5 and 6). Significantly, the $In^{1-55}$ protein was able to bind to the T30177 G4 oligonucleotide, but not the viral DNA substrate, in the presence of zinc alone (left and right panels, lanes 9 and 10). These results are in accord with the known zinc-binding ability of this domain. Bushman, et al., *Proc. Natl. Acad. Sci. U.S.A.* 90, 3428–3432 (1993); Burke, et al., *J. Biol. Chem.* 267, 9639–9644 (1992). But they also suggest that the N-terminal domain of integrase has DNA binding capabilities on its own. Finally, these experiments demonstrate comparable binding of the HIV-1 integrase zinc finger domain to an oligonucleotide containing in G4s than to a double-stranded, linear, viral DNA oligonucleotide when both manganese (or magnesium) and zinc are present but more efficient binding to the G4 oligonucleotide under non physiological conditions (zinc alone). The inventors also found that the nucleocapsid protein of HIV-1, a nucleic acid annealing protein which contains two CCHC zinc fingers and which is essential for dimerization of the retroviral RNA genome, Tsuchihashi, et al., *J. Virol.* 68, 5863–5870 (1994), was able to bind efficiently to T30177 (data not shown). The ability of zinc to confer DNA binding ability on the $IN^{1-55}$ protein was examined by replacement of this ion with other transition metals. Consistent with spectroscopic data (Burke et al., 1992), only zinc was able to induce detectable DNA binding to the G4 oligonucleotide (data not shown).

Increased potency of guanosine quartets in magnesium

Figure 28A:
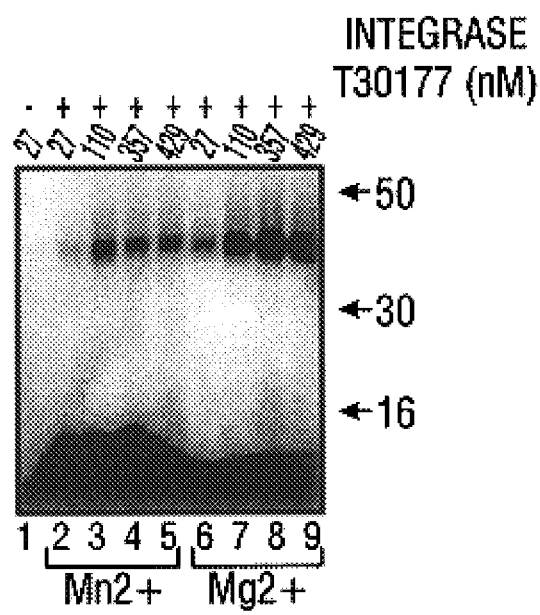
Figure 28B:
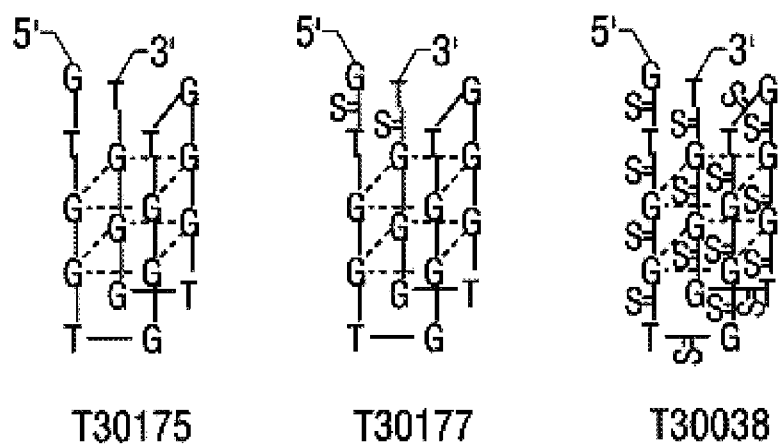
Figures 28C, 28D:
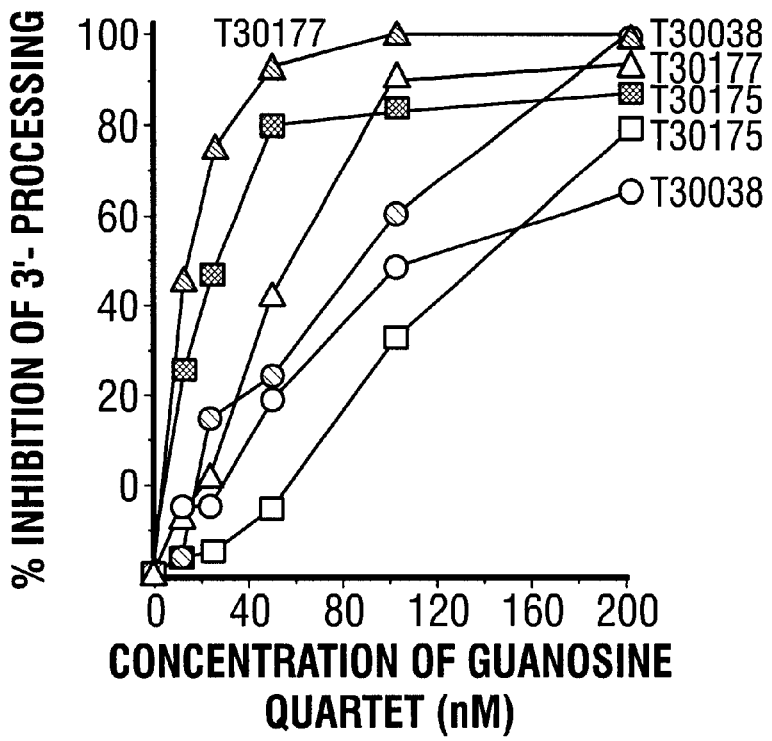

In contrast to $IN^{1-55}$, the extent of crosslinking (and presumably binding) of wild-type integrase to radiolabeled guanosine quartet was increased in the presence of magnesium relative to manganese at several concentrations of the guanosine quarter (FIG. 28A). This observation led us to examine whether the inhibitory activity of T30177 and analogs could also be enhanced by buffer containing magnesium. In order to address this question, the inventors tested three versions of T30177 as shown in FIG. 28B. T30175 has the same base sequence as T30177 (pPT variant of SEQ. ID. NO. 33) but is composed entirely of phosphorothiodiester internucleotidic linkages. The inhibition of 3'-processing catalyzed by HIV-1 integrase by these guanosine quartets is shown in FIG. 28C. Both T30175 and T30177 showed four to five-fold increases in potency when magnesium was used as the divalent metal instead of manganese. In contrast, T30038 showed no significant increase in potency when magnesium was used as the ion (FIG. 28D). These data are in accord with the increased stability constants for magnesium-nucleotide complexes when oxygen replaces sulfur (Pecoraro et al., 1984). The opposite is true for manganese. Therefore, the greater inhibitory potency of T30177 in buffer containing magnesium versus manganese may reflect a requirement for magnesium ion coordination along the phosphodiester backbone of T30177 in order to confer inhibitory activity and optimum interaction of T30177 with HIV-1 integrase. This coordination can occur with more stability when either T30177 or T30175 are assayed in buffer containing magnesium rather than manganese and is manifested in a greater potency against 3'-processing.

DNA competition experiments

The relative affinity for the G4 oligonucleotide was probed by attempting to compete off the integrase bound to radiolabeled HIV-1 viral U5 DNA with increasing concentrations of unlabeled T30177 (FIG. 29A). The converse experiment, where binding of integrase to radiolabeled G4 oligonucleotide was carried out prior to the addition of increasing concentrations of unlabeled HIV-1 viral U5 DNA, was also performed (FIG. 29B). In each case, a band having the apparent mobility of an integrase-DNA complex was evident. In FIG. 29A, the viral DNA-integrase complex has a molecular weight of 38,500 while in FIG. 29B, the T30177-integrase complex has a molecular weight of 37,000. Neither complex could not be competed off by either competitor DNA even at concentrations where the competitor was in 500-fold excess (FIG. 29A, lane 6). Similar results were seen when the $In^{1-212}$ and $IN^{50-212}$ proteins were used in competition experiments (data not shown). Therefore, the stability of the G4 oligonucleotide DNA-integrase complex is comparable to that of the viral DNA-integrase complex is comparable to that of the viral DNA-integrase complex. Ellison, et al, *Proc. Natl. Acad. Sci. U.S.A.* 91, 7316–7320 (1994); Vink, et al., *Nuc. Acids Res.* 22, 4103–4110 (1994).

Inhibition of related lentiviral integrases

T30177 was tested for inhibition of the related retroviral integrases from HIV-2 (van Gent et al., 1992), simian immunodeficiency virus (SIV) and feline immunodeficiency virus (FIV) (Vink et al., 1994b). As seen in FIGS. 30A and 30B, T30177 inhibited 3'-processing catalyzed by HIV-1 integrase in the expected concentration range (FIG. 30A, lanes 2–8; $IC_{50}=55$ nM). Inhibition of HIV-2 integrase (using HIV-1 DNA) was also observed in the same range (lanes 9–15; $IC_{50}=90$ nM). However, FIV integrase was inhibited at three-fold higher concentrations of T30177 (lanes 16–22; $IC_{50}=175$ nM), and SIV integrase was inhibited at seven-fold higher concentrations to T30177 (lanes 23–29; $IC_{50}=420$ nM). Therefore, the T30177 G4 oligonucleotide displayed some selectivity among the lentiviral integrases.

Conclusions Regarding the Site of Activity Studies

The present study demonstrates for the first time the binding of DNA guanosine quartet structures to HIV-1 integrase, and that some oligonucleotides recently shown to exhibit antiviral activity are potent HIV-1 integrase inhibitors.

Guanosine Quartet Oligonucleotides are Novel and Potent Inhibitors of HIV-1 integrase Oligonucleotides composed of deoxyguanosine and thymidine and forming guanosine-tetrads (G4) structures have previously been shown in inhibit HIV replication. Rando, et al., *J. Biol. Chem.* 270, 1754–1760 (1995); Wyatt, et al., *Proc. Natl. Acad. Sci. U.S.A.* 91, 1356–1360 (1994). Two mechanisms have been invoked. First, some oligonucleotides have been shown to bind to the V3 loop of the envelope protein gp120 and subsequently inhibit virus adsorption and cell fusion. Wyatt, et al., *Proc. Natl. Acad. Sci. U.S.A.* 91, 1356–1360 (1994). Secondly, oligonucleotides such as those described in the present study also inhibit viral-specific transcripts, Rando, et al.,*J. Biol. Chem.* 270, 1754–1760 (1995), presumably by inhibiting viral integration. Ojwang, et al., *Antimicrob. Agents Chemother.* 39, 2426–2435 (1995). The present finding that inhibition of the HIV-$1_{RF}$ strain in cell culture parallels that of purified integrase in vitro in the series of G4 oligonucleotides tested (FIG. 23D) further demonstrates the possibility that HIV-1 integrase can be targeted by some G4 oligonucleotides.

G4 oligonucleotides differ from previously published HIV-1 integrase inhibitors in several ways. (Table C-1) First, they are among the most potent inhibitors to date with IC50's in the nanomolar range. Their potency range is comparable to flavone, Fesen, et al., *Biochem. Pharmacol.* 48, 595–608 (1994), and tyrophostin derivatives, Mazumder, et al, *Biochemistry* 34, in press (1995), which, however, generally fail to show antiviral activity. Secondly, the zinc finger domain of HIV-1 integrase contributes to the inhibition by G4 oligonucleotides, as truncation mutant enzymes lacking this domain are resistant to the G4 oligonucleotides. This property is unique, as all the other inhibitors to date are active against the HIV integrase catalytic core domain. (Table C-2) Mazumder, et al., *Proc. Natl.*

Acad. Sci. 91, 5771–5775 (1994); Mazumder, et al., *Mol. Pham.* submitted (1995); Fesen, et al., *Biochem. Pharmacol.* 48, 595–608 (1994); Mazumder, et al., *Biochemistry* 34, in press (1995). Finally, G4 oligonucleotides form stable enzyme complexes that cannot be displaced by excess viral DNA oligonucleotide.

TABLE C-1

HIV-1 Integrase Inhibitor Compound Design and List

| Compound | Sequence | Description | Length | SEQ ID |
|---|---|---|---|---|
| T30177  | 5' gtggtgggtgggtgggt  -3' | pPT version of parent compound I100-15 | 17 mer | (SEQ ID NO 87) |
| T30038  | 5' gtggtgggtgggtgggt  -3' | PT, Total PT version T30177 | 17 mer | (SEQ ID NO 87) |
| T30340  | 5'  ggttggtgtggttgg  -3' | PD version of thrombin binding aptamer | 15 mer | (SEQ ID NO 53) |
| T30341  | 5'  ggttggtgtggttgg  -3' | pPT version of thrombin binding aptamer | 15 mer | (SEQ ID NO 53) |
| T30659  | 5'  ggttggtgtggttgg  -3' | PT version of thrombin binding aptamer | 15 mer | (SEQ ID NO 53) |
| T30673  | 5' gtggttggtgtggttgg  -3' | pPT variant T30177 | 17 mer | (SEQ ID NO 54) |
| T30674  | 5' gtggttggtgtggttggt -3' | pPT variant T30177 | 18 mer | (SEQ ID NO 55) |
| T30675  | 5' gtggtgggtgtggttggt -3' | pPT variant T30177 | 18 mer | (SEQ ID NO 56) |
| T30676  | 5' gtggtgggtgtggtgggt -3' | pPT variant T30177 | 18 mer | (SEQ ID NO 57) |
| T30677  | 5' gtggttggtg ggttggt  -3' | pPT variant T30177 | 17 mer | (SEQ ID NO 55) |
| T30678  | 5' gtggtgggtg ggttggt  -3' | pPT variant T30177 | 17 mer | (SEQ ID NO 56) |
| T30679  | 5' gtggttggtg ggtgggt  -3' | pPT variant T30177 | 17 mer | (SEQ ID NO 58) |
| T30660  | 5' gugguggguggguugggu  -3' | pPT version using 2'0-methyl RNA* | 17 mer | (SEQ ID NO 59) |
| T30661  | 5' gugguggguggguugggu  -3' | pPT version RNA* | 17 mer | (SEQ ID NO 59) |
| T30695  | 5' g ggtgggtgggtgggt  -3' | pPT variant remove T near 5'-end | 16 mer | (SEQ ID NO 60) |
| T30696  | 5' gtgggtggtgggtgggt  -3' | pPT variant invert loop 1 | 17 mer | (SEQ ID NO 61) |
| T30697  | 5' gtggtggggtggtgggt  -3' | pPT variant invert loop 2 | 17 mer | (SEQ ID NO 62) |
| T30698  | 5' gtggtgggtggggtggt  -3' | pPT variant invert loop 3 | 17 mer | (SEQ ID NO 63) |
| T30699  | 5' gtgggtggtggggtggt  -3' | pPT variant invert loops 1 and 3 | 17 mer | (SEQ ID NO 64) |
| T30700  | 5' gtggTgggtgggtgggt  -3' | pPT variant T = c-5 propynyl dU | 17 mer | (SEQ ID NO 65) |
| T30701  | 5' gtggtgggtgggTgggt  -3' | pPT variant T = c-5 propynyl dU | 17 mer | (SEQ ID NO 66) |
| T30702  | 5' gtggTgggtgggTgggt  -3' | pPT variant T = c-5 propynyl dU | 17 mer | (SEQ ID NO 67) |
| T30177  | 5' gtggtgggtgggtgggt  -3' | pPT version of parent compound T100-15 | 17 mer | (SEQ ID NO 87) |
| T30719  | 5' g ggTgggtgggTgggt  -3' | pPT variant T = c-5 propynyl dU | 16 mer | (SEQ ID NO 68) |
| T30720  | 5' g gggTggtgggTgggt  -3' | pPT variant T =c-5 propynyl dU | 16 mer | (SEQ ID NO 69) |
| T30721  | 5' I ggIIggIIggIIggI  -3' | pPT variant I = dI where I = inosine | 16 mer | (SEQ ID NO 70) |
| T30722  | 5' gtgggTggtgggTgggt  -3' | pPT variant T = c-5 propynyl dU | 17 mer | (SEQ ID NO 71) |
| T30075  | 5' gtggtgggtgggtgggt  -3' | 3'-cholesterol via triglycyl linker | 17 mer | (SEQ ID NO 72) |
| T30570  | 5' gtggtgggtgggBgggt  -3' | pPT version B = 5-Bromo dU | 17 mer | (SEQ ID NO 73) |
| T30571  | 5' gtggBgggBgggBgggt  -3' | pPT version B = 5-Bromo dU | 17 mer | (SEQ ID NO 74) |
| T30576  | 5' gtggIgggtgggtgggt  -3' | pPT version I = 5-Iodo dU | 17 mer | (SEQ ID NO 75) |
| T30577  | 5' gtggtgggIgggtgggt  -3' | pPT version I = 5-Iodo dU | 17 mer | (SEQ ID NO 76) |
| T30578  | 5' gtggtgggtgggIgggt  -3' | pPT version I = 5-Iodo dU | 17 mer | (SEQ ID NO 77) |
| T30579  | 5' gtggIgggIgggIgggt  -3' | pPT version I = 5-Iodo dU | 17 mer | (SEQ ID NO 78) |
| T30743  | 5' gtggCgggtgggtgggt  -3' | pPT version C = cytosine | 17 mer | (SEQ ID NO 79) |
| T30744  | 5' gtggtgggCgggtgggt  -3' | pPT version C = cytosine | 17 mer | (SEQ ID NO 80) |
| T30745  | 5' gtggtgggtgggCgggt  -3' | pPT version C = cytosine | 17 mer | (SEQ ID NO 81) |
| T30746  | 5' gtggCgggCgggCgggt  -3' | pPT version C = cytosine | 17 mer | (SEQ ID NO 82) |
| T30748  | 5' tgggaggtgggtctg  -3' | pPT New sequence - intermolecular tetrad | 15 mer | (SEQ ID NO 83) |
| T30747A | 5' tgggaggtgggtctg  -3' | All phosphodiester linkages | 15 mer | (SEQ ID NO 84) |
| T30747B | 5' tgggaggtgggtctg  -3' | All phosphodiester link. DMT at 3'-end | 15 mer | (SEQ ID NO 85) |
| T30754  | 5' gcggggctccatgggggtcg  -3' | pPT New sequence - intermolecular tetrad* | 20 mer | (SEQ ID NO 86) |
| S935833 | 5' gcggggctccatgggggtcg  -3' | pPT see below* | 20 mer | (SEQ ID NO 86) |

All compounds were synthesized using commercially available reagents except for T30075 which was synthesized with a cholesterol moiety at the 3'-end attached via a triglycyl linker as described in the paper by Rando et al. (J. Biol. Chem. 1995 270: 1754–1760] and more extensively by Vu et al. [1994 Bioconjugate Chem. 5: 666–668].
The propynyl dU building blocks contain uracil bases in which a propynyl group has been added to the c-5 position. The propynyl dC building blocks contain cytosine bases in which a propynyl group has been added to the c-5 position. These reagents are commercially available from Glen Research Reagent co. Other unusual bases used such as dI (inosine) and iodo and bromo dU are also commercially available.
pPT is shorthand for ODNs in which the linkage between the ultimate and penultimate bases has been changed from phosphodiester to phosphorothioate. PT is shorthand to indicate that all linkages are phosphorothioate.
Compounds T30660 and T30661 use RNA sugars or 2'-0-methyl RNA sugars as indicated instead of 2'-deoxy sugars as found in DNA.
The thrombin binding aptamer sequence used was the first described by Bock et al. [Nature 1992 355: 564–566] and reported to fold into an structure stabilized by an intramolecular tetrad by Want et al. Biochemistry 1993 32: 1899–1904].
Compound T30747 A/B contain only natural phosphodiester linkages. T30747B is 3'-modified in that the dimethoxy trityl capping group was left attached after removal of the oligonucleotide from the solid support and subsequent purification. Usually this group is removed after synthesis of the molecule.
Compound S935833 has the following pattern of phosphorothioate (PT) linkages where * denotes the PT linkage:
5'-g*c*gggc*t*c*a*tggggg*t*c*g-3'.
Compound T30754 has a pPT pattern in which only the 5' and 3' linkages are PT:
5'-g*cggggctccatgggggtc*g-3'.
For structures of certain of the olignucleotides listed, see FIGS. C-9, C-10, C-13, and C-14. For percentage inhibition of 3'-processing, and for inhibition of syncytium formation, of certain of these same oligonucleotides, see FIGS. C-11 and C-12, respectively.

TABLE C-2

Anti-HIV-1 Integrase Activity in vitro and Anti-HIV-1 Virus Production in Cell Culture

| | | | Enzyme (IC 50 µM) | | Cell Culture | |
|---|---|---|---|---|---|---|
| | | | Stran Trans | 3-'process | IC50 (µM) | |
| T30177 | 5' gtggtgggtgggtgggt | -3' | 0.079 | 0.049 | 0.075 | (SEQ ID NO 87) |
| T30038 | 5' gtggtgggtgggtgggt | -3' | 0.090 | 0.070 | 0.06 | (SEQ ID NO 87) |
| T30340 | 5' ggttggtgtggttgg | -3' | >0.500 | >0.500 | >50.0 | (SEQ ID NO 53) |
| T30341 | 5' ggttggtgtggttgg | -3' | 0.042 | 0.023 | 4.76 | (SEQ ID NO 53) |
| T30659 | 5' ggttggtgtggttgg | -3' | 0.870 | 0.750 | >20.0 | (SEQ ID NO 53) |
| T30673 | 5' gtggttggtgtggttgg | -3' | 0.790 | 0.600 | >35.0 | (SEQ ID NO 54) |
| T30674 | 5' gtggttggtgtggttggg | -3' | 0.760 | 0.610 | >50.0 | (SEQ ID NO 55) |
| T30675 | 5' gtggtgggtgtggttggt | -3' | 0.485 | 0.500 | >30.0 | (SEQ ID NO 56) |
| T30676 | 5' gtggtgggtgtggtgggt | -3' | 0.148 | 0.134 | 1.0 | (SEQ ID NO 57) |
| T30677 | 5' gtggttggtg ggttggt | -3' | 0.725 | 0.620 | >40.0 | (SEQ ID NO 55) |
| T30678 | 5' gtggtgggtg ggttggt | -3' | 0.098 | 0.120 | 3.95 | (SEQ ID NO 56) |
| T30679 | 5' gtggttggtg ggtgggt | -3' | 0.159 | 0.156 | 3.46 | (SEQ ID NO 58) |
| T30660 | 5' gugguggguggguggu | -3' | | | >50.0 | (SEQ ID NO 59) |
| T30661 | 5' gugguggguggguggu | -3' | 0.111 | 0.084 | 46.6 | (SEQ ID NO 59) |
| T30695 | 5' g ggtgggtgggtgggt | -3' | 0.060 | 0.020 | 0.07 | (SEQ ID NO 60) |
| T30696 | 5' gtgggtggtgggtgggt | -3' | 0.122 | 0.013 | | (SEQ ID NO 61) |
| T30697 | 5' gtggtggggtgggtgggt | -3' | 0.130 | 0.013 | | (SEQ ID NO 62) |
| T30698 | 5' gtggtgggtggggtggt | -3' | 0.150 | 0.016 | | (SEQ ID NO 63) |
| T30699 | 5' gtgggtggtggggtggt | -3' | 0.136 | 0.050 | | (SEQ ID NO 64) |
| T30700 | 5' gtggTgggtgggtgggt | -3' | 0.082 | 0.040 | | (SEQ ID NO 65) |
| T30701 | 5' gtggtgggtgggTgggt | -3' | 0.072 | 0.030 | | (SEQ ID NO 66) |
| T30702 | 5' gtggTgggtgggTgggt | -3' | 0.032 | 0.030 | 4.91 | (SEQ ID NO 67) |
| T30177 | 5' gtggtgggtgggtgggt | -3' | 0.079 | 0.049 | 0.075 | (SEQ ID NO 87) |
| T30719 | 5' g ggTgggtgggTgggt | -3' | 0.055 | 0.055 | | (SEQ ID NO 68) |
| T30720 | 5' g gggTgggTgggTgggt | -3' | 0.059 | 0.062 | | (SEQ ID NO 69) |
| T30721 | 5' I ggIIggIIggIIggI | -3' | 0.070 | 0.088 | | (SEQ ID NO 70) |
| T30722 | 5' gtgggTggtgggTgggt | -3' | 0.129 | 0.134 | | (SEQ ID NO 71) |
| T30075 | 5' gtggtgggtgggtgggt | -3' | 0.110 | 0.095 | 0.07 | (SEQ ID NO 72) |
| T30570 | 5' gtggtgggtgggBgggt | -3' | 0.090 | 0.070 | | (SEQ ID NO 73) |
| T30571 | 5' gtggBgggBgggBgggt | -3' | 0.055 | 0.050 | | (SEQ ID NO 74) |
| T30576 | 5' gtggIgggtgggtgggt | -3' | 0.065 | 0.050 | | (SEQ ID NO 75) |
| T30577 | 5' gtggtgggIgggtgggt | -3' | 0.065 | 0.055 | | (SEQ ID NO 76) |
| T30578 | 5' gtggtgggtgggIgggt | -3' | 0.060 | 0.050 | | (SEQ ID NO 77) |
| T30579 | 5' gtggIgggIgggIgggt | -3' | 0.060 | 0.055 | | (SEQ ID NO 78) |
| T30744 | 5' gtggtgggCgggtgggt | -3' | 0.105 | 0.060 | | (SEQ ID NO 80) |
| T30745 | 5' gtggtgggtgggCgggt | -3' | 0.100 | 0.100 | | (SEQ ID NO 81) |
| T30746 | 5' gtggCgggCgggCgggt | -3' | 0.150 | 0.150 | | (SEQ ID NO 82) |
| T30747A5' | tgggaggtgggtctg | -3' | | >0.250 | >0.250 | (SEQ ID NO 84) |
| T30747B5' | tgggaggtgggtctg | -3' | 0.120 | 0.120 | | (SEQ ID NO 85) |
| T30748 | 5' tgggaggtgggtctg | -3' | 0.125 | 0.125 | | (SEQ ID NO 83) |
| S93583 | 5' gcggggctccatgggggtcg | -3' | 0.060 | 0.045 | 0.63 | (SEQ ID NO 86) |
| T30745 | 5' gcggggctccatgggggtcg | -3' | 0.120 | 0.120 | | (SEQ ID NO 86) |

The integrase and viral inhibition (cell culture) assays were performed as described by Ojwang et al. [1995 Antimicrobial Agents and Chemotherapy 39: 2426–2435]. Integrase inhibition assays monitor two different enzymatic activities, the 3'-processing (3'-process) activity and the strand transfer (stran trans) activity of the enzyme. The units for the enzyme assays are in nM while the units for the cell culture inhibition assays are in µM.

Role of the HIV-1 Integrase Zinc Finger Region

Mutation and deletion analyses show that the zinc finger motif (H-H-C-C) of retroviral integrases is required for integration (3'-processing and strand transfer) activity. Engelman, et al., *J. Virol.* 66, 6361–6369 (1992). However, the structural role of this region has not been elucidated. It has been postulated too provide DNA sequence-specificity, Bushman, et al., *Proc. Natl. Acad. Sci. U.S.A.* 90, 3428–3432 (1993), stabilize DNA-enzyme, Vink, et al., *Nuc. Acids Res.* 22, 4103–4110 (1994), and enzyme multimer complexes. Ellison, et al, *J. Biol. Chem.* 270, 3320–3326 (1995). These data provide the first direct evidence that the HIV-1 integrase N-terminus region (amino acids 1–55 [FIG. 26A]) can interact directly with viral DNA in the presence of both zinc and magnesium (or manganese). The fact that the $IN^{1-55}$ protein binds to the G4 oligonucleotides in the presence but not in the absence of zinc is consistent with the formation of a zinc finger in this region. Burke, et al., *J. Biol. Chem.* 267, 9639–9644 (1992). Hence, it is possible that the zinc finger region can selectively bind to non-B DNA structures. It is noteworthy that the recently solved structure of HIV-1 integrase, Dyda, et al., *Science* 266, 1981–1984 (1994), resembles that of the Rev C Holliday junction-resolving enzyme, Ariyoshi, et al, *Cell* 78, 1063–1072 (1994), and of the bacteriophage Mu transposes core. Rice, et al., *Cell* 82, 209–220 (1995). These structurally related proteins also bind multiple double helices, generating X structure intermediates. (For review See Katz et al., *Ann. Rev. Biochem* 63:133–173 (1994) and Vink et al; *Trends in Genetics* 9:433–438 (1993).

Although the zinc finger region of integrase is required for inhibition by the G4s, the $IN^{50-212}$ protein, which contains only the central catalytic domain, was capable of binding to T30177 (FIG. 26C). The inventors also found that an HIV-1 integrase mutant with the two zinc finger histidines mutated to asparagines was able to bind to G4 oligonucleotides (data not shown). These data suggest that HIV-1 integrase may have two separate binding sites, one for viral DNA and one for target or "host" DNA. This scenarios would be expected if integrase were to bind both the viral and host DNA at sites which were instinct but in close proximity in vivo. Vincent, et al., *J. Virol.* 67, 425–437 (1993). It should be noted that the existence of a single binding site on HIV integrase for both viral and target DNA has been proposed by others. Vink, et al., *Nucleic Acids Res.* 21, 1419–1425 (1993).

Biological relevance of G4 structures

Several similarities exist between retroviral genomes and telomeric regions of eukaryotic chromosomes. The two RNA strands comprising the HIV-1 genome can potentially dimerize and form intermolecular G4s in vitro, Sundquist, et al, *Proc. Natl. Acad. Sci. U.S.A.* 90, 3393–3397 (1993); Awang, et al., *Biochemistry* 32, 11453–11457 (1993), as does telomeric DNA. Sundquist, et al., *Nature* 342, 825–829 (1989). In addition, the β subunit of the Oxytrichia telomere binding protein has bene proposed as a molecular chaperone for the formation of G4s at the end of chromosomes by enhancing the rate of a thermodynamically favored transition. Fang, et al., *Cell* 74, 875–885 (1993). In retroviruses, the nucleocapsid protein may also act as a molecular chaperone to enhance dimer formation. Sundquist, et al, *Proc. Natl. Acad. Sci. U.S.A.* 90, 3393–3397 (1993). In this manner, it may facilitate the formation of and bind to the G4. The inventors also found that G4s can bind to purified nucleocapsid protein (data not shown). Thus, G4s may be structurally important as molecular scaffolds in both retroviral preintegration complexes and telomeres, and these structures may have associated chaperones in both cases. Finally, a G4 containing structure may act as a negative regulator of telomere elongation in vivo due to its ability to inhibit telomerase in vitro. Zahler, et al., *Nature* 350, 718–720 (1991). Analogously, G4 structures may act to inhibit integrase (FIGS. 23A–D) and thereby act as a block to auto integration or digestion of the viral DNA prior to insertion into the host chromosome.

The existence of G4s in vivo has not been demonstrated. However, they have been shown to form in vitro in telomeric sequences, Sundquist, et al., *Nature* 342, 825–829 (1989); Smith, et al., *Nature* 356, 164–168 (1992); Kang, et al., *Nature* 356, 126–131 (1992), HIV-1 RNA sequences, Sundquist, et al, *Proc. Natl. Acad. Sci. U.S.A.* 90, 3393–3397 (1993); Awang, et al., *Biochemistry* 32, 11453–11457 (1993), fragile X syndrome nucleotide repeats, Fry, et al., *Proc. Natl. Acad. Sci. U.S.A.* 91, 4950–4954 (1994), the retinoblastoma susceptibility gene, Murchie, et al., *Nuc. Acids Res.* 20, 49–53 (1992), immunoglobulin switch region sequences, Sen, D., et al., *Nature* 334, 364–366 (1988), and possibly during meiotic recombination. Liu, et al., *Cell* 77, 1083–1092 (1994). Given these results, it is not surprising that proteins such as thrombin, Bock, et al., *Nature* 355, 564–566 (1992), (not normally known to bind nucleic acids), chick topoisomerase II, Chung, et al., *Nucleic Acids Res.* 20, 1973–1977 (1992), MyoD (a transcription factor that regulates myogenesis), Walsh, et al., *J. Biol. Chem.* 267, 13714–13718 (1992), an hepatocyte chromatin protein, Weisman-Shomer, et al., *J. Biol. Chem.* 268, 3306–3312 (1993), macrophage scavenger receptors, Pearson, et al., *J. Biol. Chem.* 268, 3546–2554 (1993), and a protein from *Tetrahymena thennophila*, Schierer, et al., *Biochemistry* 33, 2240–2246 (1994), have been found to bind G4 containing nucleic acids. Another G4 binding protein, KEM1, has been isolated and implicated in recombination-type reactions in vivo. Liu, et al., *Cell* 77, 1083–1092 (1994). The catalytic activities of this protein and of the integrase protein are DNA endonucleolytic cleavage and strand transfer. However, unlike KEM1, integrase does not catalyze endonucleolytic cleavage reactions on G4s (data not shown). Thus, G4s may be mechanistically relevant in a diverse set of biological processes involving enzymes with similar activities.

In summary, the inventors demonstrated that oligonucleotides containing intramolecular G4s are potent inhibitors of HIV-1 integrase. Inhibition is dependent on the zinc finger region of integrase and on the structure and sequence of the G4s. These findings also suggest that novel AIDS therapies could be based upon G4s as inhibitors of HIV-1 integrase.

D. Structure-Function Studies

As shown previously, the inventors obtained evidence for inhibition of HIV-1 infection by treatment with phosphodiester oligonucleotides containing only G and T bases. Additional studies noted above suggested to the inventors that such oligomers were potent inhibitors of HIV-1 integrase, in vitro. The highest activity was obtained using the 17 mer, referred to as T30177 (pPT variant of SEQ. ID. NO. 33), with composition G12-T5. NMR evidence suggested to the inventors that T30177 forms an intramolecular fold which is stabilized by a pair of G-tetrads, connected by three single stranded loops, with a 1–2 base tail to ether side of the fold.

Thus, the inventors undertook studies to determine sequence dependence of the intramolecular folding mechanism, in a set of four closely related 16–17 base oligonucleotide homologues, with sequences in the range G10–12-T4–7. The original T30177 compound was included, along with three derivatives which were designed so as to alter the structure of loop domains, while keeping the pair of G-tetrads intact. Based on thermal denaturation, CD and kinetic analysis, the inventors were able to show that a single base alteration within the loop or tail domains can produce a very large change in folding stability. The $K^+$ ion dependence of these data suggested a preliminary model wherein the loop and tail domains interact to form stable metal ion-binding sites. A 16 mer derivative (T30695) was designed within the context of that model, with the intent of enhancing the interaction between $K^+$ and the 5' terminus of the oligomer. The inventors showed that T30695 (a variant of SEQ. ID. NO. 33, shown in Table C-1) folding is indeed more stable than other members of the group and is highly specific for $K^+$, as assessed from the ion dependence of thermal denaturation, CD spectra and UV detected folding kinetics.

To assess the relationship between biological activity and formation of the ion-selective oligomer fold, the inventors compared tertiary structure stability at three $K^+$ concentrations with the capacity of the folded oligomers to inhibit the HIV-1 integrase enzyme in vitro, or HIV-1 infection in cell culture. The stability and activity data are found to be highly correlated, as a function of sequence alteration, suggesting that formation of the stable intramolecular fold may be a prerequisite for both integrase inhibition and anti-HIV-1 activity. Although the structure of the folded state has not yet been confirmed at high resolution, the data presented here suggested that the structure of the T30695 complex with $K^+$ ion may be of pharmaceutical significance and could serve as the basis for additional improvement of the observed HIV-1 activity.

Materials and Methods for the Structure/Function Studies

Oligonucleotide Synthesis

All oligonucleotides used in this study were synthesized on an Applied Biosystems Inc. DNA synthesizer, model 380B or 394, using standard phosphoramidite chemistry, or fast deblocking Expedite chemistry on a Milligen synthesizer. All oligomers possessed 2 phosphorothioate linkages (one on each terminus) which were introduced by the H-phosphonate method. Oligonucleotides were purified by preparative anion exchange HPLC, on Q-Sepharose. Chain purity was confirmed by analytical Q-sepbarose chromatography, and by denaturing electrophoresis of 32P labeled oligomers on a 20% polyaerylamide (19:1), 7M urea gel matrix (Rando et al., (1994) *J. Biol. Chem.* 270, 1754–1760, 17). In all instances, greater than 90% of the purified oligomer was determined to be full length. Oligomer folding was monitored by native gel electrophoresis on 15% acrylamide (19:1) matrix in TBE. Folded, 32P labeled samples were loaded subsequent to annealing in 20 mM Li3P04, pH 7.0, 10 mM KCl at 7 uM in strands, as described below.

Annealing

Prior to UV, CD or kinetic analysis, oligonucleotides were annealed at 20 mM Li3P04, pH 7 at 3–15 uM in strands. Samples were heated to 90° C. for 5 min and then incubated for 1 hour at 37° C. Metal ion could be added as the chloride either before or after the 37 ° C. incubation, with no measurable difference in final state, as assessed by UV, CD or gel analysis. As assessed by native gel electrophoresis (not shown), this annealing method was found to produce a single product with mobility consistent with a folded monomer over the strand concentration range from 3–15 uM, at all ion concentrations described.

Ultraviolet Spectroscopy

UV measurements were obtained on a HP 8452A diode array spectrometer, using a HP 89090A temperature regulator. Except where noted, thermal denaturation profiles were obtained at a rate of 1.25° C./min over the range from 20° C.–80° C., on samples at 20 mM Li3P04, pH 7, at 7 uM in strands. Absorbance was monitored at 240 nm, which was determined to be the point of maximal temperature induced change. For melting analysis, metal ion was added to the desired concentration, followed by a one hour pre-incubation at 37° C., to ensure compete annealing. Folding kinetics were obtained by manual addition of metal ion at t=0, followed by absorption measurement at 264 nm. Mixing dead time was determined to be 10 sec. Kinetics were monitored over the range from 10 sec to 15 min at 25° C.

Circular Dichroism

CD spectra were obtained at 25° C. in 20 mM Li3P04, pH 7, at 15 uM in strands, on a Jasco J-500A spectropolarimeter. Metal ion was added to the desired concentration, followed by one hour of pre-incubation at 37° C. Each spectrum in the text represents 5 averaged scans. To conform to traditional standards, data are presented in molar ellipticity (deg-cm2-dmolE-1) as measured in base, rather than strand equivalents.

Antiviral assay. The RF laboratory strain of HIV-1 was used to infect established cell lines for one hour at 37° C. prior to washing and resuspension in medium containing increasing concentrations of drug. Four to six days post-infection, drug treated and control wells were analyzed for HIV-1 induced cytopathic effects, for the presence of viral reverse transcriptase (RF) or viral p24 antigen in the culture medium as previously described by Ojwang et al. (Bishop et al., (1996) *J. Biol. Chem.* 271, 5698–5703). Purified recombinant HIV-1 integrate enzyme (wild-type) was a generous gift from Dr. Craigie, Laboratory of Molecular Biology, NIDDK. All 3'-processing and strand-transfers were performed as described previously by Fresen et al. (Fresen et al. (1993) *Proc. Natl. Acad. Sci. USA* 90, 2399–2403) and Mazurnder et al. (Mazumder et al. (1994) *Proc. Natl. Acad. Sci. USA* 91, 5771–75).

Results of Structure/Function Studies

The structure of the oligonucleotides in this study are presented in FIG. 37A. For the purposes of clarity, they have been represented in the context of a particular folding model which places eight of the guanosincs as a central octet and the remainder of the oligomer in either a loop region, or as part of a 1–2 base long tail region at the 5' or 3' terminus. Previous electrophoresis and ID NMR data (Rando et al., (1994) *J. Biol. Chem.* 270, 1754–1760) have strongly suggested that T30177 folds so as to form an intramolecular G-tetrad based structure which is stabilized by a single central G-octet. Therefore, for T30177, the simple model presented in FIG. 37A is adequately substantiated by structural data. The validity of a similar structural model for the other members of the series is legitimately assumed based upon their sequence similarity, to be tested in terms of the data presented below.

Thermal Denaturation Analysis

Based upon previous NMR data, and the general literature, the inventors postulated that folding of T30177 should be strongly dependent upon $K^+$ binding. To quantify this, they measured the thermal stability of T30177, as a function of added KC1 concentration. Coupled equilibrium theory predicts that, in the instance that $K^+$ binding stabilizes formation of an intramolecular fold, measured TM values should increase linearly with the Log of the KC1 concentration. Such data are shown in FIG. 38A, line b. It is seen that in the presence of 20 mM Li3PO4, measured Tm values for T30177 increase from 38° C. to 65° C. in the range from 0.1 to 10 mM of added KC1. This very large increase in Tm below 10 mM of added KC1, in the presence of 20 mM of Li3PO4 as buffer, argues strongly that the effect of $K^+$ binding is not a simple ionic strength effect.

The inventors have noticed that the measured Tm values for T30177 are consistently higher, by 1030° C., than has been seen for other small intramolecular folds (Smith, F. W., & Feigon, J. (1992) *Nature (London)* 344, 410–414; Schultze, et al., J. (1994) *J. Mol. Biol.* 235, 1532–1547). Since T30177 differs from these other homologues only in terms of the proposed loop domains, the inventors have synthesized homologues of T30177 where the central G-octet remains constant, but where the loop domains to either side have been modified by addition or replacement of a single base. In the context of the simple folding model (FIG. 37A) the T30676 homologue is identical to T30177, but has been modified so as to add an additional G into the topmost loop of the structure. As seen in FIG. 38A, line c, this one base addition produces a 20° C. decrease in Tm over the entire range of $K^+$ ion tested. Similarly, the T30677 (SEQ. ID. NO. 55) homologue was prepared (FIG. 37A), which is identical to T30177 (pPT variant of SEQ. ID. NO. 33), but has been modified so as to convert a pair of Gs in the bottommost loop domain. As seen in FIG. 38A, line d, this two base loop substitution produces a 30° C. decrease in Tm over the range of $K^+$ ion tested.

In the context of these substantial stability changes, the inventors sought to confirm that the general mechanism of folding had not been altered by base substitution. Thus, Tm analysis was repeated at 1 mM KC1 as a function of strand concentration in the range from 3 to 10 $\mu$M (FIG. 38C). As seen, a measurable strand concentration dependence could not be detected over this three fold range of variation, for any of the derivatives, thus verifying that the folding equilibrium remains intramolecular throughout. This was confirmed by native gel electrophoresis, which continued to display a single folded oligomer state (not shown), similarly, it was observed that the thermal difference spectrum for all three homologues was very similar (not shown).

Oligomer Design Improvement

Based upon the unusually high thermal stability of T30177, relative to intramolecular folds in the literature, and upon the 20–40° C. decrease in Tm observed as a function of what should have been a simple loop modification (FIG. 37A), the inventors concluded that interactions within the loop domains may contribute to stability. Specifically, it is proposed that $K^+$ ions may engage in stable binding to the loop domains of T30177. Simple docking calculations, performed with BIOSYM software (not shown) suggested that the TGTG loop configuration at the lower face of these folded homologues could, in cooperation with the proximal G-tetrad, give rise to tight $K^+$ coordination which is similar to that seen when $K^+$ (or $Na^+$) ion coordinates between G-tetrads (Bishop et al., (1996) *J. Biol. Chem.* 271, 5698–5703). In the context of that proposal, the inventors noticed that, if the penultimate T were removed from the 5' terminus of T30177, the distribution of nucleotide bases in the uppermost face of the fold would be similar to that of the lower face, but with one less internucleotidyl phosphate linkage.

Those considerations served as the basis for the design of the 16 mer oligonucleotide, T30695 (FIG. 37A). As seen in FIG. 38A, line a, even though T30695 is one base shorter than the T30177 homologue, it was found to melt at approximately 10° C. higher temperature, over the entire $K^+$ range tested. As for the other homologues, Tm values for T30695 were found to be strand concentration independent, confining the general similarity of the folding process (FIG. 38C).

For T30695, the $K^+$ ion dependence of thermal stability was very striking. In the presence of 20 mM of Li3PO4 as buffer, measured Tm values increase from 40° C. to 65° C. over the added KC1 range from 50 EM to 1 mM. Again, this ion dependence argues that the observed stabilization is likely to result from site-specific ion binding, rather than simple ion-screening effects.

In order to explore the selectivity of ion binding by T30695, Tm values have been measured for alkaline metal ions with differing radius: $Na^+$ (0.99A), $K^+$ (1.38A), $Rb^+$ (1.49A), and Cs+ (1.69A). As seen in FIG. 38B, significant $K^+$ ion selectivity is detected. Although $Rb^+$ is very similar to $K^+$ in general chemical properties, and differs by only +0.11A in ion radius, it is seen that the $Rb^+$ complex with T30695 melts at approximately 20–30° C. lower temperature over the entire concentration range studied. $Na^+$ ion and Cs+ ion, which differ from $K^+$ in ion radius by −0.37A and +0.29A, respectively, are seen to be even more destabilizing. Similar ion binding selectivity were obtained by this method for the T30177 homologue (not shown).

Circular Dichroism

In order to explore the nature of these ion binding effects, the inventors monitored the folding of T30695 by circular dichroism (CD) methods. It is known that G-quartet based folding, both intra and intermolecular, gives rise to large induced ellipticity values (Balagurumoorthy, P. & Brahmachari, S. K. (1994) *J. Biol. Chem.* 269, 21858–21869; Jin, et al. (1992) *Proc. Natl. Acad. Sci. USA* 89, 8832–8836; Lu et al. (1992) *Biochemistry* 31, 2455–2459; Gray et al. (1992) *Methods in Enzymology* 211, 389–406). Stable tetrad folds are characterized by nonconservative spectra, with maxima at 264 nm (~1×10+5 deg-cm2/dmol) and 210 rim (~5×10+4 deg-cm2/dmol) and a minima at 240 rim (−4×1044 deg-cm2/dmol).

In FIG. 39A, the inventors monitored the CD spectrum of T30695 at 0, 0.05 and 10rnM KC1. As seen, at the highest added KC1 concentration, the induced CD spectrum is very similar to that predicted for an orderly G-tetrad based fold. Interestingly, the spectrum obtained in the absence of added KC1 is indicative of significant folding in the absence of added $K^+$ ion, at 25° C. in the supporting 20 mM Li3PO4 buffer. Tm data for T30695 in FIG. 38A suggests an extrapolated Tm near to 20° C. in the limit of very low added $K^+$ ion. That extrapolated value is consistent with the structure evidenced at 0 mM KC1 in FIG. 39A.

Detailed $K^+$ titration data of that kind have been presented in FIG. 39B, for T30695, T30177, and T30676. As seen, all three oligomers displayed a generally similar increase in elliptic as a function of added $K^+$ ion concentration, which is consistent with the hypothesis that they fold ire a fashion similar to the simple model of FIG. 37A. However, the ion concentration dependence of the folding process is quantitatively different for the three. As would have been predicted from the Tm data of FIG. 38A, it was found that the coupling between $K^+$ ion binding and folding is stronger for T30695 (transition midpoint near to 0.02 mM), than is the case for T30177 (0.15 mM) or T30676 (0.27 mM). The T30677 oligomer, which was the least stable of the oligomers tested by Tm analysis, showed very little ellipticity change over the 0–100 mM KC1 range, and therefore has not been presented in FIG. 39B.

Closer inspection of the data in FIGS. 39A and 39B suggested that the CD titration for T30695 is biphasic, with a first step completed by 0.1 rnM, and a second step which is complete in the 1–2 rnM range. In order to confirm that the $K^+$ induced folding process involves two steps, the inventors have performed CD titrations with different alkaline metal ions (FIG. 39C). The inventors $Rb^+$ induced folding of T30695 is associated with an overall ellipticity increase which is very similar to that induced by $K^+$. This argues that the $Rb^+$ and $K^+$ complexes are folded in a similar fashion. However, as expected from the Tm differences seen in FIG. 38B, it is observed that $Rb^+$ ion induced folding is quantitatively different, occurring only at relatively high added ion concentration (0.5 rnM midpoint as compared to 0.02 rnM for $K^+$). This confirms that $Rb^+$ is a much poorer effector of the folding process. A very similar $K^+$ vs. $Rb^+$ differential was seen for T30177 (not shown), which suggests that the two oligomers display similar overall ion binding selectivity.

The biphasic character of the T30695 folding process now easily detected upon addition of $Rb^+$ (FIG. 39C). The magnitude of the CD change associated with the first and second ion induced steps are similar for both $K^+$ and $Rb^+$, confirming that the folding process has not been significantly altered in a qualitative fashion by $Rb^+$. For comparison, it was observed that folding of T30695 as a function of $Na^+$ ion binding is not biphasic, and is associated with a total ellipticity increase which is no larger than that of the first transition seen in the presence of $K^+$ and $Rb^+$ ion. One interpretation of this difference is that $Na^+$ ion is capable of driving the first, but not the second step in the folding process. This proposal will be discussed below.

Folding Kinetics

In order to investigate the two step folding process in more detail, the inventors have measured the kinetics of oligomer folding, for T30695 and T30177 at 25° C. in the standard 20 rnM Li3PO4 buffer. Data were obtained by manual addition of $K^+$ or $Rb^+$ ion at time zero, followed by measurement of UV absorbance change at 264 nm, in the 0 to 300 second time range. In FIG. 40A, $K^+$ ion has been added to T30177 at 0.2 uM (curve a), 1.0 rnM (curve b) or 10 uM (curve c). In FIG. 40B, $Rb^+$ ion has been added to T30695 at 1 uM (curve a), 5 uM (curve b) or 10 uM (curve c). These three values are approximately those required to obtain the midpoint, endpoint and ten times the endpoint of the $K^+$ induced (FIG. 39B, curve b) or $Rb^+$ induced folding process (FIG. 39C). Although not shown, the kinetic data described below were found to be nucleic acid concentration independent over the range from 3–10 uM in strands, confirming that the folding process is intramolecular.

As seen in FIG. 40A, upon addition of $K^+$ to T30177 to 0.2 mM (curve a), a single slow kinetic process is detected with a time constant near 18 sec. Interestingly, this component is hyperchromic, indicating a net loss of base stacking interaction during this first step of the folding process. Upon addition of sufficient $K^+$ to drive the folding transition to completion (1 uM, curve b), a second kinetic component is detected (~=15 sec, t2=1×104 sec). The second component is hypochromic, indicative of a net increase in base stacking, and is very slow. Upon an additional increase of $K^+$ ion to 10 μM (curve c), the first kinetic component becomes nearly too fast to be detected in the current apparatus, while the time constant for the second step has decreased to about 50 sec. Very similar kinetics, but approximately 20-fold slower, have been obtained upon addition of $Rb^+$ ion to T30177 (not shown).

In FIG. 40B, the inventors have performed a similar folding analysis on T30695, but with $Rb^+$ instead of $K^+$ ion. This was done because, for T30695, the kinetics of $K^+$ induced folding were too fast to be detected in the simple optical apparatus employed. As seen in FIG. 40B, upon addition of $Rb^+$ to 1 mM (curve a), a single slow kinetic process is detected, similar to that obtained at low $K^+$ ion concentration with T30695 (Taul=48 sec). Again, this component is hyperchromic, indicating a net loss of base stacking interaction. Upon addition of sufficient $Rb^+$ to drive the T30695 folding transition to completion (5 uM, curve b), a second kinetic component is detected. Again, the second component is hypochromic, indicative of a net increase in base stacking. Upon additional increase of $Rb^+$ ion concentration to 10 μM (curve c), the first kinetic component becomes nearly too fast to be detected, while the time constant for the second step has decreased from about 60 sec (curve b) to about 16 sec.

Although these initial kinetic data are not sufficient to solve for rate constants, the absorbance-detected kinetic data for both T30177 and T30695 are consistent with the equilibrium binding data obtained by CD (FIGS. 39B and C). Both techniques suggest that for $K^+$ and $Rb^+$, the ion induced oligomer folding process is aphasic. Kinetic data obtained with $Na^+$ ion (not shown), suggest that only the first, hyperchromic transition is obtained at any concentration in the 0–200 mM range. That observation is also generally consistent with $Na^+$ titration data (FIG. 39C). A structural model is proposed below to rationalize those observations.

A Relationship Between Structure and Function

The inventors' interest in T30177 and its derivatives has arisen because this class of oligonucleotide is a potent inhibitor of HIV infection in culture (Rando et al., (1994) *J. Biol. Chem.* 270, 1754–1760; Ojwang et al. (1994) *J. AIDS* 7, 560–570; Bishop et al., (1996) *J. Biol. Chem.* 271, 5698–5703; Ojwang et al. (1995) *Antimicrob. Agent Chemotherepy* 39, 242–635), and in vitro, has been shown herein to be the most potent inhibitor of HIV-1 integrase to have been identified thus far (see also Ojwang et al. (1995) *Antimicrob. Agent Chemotherepy* 39, 2426–35). In Table D-1, there is provided a catalog of the melting temperatures of the closely related set of derivatives used in this study, as an index of their stability as an intramolecular tetrad-based fold. Stability has been presented at three different added $K^+$ ion concentrations, spanning a range of Tm values which differ by 50° C. This was done to ensure that stability-activity correlations would not be limited to any particular $K^+$ ion concentration.

Three kinds of activity data have been presented. Integrase inhibition by these oligonucleotides has been monitored for both the 3' exonuclease and strand transfer activities of the purified HIV-1 integrase (Ojwang et al. (1995) *Antimicrob. Agent Chemotherepy* 39, 2426–35). Data are presented in Table D-1 as the IC50, in nM of added oligonucleotide. Antiviral activity has been obtained as described herein and elsewhere (Ojwang et al. (1995) *Antimicrob. Agent Chemotherepy* 39, 2426–35), and is presented as the IC50, in nM, of added oligonucleotide.

Inspection of Table D-1 suggests that, relative to any added $K^+$ ion concentration, there is a correlation between thermal stability of the folded state and the capacity to inhibit the exonuclease or strand transfer activity of purified HIV-1 integrase. A qualitative correlation is also obtained when comparing thermal stability with measured anti-HIV activity in cell culture. A relationship between thermal stability and function can only be meaningful for folded structures which are very similar. However, given the sequence similarity among these four homologues in Table D-1, and the similarity of their ion-induced folding process, the correlations are likely to be meaningful.

Conclusions Regarding the Structure/Function Studies

Data were obtained suggesting that the anti-HIV oligonucleotide drug T30177 and its homologue T30695, fold via intramolecular G-tetrad formation, to yield a structure which is stabilized by $K^+$ ion binding. It is well known from the literature that alkaline metal ions can stabilize G-tetrad formation (Williamson, J. R. (1994) *Annul Rev. Biophys. Biomal. Struct.* 27, 703–730). What distinguishes the behavior of these two oligomers is the unusually high stability of the folded state (FIG. 38A), the high selectivity shown for $K^+$ ion (FIGS. 38B and 39C) and the possibility that $K^+$ coordination may be strongly coupled to loop structure within the oligonucleotide fold (FIGS. 38A and 39B). Consistent with the idea that ion binding may occur with G-tetrads and with loops, the inventors have observed that the folding of T30695 and T30177 appears to occur as a two step process, as detected by equilibrium (FIG. 39) and kinetic methods (FIG. 40).

In order to relate these various observations, the inventors have found it useful to propose a simple, two step folding model (FIG. 37B). They suggest that the first, higher affinity ion binding step occurs by coordination of metal ion with the central-most pair of G-tetrads, thereby generating a core octet which is similar to that seen in related intramolecular folds (Williamson, et al. (1989) *Cell* 59, 871–880; Panyutin, et al. (1990) *Proc. Natl. Acad. Sci. USA* 87, 867–870; Smith, F. W., & Feigon, J. (1992) *Nature (London)* 344, 410–414; Schultze, et al. (1994) *J. Mol. Biol.* 235, 1532–1547). It is proposed that, by analogy to those other, better understood G-tetrad based structures, this first ion binding step has rather modest selectivity among the alkaline metal ions (Williamson, J. R. (1994) *Annul Rev. Biophys. Biomal. Struct.* 27, 703–730). The inventors propose that the second step in the folding process involves binding of additional ion equivalents to the loop regions of the structure. It is also proposed that this second process, which occurs at higher added ion concentration (FIG. 39) and which is associated with the slow kinetic step of FIG. 40, is coupled to a rearrangement of the loop domains to yield two additional sites for metal ion coordination.

In preliminary modeling studies (not shown), the inventors have confirmed that orderly structures of the proposed kind can be obtained in which carbonyl oxygens from T and G base plains are organized in the loops so as to complement the end of the G-octet, resulting in octahedral coordination of one $K^+$ equivalent at each of the two junctions between loop and core octet domains. It is proposed that this capacity for additional $K^+$ ion binding is the origin for the remarkable stability of T30695, the corollary being that other homologues described in this work are less stable because they have lost one or the other of the proposed $K^+$ coordination sites. A second corollary of the model is that the high ion selectivity seen for these oligomer folds is dominated by the structural requirements for ion binding to the loops, rather than from ion binding within the core octet. Preliminary NMR data (Ding & Hogan, unpublished data) suggests that the additional binding step involves 2 equivalents of $K^+$, yielding 3 $K^+$ equivalents per oligomer fold, at saturation.

Confirmation of this model awaits detailed structure analysis. However, the data at hand (Table D-1) suggest that formation of the ion-selective oligomer fold described herein may be a necessary pre-condition for anti-integrase and the overall anti-HIV activity of these compounds. As such, refinement of the present folding model could prove useful as the basis for pharmaceutical improvement.

Dosing

Twelve experimentally naive cynomolgus monkeys were assigned to four groups of three animals each. Prior to dosing, each animal was lightly sedated with a combination of ketamine (10 mg/kg) and diazepam (0.5 mg/kg), and a catheter was introduced into the femoral artery for recording central arterial pressure. Monkeys were given a single intravenous infusion of 5, 20, or 50 mg AR177/kg or saline over ten minutes through a cephalic vein catheter using a Harvard infusion pump. Arterial blood samples were drawn at −10, +10, +20, +40, +60 and +120 minutes relative to the initiation of infusion into EDTA-containing tubes for hematology, complement factors, coagulation assay, serum chemistry, and plasma AR177 determination. At 24 hours post-infusion, blood was drawn via the femoral vein into EDTA-containing tubes for these same parameters. The concentration of AR177 in dosing solutions was confirmed post experiment by absorbance at 280 nm on a spectrophotometer. For the determination of AR177 by HPLC, the plasma fraction was obtained by low speed centrifugation of

TABLE D-1

| Oligomers | 5'-Sequence-3' | $T_m$ (° C.) (1 mM KCl) | $T_m$ (° C.) (10 mM KCl) | $T_m$ (° M) (180 mM KCl) | $IC_{50}$ (nM) 3'-PROC | $IC_{50}$ (nM) STR.TRA | $IC_{50}$ (nM) HIV-1RF |
|---|---|---|---|---|---|---|---|
| T30695 | GGGTGGGTGGGTGGGT | 67 | 87* | 110* | 43 ± 17 | 24 ± 4 | 70 |
| T30177 | GTGGTGGGTGGGTGGGT | 53 | 70* | 92* | 79 ± 24[a] | 49 ± 5[a] | 75[a] |
| T30676 | GTGGTGGGTGTGGTGGGT | 33 | 46 | 65 | 148 ± 26 | 134 ± 16 | 1000 |
| T30677 | GTGGTTGGTGGGTTGGT | 17* | 27 | 40 | 725 | 620 | >40,000 |

$T_m$ with * were obtained by a calculation according to the linear fitting functions of $T_m$ vs. Log[KCl].
The data with [a] were previously reported by Ojwang et al. (Ojwang et al. (1995) Antimicrob. Agent Chemotherepy 39, 2426-35.).

Pharmacokinetic Studies

E. Single-dose hemodynamic toxicity and pharmacokinetics of a partial phosphorothioate anti-HIV oligonucleotide (AR177) following intravenous infusion to cynomolgus monkeys As part of the pre-clinical assessment of AR177, a toxicity study of AR177 (T30177) was conducted with the objective of establishing the dose-response relationship between intravenous infusion of AR177 and hemodynamic parameters in cynomolgus monkeys. Intravenous infusion is the proposed route of administration of AR177 to humans. The present study was conducted using the short term infusion protocol recommended by the Food and Drug Administration (Black et al., 1994), with measurement of central blood pressure, serum chemistry, hematology, coagulation factors, complement factors, and plasma AR177 concentrations.

Materials and Methods for Pre-Clinical Toxicology Screens

Materials

AR177 was synthesized at Aronex on a Milligen 8800 oligonucleotide synthesizer, and made into a stock solution at 25 mg/mL in sterile phosphate-buffered saline. AR177 has a molecular weight of 5793 daltons, and is a fully neutralized sodium salt. The structure of AR177 was characterized by phosphorus and proton NMR, sequencing, base composition, laser Resorption mass spectrometry, anion exchange HPLC and polyacrylamide gel electrophoresis. The AR177 was approximately 94% pure according to HPLC and electrophoretic analysis. All analyses are consistent with the proposed structure.

For HPLC analysis of plasma AR 177, tris was obtained from Fisher, NaBr and NaCl were obtained from Sigma, and methanol was purchased from J. T. Baker. The Gen-Pak Fax anion-exchange HPLC column (4.6×100 mm; cat. no. #15490) was purchased from Waters.

blood, and stored at −20° C. until used. Electrocardiograms (ECGs), central pressure, and heart rate were recorded continuously for 120 minutes following the initiation of dosing. Table E-1 summarizes the study design. The animals were observed twice daily for pharmacotoxic signs and general health beginning two days before dosing and for seven days following dosing. The monkeys were not necropsied at the end of the study.

Serum chemistry parameters

The following were determined: sodium, potassium, chloride, carbon dioxide, total bilirubin, direct bilirubin, indirect bilirubin alkaline phosphatase, lactate dehydrogenase, aspartate aminotransferase, alanine aminotransferase, gamma-glutamyltransferase, calcium, phosphorus, glucose, urea nitrogen, creatinine, uric acid total protein, albumin, globulin, cholesterol and triglycerides. The samples were analyzed at Sierra Nevada Laboratories (Reno, Nev.).

Hematology and coagulation parameters

The following were determined: red blood cell count and morphology, total and differential white blood cells, hemoglobin, hematocrit, prothrombin time, fibrinogen, mean cell hemoglobin, mean corpuscular volume, mean corpuscular hemoglobin concentration, platelet count, and activated partial thromboplastin time. Hematology parameters were determined at Sierra Nevada Laboratories (Reno, Nev.).

Complement factors

The complement split product Bb and total hemolytic complement CH50 were determined. The choice of measuring the Bb split product, as opposed to other complement factors, was based on a published study showing the involvement of the alternative pathway in complement activation induced by oligonucleotides (Galbraith et al, 1994). Complement determinations were performed in the laboratory of Dr. Patricia Giclas at the Complement Laboratory, National Jewish Center for Immunology (Denver, Colo.).
HPLC analysis of AR177 plasma concentrations AR177 was assayed in the plasma using an anion-exchange HPLC method on a Waters HPLC system with a 626 pump, 996 photodiode array detector, 717 autosampler and Millennium system software controlled by an NEC Image 466 computer. Buffer A consisted of 0.1 M Tris base, 20% methanol, pH 12, and Buffer B consisted of 0.1 M Tris base, 1.0 M NaBr, pH 12. The anion-exchange column (Gen-Pak Fax column) was equilibrated at 80% buffer A/20% buffer B for 30 minutes before each HPLC run. Fifty microliters of 0.2~filtered, neat plasma were analyzed per run. The elusion conditions were: a) five-minute isoaatic run at 80% A/20% B. during which the majority of the plasma proteins eluted, b) 25-minute linear gradient to 30% A/70% B during which AR177 elutes, c) five-minute Socratic run at 30% A/70% B. d) one-minute linear gradient to 100% B. e) two- minute run at 100% B for column clean-up, and fl two-minute linear gradient to 70% A/30% B for the step in the HPLC clean-up. The high pH (12) of the elusion buffers was necessary to dissociate AR177 from tissue constituents, which bind AR177 tightly around physiological pH. AR177 is completely stable at pH 12. This method can clearly distinguish between the full length AR177 and n-1, n-2, etc. species, which are potential metabolic products. The ultraviolet detection wavelength was 260 nm. The flow rate was 0.5 mL/minute in all steps. Column clean up between runs was performed by a 500 pL bolus injection of 0.1 M Tris base, 2 M NaCl, pH 10.5, followed by: a) ten-minute linear gradient to 60% A/40% B. b) one-minute linear gradient to 100% B. c) a three-minute isocratic run at 100% B and d) one-minute linear gradient to 80% A/20% B.

A standard curve was generated by spiking AR177 into cynomolgus monkey plasma in order to achieve concentrations of 0.04 to 128 $\mu$/mL. The plasma standards and unspiked plasma (control) were run on the anion-exchange HPLC column using e above conditions. The Waters Millennium software was used to determine the area under the peak for each AR177 standard at 260 nm. The HPLC peak area versus AR177 concentration was plotted using Cricket Graph III 1.5.1 software. There were one to three HPLC replicate runs per AR177 standard. The limit of quantitation was 25 ng/mL (50 pL injection), whereas the limit of detection was 5 ng/mL (50 pL injection). The overall correlation coefficient of the fitted lines on the standard curve plots was greater than 0.999 on two different standard curves used in this study. The standard curve was linear over an approximate 3,200-fold range. The variability of the replicates was 1–2% at all concentrations. There was one HPLC run per monkey plasma sample. This method was validated. Further details about the method will be published elsewhere (Wallace et al., submitted).

Pharmacokinetic parameters

The volume of distribution (Vd) was calculated by dividing the total dose administered by the concentration at the end of the infusion (Rowland and Tozer, 1995). The $C_{MAX}$, (maximum concentration) was taken from the plasma concentration at the conclusion of the ten-minute intravenous infusion.

Results/Clinical Observations and Hemodynamic Parameters

Aside from an anticoagulant effect described below, there were no indications of significant toxicity. No clearly treatment-related changes in blood pressure (FIG. 41), heart rate (data not shown) or electrocardiographic activity (data not shown) were observed, no animals died following AR177 infusion. One high-dose (50 mg/kg) monkey exhibited a rise in arterial pressure during the infusion followed by a decline to approximately 20–30 mm Hg below the pre-infusion blood pressure. These changes are qualitatively similar to, but less pronounced, than those seen in monkeys given total phosphorothioateoligonucleotides (Galbraith et al., 1994). Although suggestive of a treatment effect, the alterations in blood pressure in the subject animal could not be clearly distinguished from normal fluctuations that occurred in other animals, including one control monkey. The only treatment related clinical sign was emesis during the infusion, which occurred in two of the three animals in the 50 mg/kg group and all of the monkeys that received the 20 mg/kg dose.

Serum Chemistry

There were no changes in any of the serum chemistry parameters that could be attributed to AR177.

Hematology

There were no changes in hematology values attributable to AR 177. Neutrophil counts were increased to a similar extent in all groups, including the saline control group, probably as a result of the stress associated with the experimental procedure (FIG. 42). The characteristic neutropenia and rebound neutrophilia that has been reported with other oligonucleotides did not occur in the AR177-treated monkeys, which is consistent with the relatively small changes in complement Bb split product (FIG. 44) and CH50 (FIG. 45) levels.

Coagulation parameters

The most salient effect of AR177 observed in this study was a pronounced, albeit transient, dose-dependent, reversible prolongation of aPTT in the 20 and 50 mg/kg groups, which reflected inhibition of the intrinsic coagulation pathway. There was at least a four-fold prolongation of aPTT in the 20 and 50 mg/kg dose groups at the conclusion of the infusion of AR177. Determination of the upper aPTT value was limited by the range of the assay. (See FIG. 43). This change was reversible in both dose groups. The aPTT was increased beyond the upper limit of the assay in the 50 mg/kg group for all or most of the two-hour monitoring period, but had returned to normal by the following day. Baseline aPTT values were reestablished by two hours after termination of dosing with the 20 mg/kg dose. In the 5 mg/kg group, only a small and transient rise in aPTT was observed, and there was no change in prothrombin time (PT). Similar changes have been observed with other oligonucleotides, and are believed to be, at least in part, attributable to direct and reversible binding of the oligonucleotide to thrombin (Henry et al., 1994, *Pharmaceutical Res.* 11: S353, 1994). PT was affected to a much lesser extent than aPTT in the 20 and 50 mg AR177/kg groups (data not shown), indicating little or no effect on the extrinsic pathway.

Complement activation

Plasma levels of the complement split product Bb, a marker for activation of the alternative pathway, were increased 60–85% over baseline in the 5 mg/kg group, approximately 2-fold over baseline in the 20 mg/kg group, and approximately 2- to 4-fold in the 50 mg/kg group at the end of infusion. (See FIG. 44). The elevation in Bb persisted through the duration of the 2-hour monitoring period, but the values had returned to normal by the following day. These increases in Bb were small in magnitude. There were also small and transient decreases in the CH50 levels (FIG. 45) in the 20 and 50 mg/kg doses, but there was no dose-CH50 level relationship. In confirmation of this minimal change in CH50, AR177 had no effect on complement CH50 at doses up to 236 $\mu$/mL when it was tested in vitro in human or cynomolgus monkey plasma. (See below). Thus, a large increase in complement activation, and resulting characteristic neutropenia and rebound neutrophilia, that has been reported with other oligonucleotides (Galbraith et al., 1994) did not occur in the AR177-treated monkeys (FIG. 42).

Plasma AR177 concentration

Plasma concentrations of AR177 were maximal at the end of the infusion and declined thereafter with an approximate initial half-life of 20–30 minutes (FIG. 46). Another more complete study in cynomolgus monkeys has shown the terminal half-life to be approximately 24 hours (See below). These half-lives are much longer than that reported by Lee et al. ((1995) *Pharnaceut. Res.* 12:1943–1947) in cynomolgus monkeys for GS-522, a 15 mer oligonucleotide that has a tetrad structure similar to AR177. No metabolites of AR 177 could be observed in the plasma at any time point or dose. This contrasts with the results of Lee et al. (1995), who found significant amounts of shorter species of GS522 in monkey plasma following intravenous infusion. The results with AR177 suggest that AR177 does not undergo metabolism. There was a direct relationship between the AR177 plasma Cmax and the dose that was administered as a ten-minute intravenous infusion to the monkeys (FIG. 45). Plasma Cmaxs of 83.2+/−7.2, 397.8 +/−30.8, and 804.7+/−226.3 μg/mL were achieved for the 5, 20, or 50 mg/kg doses, respectively, at the end of the infusion (+10 minute time point) (Table E-2; FIG. 47).

The initial volume of distribution (Vd) of the three doses ranged from 200–248 mL (mean +s.d.) (Table E-2) at the conclusion of the intravenous infusion. The mean body weight of the monkeys in the AR177 dose groups was 3.67 kg. Assuming that plasma volume is 4% of body weight (Davies and Morris, 1993, *Pharmaceutical Res.* 10: 1093–1095), the plasma volume would be 147 mL. Thus, the initial Vd was slightly greater than the plasma volume.

In general, there was a direct relationship between the plasma concentration of AR177 and aPTT Atomated Partial Thromboplastin Time for the 5 (FIG. 48) and 20 (FIG. 49) mg/kg doses. For the 50 mg/kg dose (FIG. 50), the aPTT values were off-scale during the two-hour sampling period so it was not possible to determine the relationship between the plasma concentration and aPTT. There was a no effect plasma AR177 concentration versus aPTT of approximately 60–100 ug AR177/mL, above which there was prolongation of aPTT. Doubling of aPTT was observed at plasma AR177 concentrations of approximately 100–250 ug AR177/mL. Tripling of aPTT was observed at plasma AR177 concentrations of approximately 250–300 fig AR177/mL, after which no correlation was possible because the aPTT values were beyond the aPTT assay range. The disappearance of AR177 from plasma was roughly correlated with the return of the aPTT to baseline, which is consistent with direct and reversible binding of the oligonucleotide to one or more clotting factors. By contrast, there did not appear to be a correlation between the plasma concentration of AR177 and complement split product Bb (data not shown).

In addition to the in vivo study in cynomolgus monkeys, an in vitro study was performed which investigated the effect of AR177 on the coagulation- cascade and complement activity in cynomolgus monkey and human plasma (coagulation) and serum (complement), respectively. AR177 caused a two-fold increase in aPTT at a concentration between 30 and 59 μg/mL of human plasma, whereas the compound caused a two-fold increase in aPTT at a concentration between 118 and 236 μg/mL of cynomolgus monkey plasma in vitro. AR177 had no effect on thrombin time in human plasma, but caused approximately a 2.5-fold increase in thrombin time in cynomolgus monkey plasma at 236 μg/mL. AR177 had no effect on either fibrinogen or complement CH50 at doses up to 236 ug/mL in human or cynomolgus monkey plasma. AR177 caused a 30% increase in prothrombin time in human plasma and approximately a 15% increase in prothrombin time in cynomolgus monkey plasma at 236 μg/mL.

Discussion

Using an identical dosing regimen to that used in previous experiments that resulted in profound hemodynamic effects, the present study showed that AR177 was very safe. Although limited conclusions can be drawn from the present study because only one partial phosphorothioate (AR177) was examined, it is possible that the lack of the cardiovascular toxicity is due to the limited number of phosphorothioate linkages (two) in AR177. It is also speculated that the lack of toxicity could be due to the three-dimensional (i.e. tetrad) shape of AR177 (Rando et al., 1995, *J. Biol. Chem.* 270: 1754–1760). In confirmation of the lack of toxicity of AR177 found in the present study, AR177 does not cause toxicity when it is administered as a bolus intravenous injection to cynomolgus monkeys every other day at 40 mg/kg for a total of 12 doses (see below).

There was minimal activation of the complement system following administration of AR177. Small increases (2–4 fold) in plasma Bb levels occurred at plasma AR177 concentrations as high as 750 μ/mL after a dose of 50 mg/kg given as a ten-minute intravenous infusion. Minimal changes (−25%) in the CHX levels occurred at plasma AR177 concentrations as high as 750 μg/mL after a dose of 50 mg/kg given as a ten-minute intravenous infusion. The complement activation that was seen with AR177 at these high doses did not even result in hypotension. By contrast, Galbraith et al. (1994) have reported that GEM91, a 25-mer phosphorothioate oligonucleotide, caused an 80% decrease in complement CH50, a 700% increase in the level of complement C5a, and death in two out of four monkeys following the intravenous infusion of 20 mg/kg over ten minutes. The mechanism by which oligonucleotides activate the complement system is unknown. However, this phenomenon bears resemblance to a similar phenomenon in human patients during dialysis in which contact between blood and dialyser membrane induces complement activation and profound neutropenia (Heierli et al., 1988, *Nephrol. Dial. Transplant* 3: 773–783; Jacobs et al., 1989, *Nephron* 52: 119–124). The present work indicates that although AR177 induces some minimal complement activation, this is not translated into the hemodynamic toxicity that has been seen with other oligonucleotides.

AR177 administration resulted in the dose-dependent inhibition of the intrinsic coagulation pathway, reflected by prolongation of aPTT. The effect was maximal at the end of infusion and was reversed in parallel with clearance of AR177 from plasma. The inhibition of coagulation was significant at the highest dose level, but marginal and not considered clinically significant at the 5 mg/kg dose level. An anticoagulant effect has been reported to be a class effect of oligonucleotides (Henry et al., 1994). The anticoagulant results with AR177 thus agree with results that have been seen with other oligonucleotides, although AR177 is 40-fold less potent than the thrombin-binding aptamer oligonucleotide that has been reported by Griffin et al. (1993).

In conclusion, AR177 does not cause mortality, cardiovascular toxicity, or alterations in clinical chemistry in cynomolgus monkeys receiving doses up to 50 mg/kg as a ten-minute intravenous infusion. However, there was a reversible prolongation of coagulation time at doses of 20 and 50 mg/kg. Taken together, the data suggest that AR 177 does not have the hemodynamic toxicities that are associated with total phosphorothioate oligonucleotides, and can be administered safely as an intravenous infusion over ten minutes.

TABLE E-1

Monkey Dosing Information

| Group | Treatment | Dose level (mg/kg) | Dose Conc. (mg/mL) | Dose volume (mL/kg) | Male | Female | Monkey weight (kg) mean ± s.d. |
|---|---|---|---|---|---|---|---|
| 1 | Placebo | 0 | 0 | 4.0 | 1 | 2 | 3.67 ± 0.38 |
| 2 | AR177 | 5 | 1.25 | 4.0 | 2 | 1 | 4.12 ± 0.83 |
| 3 | AR177 | 20 | 5.0 | 4.0 | 2 | 1 | 3.67 ± 0.29 |
| 4 | AR177 | 50 | 4.0 | 4.0 | 1 | 2 | 3.23 ± 0.76 |

Table E-1 - Monkey dosing information

Cynomolgus monkeys were given ten-minute, intravenous infusions of 5, 20 or 50 mg AR177/kg at a volume of 4 mL/kg.

TABLE E-2

Plasma AR177, Vd, aPTT and complement Bb values at $C_{MAX}$

| Dose (mg/kg) | AR177 plasma ($\mu$g/mL) | Vd (mL) | a PTT (seconds) | Bb ($\mu$g/mL) |
|---|---|---|---|---|
| 5 | 83.2 ± 7.2 | 247.6 ± 21.4 | 45.9 ± 11.4 | 0.59 ± 0.07 |
| 20 | 397.8 ± 30.8 | 184.5 ± 14.3 | >166.8 ± 23.8 | 1.48 ± 0.44 |
| 50 | 804.7 ± 226.3 | 200.7 ± 56.4 | >170.0 ± 34.6 | 1.28 ± 0.46 |

Table E-2 - Plasma AR177 Cm, x, aPTT and complement Bb levels

The AR177 plasma $C_{MAX}$, aPTT, and Bb values are the means ± standard deviations of data at the +10 minute tune point (end of the infusion). The baseline (10 minutes prior to dosing) aPTT levels were 32.1±4.4, 41.6, 6.7 and 33.2±4.8 seconds for the 5, 20, and 50 mg/kg doses, respectively (mean ±s.d.). The baseline (10 minutes prior to dosing) Bb levels were 0.44±0.14, 0.78±0.46 and 0.49±0.21 $\mu$/mL for Me 5, 20, and 50 mg/kg doses. Volume of distribution (Vd)=dose/plasma $C_{MAX}$, where the dose is the total mg of AR177.

| | | | Serum Chemistry Values | | | | |
|---|---|---|---|---|---|---|---|
| | Pre-dose | 60 min | 24 hr | | Pre-dose | 60 min | 24 hr |
| Group | Alkaline phosphatase (Units/L) | | | Group | Lactate deyhdrogenase (Units/L) | | |
| Saline | 315.0 ± 21.6 | 293.3 ± 209.3 | 314.0 ± 234.7 | Saline | 340.0 ± 190.7 | 337.3 ± 133.1 | 1138.3 ± 1248.1 |
| 5 mg/kg | 257.7 ± 141.8 | 256.7 ± 142. | 344.7 ± 195.1 | 5 mg/kg | 228.7 ± 14.8 | 219.3 ± 11.9 | 799.0 ± 528.7 |
| 20 mg/kg | 269.3 ± 157.3 | 245.0 ± 121.5 | 238.0 ± 136.0 | 20 mg/kg | 266.0 ± 74. | 242.7 ± 61.5 | 583.3 ± 177.4 |
| 50 mg/kg | 143.0 ± 21.1 | 140.0 ± 33.8 | 149.3 ± 28.7 | 50 mg/kg | 203.3 ± 7.1 | 189.3 ± 19.7 | 409.7 ± 18.6 |
| | Asparate aminotransferase (Units/L) | | | | Alanine aminotransferase (Units/L) | | |
| Saline | 36.3 ± 16.7 | 36.7 ± 10.0 | 193.7 ± 188.9 | Saline | 49.3 ± 27.5 | 42.7 ± 23.8 | 93.3 ± 55.3 |
| 5 mg/kg | 35.0 ± 7.5 | 31.7 ± 7.6 | 258.0 ± 218.4 | 5 mg/kg | 27.7 ± 3.5 | 27.0 ± 4.0 | 148.3 ± 136.9 |
| 20 mg/kg | 48.7 ± 6.8 | 51.0 ± 12.3 | 119.7 ± 22.6 | 20 mglkg | 56.3 ± 34.0 | 49.3 ± 30.0 | 97.3 ± 19.9 |
| 50 mg/kg | 39.7 ± 16.5 | 41.7 ± 20.2 | 128.3 ± 21.2 | 50 mg/kg | 31.3 ± 7.4 | 30.3 ± 10.3 | 62.7 ± 7.6 |
| | Urea nitrogen (mg/dL) | | | | Creatinine (mg/dL) | | |
| Saline | 20.7 ± 1.5 | 20.7 ± 2.3 | 23.7 ± 2.5 | Saline | 0.90 ± 0.45 | 0.63 ± 0.12 | 0.90 ± 0.10 |
| 5 mg/kg | 16.7 ± 0.6 | 17.0 ± 1.0 | 20.7 ± 3.1 | 5 mg/kg | 0.63 ± 0.06 | 0.60 ± 0.00 | 0.97 ± 0.06 |
| 20 mg/kg | 21.7 ± 2.9 | 21.7 ± 2.1 | 27.3 ± 0.6 | 20 mg/kg | 0.67 ± 0.05 | 0.67 ± 0.15 | 0.83 ± 0.15 |
| 50 mg/kg | 14.7 ± 3.5 | 15.7 ± 2.5 | 25.0 ± 6.6 | 50 mg/kg | 0.50 ± 0.10 | 0.53 ± 0.06 | 0.67 ± 0.15 |

Serum chemistry was evaluated at pre-dose, and 1 and 24 hours following initiation of intravenous AR177 infusion. Values represent the mean ± s.d. of 3 monkeys.

| | Pre-dose | 10 min | 20 min | 40 min | 60 min | 120 min | 24 hr |
|---|---|---|---|---|---|---|---|
| Group | | | White blood cells ($10^3$/mm$^3$) | | | | |
| Saline | 14.1 ± 40 | 13.6 ± 3.3 | 13.9 ± 3.0 | 14.2 ± 2.7 | 14.0 ± 2.0 | 17.8 ± 2.2 | 21.1 ± 2.0 |
| 5 mg/kg | 9.3 ± 1.0 | 9.2 ± 2.3 | 9.5 ± 1.7 | 9.8 ± 1.2 | 8.6 ± 3.0 | 11.3 ± 2.7 | 13.2 ± 0.2 |
| 20 mg/kg | 8.1 ± 1.7 | 12.3 ± 0.3 | 12.0 ± 0.6 | 11.5 ± 2.2 | 11.8 ± 02.2 | 14.9 ± 0.7 | 14.4 ± 5.5 |
| 50 mg/kg | 6.7 ± 1.4 | 11.8 ± 1.7 | 10.9 ± 0 | 11.6 ± 3.1 | 13.8 ± 1.9 | 21.3 ± 4.0 | 13.2 ± 0.8 |
| | | | Lymphocytes ($10^3$/mm$^3$) | | | | |
| Saline | 8.2 ± 1.5 | 7.9 ± 1.7 | 8.4 ± 1.0 | 8.8 ± 0.2 | 9.2 ± 0.5 | 7.7 ± 1.5 | 11.6 ± 5.3 |
| 5 mg/kg | 6.2 ± 0.8 | 5.6 ± 10 | 6.5 ± 0.3 | 6.8 ± 1.1 | 5.7 ± 1.6 | 5.9 ± 0.8 | 5.5 ± 1.6 |
| 20 mg/kg | 5.0 ± 1.3 | 8.5 ± 0.3 | 8.3 ± 0.5 | 8.8 ± 1.9 | 8.5 ± 1.5 | 7.9 ± 1.2 | 5.3 ± 2.5 |
| 50 mg/kg | 4.1 ± 1.0 | 7.6 ± 0.7 | 7.7 ± 1.5 | 8.0 ± 1.1 | 10.5 ± 0.4 | 10.9 ± 1.9 | 5.3 ± 2.4 |

-continued

| | Monocytes ($10^3/mm^3$) | | | | | | |
|---|---|---|---|---|---|---|---|
| Saline | 0.54 ± 0.25 | 0.71 ± 0.17 | 0.62 ± 0.20 | 0.58 ± 0.20 | 0.59 ± 0.43 | 0.98 ± 0.53 | 1.64 ± 1.06 |
| 5 mg/kg | 0.37 ± 0.09 | 0.36 ± 0.22 | 0.35 ± 0.13 | 0.45 ± 0.06 | 0.36 ± 0.21 | 0.52 ± 0.30 | 1.37 ± 1.00 |
| 20 mg/kg | 0.24 ± 0.05 | 0.66 ± 0.32 | 0.59 ± 0.30 | 0.31 ± 0.15 | 0.60 ± 0.17 | 0.59 ± 0.30 | 0.99 ± 0.59 |
| 50 mg/kg | 0.16 ± 0.09 | 0.94 ± 0.69 | 0.33 ± 0.15 | 0.32 ± 0.18 | 0.32 ± 0.23 | 0.75 ± 0.48 | 0.53 ± 0.35 |
| | Platelet ($10^3 mm^3$) | | | | | | |
| Saline | 266.8 ± 41.9 | 251.3 ± 28.3 | 258.0 ± 47.8 | 262.3 ± 51.7 | 270.0 ± 47.6 | 278.0 ± 46.5 | 183.7 ± 124.5 |
| 5 mg/kg | 297.3 ± 34.4 | 362.3 ± 5.8 | 369.7 ± 14.6 | 367.3 ± 52.9 | 371.7 ± 44.5 | 292.3 ± 33.0 | 383.0 |
| 20 mg/kg | 272.3 ± 45.8 | 172.0 | 178.0 | 173.0 ± 48.1 | 206.0 ± 48.1 | 258.3 ± 29.0 | 158.7 ± 132.4 |
| 50 mg/kg | 329.3 ± 70.8 | UA | UA | 144.0 | UA | 278.0 ± 151.3 | 325.3 ± 105.6 |

Hematology was evaluated at pre-dose, at 10, 20, 40, 60 and 120 minutes and 24 hours following initiation of intravenous AR177 infusion. Values represent the mean ± s.d. of 2 to 3 monkeys. UA = sample unavailable.

Red Blood Cell, Hemoglobin and Hematocrit Values

| | Red blood cells ($10^6/mm^3$) | | | | | | |
|---|---|---|---|---|---|---|---|
| Saline | 5.7 ± 0.4 | 5.4 ± 0.4 | 5.3 ± 0.4 | 5.3 ± 0.4 | 5.2 ± 0.5 | 5.2 ± 0.6 | 4.7 ± 0.6 |
| 5 | 5.1 ± 0.5 | 4.9 ± 0.4 | 5.1 ± 0.6 | 5.1 ± 0.5 | 5.1 ± 0.5 | 5.0 ± 0.5 | 4.7 ± 0.4 |
| 20 | 5.5 ± 0.4 | 5.1 ± 0.4 | 5.4 ± 0.2 | 5.2 ± 0.2 | 4.9 ± 0.3 | 5.0 ± 0.3 | 4.0 ± 0.8 |
| 50 | 5.3 ± 0.4 | 5.1 ± 0.3 | 5.4 ± 0.1 | 4.9 ± 0.6 | 5.1 ± 0.4 | 4.9 ± 0.8 | 3.7 ± 1.0 |
| | Hemoglobin (g/dL) | | | | | | |
| Saline | 13.9 ± 1.6 | 13.1 ± 1.3 | 13.1 ± 1.4 | 13.2 ± 1.4 | 128 ± 1.9 | 12.6 ± 2.0 | 11.7 ± 1.6 |
| 5 | 12.3 ± 0.8 | 11.7 ± 0.5 | 12.1 ± 0.7 | 12.2 ± 0.5 | 12.1 ± 0.7 | 12.0 ± 0.8 | 11.3 ± 0.4 |
| 20 | 12.8 ± 0.9 | 12.3 ± 0.7 | 12.7 ± 0.9 | 12.1 ± 0.3 | 11.6 ± 0.5 | 11.9 ± 0.7 | 9.5 ± 1.7 |
| 50 | 12.7 ± 0.9 | 12.7 ± 0.7 | 13.1 ± 0.0 | 12.1 ± 1.2 | 12.6 ± 0.8 | 12.1 ± 1.7 | 0.2 ± 2.4 |
| | Hematocrit (%) | | | | | | |
| Saline | 42.1 ± 4.4 | 40.2 ± 2.5 | 39.9 ± 3.6 | 40.3 ± 3.6 | 39.6 ± 4.2 | 39.0 ± 5.4 | 35.6 ± 5.1 |
| 5 | 37.8 ± 2.0 | 35.8 ± 1.6 | 37.1 ± 2.1 | 37.5 ± 1.3 | 37.1 ± 20 | 36.5 ± 1.9 | 34.1 ± 0.4 |
| 20 | 39.6 ± 2.9 | 37.5 ± 2.2 | 39.3 ± 2.7 | 37.4 ± 1.0 | 35.8 ± 1.3 | 36.6 ± 1.9 | 29.2 ± 5.4 |
| 50 | 39.8 ± 2.2 | 393. ± 1.7 | 40.4 ± 0.4 | 37.5 ± 3.2 | 38.9 ± 2.3 | 37.3 ± 5.1 | 28.1 ± 6.9 |

Hematology was evaluated at pre-dose, at 10, 20, 40, 60 and 120 minutes and 24 hours following initiation of intravenous AR177 infusion. Values represent the mean ± s.d. of 3 monkeys.

F. Repeat-dose toxicity and pharmacokinetics of a partial phosphorothioate anti-HIV oligonucleotide (AR177) following bolus intravenous administration to cynomolgus monkeys AR177 is a 17-mer partial phosphorothioate oligonucleotide with the sequence 5'GTGGTGGGTGGGTGGGT-3' (SEQ. ID. NO. 33), with sulfurs at the terminal internucleoside linkages at the 3' and 5' ends. It is a potent inhibitor of HIV integrase and HIV production in vitro (Rando et al., 1995; Ojwang et al., 1995), and has a long tissue half-life in rodents (unpublished data). AR177 does not have an antisense- or triplex-based mechanism of action. A previous study has shown that AR177 does not cause the characteristic hypotension or neutropenia of other oligonucleotides (Cornish et al., 1993; Galbraith et al., 1994) following a ten-minute intravenous infusion, at doses up to 50 mg/kg (Wallace et al., submitted, 1996). As part of the pre-clinical assessment of AR177, an intravenous toxicity study of AR177 was conducted in cynomolgus monkeys with the objective of establishing the clinical and histopathological changes that occur following repeated doses.

Materials and Methods for Repeat Dose Studies

Materials

For HPLC analysis of plasma AR177 concentrations, tris was obtained from Fisher, NaBr and NaCl were obtained from Sigma, and methanol was purchased from J. T. Baker. The Gen-Pak Fax anion-exchange HPLC column (4.6×100 mm, cat. no. #15490) was purchased from Waters.

AR177 was synthesized at Biosearch, a division of PerSeptive Biosystems, on a Milligen 8800 oligonucleotide synthesizer, and vialed at 25 mg/mL in phosphate buffered saline. AR177 has a molecular weight of 5793, and is a fully neutralized sodium salt. The structure of AR177 was characterized by phosphorus and proton NMR, sequencing, base composition, laser Resorption mass spectrometry, anion exchange HPLC and polyacrylamide gel electrophoresis. All analyses were consistent with the proposed structure. The AR177 was approximately 94% pure according to HPLC and electrophoresis analysis.

The monkeys used in this study were laboratory bred (C.V. Primates, Indonesia or Yunnan National Laboratory, China) and were experimentally naive prior to the study. The age of the monkeys was 3 to 6 1/2 years.

Dosing

AR177 was administered intravenously over 1–2 minutes into unsedated monkeys every other day for 23 days (12 doses) by injection into the femoral vein. (See Table E-1). The monkeys were not sedated, but were restrained during dosing. The highest dose level (40 mg/kg/injection) was selected based on observations in a previous single-dose study of pronounced anticoagulant activity of AR177 at a dose of 50 mg/kg infused over 10 minutes (Wallace et al., submitted). A comparable or greater degree of anticoagulation was expected to occur with fast (1–2 minute) infusion of 40 mg/kg, and was confirmed by the results of this study. The dosing schedule (every other day) was chosen in order to avoid excessive accumulation of the test material, which, based on pharmacokinetic data obtained in rats (Wallace et al., submitted), would be expected to occur with daily administration.

The monkeys were observed twice daily for general health, changes in appetite and clinical signs of adverse events. Body weights were measured within a few days prior to the first dose (Day 1) and approximately weekly thereafter. Electrocardiographic (ECG) recordings were obtained from all animals prior to the study and on Day 22, and from recovery animals on Day 35. Blood samples were collected for evaluation of serum chemistry, hematology and coagulation parameters from all animals prior to the initiation of the study, on the first day of dosing (Dose 1; Day 1), and on the last day of dosing (Dose 12; Day 23). The sample collection on Days 1 and 23 was timed relative to dose administration in order to characterize possible acute effects on hematology parameters. An additional clinical pathology evaluation was conducted for all animals on Day 24, as well as for recovery animals on Day 37. Blood was collected from all animals at 5 minutes, 30 minutes and 4 hours post-dosing on Days 1 and 23 for analysis of the plasma AR177 concentration.

On Day 25 (two days after the last dose), three males and three females from each group were humanely euthanized and necropsied, while the remaining two animals each in the high-dose and control groups were continued on study for an additional two-week treatment-free "recovery" period, and were euthanized on Day 38. Complete gross necropsies were performed on all animals at their scheduled termination. Urine was collected from each animal during necropsy by bladder puncture and submitted for routine urinalysis. Weights of 13 major organs were recorded, and numerous tissues were collected, preserved and processed for histology.

Serum chemistry parameters

Serum chemistry was determined pre-study, on day 24 (one day after the 12th dose), and on day 37 in the recovery monkeys. The following were determined: sodium, potassium, chloride, carbon dioxide, total bilirubin, direct bilirubin, indirect bilirubin alkaline phosphatase, lactate dehydrogenase, aspartate aminotransferase, alanine aminotransferase, gammaglutamyltransferase, calcium, phosphorus, glucose, urea nitrogen, creatinine, uric acid total protein, albumin, globulin, cholesterol and triglycerides. Serum chemistry was determined at Sierra Nevada Laboratories (Reno, Nev.).

Hematology and coagulation parameters

Hematology and coagulation parameters were determined 9–11 days prior to the start of the study, just prior to administering doses 1 (day 1) and 12 (day 23), five minutes after dosing (coagulation only), 30 minutes and 4 hours following dosing, one day after the 12th dose (day 24), and in recovery monkeys at sacrifice (day 37). The following were determined: red blood cell count and morphology, total and differential white blood cells, hemoglobin, hematocrit, prothrombin time, fibrinogen, mean cell hemoglobin, mean corpuscular volume, mean corpuscular hemoglobin concentration, platelet count, activate partial thromboplastin time, and D-dimer. Hematology was determined at Sierra Nevada Laboratories (Reno, Nev.).

AR177 plasma HPLC analysis

Blood was taken for plasma analysis of AR 177 just prior to, and at 5, 30 and 240 minutes following administration of doses 1 and 12. The plasma fraction was obtained by low speed centrifugation of blood, and stored at $-20°$ C. until analyzed for the AR177 concentration. Plasma AR177 concentrations were assayed using an anion-exchange HPLC method on a Waters HPLC system with a 626 pump, 996 photodiode array detector, 717 autosampler and Millennium system software controlled by an NEC Image 466 computer. Buffer A was 0.1 M Tris base, 20% methanol, pH 12, and Buffer B was 0.1 M Tris base, 1.0 M NaBr, pH 12. anion-exchange column tGen-Pak Fax column) was equilibrated at 80% buffer A/20% buffer B for 30 minutes before each HPLC run. Fifty microliters of plasma were analyzed per run. The elusion conditions were: a) five-minute isocratic run at 80% A/20% B. during which the majority of the plasma proteins eluted, b) 30-minute linear gradient to 30% A/70% B during which the AR177 eluted, c) five-minute isocratic run at 30% A/70% B. d) one minute linear gradient to 100% B. e) two- minute run at 100% B for initial column cleanup, and fl two-minute linear gradient to 70% A/30% B for the initial step in the clean-up method for HPLC column clean-up. The high pH (12) of the elusion buffers was necessary to dissociate AR177 from tissue constituents, which bind AR177 tightly around physiological pH. AR177 is completely stable at pH 12. This method can clearly distinguish between the full length AR177 and n-1, n-2, etc. species, which are potential metabolic products. The W detection wavelength was 260 nm. The flow rate was 0.5 mL/minute in all steps. All runs were performed at room temperature. Column clean up between runs was performed by a 500 $\mu$L bolus injection of 0.1 M Tris base, 2 M NaCl, pH 10.5, followed by: a) ten-minute linear gradient to 60% A/40% B. b) one-minute linear gradient to 100% B. c) a three-minute isocratic run at 100% B and d) one-minute linear gradient to 80% A/20% B.

AR177 was spiked into cynomolgus monkey plasma in order to achieve concentrations of 0.0635 to 125 $\mu$g/mL for the standard curve. The plasma standards and unspiked plasma (control) were run on the anion-exchange HPLC column using the above conditions. The Waters Millennium software was used to determine the area under the peak for each AR177 standard at 260 nm. The HPLC area versus AR177 concentration was plotted using Cricket Graph m 1.5.1 software. There were two HPLC replicate runs per AR177 standard. The areas which represented the lowest concentration were at least two times the background area at 260 nm. The overall correlation coefficient of the fitted lines on the standard curve plots was greater than 0.999. There was a linear concentration versus A260 relationship over a minimum 6,500 fold range. The variability of the replicates was 1–2%. This method was validated.

Necropsy and histopathology

A complete necropsy was conducted on all monkeys, and included examination of the external surface of body (body orifices; dosing site; cranial, nasal, paranasal, thoracic, abdominal and pelvic cavities), and the external surface of the brain and spinal cord. The organ weights of the adrenals, epididymies, liver, pituitary, spleen, thyroids, parathyroids, brain, heart, lungs, prostate, testes, uterus, cervix, kidney, ovaries, seminal vesicles, and thymus were recorded.

A histopathological assessment was made of 46 hematoxylin and eosin-stained tissues by a veterinary pathologist. These included tissues from the cardiovascular, digestive, respiratory, urogenital, lymphoid/hematopoietic, skin/musculoskeletal and nervous systems, and all major organs.

Results

Clinical observations

No animals died during the course of the study, and there were no effects on body weight. The only treatment-related clinical sign was an incidence of discoloration around the eyes in three high-dose animals, which occurred on only one occasion (Day 16 or 18) for two of the animals, and on four consecutive days (Days 18–21) in the third animal. The latter monkey also had swelling around the eyes on Day 18. The reaction was transient and was limited to the high-dose group.

ECG, clinical chemistry, urinalysis and hematology

No abnormalities in the ECG recordings were noted, and there were no treatment-related changes in serum chemistry or urinalysis parameters. The only changes in hematology parameters considered possibly treatment-related were an acute and transient increase in lymphocytes in the high-dose group, and an acute decrease in eosinophils which was seen in all groups, but appeared to be more pronounced in the AR177-treated groups. Both of these changes were observed shortly following dosing on Days 1 and 23 (i.e., those days when clinical pathology was evaluated at several time points post-dosing), but were largely absent on Day 24 (one day after the last dose). The values generally remained within the normal range and were not considered indicative of significant toxicity.

Necropsy and Histopathology

No clearly treatment-related histopathologic changes were seen in any organs or tissues, and no effects on organ weight were evident. Eosinophilic material was seen in a few tubules in the medullary area of the kidneys of three monkeys in the high dose group on day 25, but was not seen in the controls or in the recovery animals. Although this may be treatment-related, eosinophilic material can sometimes be observed in the renal tubules of healthy, untreated monkeys.

Plasma AR177 concentration

FIG. 51 shows that there was no difference between the AR177 plasma concentrations that were achieved after the first and twelfth (last) doses at either 2.5, 10 or 40 mg/kg. The plasma concentration versus time profile of AR177 is shown in FIG. 52. At the earliest sampling time point (five minutes after initiation of dosing), maximal plasma levels of 35.79±5.99, 135.43±16.19 and 416.54±54.55 $\mu$/mL were achieved for dose #1 at 2.5, 10 and 40 mg/kg (FIG. 52). At the earliest sampling time point (five minutes after initiation of dosing), maximal plasma levels of 33.98+9.98, 113.71±26.55 and 386.39±70.29 $\mu$/mL were achieved for dose #12 at 2.5, 10 and 40 mg/kg. The decay kinetics of the 2.5 mg/kg dose appeared to be different than the decay kinetics of the 10 and 40 mg/kg doses after either dose 1 (FIG. 52), although no definite conclusions can be drawn because of the limited number of time points. No metabolites (i.e. n-1, n-2, etc.) could be observed in the plasma at any time or any dose. This confirms results in rats showing no metabolism of AR177 (Wallace et al., submitted).

Coagulation parameters

Dose-dependent anticoagulant activity was manifested at the 10 (FIG. 54) and 40 (FIG. 55) mg/kg doses, whereas there was no anticoagulant activity following the 2.5 mg/kg dose (FIG. 53). This activity was evident from the prolongation of activated partial thromboplastin time (aPTT), which reflects a primary effect on the intrinsic coagulation pathway. Following both the 1st and 12th doses, mean aPTT in the 10 mg/kg group was increased to approximately twice the pre-dose value by 5 minutes post-dosing, but had returned to baseline levels by four hours. Following both the 1st and 12th doses, mean aPTT in the 40 mg/kg group exceeded the upper limit of the assay five minutes after dosing. By 30 minutes post-dosing, aPTT values in the 40 mg/kg group had declined to approximately 2 to 4-fold above the pre-dose level. By four hours, the aPTT had returned to the pre-dose levels in all but one monkey.

The relationship between the AR177 plasma concentration and aPTT is also shown in FIGS. 53, 54, and 55 for doses 2.5, 10, and 40 mg/kg, respectively. There was a no effect plasma AR177 concentration versus aPTT of approximately 60–100 $\mu$g AR177/mL, above which there was prolongation of aPTT. Doubling of aPTT was observed at plasma AR177 concentrations of approximately 100–220 $\mu$g AR177/mL. Tripling of aPTT was observed at plasma AR177 concentrations of approximately 220–300 $\mu$g AR177/mL, after which no correlation was possible because the aPTT values were off-scale. There was no change in aPTT after the first or twelfth doses of 2.5 mg/kg (FIG. 53), since the AR177 plasma concentration did not reach the threshold of approximately 60–100 $\mu$g/mL. There was a maximal two-fold increase in aPTT after the first or twelfth 10 mg/kg doses (FIG. 54). The elimination kinetics of AR177 and the return of aPTT to baseline levels were similar after the first or twelfth doses.

Discussion

These results indicate that AR177, administered as bolus intravenous injections up to 40 mg/kg every other day for 12 doses, did not cause mortality, histopathological or cardiovascular events that have been described for other oligonucleotides (Galbraith et al., 1994; Srinivasan and Iversen, 1995). The only significant change that was observed was a prolongation of aPTT, which was reversible. To our knowledge, this is the first oligonucleotide that has not been observed to cause liver and kidney toxicity following intravenous administration.

The structure of AR177 may contribute to its lack of general toxicity. AR177 contains only two phosphorothioate bonds at the 3' and 5' termini. These phosphorothioate bonds were designed to help prevent endonuclease-induced cleavage of AR177. We speculate that the small number of sulfurs may have reduced the propensity to bind to proteins, a phenomenon that has been observed for full phosphorothioates, which has been speculated to cause toxicity (Srinivasan and Iversen, 1995). AR177's three-dimensional shape may also contribute to its lack of toxicity. AR177 has been shown to form a structure in which hydrogen bonds form between deoxyguanosine residues to create a "G-tetrad" (Rando et al., 1995). This tetrad structure imparts a compact shape which makes it resistant to degradation (Bishop et al., 1996) and may make it relatively non-toxic by minimizing reactive sites. The resistance to degradation has been noted in single and repeat dose pharmacokinetics studies in rodents (Wallace et al., submitted), and in a more complete pharmacokinetic study in cynomolgus monkeys which showed a terminal plasma half-life of greater than 24 hours (data not shown).

The results of the AR177 plasma analysis demonstrated that there was no difference between the AR177 plasma concentrations that were achieved after the first or twelfth (last) doses of 2.5, 10 or 40 mg/kg. These results can be interpreted to mean that AR177 does not induce metabolic enzymes that would, if they were induced, reduce the concentration of AR177 by increasing its metabolism. This has the important implication that repeat doses of AR177, at least when given every other day for 23 days, will not result in pharmacokinetic tolerance.

The results of the AR177 plasma analysis demonstrated that there was a close relationship between the AR177 plasma concentration and aPTT. There was a no effect plasma AR177 concentration versus aPTT of approximately 60–100 $\mu$g AR177/mL, above which there was prolongation of aPTT. The ability to prolong coagulation has been noted to be a feature of other oligonucleotides (Bock et al., 1992; Henry et al., 1994). An oligonucleotide composed of deoxyguanosines and thymidines has been described that binds to thrombin (Paborsky et al., 1993), demonstrates sequence dependent inhibition of coagulation in vitro (Bock et al. 1992), has a G-tetrad structure (Wang et al., 1993), and is active as a short acting anticoagulant in vivo (Griffin et al., 1993; DeAnda et al., 1994). The structure of the oligonucleotide, (GGTTGGTGTGGTTGG) bears some resemblance to AR177 (GTGGTGGGTGGGTGGGT). Both oligonucleotides form G-tetrad structures. A comparison of the anticoagulant properties of these oligonucleotides indicates that the oligonucleotide is approximately 10–100 times more potent than AR177. An examination of the anti-HIV properties of the oligonucleotide showed that it had little or no anti-HIV activity (unpublished data). Thus, although both oligonucleotides are composed of deoxyguanosines and thymidine, and form G-tetrads, they have distinct biological properties.

In conclusion, administration of up to 40 mg/kg of AR177 to cynomolgus monkeys by bolus intravenous injection every other day for 23 days was well tolerated. No mortality or clinical signs of significant toxicity occurred. The most salient alteration in clinical pathology parameters was the prolongation of aPTT in the 10 and 40 mg/kg groups, which reflects inhibition of the intrinsic coagulation pathway. The approximate doubling of aPTT observed in the middle-dose group (10 mg/kg) is considered to be marginally clinically significant following bolus intravenous injection. The severe inhibition of coagulation in the 40 mg/kg group may not be dose limiting since aPTT values had returned to baseline levels fours hours following dosing. It is probable that prolongation of aPTT at these doses could be circumvented by administering AR177 as a slow infusion over the course of several hours in order to stay below the threshold for anticoagulation, which was established to be 60–100 $\mu$g/mL of AR177. The absence of clinical pathology abnormalities or tissue histopathology at even the highest dose (40 mg/kg) after repeated intravenous administration suggests that there is little potential for cumulative toxicity with T31077 with any type of administration.

TABLE F-1

Monkey dosing information

| Group | Treatment | Dose level (mg/kg) | Dose Conc. (mg/mL) | Dose volume (ML/kg) | # of animals Male | # of animals Female | Number sacrificed on: Day 25 (m/f) | Number sacrificed on: Day 38 (m/f) | Weight (kg) mean ± s.d. |
|---|---|---|---|---|---|---|---|---|---|
| 1 | Placebo | 0 | 0 | 3.2 | 3 | 5 | 3/3 | 0/2 | 3.0 ± 0.6 |
| 2 | AR177 | 2.5 | 0.781 | 3.2 | 3 | 3 | 3/3 | | 3.0 ± 0.5 |
| 3 | AR177 | 10 | 3.125 | 3.2 | 3 | 3 | 3/3 | | 3.2 ± 0.7 |
| 4 | AR177 | 40 | 12.5 | 3.2 | 4 | 4 | 3/3 | 1/1 | 3.2 ± 0.6 |

Table 1 - Monkey dosing information. Cynomolgus monkeys were given bolus intravenous injections of AR177 at 2.5, 10 or 40 mg/kg/day at a constant volume every other day for a total of 12 doses. Control monkeys received sterile saline. There were 8 monkeys per group, evenly split between males and females, except for the placebo group, which inadvertently had an extra female. The main group was sacrificed on day 25 following initiation of dosing, which was two days following the twelfth dose on day 23. Two monkeys in the placebo and 40 mg/kg groups were in a recovery group. The recovery group monkeys were sacrificed two weeks (on day 38 after initiation of dosing) after the other monkeys.

TABLE F-2

Body Weights

| Group | Prestudy | Day 7 | Day 14 | Day 21 | Day 25 | Day 28 | Day 35 | Day 38 |
|---|---|---|---|---|---|---|---|---|
| Saline | 3.0 ± 0.6 | 3.1 ± 0.6 | 3.1 ± 0.7 | 3.1 ± 0.7 | 3.3 ± 0.6 | 2.4 ± 0.2 | 2.5 ± 0.2 | 2.5 ± 0.2 |
| 2.5 | 3.1 ± 0.5 | 3.1 ± 0.6 | 3.2 ± 0.6 | 3.2 ± 0.6 | 3.1 ± 0.6 | * | * | * |
| 10 | 3.2 ± 0.7 | 3.2 ± 0.7 | 3.3 ± 0.7 | 3.3 ± 0.7 | 3.2 ± 0.7 | * | * | * |
| 40 | 3.2 ± 0.6 | 3.2 ± 0.6 | 3.3 ± 0.6 | 3.2 ± 0.6 | 3.1 ± 0.6 | 3.4 ± 0.9 | 3.5 * 0.9 | 3.5 ± 1.0 |

* All monkeys were sacrificed on day 25. Monkeys were weighed at pre-study and approximately weekly thereafter. The weights listed for days 28, 35 and 38 are the recovery group monkeys. Values represent the mean ± s.d. of 2–8 monkeys. There were two monkeys per group in the saline and 40 mg/kg recovery groups, and six monkeys per group in the non-recovery groups.

TABLE F-3

Serum Chemistry Values

| | Prestudy | Day 24 | Day 37 | | Prestudy | Day 24 | Day 37 |
|---|---|---|---|---|---|---|---|
| | Alkaline phosphatase (Units/L) | | | | Lactate dehydrogenase (Units/L) | | |
| Saline | 426.8 ± 194.3 | 379.4 ± 176.7 | 222.0 ± 134.4 | Saline | 506.4 ± 530.6 | 1091.6 ± 1057.1 | 206.0 ± 0.0 |
| 2.5 | 459.0 ± 269.9 | 389.3 ± 211.5 | * | 2.5 | 432.5 ± 218.7 | 625.5 ± 170.2 | * |
| 10 | 19.3 ± 237.1 | 343.5 ± 184.3 | * | 10 | 460.3 ± 246.7 | 391.0 ± 151.0 | * |
| 40 | 355.1 ± 194.5 | 294.6 ± 112.7 | 289.5 ± 130.8 | 40 | 1985.4 ± 3242.6 | 764.3 ± 655.7 | 169.5 ± 20.5 |
| | Aspartate aminotransferase (Units/L) | | | | Alanine aminotransferase (Units/L) | | |
| Saline | 54.1 ± 62.1 | 115.3 ± 96.8 | 28.0 ± 7.1 | Saline | 55.8 ± 23.6 | 62.6 ± 27.9 | 58.5 ± 6.4 |
| 2.5 | 59.0 ± 56.7 | 80.5 ± 36.9 | * | 2.5 | 54.0 ± 16.5 | 65.0 ± 15.5 | * |
| 10 | 74.3 ± 798.2 | 54.0 ± 15.1 | * | 10 | 53.7 ± 13.7 | 41.2 ± 6.2 | * |
| 40 | 203.3 ± 335.7 | 160.9 ± 127.3 | 24.0 ± 9.9 | 40 | 91.3 ± 106.7 | 61.3 ± 28.5 | 30.0 ± 57 |

TABLE F-3-continued

Serum Chemistry Values

| | Prestudy | Day 24 | Day 37 | | Prestudy | Day 24 | Day 37 |
|---|---|---|---|---|---|---|---|
| | Blood Urea nitrogen (mg/dL) | | | | Creatinine (mg/dL) | | |
| Saline | 16.4 ± 4.5 | 20.3 ± 5.9 | 22.5 ± 0.7 | Saline | 0.79 ± 0.14 | 0.64 ± 0.07 | 0.50 ± 0.00 |
| 2.5 | 16.2 ± 5.9 | 22.7 ± 5.1 | * | 2.5 | 0.78 ± 0.17 | 0.67 ± 0.10 | * |
| 10 | 19.0 ± 3.2 | 19.8 ± 2.7 | * | 10 | 0.73 ± 0.05 | 0.62 ± 0.04 | * |
| 40 | 16.1 ± 3.9 | 21.4 ± 4.8 | 17.5 ± 4.9 | 40 | 0.79 ± 0.11 | 0.71 ± 0.11 | 0.60 ± 0.14 |

Serum chemistry was evaluated at pre-study, and at days 24 and 37 (recovery monkeys only) following initiation of intravenous AR177 administration. Values represent the mean ± s.d. of 2–8 monkeys. There were two monkeys per group in the saline and 40 mg/kg recovery groups, and six monkeys per group in the non-recovery groups.

TABLE F-4

White Blood Cell, Lymphocytes, Monocytes and Platelet Values

| | Day 1 | | | Day 23 | | | | |
|---|---|---|---|---|---|---|---|---|
| Group | Predose | 30 min | 4 hr | Pre-dose | 30 min | 4 hr | Day 24 | Day 37 |
| | White blood cells ($10^3$/mm$^3$) | | | | | | | |
| Saline | 13.4 ± 2.8 | 19.4 ± 5.9 | 17.5 ± 5.1 | 14.8 ± 5.3 | 20.6 ± 10.2 | 18.7 ± 5.3 | 11.1 ± 3.1 | 9.8 ± 5.4 |
| 2.5 | 15.7 ± 4.3 | 22.4 ± 4.7 | 18.5 ± 4.7 | 13.6 ± 41 | 18.8 ± 9.1 | 16.2 ± 6.4 | 12.4 ± 7.2 | * |
| 10 | 11.1 ± 2.7 | 19.2 ± 4.7 | 20.1 ± 4.1 | 11.4 ± 3.2 | 16.3 ± 4.0 | 19.1 ± 5.5 | 9.1 ± 2.5 | * |
| 40 | 16.0 ± 1.7 | 28.1 ± 4.5 | 25.0 ± 5.4 | 12.3 ± 2.8 | 20.1 ± 5.6 | 20.2 ± 6.0 | 8.9 ± 2.7 | 15.4 ± 6.2 |
| | Lymphocytes ($10^3$/mm$^3$) | | | | | | | |
| Saline | 9.4 ± 3.3 | 7.0 ± 1.8 | 58 ± 1.7 | 7.6 ± 3.4 | 7.0 ± 3.8 | 5.0 ± 1.0 | 5.4 ± 1.7 | 4.7 ± 1.2 |
| 2.5 | 9.4 ± 3.8 | 7.0 ± 3.0 | 6.3 ± 2.4 | 7.6 ± 2.3 | 7.2 ± 4.0 | 5.1 ± 3.1 | 5.7 ± 2.5 | * |
| 10 | 7.0 ± 2.4 | 9.7 ± 2.6 | 6.9 ± 2.0 | 6.2 ± 2.5 | 6.6 ± 1.9 | 4.4 ± 2.0 | 4.9 ± 1.4 | * |
| 40 | 10.6 ± 2.1 | 13.8 ± 3.4 | 6.9 ± 1.4 | 7.4 ± 2.5 | 11.3 ± 4.9 | 5.8 ± 1.9 | 4.6 ± 1.5 | 8.7 ± 5.3 |
| | Monocytes ($10^3$/mm$^3$) | | | | | | | |
| Saline | 0.35 ± 0.25 | 0.69 ± 0.64 | 1.00 ± 0.28 | 0.55 ± 0.38 | 0.48 ± 0.30 | 0.89 ± 0.40 | 0.44 ± 0.10 | 0.49 ± 0.31 |
| 2.5 | 0.29 ± 0.26 | 0.58 ± 0.48 | 0.88 ± 0.53 | 0.56 ± 0.29 | 0.51 ± 0.47 | 0.64 ± 0.36 | 0.45 ± 0.34 | * |
| 10 | 0.36 ± 0.15 | 0.61 ± 0.60 | 0.98 ± 0.788 | 0.43 ± 0.33 | 0.40 ± 0.20 | 0.76 ± 0.45 | 0.39 ± 0.25 | * |
| 40 | 0.37 ± 0.29 | 0.92 ± 0.57 | 1.07 ± 0.45 | 0.65 ± 0.40 | 0.72 ± 0.39 | 1.10 ± 0.74 | 0.39 ± 0.24 | 0.46 ± 0.18 |
| | Platelet ($10^3$mm$^3$) | | | | | | | |
| Saline | 309.0 ± 92. | 323.0 ± 100.7 | 296.3 ± 138.2 | 336.5 ± 81.7 | 337.3 ± 71.3 | 334.9 ± 74.6 | 335.1 ± 87.8 | 331.5 ± 112.4 |
| 2.5 | 319.5 ± 80.6 | 321.2 ± 84.8 | 303.0 ± 77.1 | 376.5 ± 92.0 | 281.4 ± 110.2 | 299.6 ± 65.8 | 341.0 ± 75.6 | * |
| 10 | 391.4 ± 154.3 | 352.2 ± 177.7 | 337.8 ± 199.5 | 463.7 ± 137.9 | 458.3 ± 132.3 | 417.2 ± 58.5 | 431.3 ± 85.7 | * |
| 40 | 358.6 ± 52.6 | 159.5 ± 24.7 | 337.3 ± 81.6 | 431.4 ± 71.5 | 353.5 ± 178.9 | 399.5 ± 65.8 | 394.4 ± 86.8 | 393.0 ± 38.2 |

Leukocytes and platelet hematology were evaluated at predose, 30 minutes and 4 hours on days 1 and 23, and on day 24 and 37 following initiation of intravenous AR177 administration. Values represent the mean ± s.d. of 2 to 8 monkeys. (*) = All monkeys were sacrificed on day 25.

TABLE F-5

Red Blood Cell, Reticulocyte, Hemoglobin and Hematocrit Values

| | Day 1 | | | Day 23 | | | | |
|---|---|---|---|---|---|---|---|---|
| Group | Pre-dose | 30 min | 4 hr | Pre-dose | 30 min | 4 hr | Day 24 | Day 37 |
| | Red blood cells ($10^3$/mm$^3$) | | | | | | | |
| Saline | 6.0 ± 0.4 | 5.8 ± 0.4 | 5.6 ± 0.3 | 6.0 ± 0.6 | 5.8 ± 0.4 | 5.6 ± 0.4 | 4.8 ± 0.4 | 6.1 ± 0.3 |
| 2.5 | 6.0 ± 0.4 | 5.6 ± 0.4 | 5.5 ± 0.3 | 6.0 ± 0.5 | 5.6 ± 0.5 | 5.4 ± 0.5 | 4.7 ± 0.4 | * |
| 10 | 5.6 ± 0.5 | 5.4 ± 0.5 | 5.3 ± 0.4 | 5.8 ± 0.6 | 5.6 ± 0.5 | 5.4 ± 0.4 | 4.6 ± 0.4 | * |
| 40 | 5.8 ± 0.6 | 5.5 ± 0.6 | 5.4 ± 0.5 | 5.8 ± 0.7 | 5.5 ± 0.6 | 5.3 ± 0.6 | 4.6 ± 0.6 | 6.4 ± 0.2 |
| | Reticulocytes ($10^5$/mm$^3$) | | | | | | | |
| Saline | 0.77 ± 0.29 | 0.87 ± 0.27 | 0.82 ± 0.22 | 1.08 ± 0.49 | 0.82 ± 0.37 | 0.81 ± 0.31 | 0.72 ± 0.34 | 0.54 ± 0.23 |
| 2.5 | 0.83 ± 0.21 | 0.79 ± 0.26 | 0.68 ± 0.15 | 0.97 ± 0.45 | 0.82 ± 0.24 | 0.72 ± 0.27 | 0.84 ± 0.32 | * |
| 10 | 0.59 ± 0.16 | 0.53 ± 0.13 | 0.66 ± 0.20 | 1.09 ± 0.31 | 0.72 ± 0.25 | 0.81 ± 0.26 | 0.63 ± 0.14 | * |
| 40 | 0.99 ± 0.56 | 0.60 ± 0.20 | 0.99 ± 0.44 | 1.09 ± 0.33 | 0.60 ± 0.23 | 0.87 ± 0.27 | 0.92 ± 0.33 | 0.80 ± 0.07 |
| | Hemoglobin (g/dL) | | | | | | | |
| Saline | 13.4 ± 1.4 | 12.8 ± 1.4 | 12.3 ± 1.3 | 13.3 ± 0.7 | 12.8 ± 1.1 | 12.4 ± 1.0 | 10.8 ± 1.1 | 11.7 ± 0.2 |
| 2.5 | 14.0 ± 1.1 | 13.3 ± 1.0 | 13.0 ± 12. | 14.0 ± 0.9 | 13.3 ± 1.0 | 12.8 ± 1.0 | 11.2 ± 0.8 | * |
| 10 | 12.9 ± 0.7 | 12.5 ± 0.9 | 12.3 ± 0.8 | 13.2 ± 0.9 | 12.9 ± 0.8 | 12.5 ± 1.1 | 10.6 ± 0.8 | * |
| 40 | 13.6 ± 1.4 | 13.0 ± 1.3 | 12.7 ± 1.5 | 13.5 ± 1.2 | 12.9 ± 1.1 | 12.3 ± 1.1 | 10.8 ± 1.4 | 12.4 ± 2.4 |

TABLE F-5-continued

Red Blood Cell, Reticulocyte, Hemoglobin and Hematocrit Values

| Group | Day 1 | | | Day 23 | | | Day 24 | Day 37 |
|---|---|---|---|---|---|---|---|---|
| | Pre-dose | 30 min | 4 hr | Pre-dose | 30 min | 4 hr | | |
| | | | | Hematocrit (%) | | | | |
| Saline | 41.3 ± 3.5 | 39.6 ± 3.6 | 37.6 ± 3.3 | 45.1 ± 1.8 | 40.1 ± 3.0 | 38.8 ± 2.2 | 33.3 ± 3.1 | 37.5 ± 1.2 |
| 2.5 | 42.6 ± 3.3 | 40.0 ± 2.4 | 39.2 ± 2.8 | 43.1 ± 2.7 | 40.5 ± 3.1 | 39.1 ± 2.9 | 34.0 ± 2.4 | * |
| 10 | 38.9 ± 1.9 | 38.0 ± 2.5 | 37.2 ± 1.8 | 40.9 ± 2.6 | 39.6 ± 2.7 | 38.1 ± 3.3 | 32.3 ± 2.0 | * |
| 40 | 41.6 ± 2.8 | 39.5 ± 3.1 | 38.6 ± 4.0 | 41.7 ± 3.3 | 39.8 ± 23. | 37.8 ± 3.0 | 32.7 ± 3.6 | 39.3 ± 6.2 |

Red blood cell hematology was evaluated at pre-dose, 30 minutes and 4 hours on days 1 and 23, and on day 24 and 37 following initiation of intravenous AR177 administration. Values represent the mean ± s.d. of 2 to 8 monkeys. (*) = All monkeys were sacrificed on day 25.

G. Human Clinical Trials

Four HIV-infected patients/group were dosed with AR177 at 0.75 mg/kg and 115 mg/kg, and two HIV-infected patients were dosed so far with AR177 at 3.0 mg/kg by intravenous infusion over two hours.

Methods

Blood was collected in EDTAp coated tubes at 0.25, 0.5, 1, 2, 2.05, 2.5, 3, 3.5, 4, 6, 8, 11, 14, 26, 48, 98, and 122 hours following initiation of drug administration. Plasma was obtained by low speed centrifugation of the blood, and was stored frozen until analyzed by HPLC for AR177 concentration. The concentration of AR177 was determined in patient plasma using a validated anion-exchange HPLC method at the Division of Clinical Pharmacy of the University of California, San Francisco. This method has a limit of quantitation of 15 ng/mL in human plasma.

Pharmacokinetic analysis

Pharmacokinetic parameters were calculated using PKAnalyst software (MicroMath, Salt Lake City, Utah). The pharmacokinetic data best fit a two compartment model for all of the patients. The alpha and beta half-lives were almost identical in each of the patients, based on the software interpretation of the AR177 plasma concentration versus time plot (FIGS. 56–59). For this reason, only one half-life is reported. (Note that in monkeys, a third half-life of approximately 24 hours was observed at a dose of 5 mg/kg given as an intravenous infusion over two hours. A third half-life was not evident in human data, except perhaps for patient #10.) For each pharmacokinetic parameter, the mean ±s.d. of n=4 was calculated for the 0.75 and 1.5 mg/kg groups and the mean ±s.d. of n=2 was calculated for the 3.0 mg/kg group.

Results

The plasma concentrations of AR177 following intravenous infusion are shown in FIG. 56 (0.75 mg/kg), FIG. 57 (1.5 mg/kg), FIG. 58 (3.0 mg/kg) and FIG. 59 (all doses). Analysis of this data indicate that the plasma pharmacokinetics of AR177 are not directly proportional to the dose (Table G-1). The increase in the $C_{max}$ and AUC were proportionally much greater than the increase in the dose from 0.75 to 3.0 mg/kg. The increase in the $C_{max}$ and AUC were much greater than the increase in the dose. The $C_{max}$ value in the 0.75 mg/kg group was 5.1±1.4 µg/mL and the $C_{max}$ value in the 3.0 mg/kg group was 37.5±0.1 µg/mL, approximately a seven-fold increase (FIG. 60). The AUC value in the 0.75 mg/kg group was 703.6±154.7 µg-min/mL and the AUC value in the 3.0 mg/kg group was 8,277.8±2.937.4 µg-min/mL, approximately a 12-fold increase (Table 1).

The plasma clearance and Vd values reflected the $C_{max}$ and AUC data. The plasma clearance in the 0.75 mg/kg group was 1.1±0.2 mL/min/kg and the clearance in the 3.0 mg/kg group was 0.4±0.2 mL/min/kg, approximately a 65% decrease (FIG. 61). the initial and steady-state volumes of distribution in the 0.75 mg/kg group were 0.16±0.05 L/kg and 0.14±0.05 L/kg, respectively, whereas the initial and steady-state volumes of distribution (Vd) in the 3.0 mg/kg group were 0.08±0.00 L/kg and 0.05±0.03 L/kg, respectively (Table 1).

In agreement with the above data, the plasma half-life in the 0.75 mg/kg group was 28.0±12.7 minutes, and the half-life in the 3.0 mg/kg group was 120.1±60.7 minutes, approximately a four fold increase (FIG. 60).

Conclusions

These results indicate that the plasma pharmacokinetics of AR177 are non-linear and suggest that there is a saturable mechanism for the elimination of the drug.

TABLE G-1

Phase I plasma AR177 pharmacokinetic parameters

| Parameter | Patient #01 | Patient #02 | Patient #03 | Patient #04 | mean ± s.d. |
|---|---|---|---|---|---|
| Dose (mg/kg) | 0.75 | 0.75 | 0.75 | 0.75 | |
| Total dose (mg) | 65.1 | 49.23 | 50.78 | 54.23 | |
| Body weight (kg) | 86.9 | 65.9 | 67.1 | 72.3 | |
| $C_{MAX}$ (µg/mL) | 5.3 | 6.7 | 3.3 | 5.1 | 5.1 ± 1.4 |
| $AUC_{O\text{-infinity}}$ (µg-min/mL) | 730.6 | 910.2 | 563.9 | 609.7 | 703.6 ± 154.7 |
| Terminal T½ (min) | 24.2 | 33.3 | 42.3 | 12.5 | 28.0 ± 12.7 |
| CL (mL/min) | 89.1 | 54.1 | 90.0 | 89.0 | 80.5 ± 17.6 |
| CL (mL/min/kg) | 1.0 | 0.8 | 1.3 | 1.2 | 1.1 ± 0.2 |
| $Vd_{init}$ (L) | 12.30 | 7.40 | 15.20 | 10.60 | 11.38 ± 3.26 |
| $Vd_{init}$ (L/kg) | 0.14 | 0.11 | 0.23 | 0.15 | 0.16 ± 0.05 |
| $Vd_{SS}$ (L) | 11.0 | 6.3 | 13.9 | 8.9 | 10.02 ± 3.19 |
| $Vd_{SS}$ (L/kg) | 0.13 | 0.10 | 0.21 | 0.12 | 0.14 ± 0.05 |

TABLE G-1-continued

Phase I plasma AR177 pharmacokinetic parameters

| Parameter | Patient #05 | Patient #06 | Patient #07 | Patient #08 | mean ± s.d |
|---|---|---|---|---|---|
| $AUMC_{(O\text{-infinity})}$ ($\mu$g-min$^2$/mL) | 90197.3 | 106558.0 | 86825.3 | 609803.1 | 86120.9 ± 18892.0 |
| Dose (mg/kg) | 1.5 | 1.5 | 1.5 | 1.5 | |
| Total dose (mg) | 93.75 | 93.15 | 110.7 | 135.6 | |
| Body weight (kg) | 62.5 | 62.1 | 74 | 90.4 | |
| $C_{MAX}$ ($\mu$g/mL) | 11.6 | 12.9 | 11.9 | 15.2 | 12.9 ± 1.6 |
| $AUC_{(O\text{-infinity})}$ ($\mu$g-min/mL) | 1,745.6 | 1,949.0 | 1,953.0 | 2,794.7 | 2110.6 ± 466.3 |
| Terminal T½ (min) | 110.1 | 75.4 | 29.3 | 42.3 | 64.3 ± 36.2 |
| CL (mL/min) | 53.7 | 47.8 | 56.7 | 48.5 | 51.7 ± 4.3 |
| CL (mL/min/kg) | 0.9 | 0.8 | 0.8 | 0.5 | 0.7 ± 0.1 |
| $VD_{init}$ (L) | 8.10 | 7.20 | 9.30 | 8.90 | 8.38 ± 0.93 |
| $Vd_{init}$ (L/kg) | 0.13 | 0.12 | 0.13 | 0.10 | 0.12 ± 0.01 |
| $Vd_{SS}$ (L) | 5.40 | 6.26 | 8.76 | 8.11 | 7.13 ± 1.57 |
| $Vd_{SS}$ (L/kg) | 0.09 | 0.10 | 0.12 | 0.09 | 0.10 ± 0.01 |
| $AUMC_{(O\text{-infinity})}$ ($\mu$g-min$^2$/mL) | 175479.1 | 255258.6 | 301785.9 | 467118.0 | 299910.4 ± 123070.2 |

| Parameter | Patient #09 | Patient #10 | Patient #11 | Patient #12 | mean ± s.d |
|---|---|---|---|---|---|
| Dose (mg/kg) | 3 | 3 | | | |
| Total dose (mg) | 224.7 | 233.4 | | | |
| Body weight (kg) | 74.9 | 77.8 | | | |
| $C_{MAX}$ ($\mu$g/mL) | 37.4 | 37.6 | | | 37.5 ± 0.1 |
| $AUC_{(O\text{-infinity})}$ ($\mu$g-min/,L) | 6,200.8 | 10,354.9 | | | 8277.8 ± 2937.4 |
| Terminal T½ (min) | 163.0 | 77.2 | | | 120.1 ± 60.7 |
| CL (mL/min) | 36.2 | 22.5 | | | 29.4 ± 9.7 |
| CL (mL/min/kg) | 0.5 | 0.3 | | | 0.4 ± 0.1 |
| $Vd_{init}$ (L) | 6.00 | 6.20 | | | 6.10 ± 0.14 |
| $Vd_{init}$ (L/kg) | 0.08 | 0.08 | | | 0.08 ± 0.00 |
| $Vd_{SS}$ (L) | 1.58 | 5.40 | | | 3.49 ± 2.70 |
| $Vd_{SS}$ (L/kg) | 0.02 | 0.07 | | | 0.05 ± 0.03 |
| $AUMC_{(O\text{-infinity})}$ ($\mu$g-min$_2$/mL) | 269622.5 | 2478968.5 | | | 1374295.5 ± 1562243.5 |

Multi-Dose Trials

Zintevir™ (AR177; T30177) was next used in multiple dosing experiments with AIDS patients. Supporting rationale include:
  anti-HIV-1 activity at sub-micromolar concentrations in lymphocytes infected with clinical isolates of HIV-1;
  prevention of cytopathic effects if HIV-1 in primary $CD_4$+T-cell lymphocytes;
  activity at high multiplicities of infection (MOI); and
  a novel mechanism of action that does not involve inhibition of either reverse transcriptase (RT) or protease activity.

Study Design

This was an open-label, single-center, study to evaluate the safety, pharmacokinetic profile and virologic/immunologic activity of AR177 in HIV patients. Patients that met the screening criteria received multiple doses of AR177 infused every other day for 14 days (seven doses). Patients were allowed to participate in the study at ONLY one dose level. Patients were confined to the Research Unit from Day 0 through Day 18. Patient activities outside the unit had to be acceptable to, and agreed upon prior to study initiation.

Drugs

AR177 was provided by Aronex Pharmaceuticals, Inc. AR177 was obtained from multiple lots during the course of the study. The study drug was available in two vial sizes. These clear glass vials contained 2.2 cc or 15.9 cc of product. Each ml of active drug will deliver a 25 mg dose; thus, the expected total mg dose per vial is 55.0 milligrams and 397.50 milligrams, respectively.

Dosages

Patients meeting all entry criteria were given a two-hour continuous infusion of AR177 every other day for a total of seven infusions. The dosing schedule utilized is shown in the following table (G-2).

| DOSAGE SCHEDULE | | | |
|---|---|---|---|
| Group | Study Medication | Dose Level | Number of Patients |
| 1 | AR177 | 1.5 mg/kg | 3 |
| *2 | AR177 | 3.0 mg/kg | 8 |

*Escalation will occur at a 100% increment from 1.5 mg/kg (Group 1) to 3.0 mg/kg (Group 2), if no ≧Grade III toxicity(ies) occurs.

Dose escalation occurred at a 100% increment from the starting does of 1.50 mg/kg (Group 1) to 3.0 mg/kg (Group 2), if no ≧Grade III toxicities are observed. Details regarding does escalation and/or decalation, and the number of patients to be enrolled at each dose level if toxicity is observed, was determined.

DOSE ADMINISTRATION

The intravenous infusion of study medication will be administered continuously via an indwelling I.V. catheter at a rate of 2 mL/min for two hours.

RESULTS

The plasma levels of HIV-1 RNA are an accepted measure of the plasma viral titer and are directly related to the progression of HIV infection to acquired immunodeficiency disease syndrome (AIDS) and death in humans. Mellors et al. (1996) *Science* 272:1167–1170. Striking results were obtained over the course of a 14-day treatment. In each of the three patients given 3.0 mg/kg dosages, viral load was significantly reduced.

TABLE G-3

Viral Load Data
Plasma PCR/HIV-1 RNA Number or copies/ml)
Dose Level: 3.0 mg/kg

| Patient I.D. No. | Day 0 | Day 7 | Day 13 | % Decrease | Day 18 (4 days post) |
|---|---|---|---|---|---|
| MMJ/038 | 111,560 | 85,020 | 74,350 | 33% | 106,190 |
| RLV/050 | 21,400 | 24,380 | 18,890 | 12% | 26,450 |
| RAH/055 | 187,740 | 152–820 | 84,580 | 55% | 114,260 |

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned as well as those inherent therein. The oligonucleotides, compounds, methods, procedures and techniques described herein are presently representative of preferred embodiments, are intended to be exemplary and are not intended as limitations on the scope. Changes therein and other uses will occur to those skilled in the art which are encompassed within the spirit of the invention or defined by the scope of the appended claims. It will be readily apparent to one skilled in the art that various substitutions and modifications may be made to the invention disclosed herein without departing from the scope and spirit of the invention.

What is claimed is:

1. An oligonucleotide having a nucleotide sequence chosen from the group consisting of SEQ ID NOS 2–27, 29, 31–39, 46–52 and 53–87, wherein said nucleotide sequence is optionally modified at the 3' terminus or 5' terminus by attachment of a substituent moiety selected from the group consisting of propylamine, poly-L-lysine, cholesterol, fatty acid chains of length 2 to 24 carbons, and vitamin E.

2. An oligonucleotide having a nucleotide sequence chosen from the group consisting of SEQ ID NOS 2–27 29, 31–39, 46–52 and 53–87, wherein said nucleotide sequence includes at least one modification selected from the group consisting of:

a modified 3' terminus by attachment of a substituent moiety selected from the group consisting of propylamine, poly-L-lysine, cholesterol, fatty acid chains of length 2 to 24 carbons, and vitamin E;

a modified 5' terminus by attachment of a substituent moiety selected from the group consisting of propylamine, poly-L-lysine, cholesterol, fatty acid chains of length 2 to 24 carbons, and vitamin E;

a replacement of at least one phosphodiester moiety with a phosphorothioate moiety;

a deletion of a thymidine base from at least one nucleotide;

a substitution of a guanosine for at least one thymidine;

a substitution of 5- propynyl-2'-deoxyuridine for at least one thymidine;

a substitution of 5-bromo-2'-deoxyuridine for at least one thymidine;

a substitution of 5-iodo-2'-deoxyuridine for at least one thymidine;

a substitution of 2'-deoxyinosine for at least one thymidine; and a substitution of at least one cytidine for at least one thymidine.

3. An oligonucleotide having the basic sequence of

5'-gtggtgggtgggtgggt-3'    (SEQ ID NO 33, 87), said basic sequence optionally modified by addition to or deletion of at least one nucleotide from the 3' or 5' terminus such that said oligonucleotide has a nucleotide sequence from 9 to 45 nucleotides in length;

optionally modified at the 3' terminus by attachment of a substituent moiety selected from the group consisting of propylamine, poly-L-lysine, cholesterol and cholesterol with a triglycyl linker;

optionally modified at the 5' terminus by attachment of a substituent moiety selected from the group consisting of propylamine, poly-L-lysine, cholesterol and cholesterol with a triglycyl linker;

optionally modified by replacement of at least one phosphodiester moiety with a phosphorothioate moiety;

optionally modified by deletion of a thymidine base from at least one nucleotide;

optionally modified by substitution of 5–1propynyl-2'-deoxyuridine for at least one thymidine, optionally modified by substitution of 5-bromo-2'-deoxyuridine for at least one thymidine, optionally modified by substitution of 5-iodo-2'-deoxyuridine for at least one thymidine, optionally modified by substitution of 2'-deoxyinosine for at least one thymidine, optionally modified by substitution of at least one cytidine for at least one thymidine, and optionally modified by substitution of ribose 2'-O-alkylribose, or 2'-arylribose for the deoxyribose of at least one nucleotide.

4. The oligonucleotide of claim 3 wherein at least one nucleotide is modified by deletion of a thymidine base.

5. The oligonucleotide of claim 3 having the nucleotide sequence and phosphorothioate linkage distribution 5'-g*tggtgggtgggtggg*t-3'    (SEQ ID NO 33, 87)

wherein * indicates a phosphorothioate linkage.

6. An oligonucleotide having a sequence selected from the group consisting of

| | |
|---|---|
| 5'-gtggtgggtgggtgggg-3' | (SEQ ID NO 46), |
| 5'-gtggtgggtgggtggg-3' | (SEQ ID NO 47), |
| 5'-ggtgggtgggtgggt-3' | (SEQ ID NO 48), |
| 5'-gtggtgggtgggt-3' | (SEQ ID NO 49), |
| 5'-gtggtgggt-3' | (SEQ ID NO 50), |
| 5'-   gtgggtgggtgggt-3' | (SEQ ID NO 51), |
|     5'-gtgggtgggt-3' | (SEQ ID NO 52), |
| 5'-gtggttggtgtggttgg-3' | (SEQ ID NO 54), |
| 5'-ggttggtgtggttggg-3' | (SEQ ID NO 55), |
| 5'-gtggtgggtgtggttggt-3' | (SEQ ID NO 56), |
| 5'-gtggtgggtgtggtgggt-3' | (SEQ ID NO 57), |
| 5'-gtggttggtg_gttggt-3' | (SEQ ID NO 55), |
| 5'-gtggtgggtg_ggttggt-3' | (SEQ ID NO 56), |
| 5'-gtggttggtg_ggtgggt-3' | (SEQ ID NO 58), |
| 5'-g_ggtgggtgggtgggt-3' | (SEQ ID NO 60), |
| 5'-gtgggtggtgggtgggt-3' | (SEQ ID NO 61), |
| 5'-gtggtggggtggtgggt-3' | (SEQ ID NO 62), |
| 5'-gtggtgggtggggtggt-3' | (SEQ ID NO 63), and |
| 5'-gtgggtggtggggtggt-3' | (SEQ ID NO 64) | wherein _ denotes a nucleotide lacking a base;

optionally modified at the 3'terminus by attachment of a substituent moiety selected from the group consisting of propylamine, poly-L-lysine cholesterol and cholesterol with a triglycyl linker;

optionally modified at the 5'terminus by attachment of a substituent moiety selected from the group consisting of propylamine poly-L-lysine, cholesterol and cholesterol with a triglycyl linker;

optionally modified by replacement of at least one phosphodiester moiety with a phosphorothioate moiety;

optionally modified by deletion of a thymidine base from at least one nucleotide;

optionally modified by substitution of 5-propynyl-2'-deoxyuridine for at least one thymidine, optionally modified by substitution of 5-bromo-2'-deoxyuridine for at least one thymidine, optionally modified by substitution of 5-iodo -2'-deoxyuridine for at least one thymidine, optionally modified by substitution of 2'-deoxyinosine for at least one thymidine, optionally modified by substitution of at least one cytidine for at least one thymidine, and optionally modified by substitution of ribose 2'-O-alkylribose, or 2'-O-arylribose for the deoxyribose of at least one nucleotide.

7. An oligonucleotide having a sequence selected from the group consisting of

```
5'-guggugggugggugggu-3'      (SEQ ID NO 59),
5'-g_ggtgggtgggtgggt-3'      (SEQ ID NO 60),
5'-g_ggPgggtgggPgggt-3'      (SEQ ID NO 68),
5'-g_gggPggtgggPgggt-3'      (SEQ ID NO 69),
5'-I_ggIIggIIggIIggI-3'      (SEQ ID NO 70),
5'-gtgggPggtgggpgggt-3'      (SEQ ID NO 71),
5'-gtggtgggtgggtgggt-3'      (SEQ ID NO 72),
5'-gtggtgggtgggBgggt-3'      (SEQ ID NO 73),
5'-gtggBgggBgggBgggt-3'      (SEQ ID NO 74),
5'-gtggIgggtgggtgggt-3'      (SEQ ID NO 75),
5'-gtggtgggIgggtgggt-3'      (SEQ ID NO 76),
5'-gtggtgggtgggIgggt-3'      (SEQ ID NO 77),
5'-gtggIgggIgggIgggt-3'      (SEQ ID NO 78),
5'-gtggcgggtgggtgggt-3'      (SEQ ID NO 79),
5'-gtggtgggcgggtgggt-3'      (SEQ ID NO 80),
5'-gtggtgggtgggcgggt-3'      (SEQ ID NO 81),
5'-gtggcgggcgggcgggt-3'      (SEQ ID NO 82),
5'-gggaggtgggtctg-3'         (SEQ ID NO 84),
5'-gggaggtgggtctg-3'         (SEQ ID NO 85),
5'-tgggaggtgggtctg-3'        (SEQ ID NO 83), and
5'-gcggggctccatgggggtcg-3'   (SEQ ID NO 86)
``` wherein

P is 5-propynyl-2'-deoxyuridine

I is 2'-deoxyinosine

B is 5-bromo 2'-deoxyuridine, and u is uridine or 2'-O-methyluridine;

optionally modified at the 3'terminus by attachment of a substituent moiety selected from the group consisting of propylamine, poly-L-lysine, cholesterol and cholesterol with a triglycyl linker;

optionally modified at the 5'terminus by attachment of a substituent moiety selected from the group consisting of propylamine, poly-L-lysine cholesterol and cholesterol with a triglycyl linker; and optionally modified by replacement of at least one phosphodiester moiety with a phosphorothioate moiety.

8. An oligonucleotide having the nucleotide and phosphorothioate linkage distribution 5'-g*_ggtgggtgggtggg*t-3'      (SEQ ID NO 60)

wherein * indicates a phosphorothioate linkage, and _ indicates a nucleotide lacking a base optionally modified at the 3 'terminus by attachment of a substituent moiety selected from the group consisting of propylamine, poly-L-lysine, cholesterol and cholesterol with a triglycyl optionally modified at the 5'terminus by attachment of a substituent moiety selected from the group consisting of propylamine, poly-L-lysine, cholesterol and cholesterol with a triglycyl linker;

optionally modified by replacement of at least one phosphodiester moiety with a phosphorothioate moiety;

optionally modified by deletion of a thymidine base from at least one nucleotide;

optionally modified by substitution of 5-propynyl-2'-deoxyuridine for at least one thymidine, optionally modified by substitution of 5-bromo-2'-deoxyuridine for at least one thymidine, optionally modified by substitution of 5-iodo-2'-deoxyuridine for at least one thymidine, optionally modified by substitution of 2'-deoxyinosine for at least one thymdine, optionally modified by substitution of at least one cytidine for at least one thymidine, and optionally modified by substitution of ribose 2'-O-alkylribose, or 2'-O-arylribose for the deoxyribose of at least one nucleotide.

9. An oligonucleotide selected from the group consisting of

5'-g*c*ggggc*t*c*c*a*tggggg*t*c*g-3'      (SEQ ID NO 86)

and

5'-g*cggggctccatgggggtc*g-3'      (SEQ ID NO 86)

wherein * indicates a phosphorothioate linkage optionally modified at the 3'terminus by attachment of a substituent moiety selected from the group consisting of propylamine, poly-L-lysine, cholesterol and cholesterol with a triglycyl linker;

optionally modified at the 5'terminus by attachment of a substituent moiety selected from the group consisting of propylamine, poly-L-lysine, cholesterol and cholesterol with a triglycyl linker;

optionally modified by substitution of 5-propynyl-2'deoxyuridine for at least one thymidine, optionally modified by substitution of5-bromo-2'-deoxyuridine for at least one thymidine, optionally modified by substitution of 5-iodo-2'-deoxyuridine for at least one thymidine, optionally modified by substitution of 2'-deoxyinosine for at least one thymidine, and optionally modified by substitution of ribose or 2'-O-arylribose for the deoxyribose of at least one nucleotide.

10. An oligonucleotide having the nucleotide sequence

5'-gtggtgggtgggtgggtggtgggtggtggttgtgggtgggt ggtg-3' (SEQ ID NO 24), optionally modified by substitution of phosphorothioate for phosphodiester linkages; and modified at the 3' end by attachment of a substituent moiety selected from the group consisting of propylamine, poly-L-lysine, cholesterol and similar lipophilic or amine groups which enhance cellular uptake or stability of the oligonucleotide.

11. A pharmaceutical composition for inhibiting production of human immunodeficiency virus type 1 (HIV-1) comprising an oligonucleotide of any one of claim 1 and a pharmaceutically acceptable carrier.

12. A method of treating a disease associated with HIV-1 infection pharmacologically effective dose comprising administering to a person in need thereof a of the composition of claim 11 said dose being sufficient to inhibit the production of HIV-1 virus.

13. The method of claim 12 wherein said dose is at least 3.0 mg/kg of patient body weight.

14. A method of treating an infection by a human immunodeficiency virus, comprising administering to a person in need thereof a pharmacological dose of the composition of claim 11.

15. The method of claim 14 wherein said dose is at least 3.0 mg/kg of patient body weight administered in seven equal doses over 14 days.

16. The method of claim 14 further comprising administering another drug, having a different antiviral mechanism of action than that of said oligonucleotide, optionally before or after said administering of said composition such that resistance to said other drug or to said composition is avoided.

17. A method of making a pharmaceutical composition for the treatment of HIV-1 infection comprising synthesizing at least one of the oligonucleotides of claim 5 or 8, in the form of a fully neutralized salt, dissolving said oligonucleotide in phosphate-buffered saline;

sterilizing said phosphate-buffered saline solution of said oligonucleotide; and preparing said solution at a concentration of about 25 mg/mL.

* * * * *

```
                      SEQUENCE LISTING (1) GENERAL INFORMATION:

(iii) NUMBER OF SEQUENCES: 87

(2) INFORMATION FOR SEQ ID NO:1:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 38
        (D) OTHER INFORMATION: /note= "Amine moiety
             attached to 3' end"

(xi) SEQUENCE DESCRIPTION: SEQ ID NO:1:

TGGGTGGGGT GGGGTGGGGG GGTGTGGGGT GTGGGGTG                             38

(2) INFORMATION FOR SEQ ID NO:2:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GTGGGGTGTG GGGTGTGGGG GGGTGGGGTG GGGTGGGT                             38

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

GGGTGGGTGG GTGGGTGG                                              18

(2) INFORMATION FOR SEQ ID NO:4:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGTGGTGGGG GGGGGTGGGG TGGTGGTGGG GGTGTTGG                         38

(2) INFORMATION FOR SEQ ID NO:5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTGGTGGTGG TGTTGGTGGT GGTTTGGGGG GTGGGG                           36

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GTGGTTGGTG GTGGTGTGTG GGTTTGGGGT GGGGGG                           36

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 36
        (D) OTHER INFORMATION: /note= "phosphorothioate
            backbone"

(xi) SEQUENCE DESCRIPTION: SEQ ID NO:7:

GTGGTGGTGG TGTTGGTGGT GGTTTGGGGG GTGGGG                           36

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

```
    (ix) FEATURE:
         (A) NAME/KEY: misc_feature
         (B) LOCATION: 36
         (D) OTHER INFORMATION: /note= "phosphorothioate
             backbone"

(xi) SEQUENCE DESCRIPTION: SEQ ID NO:8:

GTGGTTGGTG GTGGTGTGTG GGTTTGGGGT GGGGGG                              36

(2) INFORMATION FOR SEQ ID NO:9:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGTGGGGTGG TGGTGGTTGG GGGGGGGGGG T                                   31

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

GGTGGTTGGG GGGTGGGGGG G                                              21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGGTGGGGTG GTGGGTGGGG G                                              21

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGTGGGTGGT TTGTGTGGTT GGTGGGTTTT                                     30

(2) INFORMATION FOR SEQ ID NO:13:

(i) SEQUENCE CHARACTERISTICS:
        (A) LENGTH: 31 base pairs
        (B) TYPE: nucleic acid
        (C) STRANDEDNESS: single
        (D) TOPOLOGY: linear
```

(ii) MOLECULE TYPE: DNA (genomic)

(xi) SEQUENCE DESCRIPTION: SEQ ID NO:13:

GGGGGGGGGG TGTGGGGGGG GGTTGTGGTG G                              31

(2) INFORMATION FOR SEQ ID NO:14:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:14:

GGTGGGTGGG TTGGGGGGTG GGTGGGG                                   27

(2) INFORMATION FOR SEQ ID NO:15:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:15:

TGGGGTTTGG GTGGGGGGTT GGGTGGTTG                                 29

(2) INFORMATION FOR SEQ ID NO:16:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:16:

GGGTGGTGGT GTTGGTGTTG TGTG                                      24

(2) INFORMATION FOR SEQ ID NO:17:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:17:

GGTGGGGGGG TTGGTGTGTT TG                                        22

(2) INFORMATION FOR SEQ ID NO:18:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:18:

```
                                      -continued

GTGTGGGGGG GTGGGGTGGG GTGGGT                                              26

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GGGTGGGTGG GTGGGTGGGT GGGTGG                                              26

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 26
        (D) OTHER INFORMATION: /note= "Amine moiety
            attached to 3' end"

(xi) SEQUENCE DESCRIPTION: SEQ ID NO:20:

GTTGGGGGTT GTTGGTGGGG TGGTGG                                              26

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "Amine moiety
            attached to 3' end"

(xi) SEQUENCE DESCRIPTION: SEQ ID NO:21:

TGGTGGGTGT GTGGGGGGTG TTGGGGGTTG TTGGTGGGGT GGTGG                          45

(2) INFORMATION FOR SEQ ID NO:22:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "cholesterol moiety
            attached to 3' end"

(xi) SEQUENCE DESCRIPTION: SEQ ID NO:22:

TGGTGGGTGT GTGGGGGGTG TTGGGGGTTG TTGGTGGGGT GGTGG                          45
```

(2) INFORMATION FOR SEQ ID NO:23:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "cholesterol moiety
            attached to 3' end"

(xi) SEQUENCE DESCRIPTION: SEQ ID NO:23:

GTGGTGGGTG GGTGGGTGGT GGGTGGTGGT TGTGGGTGGG TGGTG                    45

(2) INFORMATION FOR SEQ ID NO:24:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "Amine moiety
            attached to 3' end"

(xi) SEQUENCE DESCRIPTION: SEQ ID NO:24:

GTGGTGGGTG GGTGGGTGGT GGGTGGTGGT TGTGGGTGGG TGGTG                    45

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 26
        (D) OTHER INFORMATION: /note= "cholesterol moiety
            attached to 3' end"

(xi) SEQUENCE DESCRIPTION: SEQ ID NO:25:

GTTGGGGGTT GTTGGTGGGG TGGTGG                                      26

(2) INFORMATION FOR SEQ ID NO:26:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 45
        (D) OTHER INFORMATION: /note= "Amine moiety attached to 3' end"

(xi) SEQUENCE DESCRIPTION: SEQ ID NO:26:

GATCCATGTC AGTGACACTG CGTAGATCCG ATGATCCAGT CGATG          45

(2) INFORMATION FOR SEQ ID NO:27:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(ix) FEATURE:
       (A) NAME/KEY: misc_feature
       (B) LOCATION: 26
       (D) OTHER INFORMATION: /note= "phosphorothioate
           backbone and amine moiety attached to
           backbone"

(xi) SEQUENCE DESCRIPTION: SEQ ID NO:27:

GTTGGGGGTT GTTGGTGGGG TGGTGG          26

(2) INFORMATION FOR SEQ ID NO:28:

(i) SEQUENCE CHARACTERISTICS:
       (A) LENGTH: 26 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:28:

GGTGGTGGGG TGGTTGTTGG GGGTTG          26

(2) INFORMATION FOR SEQ ID NO:29:

(i) SEQUENCE CHARACTERISTICS:
       (A) LENGTH: 45 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:29:

GGTGGTGGGG TGGTTGTTGG GGGTTGTTGG GGGTGTGTGG GTGGT          45

(2) INFORMATION FOR SEQ ID NO:30:

(i) SEQUENCE CHARACTERISTICS:
       (A) LENGTH: 18 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:30:

GGGTGGTTGG GTGGTTGG          18

(2) INFORMATION FOR SEQ ID NO:31:

(i) SEQUENCE CHARACTERISTICS:
       (A) LENGTH: 18 base pairs
       (B) TYPE: nucleic acid

```
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 18
            (D) OTHER INFORMATION: /note= "Amine moiety
                attached to 3' end"

(xi) SEQUENCE DESCRIPTION: SEQ ID NO:31:

GGGTGGGTGG GTGGGTGG                                                  18

(2) INFORMATION FOR SEQ ID NO:32:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 18
            (D) OTHER INFORMATION: /note= "Amine moiety
                attached to 3' end and phosphothioate
                backbone"

(xi) SEQUENCE DESCRIPTION: SEQ ID NO:32:

GGGTGGGTGG GTGGGTGG                                                  18

(2) INFORMATION FOR SEQ ID NO:33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 17
            (D) OTHER INFORMATION: /note= "Amine moiety
                attached to 3' end"

(xi) SEQUENCE DESCRIPTION: SEQ ID NO:33:

GTGGTGGGTG GGTGGGT                                                   17

(2) INFORMATION FOR SEQ ID NO:34:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 27
            (D) OTHER INFORMATION: /note= "Amine moiety
                attached to 3' end"

(xi) SEQUENCE DESCRIPTION: SEQ ID NO:34:

GTGGTGGGTG GGTGGGTGGT GGGTGGT                                        27
```

(2) INFORMATION FOR SEQ ID NO:35:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 37
        (D) OTHER INFORMATION: /note= "Amine moiety
            attached to 3' end"

(xi) SEQUENCE DESCRIPTION: SEQ ID NO:35:

GTGGTGGGTG GGTGGGTGGT GGGTGGTGGT TGTGGGT                37

(2) INFORMATION FOR SEQ ID NO:36:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 16
        (D) OTHER INFORMATION: /note= "Amine moiety
            attached to 3' end"

(xi) SEQUENCE DESCRIPTION: SEQ ID NO:36:

TTGTGGGTGG GTGGTG                                          16

(2) INFORMATION FOR SEQ ID NO:37:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 29
        (D) OTHER INFORMATION: /note= "Amine moiety
            attached to 3' end"

(xi) SEQUENCE DESCRIPTION: SEQ ID NO:37:

TGGTGGGTGG TGGTTGTGGG TGGGTGGTG                      29

(2) INFORMATION FOR SEQ ID NO:38:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 38
        (D) OTHER INFORMATION: /note= "Amine moiety
            attached to 3' end"

```
        (xi) SEQUENCE DESCRIPTION: SEQ ID NO:38:

GTGGGTGGGT GGTGGGTGGT GGTTGTGGGT GGGTGGTG                              38

(2) INFORMATION FOR SEQ ID NO:39:

(i) SEQUENCE CHARACTERISTICS:
           (A) LENGTH: 45 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: misc_feature
           (B) LOCATION: 45
           (D) OTHER INFORMATION: /note= "phosphorothioate
               backbone and amine moiety attached to 3' end"

(xi) SEQUENCE DESCRIPTION: SEQ ID NO:39:

GTGGTGGGTG GGTGGGTGGT GGGTGGTGGT TGTGGGTGGG TGGTG                      45

(2) INFORMATION FOR SEQ ID NO:40:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: misc_feature
           (B) LOCATION: 18
           (D) OTHER INFORMATION: /note= "Amine moiety
               attached to 3' end"

(xi) SEQUENCE DESCRIPTION: SEQ ID NO:40:

GATCCATGTC AGTGACAC                                                    18

(2) INFORMATION FOR SEQ ID NO:41:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)

(ix) FEATURE:
           (A) NAME/KEY: misc_feature
           (B) LOCATION: 18
           (D) OTHER INFORMATION: /note= "Amine moiety
               attached to 3' end and phosphorothioate
               backbone"

(xi) SEQUENCE DESCRIPTION: SEQ ID NO:41:

GATCCATGTC AGTGACAC                                                    18

(2) INFORMATION FOR SEQ ID NO:42:

(i) SEQUENCE CHARACTERISTICS:
           (A) LENGTH: 18 base pairs
           (B) TYPE: nucleic acid
           (C) STRANDEDNESS: single
           (D) TOPOLOGY: linear (ii) MOLECULE TYPE: DNA (genomic)
```

(ix) FEATURE:
        (A) NAME/KEY: misc_feature
        (B) LOCATION: 18
        (D) OTHER INFORMATION: /note= "Amine moiety
            attached to 3' end"

(xi) SEQUENCE DESCRIPTION: SEQ ID NO:42:

CCCCCCCCCC CCCCCCCC                                                    18

(2) INFORMATION FOR SEQ ID NO:43:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 18
        (D) OTHER INFORMATION: /note= "Amine moiety
            attached to 3' end and phosphorothioate
            backbone"

(xi) SEQUENCE DESCRIPTION: SEQ ID NO:43:

CCCCCCCCCC CCCCCCCC                                                    18

(2) INFORMATION FOR SEQ ID NO:44:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

TTCATTTGGG AAACCCTTGG AACCTGACTG ACTGGCCGTC GTTTTAC                    47

(2) INFORMATION FOR SEQ ID NO:45:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

GTAAAACGAC GGCCA                                                       15

(2) INFORMATION FOR SEQ ID NO:46:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

GTGGTGGGTG GGTGGGG                                                     17

(2) INFORMATION FOR SEQ ID NO:47:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:47:

GTGGTGGGTG GGTGGG                                                16

(2) INFORMATION FOR SEQ ID NO:48:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:48:

TGGTGGGTGG GTGGGT                                                16

(2) INFORMATION FOR SEQ ID NO:49:

(i) SEQUENCE CHARACTERISTICS:
      (A) LENGTH: 13 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:49:

GTGGTGGGTG GGT                                                   13

(2) INFORMATION FOR SEQ ID NO:50:

(i) SEQUENCE CHARACTERISTICS:
      (A) LENGTH: 9 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:50:

GTGGTGGGT                                                         9

(2) INFORMATION FOR SEQ ID NO:51:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:51:

GTGGGTGGGT GGGT                                                  14

(2) INFORMATION FOR SEQ ID NO:52:

(i) SEQUENCE CHARACTERISTICS:
      (A) LENGTH: 10 base pairs (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:52:

GTGGGTGGGT                                                              10

(2) INFORMATION FOR SEQ ID NO:53:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:53:

GGTTGGTGTG GTTGG                                                        15

(2) INFORMATION FOR SEQ ID NO:54:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:54:

GTGGTTGGTG TGGTTGG                                                      17

(2) INFORMATION FOR SEQ ID NO:55:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:55:

GTGGTTGGTG TGGTTGGT                                                     18

(2) INFORMATION FOR SEQ ID NO:56:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:56:

GTGGTGGGTG TGGTTGGT                                                     18

(2) INFORMATION FOR SEQ ID NO:57:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:57:

GTGGTGGGTG TGGTGGGT                                                         18

(2) INFORMATION FOR SEQ ID NO:58:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 11
            (D) OTHER INFORMATION: /note= "the base is
                removed from this nucleotide"

(xi) SEQUENCE DESCRIPTION: SEQ ID NO:58:

GUGGUGGGUG GGUGGGU                                                          17

(2) INFORMATION FOR SEQ ID NO:59:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: RNA (genomic)

(xi) SEQUENCE DESCRIPTION: SEQ ID NO:59:

GUGGUGGGUG GGUGGGU                                                          17

(2) INFORMATION FOR SEQ ID NO:60:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (A) NAME/KEY: misc_feature
            (B) LOCATION: 2
            (D) OTHER INFORMATION: /note= "the base is
                removed from this nucleotide"

(xi) SEQUENCE DESCRIPTION: SEQ ID NO:60:

GNGGTGGGTG GGTGGGT                                                          17

(2) INFORMATION FOR SEQ ID NO:61:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:61:

GTGGGTGGTG GGTGGGT                                                          17

(2) INFORMATION FOR SEQ ID NO:62:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:62:

GTGGTGGGGT GGTGGGT                                       17

(2) INFORMATION FOR SEQ ID NO:63:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:63:

GTGGTGGGTGG GGTGGT                                      17

(2) INFORMATION FOR SEQ ID NO:64:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

GTGGGTGGTGG GGTGGT                                      17

(2) INFORMATION FOR SEQ ID NO:65:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 5
        (D) OTHER INFORMATION: /note= "C-5 propynl dU"

(xi) SEQUENCE DESCRIPTION: SEQ ID NO:65:

GTGGNGGGGT GGTGGGT                                      17

(2) INFORMATION FOR SEQ ID NO:66:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13
        (D) OTHER INFORMATION: /note= "C-5 propynl dU"

(xi) SEQUENCE DESCRIPTION: SEQ ID NO:66:

GTGGTGGGTG GGNGGGT                                                      17

(2) INFORMATION FOR SEQ ID NO:67:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 5,13
        (D) OTHER INFORMATION: /note= "C-5 propynl dU"

(xi) SEQUENCE DESCRIPTION: SEQ ID NO:67:

GTGGNGGGTG GGNGGGT                                                      17

(2) INFORMATION FOR SEQ ID NO:68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 2
        (D) OTHER INFORMATION: /note= "the base is
            removed from this nucleotide"

(ix) FEATURE:
        (A) NAME/KEY: misc_feature
        (B) LOCATION: 5,13
        (D) OTHER INFORMATION: /note= "C-5 propynl dU"

(xi) SEQUENCE DESCRIPTION: SEQ ID NO:68:

GUGGUGGGUG GGUGGGU                                                      17

(2) INFORMATION FOR SEQ ID NO:69:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 2
        (D) OTHER INFORMATION: /note= "the base is
            removed from this nucleotide"

(ix) FEATURE:
        (A) NAME/KEY: misc_feature
        (B) LOCATION: 6,13
        (D) OTHER INFORMATION: /note= "C-5 propynl dU"

(xi) SEQUENCE DESCRIPTION: SEQ ID NO:69:

GNGGGTGGTG GGTGGGT                                                      17

(2) INFORMATION FOR SEQ ID NO:70:

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 2
        (D) OTHER INFORMATION: /note= "the base is
            removed from this nucleotide"

(ix) FEATURE:
        (A) NAME/KEY: misc_feature
        (B) LOCATION: 1,5,6,9,10,13,14,17
        (D) OTHER INFORMATION: /note= "deoxyinosine"

(xi) SEQUENCE DESCRIPTION: SEQ ID NO:70:

NNGGNNGGNN GGNNGGN                                                    17

(2) INFORMATION FOR SEQ ID NO:71:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 6,13
        (D) OTHER INFORMATION: /note= "C-5 propynl dU"

(xi) SEQUENCE DESCRIPTION: SEQ ID NO:71:

GNGGGTGGTG GGTGGGT                                                    17

(2) INFORMATION FOR SEQ ID NO:72:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13
        (D) OTHER INFORMATION: /note= "3' cholesterol via
            triglycyl linker"

(xi) SEQUENCE DESCRIPTION: SEQ ID NO:72:

GTGGTGGGTG GGTGGGT                                                    17

(2) INFORMATION FOR SEQ ID NO:73:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 13
```

(D) OTHER INFORMATION: /note= "5-bromo dU"

(xi) SEQUENCE DESCRIPTION: SEQ ID NO:73:

GTGGTGGGTG GGNGGGT                                                              17

(2) INFORMATION FOR SEQ ID NO:74:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 5,9,13
        (D) OTHER INFORMATION: /note= "5-bromo dU"

(xi) SEQUENCE DESCRIPTION: SEQ ID NO:74:

GTGGNGGGNG GGNGGGT                                                              17

(2) INFORMATION FOR SEQ ID NO:75:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 5
        (D) OTHER INFORMATION: /note= "5-iodo dU"

(xi) SEQUENCE DESCRIPTION: SEQ ID NO:75:

GTGGNGGGTG GGTGGGT                                                              17

(2) INFORMATION FOR SEQ ID NO:76:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature
        (B) LOCATION: 9
        (D) OTHER INFORMATION: /note= "5-iodo dU"

(xi) SEQUENCE DESCRIPTION: SEQ ID NO:76:

GTGGTGGGNG GGTGGGT                                                              17

(2) INFORMATION FOR SEQ ID NO:77:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: misc_feature (B) LOCATION: 13
          (D) OTHER INFORMATION: /note= "5-iodo dU"

(xi) SEQUENCE DESCRIPTION: SEQ ID NO:77:

GTGGTGGGTG GGNGGGT                                              17

(2) INFORMATION FOR SEQ ID NO:78:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(ix) FEATURE:
          (A) NAME/KEY: misc_feature
          (B) LOCATION: 5,9,13
          (D) OTHER INFORMATION: /note= "5-iodo dU"

(xi) SEQUENCE DESCRIPTION: SEQ ID NO:78:

GTGGNGGGNG GGNGGGT                                              17

(2) INFORMATION FOR SEQ ID NO:79:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:79:

GTGGCGGGTG GGTGGGT                                              17

(2) INFORMATION FOR SEQ ID NO:80:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:80:

GTGGTGGGCG GGTGGGT                                              17

(2) INFORMATION FOR SEQ ID NO:81:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO:81:

GTGGTGGGTG GGCGGGT                                              17

(2) INFORMATION FOR SEQ ID NO:82:

(i) SEQUENCE CHARACTERISTICS:
          (A) LENGTH: 17 base pairs
          (B) TYPE: nucleic acid
          (C) STRANDEDNESS: single (D) TOPOLOGY: linear (ii) MOLECULE TYPE: DNA (genomic)

(xi) SEQUENCE DESCRIPTION: SEQ ID NO:82:

GTGGCGGGCG GGCGGGT                                                    17

(2) INFORMATION FOR SEQ ID NO:83:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:83:

TGGGAGGTGG GTCTG                                                      15

(2) INFORMATION FOR SEQ ID NO:84:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:84:

TGGGAGGTGG GTCTG                                                      15

(2) INFORMATION FOR SEQ ID NO:85:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:85:

TGGGAGGTGG GTCTG                                                      15

(2) INFORMATION FOR SEQ ID NO:86:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:86:

GCGGGGCTCC ATGGGGTCG                                                  20

(2) INFORMATION FOR SEQ ID NO:87:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

-continued (xi) SEQUENCE DESCRIPTION: SEQ ID NO:87:

GTGGTGGGTG GGTGGGT                    17